(12) United States Patent
Cong et al.

(10) Patent No.: US 11,434,269 B2
(45) Date of Patent: *Sep. 6, 2022

(54) METHODS FOR TREATING DISEASE USING INHIBITORS OF BONE MORPHOGENETIC PROTEIN 6 (BMP6)

(71) Applicant: Novartis AG, Basel (CH)

(72) Inventors: Feng Cong, Quincy, MA (US); William Dietrich, Cambridge, MA (US); Nathalie George, Village-Neuf (FR); Dong Liu, Natick, MA (US); Asher Schachter, Needham, MA (US); Aditi Soni, Cambridge, MA (US); Jing Zhou, Boxborough, MA (US)

(73) Assignee: Novartis AG, Basel (CH)

( * ) Notice: Subject to any disclaimer, the term of this patent is extended or adjusted under 35 U.S.C. 154(b) by 651 days.

This patent is subject to a terminal disclaimer.

(21) Appl. No.: 16/464,113

(22) PCT Filed: Jun. 13, 2017

(86) PCT No.: PCT/IB2017/053507
§ 371 (c)(1),
(2) Date: May 24, 2019

(87) PCT Pub. No.: WO2017/216724
PCT Pub. Date: Dec. 21, 2017

(65) Prior Publication Data
US 2021/0130428 A1 May 6, 2021

Related U.S. Application Data

(60) Provisional application No. 62/350,257, filed on Jun. 15, 2016.

(51) Int. Cl.
| | |
|---|---|
| *A61K 39/00* | (2006.01) |
| *A61K 38/00* | (2006.01) |
| *C07K 14/505* | (2006.01) |
| *C07K 16/22* | (2006.01) |
| *A61P 7/06* | (2006.01) |
| *A61K 38/18* | (2006.01) |

(52) U.S. Cl.
CPC .............. *C07K 14/505* (2013.01); *A61P 7/06* (2018.01); *C07K 16/22* (2013.01); *A61K 38/1816* (2013.01); *A61K 39/00* (2013.01); *C07K 2317/24* (2013.01); *C07K 2317/55* (2013.01); *C07K 2317/565* (2013.01); *C07K 2317/622* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,187,076 A | 2/1993 | Wozney et al. | |
| 5,242,813 A | 9/1993 | Pastan et al. | |
| 5,562,903 A | 10/1996 | Co et al. | |
| 5,610,021 A | 3/1997 | Rueger et al. | |
| 5,830,671 A | 11/1998 | Dennis et al. | |
| 7,612,181 B2 | 11/2009 | Wu et al. | |
| 7,674,605 B2 | 3/2010 | Lin et al. | |
| 8,318,167 B2 | 11/2012 | Lin et al. | |
| 8,795,665 B2 | 8/2014 | Seo et al. | |
| 8,980,582 B2 | 3/2015 | Seo et al. | |
| 9,334,331 B2* | 5/2016 | Igawa | C07K 16/36 |
| 9,862,764 B2 | 1/2018 | Cong | |
| 10,421,807 B2* | 9/2019 | Gonzales | A61P 17/08 |
| 10,683,346 B2 | 6/2020 | Cong et al. | |
| 2003/0224501 A1 | 12/2003 | Young et al. | |
| 2008/0171043 A1 | 7/2008 | Lin et al. | |
| 2008/0260736 A1 | 10/2008 | Lin et al. | |
| 2010/0136015 A1 | 6/2010 | Lin et al. | |
| 2010/0209926 A1 | 8/2010 | Alaoui et al. | |
| 2011/0070242 A1 | 3/2011 | Roth et al. | |
| 2014/0056902 A1 | 2/2014 | Shimizu et al. | |
| 2014/0086919 A1 | 3/2014 | Lin et al. | |
| 2014/0170161 A1 | 6/2014 | Seo et al. | |
| 2014/0199314 A1 | 7/2014 | Lin et al. | |
| 2014/0309404 A1 | 10/2014 | Seo et al. | |
| 2016/0115545 A1 | 4/2016 | Clube | |
| 2016/0158357 A1* | 6/2016 | Clube | C07K 16/18 424/134.1 |
| 2016/0176956 A1 | 6/2016 | Cong et al. | |

FOREIGN PATENT DOCUMENTS

| | | |
|---|---|---|
| WO | 9639518 A1 | 12/1996 |
| WO | 2007027713 | 3/2007 |
| WO | 2008033408 A2 | 3/2008 |
| WO | 2010056981 A2 | 5/2010 |
| WO | 2012150973 A1 | 11/2012 |
| WO | 2012151609 A1 | 11/2012 |

(Continued)

OTHER PUBLICATIONS

Al Qaraghuli et al. Antibody-protein binding and conformational changes: identifying allosteric signaling pathways to engineer a better effector response. Nature Scientific Reports 10:13969; (2020). (Year: 2020).*

Tokuriki et al. Stability effects of mutations and protein evolvability, Current Opinion in Structural Biology, 19:596-604 (2009). (Year: 2009).*

Bhattacharya et al. Impact of genetic variation on three dimensional structure and function of proteins; PLOS One 12(3): e0171355, pp. 1-22, (Mar. 2017). (Year: 2017).*

(Continued)

*Primary Examiner* — Elizabeth C. Kemmerer
*Assistant Examiner* — Regina M DeBerry
(74) *Attorney, Agent, or Firm* — Jana E. Harris

(57) ABSTRACT

The present invention relates methods of treatment using BMP6 antagonists.

25 Claims, 15 Drawing Sheets

Specification includes a Sequence Listing.

(56) References Cited

FOREIGN PATENT DOCUMENTS

| WO | 2014099391 A1 | 6/2014 |
|---|---|---|
| WO | 2016098079 A2 | 6/2016 |

OTHER PUBLICATIONS

Edwards et al. The remarkable flexibility of the human antibody repertoire; isolation of over one thousand different antibodies to a single protein, BLyS. Journal of Molecular Biology 334:103-118; (2003). (Year: 2003).*

Lloyd et al. Modelling the human immune response: performance of a 10(11) human antibody repertoire against a broad panel of therapeutically relevant antigens. Protein Engineering, Eng. Design & Selection 22(3): 159-168; (2009). (Year: 2009).*

Goel et al. Plasticity within the antigen-combining site may manifest as molecular mimicry in the humoral immune response. J. Immunol. 173: 7358-7367; (2004). (Year: 2004).*

Khan et al. Adjustable locks and flexible keys: plasticity of epitope-paratope interactions in germline antibodies. J. Immunol. 192: 5398-5405; (2014). (Year: 2014).*

Poosarla et al. Computational De Novo Design of Antibodies Binding to a Peptide With High Affinity. Biotechn. Bioeng. 114(6): 1331-1342; (2017). (Year: 2017).*

Rabia, et al. Understanding and overcoming trade-offs between antibody affinity, specificity, stability and solubility. Biochemical Engineering Journal 137:365-374; (2018). (Year: 2018).*

Igor et al. Pharmacologic inhibition of hepcidin expression reverses anemia of chronic inflammation in rats. Blood vol. 118/No. 18:4977; (2011). (Year: 2011).*

Shalev et al. Clinical and laboratory manifestations of congenital dyserythropoietic anemia type I in young adults. European Journal of Haematology vol. 68/No. 3:p. 170-174, (2002). (Year: 2002).*

Sun et al., "Targeting the hepciding-ferroportin axis to develop new treatment strategies for anemia of chronic disease and anemia of inflammation", American Journal of Hematology, 87(4):392-400. 2012.

Corradini et al., "BMP6 Treatment Compensates for the Molecular Defect and Ameliorates Hemochromatosis in Hfe Knockout Mice", Gastroenterology, 139(5):1721-1729. 2010.

Coyne, et al., "Ferric Gluconate Is Highly Efficacious in Anemic Hemodialysis Patients with High Serum Ferritin and Low Trasnferrin Saturation: Results of the Dialysis Patents' Response to IV Iron with Elevated Ferritin (DRIVE) Study", Journal of the American Society of Nephrology, 18(3):975-984. 2007.

Andriopoulos, Jr, et al., "BMP6 is a key endogenous regulator of hepcidin expression and iron metabolism", Nature Genetics, 2009, 41(4):482-487.

Babitt et al., "Modulation of bone morphogenetic protein signaling in vivo regulates systemic iron balance", Journal of Clinical Investigation, 2007, 117(7)1933-1939.

Celeste et al., "Identification of transforming growth factor B family members present in bone-inductive protein purified from bovine bone", Proc. Natl. Acad. Sci. USA, 1990, 87:9843-9847.

Chia Chi Sun et al. "Targeting the hepcidin-ferroportin axis to develop new treatment strategies for anemia of chronic disease and anemia of inflammation" American Journal of Hematology, (2012), vol. 87, No. 4, pp. 392-400.

Collins et al., "Hepcidin Regulation of Iron Transport", The Journal of Nutrition, 2008, 138:2284-2288.

D.W. Coyne et al. "Ferric Gluconate is Highly Efficacious in Anemic Hemodialysis Patients with High Serum Ferritin and Low Transferrin Saturation: Results of the Dialysis Patients' Response to IV Iron with Elevated Ferritin (DRIVE) Study", Journalof the American Society of Nephrology, (2007), vol. 18, pp. 975-984.

Dondelinger et al., "Understanding the Significance and Implications of Antibody Numbering and Antigen-Binding Surface/Residue Definition," Frontiers in Immunology, vol. 9, No. 2278, Oct. 2018 (pp. 1-15).

Elena Corradini et al. "BMP6 Treatment Compensates for the Molecular Defect and Ameliorates Hemochromatosis in Hfe Knockout Mice" Gastroenterology (2010), vol. 139, No. 5, pp. 1721-1729.

Falzacappa et al., "A bone morphogenetic protein (BMP)-responsive element in the hepcidin promoter controls HFE2-mediated hepatic hepcidin expression and its response to IL-6 in cultured cells", J. Mol. Med, 2008, 86:531-540.

Herrera et al., "A rapid and sensitive bioassay for the simultaneous measurement of multiple bone morphogenetic proteins. Identification and quantification of BMP4, BMP6 and BMP9 in bovine and human serum," BMC Cell Biol. Mar. 19, 2009; 10:20.

International Search Report and Written Opinion for International Application No. PCT/IB2015/059797, dated Jun. 10, 2016 (14 pages).

International Search Report and Written Opinion for International Application No. PCT/IB2017/053507 dated Oct. 13, 2017.

Kautz et al., "BMP/Smad signaling is not enhanced in Hfe-deficient mice despite increased Bmp6 expression", Blood, 2009, 114(12):2515-2520.

Kautz et al., "Iron regulates phosphorylation of SmadJan. 5, 2008 and gene expression of Bmp6, Smad7, Id1 and Atoh8 in the mouse liver", Blood, 2008, 112(4): 1503-1509.

Wall et al., "Biosynthesis and In Vivo Localization of the Decapentaplegic-Vg-related Protein, DVR-6 (Bone Morphogenetic Proten-6)", J. Cell Biology, 1993, 120(2):493-502.

Xia et al., "Hemojuvelin regulates hepcidin expression via a selective subset of BMP ligands and receptors independently of neogenin", Blood, 2008, 111(10):5195-5204.

Yu et al., "Dorsomorphin inhibits BMP signals required for embryogenesis and iron metabolism", Nat. Chem. Biol., 2008, 4(1):33-41.

Van Der Weerd et al., Poor Compliance with Guidelines on Anemia Treatment in a Cohort of Chronic Hemodialysis Patients, Blood Purification, Aug. 8, 2012, 19-27, 34.

* cited by examiner

Shaded amino acids represent sequence identity among mature BMP5, 6, and 7
Boxed area indicates peptide of BMP6 recognized by NOV0442 (parental IgG) and Antibody 7

SEQUENCE LISTING

```
<160> NUMBER OF SEQ ID NOS: 99

<210> SEQ ID NO 1
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Arg Ser Ser Glu Asn Ile Tyr Arg Asn Leu Ala
1               5                   10

<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Ala Ala Thr Asn Leu Ala Asp
1               5

<210> SEQ ID NO 3
```

```
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gln Gly Ile Trp Gly Thr Pro Leu Thr
1               5

<210> SEQ ID NO 4
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Asn Ile Tyr Arg Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ile Trp Gly Thr Pro Leu
                85                  90                  95

Thr Phe Gly Gly Gly Thr Lys Val Glu Ile Lys
            100                 105

<210> SEQ ID NO 5
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 5

Asp Ile Gln Met Thr Gln Ser Pro Ser Ser Leu Ser Ala Ser Val Gly
1               5                   10                  15

Asp Arg Val Thr Ile Thr Cys Arg Ser Ser Glu Asn Ile Tyr Arg Asn
            20                  25                  30

Leu Ala Trp Tyr Gln Gln Lys Pro Gly Lys Ala Pro Lys Leu Leu Ile
        35                  40                  45

Tyr Ala Ala Thr Asn Leu Ala Asp Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gly Ile Trp Gly Thr Pro Leu
                85                  90                  95

Thr Phe Gly Gly Gly Thr Lys Val Glu Ile Lys Arg Thr Val Ala Ala
            100                 105                 110
```

```
Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 6
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gly Tyr Thr Phe Thr Ser Tyr Ala Met His
1               5                   10

<210> SEQ ID NO 7
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Tyr Ile Asn Pro Tyr Asn Asp Gly Thr Lys Tyr Asn Glu Asn Phe Lys
1               5                   10                  15

<210> SEQ ID NO 8
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Arg Pro Phe Gly Asn Ala Met Asp Ile
1               5

<210> SEQ ID NO 9
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 9

Ser Tyr Val Val His
```

```
1               5
```

<210> SEQ ID NO 10
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

```
Arg Ile Lys Asp His Lys Gln Gly Tyr Thr Thr Ala Tyr Ala Ala Ser
1               5                   10                  15

Val Lys Gly
```

<210> SEQ ID NO 11
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

```
Val Glu Arg Ser Lys Ser Gly Phe Asp Asn
1               5                   10
```

<210> SEQ ID NO 12
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

```
Gly Phe Thr Phe Ser Ser Tyr
1               5
```

<210> SEQ ID NO 13
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

```
Lys Asp His Lys Gln Gly Tyr Thr
1               5
```

<210> SEQ ID NO 14
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 14

```
Val Glu Arg Ser Lys Ser Gly Phe Asp Asn
1               5                   10
```

<210> SEQ ID NO 15
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 15

```
Gln Val Gln Leu Val Glu Ser Gly Gly Gly Leu Val Lys Pro Gly Gly
  1               5                  10                  15
Ser Leu Arg Leu Ser Cys Ala Ala Ser Gly Phe Thr Phe Ser Ser Tyr
             20                  25                  30
Val Val His Trp Val Arg Gln Ala Pro Gly Lys Gly Leu Glu Trp Val
         35                  40                  45
Gly Arg Ile Lys Asp His Lys Gln Gly Tyr Thr Thr Ala Tyr Ala Ala
     50                  55                  60
Ser Val Lys Gly Arg Phe Thr Ile Ser Arg Asp Asp Ser Lys Asn Thr
 65                  70                  75                  80
Leu Tyr Leu Gln Met Asn Ser Leu Lys Thr Glu Asp Thr Ala Val Tyr
                 85                  90                  95
Tyr Cys Ala Arg Val Glu Arg Ser Lys Ser Gly Phe Asp Asn Trp Gly
            100                 105                 110
Gln Gly Thr Leu Val Thr Val Ser Ser
            115                 120
```

<210> SEQ ID NO 16
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 16

```
caggtgcaat tggtggaaag cggcggtggc ctggtgaaac caggcggcag cctgcgcctg      60
agctgcgccg cctccggatt caccttttct tcttacgttg ttcattgggt gcgccaggcc     120
ccgggcaaag gtctcgagtg ggtgggccgt atcaaagacc acaaacaggg ctacactact     180
gcttatgccg cctctgtgaa aggccgcttt accattagcc gcgatgattc gaaaaacacc     240
ctgtatctgc aaatgaacag cctgaaaacc gaagatacgg ccgtgtatta ttgcgcgcgt     300
gttgaacgtt ctaaatctgg tttcgataac tggggccaag gcaccctggt gactgttagc     360
tca                                                                   363
```

<210> SEQ ID NO 17
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 17

```
Gln Val Gln Leu Val Glu Ser Gly Gly Gly Leu Val Lys Pro Gly Gly
  1               5                  10                  15
Ser Leu Arg Leu Ser Cys Ala Ala Ser Gly Phe Thr Phe Ser Ser Tyr
             20                  25                  30
```

-continued

```
Val Val His Trp Val Arg Gln Ala Pro Gly Lys Gly Leu Glu Trp Val
         35                  40                  45

Gly Arg Ile Lys Asp His Lys Gln Gly Tyr Thr Thr Ala Tyr Ala Ala
50                  55                  60

Ser Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                    85                  90                  95

Tyr Cys Ala Arg Val Glu Arg Ser Lys Ser Gly Phe Asp Asn Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
                180                 185                 190

Pro Ser Ser Ser Leu Gly Thr Gln Thr Tyr Ile Cys Asn Val Asn His
                195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
                260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
        290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
                340                 345                 350

Tyr Thr Leu Pro Pro Ser Arg Glu Glu Met Thr Lys Asn Gln Val Ser
                355                 360                 365

Leu Thr Cys Leu Val Lys Gly Phe Tyr Pro Ser Asp Ile Ala Val Glu
        370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
        435                 440                 445
```

Pro Gly Lys
    450

<210> SEQ ID NO 18
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 18

| | | | | | |
|---|---|---|---|---|---|
| caggtgcaat | tggtggaaag | cggcggtggc | ctggtgaaac | caggcggcag | cctgcgcctg | 60 |
| agctgcgccg | cctccggatt | cacctttctct | tcttacgttg | ttcattgggt | gcgccaggcc | 120 |
| ccgggcaaag | gtctcgagtg | gtgggccgt | atcaaagacc | acaaacaggg | ctacactact | 180 |
| gcttatgccg | cctctgtgaa | aggccgcttt | accattagcc | gcgatgattc | gaaaaacacc | 240 |
| ctgtatctgc | aaatgaacag | cctgaaaacc | gaagatacgg | ccgtgtatta | ttgcgcgcgt | 300 |
| gttgaacgtt | ctaaatctgg | tttcgataac | tggggccaag | gcaccctggt | gactgttagc | 360 |
| tcagcctcca | ccaagggtcc | atcggtcttc | cccctggcac | cctcctccaa | gagcacctct | 420 |
| gggggcacag | cggccctggg | ctgcctggtc | aaggactact | tccccgaacc | ggtgacggtg | 480 |
| tcgtggaact | caggcgccct | gaccagcggc | gtgcacacct | tcccggctgt | cctacagtcc | 540 |
| tcaggactct | actccctcag | cagcgtggtg | accgtgccct | ccagcagctt | gggcacccag | 600 |
| acctacatct | gcaacgtgaa | tcacaagccc | agcaacacca | aggtggacaa | gagagttgag | 660 |
| cccaaatctt | gtgacaaaac | tcacacatgc | ccaccgtgcc | cagcacctga | actcctgggg | 720 |
| ggaccgtcag | tcttcctctt | ccccccaaaa | cccaaggaca | ccctcatgat | ctcccggacc | 780 |
| cctgaggtca | catgcgtggt | ggtggacgtg | agccacgaag | accctgaggt | caagttcaac | 840 |
| tggtacgtgg | acggcgtgga | ggtgcataat | gccaagacaa | agccgcggga | ggagcagtac | 900 |
| aacagcacgt | accgggtggt | cagcgtcctc | accgtcctgc | accaggactg | gctgaatggc | 960 |
| aaggagtaca | agtgcaaggt | ctccaacaaa | gccctcccag | cccccatcga | gaaaaccatc | 1020 |
| tccaaagcca | aagggcagcc | ccgagaacca | caggtgtaca | ccctgccccc | atcccgggag | 1080 |
| gagatgacca | agaaccaggt | cagcctgacc | tgcctggtca | aaggcttcta | tcccagcgac | 1140 |
| atcgccgtgg | agtgggagag | caatgggcag | ccggagaaca | actacaagac | cacgcctccc | 1200 |
| gtgctggact | ccgacggctc | cttcttcctc | tacagcaagc | tcaccgtgga | caagagcagg | 1260 |
| tggcagcagg | ggaacgtctt | ctcatgctcc | gtgatgcatg | aggctctgca | caaccactac | 1320 |
| acgcagaaga | gcctctccct | gtctccgggt | aaa | | | 1353 |

<210> SEQ ID NO 19
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19

Thr Gly Ser Ser Ser Asn Ile Gly Ala Gly Tyr Ser Val His
1               5                   10

<210> SEQ ID NO 20
<211> LENGTH: 7

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Gly Ser Ser Glu Arg Pro Ser
1               5

<210> SEQ ID NO 21
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln Ser Trp Asp Ser Ser Gln Thr Leu Val Val
1               5                   10

<210> SEQ ID NO 22
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Ser Ser Ser Asn Ile Gly Ala Gly Tyr Ser
1               5                   10

<210> SEQ ID NO 23
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gly Ser Ser
1

<210> SEQ ID NO 24
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Trp Asp Ser Ser Gln Thr Leu Val
1               5

<210> SEQ ID NO 25
<211> LENGTH: 111
<212> TYPE: PRT
<213> ORGANISM: Artificial Sequence
<220> FEATURE:
<221> NAME/KEY: source
```

<223> OTHER INFORMATION: /note="Description of Artificial Sequence:
       Synthetic polypeptide"

<400> SEQUENCE: 25

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Ser Val His Trp Tyr Gln Gln Leu Pro Gly Thr Ala Pro Lys Leu
        35                  40                  45

Leu Ile Tyr Gly Ser Ser Glu Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Trp Asp Ser Ser
                85                  90                  95

Gln Thr Leu Val Val Phe Gly Gly Gly Thr Lys Leu Thr Val Leu
            100                 105                 110

<210> SEQ ID NO 26
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
       Synthetic polynucleotide"

<400> SEQUENCE: 26
cagagcgtgc tgacccagcc gccgagcgtg agcggtgcac cgggccagcg cgtgaccatt      60
agctgtaccg gcagcagcag caacattggt gctggttact ctgtgcattg gtaccagcag     120
ctgccgggca cggcgccgaa actgctgatc tatggtagct ctgaacgccc gagcggcgtg     180
ccggatcgct ttagcggatc caaaagcggc accagcgcca gcctggcgat taccggcctg     240
caagcagaag acgaagcgga ttattactgc cagtcttggg actcttctca gactctggtt     300
gtgtttggcg gcggcacgaa gttaaccgtc cta                                  333

<210> SEQ ID NO 27
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
       Synthetic polypeptide"

<400> SEQUENCE: 27

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Ser Val His Trp Tyr Gln Gln Leu Pro Gly Thr Ala Pro Lys Leu
        35                  40                  45

Leu Ile Tyr Gly Ser Ser Glu Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Trp Asp Ser Ser
                85                  90                  95

```
Gln Thr Leu Val Val Phe Gly Gly Thr Lys Leu Thr Val Leu Gly
            100                 105                 110

Gln Pro Lys Ala Ala Pro Ser Val Thr Leu Phe Pro Pro Ser Ser Glu
            115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
                195                 200                 205

Lys Thr Val Ala Pro Thr Glu Cys Ser
            210                 215
```

```
<210> SEQ ID NO 28
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 28
cagagcgtgc tgacccagcc gccgagcgtg agcggtgcac cgggccagcg cgtgaccatt      60
agctgtaccg gcagcagcag caacattggt gctggttact ctgtgcattg gtaccagcag     120
ctgccgggca cggcgccgaa actgctgatc tatggtagct ctgaacgccc gagcggcgtg     180
ccggatcgct ttagcggatc caaaagcggc accagcgcca gcctggcgat taccggcctg     240
caagcagaag acgaagcgga ttattactgc cagtcttggg actcttctca gactctggtt     300
gtgtttggcg gcggcacgaa gttaaccgtc ctaggtcagc ccaaggctgc cccctcggtc     360
actctgttcc cgccctcctc tgaggagctt caagccaaca ggccacact ggtgtgtctc      420 ataagtgact tctacccggg agccgtgaca gtggcctgga aggcagatag cagccccgtc     480
aaggcgggag tggagaccac cacaccctcc aaacaaagca caacaagta cgcggccagc     540 agctatctga gcctgacgcc tgagcagtgg aagtcccaca gaagctacag ctgccaggtc     600
acgcatgaag ggagcaccgt ggagaagaca gtggccccta cagaatgttc a              651
```

```
<210> SEQ ID NO 29
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 29

Ser Tyr Val Val His
1               5
```

```
<210> SEQ ID NO 30
<211> LENGTH: 19
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 30

Arg Ile Lys Arg Glu Ser Ser Ser Tyr Thr Thr Met Tyr Ala Ala Pro
1               5                   10                  15

Val Lys Gly

<210> SEQ ID NO 31
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 31

Val Glu Arg Ser Lys Ser Gly Phe Asp Asn
1               5                   10

<210> SEQ ID NO 32
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 32

Gly Phe Thr Phe Ser Ser Tyr
1               5

<210> SEQ ID NO 33
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 33

Lys Arg Glu Ser Ser Ser Tyr Thr
1               5

<210> SEQ ID NO 34
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 34

Val Glu Arg Ser Lys Ser Gly Phe Asp Asn
1               5                   10

<210> SEQ ID NO 35
<211> LENGTH: 121
<212> TYPE: PRT
<213> ORGANISM: Artificial Sequence
<220> FEATURE:
<221> NAME/KEY: source
```

<223> OTHER INFORMATION: /note="Description of Artificial Sequence:
      Synthetic polypeptide"

<400> SEQUENCE: 35

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Val Val His Trp Val Arg Gln Ala Pro Gly Lys Gly Leu Glu Trp Val
        35                  40                  45

Gly Arg Ile Lys Arg Glu Ser Ser Tyr Thr Thr Met Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Glu Arg Ser Lys Ser Gly Phe Asp Asn Trp Gly
            100                 105                 110

Gln Gly Thr Leu Val Thr Val Ser Ser
        115                 120

<210> SEQ ID NO 36
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 36
caggtgcagc tggtggaatc aggcggcgga ctggtcaagc ctggcggtag cctgagactg       60
agctgcgctg ctagtggctt caccttctct agctacgtgg tgcactgggt cagacaggcc     120
cctggtaaag gcctggagtg ggtcggacgg attaagagag agtcctctag ctacactact     180
atgtacgccg ctcccgtgaa gggccggttc actatctcta gggacgactc taagaacacc     240
ctgtacctgc agatgaatag cctgaaaacc gaggacaccg ccgtctacta ctgcgctaga     300
gtggaacggt ctaagtcagg cttcgataac tggggtcagg gcaccctggt caccgtgtct     360
agc                                                                   363

<210> SEQ ID NO 37
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Val Val His Trp Val Arg Gln Ala Pro Gly Lys Gly Leu Glu Trp Val
        35                  40                  45

Gly Arg Ile Lys Arg Glu Ser Ser Tyr Thr Thr Met Tyr Ala Ala
    50                  55                  60

```
Pro Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                 85                  90                  95

Tyr Cys Ala Arg Val Glu Arg Ser Lys Ser Gly Phe Asp Asn Trp Gly
            100                 105                 110

Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 38
<211> LENGTH: 1353
<212> TYPE: DNA
```

<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 38

```
caggtgcagc tggtggaatc aggcggcgga ctggtcaagc tggcggtag cctgagactg      60
agctgcgctg ctagtggctt caccttctct agctacgtgg tgcactgggt cagacaggcc    120
cctggtaaag gcctggagtg ggtcggacgg attaagagag agtcctctag ctacactact    180
atgtacgccg ctcccgtgaa gggccggttc actatctcta gggacgactc taagaacacc    240
ctgtacctgc agatgaatag cctgaaaacc gaggacaccg ccgtctacta ctgcgctaga    300
gtggaacggt ctaagtcagg cttcgataac tggggtcagg gcaccctggt caccgtgtct    360
agcgctagca ctaagggccc aagtgtgttt ccctggccc ccagcagcaa gtctacttcc     420
ggcggaactg ctgccctggg ttgcctggtg aaggactact ccccgagcc cgtgacagtg     480
tcctggaact ctggggctct gacttccggc gtgcacacct ccccgccgt gctgcagagc     540
agcggcctgt acagcctgag cagcgtggtg acagtgccct ccagctctct gggaacccag    600
acctatatct gcaacgtgaa ccacaagccc agcaacacca aggtggacaa gagagtggag    660
cccaagagct gcgacaagac ccacacctgc ccccctgcc cagctccaga actgctggga     720
gggccttccg tgttcctgtt ccccccaag cccaaggaca ccctgatgat cagcaggacc     780
cccgaggtga cctgcgtggt ggtggacgtg tcccacgagg acccagaggt gaagttcaac    840
tggtacgtgg acggcgtgga ggtgcacaac gccaagacca gcccagaga ggagcagtac     900
aacagcacct acagggtggt gtccgtgctg accgtgctgc accaggactg gctgaacggc    960
aaagaataca agtgcaaagt ctccaacaag gccctgccag ccccaatcga aaagacaatc   1020
agcaaggcca agggccagcc acgggagccc caggtgtaca ccctgccccc cagccgggag   1080
gagatgacca gaaaccaggt gtccctgacc tgtctggtga agggcttcta ccccagcgat   1140
atcgccgtgg agtgggagag caacggccag ccgagaaca actacaagac cacccccca    1200
gtgctggaca gcgacggcag cttcttcctg tacagcaagc tgaccgtgga caagtccagg   1260
tggcagcagg gcaacgtgtt cagctgcagc gtgatgcacg aggccctgca caaccactac   1320
acccagaagt ccctgagcct gagccccggc aag                                1353
```

<210> SEQ ID NO 39
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 39

```
Thr Gly Ser Ser Ser Asn Ile Gly Ala Gly Tyr Ser Val His
1               5                   10
```

<210> SEQ ID NO 40
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

```
<400> SEQUENCE: 40

Gly Gln Ser Glu Arg Pro Ser
1               5

<210> SEQ ID NO 41
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 41

Gln Ser Trp Asp Ser Ser Gln Thr Leu Val Val
1               5                   10

<210> SEQ ID NO 42
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 42

Ser Ser Ser Asn Ile Gly Ala Gly Tyr Ser
1               5                   10

<210> SEQ ID NO 43
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 43

Gly Gln Ser
1

<210> SEQ ID NO 44
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 44

Trp Asp Ser Ser Gln Thr Leu Val
1               5

<210> SEQ ID NO 45
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gln Ser Val Leu Thr Gln Pro Pro Ser Val Ser Gly Ala Pro Gly Gln
1               5                   10                  15
```

Arg Val Thr Ile Ser Cys Thr Gly Ser Ser Ser Asn Ile Gly Ala Gly
            20                  25                  30

Tyr Ser Val His Trp Tyr Gln Gln Leu Pro Gly Thr Ala Pro Lys Leu
        35                  40                  45

Leu Ile Tyr Gly Gln Ser Glu Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Trp Asp Ser Ser
                85                  90                  95

Gln Thr Leu Val Val Phe Gly Gly Gly Thr Lys Leu Thr Val Leu
            100                 105                 110

<210> SEQ ID NO 46
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 46
cagtcagtcc tgactcagcc ccctagcgtc agcggcgctc ccggtcagag agtgactatt     60
agctgcaccg gctctagctc taatatcggc gctggctata gcgtgcactg gtatcagcag    120
ctgcccggca ccgcccctaa gctgctgatc tacggtcagt cagagcggcc tagcggcgtg    180
cccgataggt ttagcggctc taagtcaggc actagcgcta gtctggctat caccggcctg    240
caggctgagg acgaggccga ctactactgt cagtcctggg actctagtca gaccctggtg    300
gtgttcggcg gaggcactaa gctgaccgtg ctg                                 333

<210> SEQ ID NO 47
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 47

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Ser Val His Trp Tyr Gln Gln Leu Pro Gly Thr Ala Pro Lys Leu
        35                  40                  45

Leu Ile Tyr Gly Gln Ser Glu Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Trp Asp Ser Ser
                85                  90                  95

Gln Thr Leu Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
                180                 185                 190

His Arg Ser Tyr Ser Cys Gln Val Thr His Glu Gly Ser Thr Val Glu
            195                 200                 205

Lys Thr Val Ala Pro Thr Glu Cys Ser
    210                 215

<210> SEQ ID NO 48
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 48
cagtcagtcc tgactcagcc ccctagcgtc agcggcgctc ccggtcagag agtgactatt    60
agctgcaccg gctctagctc taatatcggc gctggctata gcgtgcactg gtatcagcag   120
ctgcccggca ccgcccctaa gctgctgatc tacggtcagt cagagcggcc tagcggcgtg   180
cccgataggt ttagcggctc taagtcaggc actagcgcta gtctggctat caccggcctg   240
caggctgagg acgaggccga ctactactgt cagtcctggg actctagtca gaccctggtg   300
gtgttcggcg gaggcactaa gctgaccgtg ctgggtcagc taaggctgc ccccagcgtg   360 accctgttcc cccccagcag cgaggagctg caggccaaca aggccaccct ggtgtgcctg   420
atcagcgact ctacccagg cgccgtgacc gtggcctgga aggccgacag cagccccgtg   480
aaggccggcg tggagaccac cacccccagc aagcagagca acaacaagta cgccgccagc   540
agctacctga gcctgacccc cgagcagtgg aagagccaca ggtcctacag ctgccaggtg   600
acccacgagg gcagcaccgt ggaaaagacc gtggccccaa ccgagtgcag c            651

<210> SEQ ID NO 49
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 49

Ser Tyr Val Val His
1               5

<210> SEQ ID NO 50
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 50

```
Arg Thr Arg His Ser Asp Met Gly Tyr Ala Thr Ser Tyr Ala Ala Pro
1               5                   10                  15

Val Lys Gly
```

<210> SEQ ID NO 51
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 51

```
Val Glu Arg Ser Lys Ser Gly Phe Asp Asn
1               5                   10
```

<210> SEQ ID NO 52
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 52

```
Gly Phe Thr Phe Ser Ser Tyr
1               5
```

<210> SEQ ID NO 53
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 53

```
Arg His Ser Asp Met Gly Tyr Ala
1               5
```

<210> SEQ ID NO 54
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 54

```
Val Glu Arg Ser Lys Ser Gly Phe Asp Asn
1               5                   10
```

<210> SEQ ID NO 55
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

```
Gln Val Gln Leu Val Glu Ser Gly Gly Gly Leu Val Lys Pro Gly Gly
1               5                   10                  15
```

```
Ser Leu Arg Leu Ser Cys Ala Ala Ser Gly Phe Thr Phe Ser Ser Tyr
            20                  25                  30

Val Val His Trp Val Arg Gln Ala Pro Gly Lys Gly Leu Glu Trp Val
        35                  40                  45

Gly Arg Thr Arg His Ser Asp Met Gly Tyr Ala Thr Ser Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Glu Arg Ser Lys Ser Gly Phe Asp Asn Trp Gly
            100                 105                 110

Gln Gly Thr Leu Val Thr Val Ser Ser
            115                 120
```

<210> SEQ ID NO 56
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence: Synthetic polynucleotide"

<400> SEQUENCE: 56

```
caggtgcagc tggtggaatc aggcggcgga ctggtcaagc ctggcggtag cctgagactg      60
agctgcgctg ctagtggctt caccttctct agctacgtgg tgcactgggt cagacaggcc     120
cctggtaaag gcctggagtg ggtcggacgg actagacact cagatatggg ctacgctact     180
agctacgccg ctcccgtgaa gggccggttc actatctcta gggacgactc taagaacacc     240
ctgtacctgc agatgaatag cctgaaaacc gaggacaccg ccgtctacta ctgcgctaga     300
gtggaacggt ctaagtcagg cttcgataac tggggtcagg gcacccttggt caccgtgtct    360
agc                                                                   363
```

<210> SEQ ID NO 57
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 57

```
Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Val Val His Trp Val Arg Gln Ala Pro Gly Lys Gly Leu Glu Trp Val
        35                  40                  45

Gly Arg Thr Arg His Ser Asp Met Gly Tyr Ala Thr Ser Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Ala Arg Val Glu Arg Ser Lys Ser Gly Phe Asp Asn Trp Gly
```

```
            100                 105                 110
Gln Gly Thr Leu Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 58
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 58
```

```
caggtgcagc tggtggaatc aggcggcgga ctggtcaagc ctggcggtag cctgagactg    60
agctgcgctg ctagtggctt caccttctct agctacgtgg tgcactgggt cagacaggcc   120
cctggtaaag gcctggagtg ggtcggacgg actagacact cagatatggg ctacgctact   180
agctacgccg ctcccgtgaa gggccggttc actatctcta gggacgactc taagaacacc   240
ctgtacctgc agatgaatag cctgaaaacc gaggacaccg ccgtctacta ctgcgctaga   300
gtggaacggt ctaagtcagg cttcgataac tggggtcagg gcaccctggt caccgtgtct   360
agcgctagca ctaagggccc aagtgtgttt cccctggccc ccagcagcaa gtctacttcc   420
ggcggaactg ctgccctggg ttgcctggtg aaggactact cccccgagcc cgtgacagtg   480
tcctggaact ctggggctct gacttccggc gtgcacacct ccccgccgt gctgcagagc    540
agcggcctgt acagcctgag cagcgtggtg acagtgccct ccagctctct gggaacccag   600
acctatatct gcaacgtgaa ccacaagccc agcaacacca aggtggacaa gagagtggag   660
cccaagagct gcgacaagac ccacacctgc ccccccctgcc cagctccaga actgctggga   720
gggccttccg tgttcctgtt cccccccaag cccaaggaca ccctgatgat cagcaggacc   780
cccgaggtga cctgcgtggt ggtggacgtg tcccacgagg acccagaggt gaagttcaac   840
tggtacgtgg acggcgtgga ggtgcacaac gccaagacca gcccagaga ggagcagtac    900
aacagcacct acagggtggt gtccgtgctg accgtgctgc accaggactg gctgaacggc   960
aaagaataca agtgcaaagt ctccaacaag gccctgccag ccccaatcga aagacaatc   1020
agcaaggcca agggccagcc acgggagccc caggtgtaca ccctgccccc cagccgggag  1080
gagatgacca agaaccaggt gtccctgacc tgtctggtga agggcttcta ccccagcgat  1140
atcgccgtgg agtgggagag caacggccag cccgagaaca actacaagac cacccccca   1200
gtgctggaca gcgacggcag cttcttcctg tacagcaagc tgaccgtgga caagtccagg  1260
tggcagcagg gcaacgtgtt cagctgcagc gtgatgcacg aggccctgca caaccactac  1320
acccagaagt ccctgagcct gagccccggc aag                                1353
```

<210> SEQ ID NO 59
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 59

Thr Gly Ser Ser Ser Asn Ile Gly Ala Gly Tyr Ser Val His
1               5                   10

<210> SEQ ID NO 60
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"

<400> SEQUENCE: 60

Gly Gln Ser Glu Arg Pro Ser
1               5

<210> SEQ ID NO 61

-continued

```
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 61

Gln Ser Trp Asp Ser Ser Gln Thr Leu Val Val
1               5                   10

<210> SEQ ID NO 62
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 62

Ser Ser Ser Asn Ile Gly Ala Gly Tyr Ser
1               5                   10

<210> SEQ ID NO 63
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 63

Gly Gln Ser
1

<210> SEQ ID NO 64
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 64

Trp Asp Ser Ser Gln Thr Leu Val
1               5

<210> SEQ ID NO 65
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 65

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Ser Val His Trp Tyr Gln Gln Leu Pro Gly Thr Ala Pro Lys Leu
        35                  40                  45
```

Leu Ile Tyr Gly Gln Ser Glu Arg Pro Ser Gly Val Pro Asp Arg Phe
            50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Trp Asp Ser Ser
                 85                  90                  95

Gln Thr Leu Val Val Phe Gly Gly Gly Thr Lys Leu Thr Val Leu
            100                 105                 110

<210> SEQ ID NO 66
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 66
cagtcagtcc tgactcagcc ccctagcgtc agcggcgctc ccggtcagag agtgactatt      60
agctgcaccg gctctagctc taatatcggc gctggctata gcgtgcactg gtatcagcag     120
ctgcccggca ccgcccctaa gctgctgatc tacggtcagt cagagcggcc tagcggcgtg     180
cccgataggt ttagcggctc taagtcaggc actagcgcta gtctggctat caccggcctg     240
caggctgagg acgaggccga ctactactgt cagtcctggg actctagtca gaccctggtg     300
gtgttcggcg gaggcactaa gctgaccgtg ctg                                  333

<210> SEQ ID NO 67
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Gln Ser Val Leu Thr Gln Pro Pro Ser Val Ser Gly Ala Pro Gly Gln
 1               5                  10                  15

Arg Val Thr Ile Ser Cys Thr Gly Ser Ser Ser Asn Ile Gly Ala Gly
                 20                  25                  30

Tyr Ser Val His Trp Tyr Gln Gln Leu Pro Gly Thr Ala Pro Lys Leu
             35                  40                  45

Leu Ile Tyr Gly Gln Ser Glu Arg Pro Ser Gly Val Pro Asp Arg Phe
         50                  55                  60

Ser Gly Ser Lys Ser Gly Thr Ser Ala Ser Leu Ala Ile Thr Gly Leu
 65                  70                  75                  80

Gln Ala Glu Asp Glu Ala Asp Tyr Tyr Cys Gln Ser Trp Asp Ser Ser
                 85                  90                  95

Gln Thr Leu Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
         115                 120                 125

Glu Leu Gln Ala Asn Lys Ala Thr Leu Val Cys Leu Ile Ser Asp Phe
     130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys

```
                165                 170                 175
Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205

Lys Thr Val Ala Pro Thr Glu Cys Ser
    210                 215

<210> SEQ ID NO 68
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 68
cagtcagtcc tgactcagcc ccctagcgtc agcggcgctc ccggtcagag agtgactatt      60
agctgcaccg gctctagctc taatatcggc gctggctata gcgtgcactg gtatcagcag     120
ctgcccggca ccgcccctaa gctgctgatc tacggtcagt cagagcggcc tagcggcgtg     180
cccgataggt ttagcggctc taagtcaggc actagcgcta gtctggctat caccggcctg     240
caggctgagg acgaggccga ctactactgt cagtcctggg actctagtca daccctggtg     300
gtgttcggcg gaggcactaa gctgaccgtg ctgggtcagc ctaaggctgc ccccagcgtg     360
accctgttcc cccccagcag cgaggagctg caggccaaca aggccaccct ggtgtgcctg     420
atcagcgact tctacccagg cgccgtgacc gtggcctgga aggccgacag cagccccgtg     480
aaggccggcg tggagaccac cacccccagc aagcagagca caacaagta cgccgccagc     540 agctacctga gcctgacccc cgagcagtgg aagagccaca ggtcctacag ctgccaggtg     600
acccacgagg gcagcaccgt ggaaaagacc gtggccccaa ccgagtgcag c               651

<210> SEQ ID NO 69
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 69

Ser Tyr Val Val His
1               5

<210> SEQ ID NO 70
<211> LENGTH: 19
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 70

Arg Ile Arg Leu Glu Thr His Gly Tyr Ala Ala Glu Tyr Ala Ala Ser
1               5                   10                  15

Val Lys Gly

<210> SEQ ID NO 71
```

```
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 71

Val Glu Arg Ser Lys Ser Gly Phe Asp Asn
1               5                   10

<210> SEQ ID NO 72
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 72

Gly Phe Thr Phe Ser Ser Tyr
1               5

<210> SEQ ID NO 73
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 73

Arg Leu Glu Thr His Gly Tyr Ala
1               5

<210> SEQ ID NO 74
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 74

Val Glu Arg Ser Lys Ser Gly Phe Asp Asn
1               5                   10

<210> SEQ ID NO 75
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Ser Tyr
            20                  25                  30

Val Val His Trp Val Arg Gln Ala Pro Gly Lys Gly Leu Glu Trp Val
        35                  40                  45
```

Gly Arg Ile Arg Leu Glu Thr His Gly Tyr Ala Ala Glu Tyr Ala Ala
            50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                    85                  90                  95

Tyr Cys Ala Arg Val Glu Arg Ser Lys Ser Gly Phe Asp Asn Trp Gly
                100                 105                 110

Gln Gly Thr Leu Val Thr Val Ser Ser
            115                 120

<210> SEQ ID NO 76
<211> LENGTH: 363
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 76
caggtgcagc tggtggaatc aggcggcgga ctggtcaagc ctggcggtag cctgagactg      60
agctgcgctg ctagtggctt caccttctct agctacgtgg tgcactgggt cagacaggcc    120
cctggtaaag gcctggagtg gtcggacgg attagactgg aaactcacgg ctacgccgcc     180
gagtacgccg ctagtgtgaa gggccggttc actatctcta gggacgactc taagaacacc    240
ctgtacctgc agatgaatag cctgaaaacc gaggacaccg ccgtctacta ctgcgctaga    300
gtggaacggt ctaagtcagg cttcgataac tggggtcagg gcaccctggt caccgtgtct    360
agc                                                                  363

<210> SEQ ID NO 77
<211> LENGTH: 451
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 77

Gln Val Gln Leu Val Glu Ser Gly Gly Gly Leu Val Lys Pro Gly Gly
 1               5                  10                  15

Ser Leu Arg Leu Ser Cys Ala Ala Ser Gly Phe Thr Phe Ser Ser Tyr
                20                  25                  30

Val Val His Trp Val Arg Gln Ala Pro Gly Lys Gly Leu Glu Trp Val
            35                  40                  45

Gly Arg Ile Arg Leu Glu Thr His Gly Tyr Ala Ala Glu Tyr Ala Ala
            50                  55                  60

Ser Val Lys Gly Arg Phe Thr Ile Ser Arg Asp Asp Ser Lys Asn Thr
 65                  70                  75                  80

Leu Tyr Leu Gln Met Asn Ser Leu Lys Thr Glu Asp Thr Ala Val Tyr
                    85                  90                  95

Tyr Cys Ala Arg Val Glu Arg Ser Lys Ser Gly Phe Asp Asn Trp Gly
                100                 105                 110

Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

```
Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
            165                 170                 175

Val Leu Gln Ser Ser Gly Leu Tyr Ser Leu Ser Ser Val Thr Val
        180                 185                 190

Pro Ser Ser Ser Leu Gly Thr Gln Thr Tyr Ile Cys Asn Val Asn His
            195                 200                 205

Lys Pro Ser Asn Thr Lys Val Asp Lys Arg Val Glu Pro Lys Ser Cys
        210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Glu Glu Met Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 78
<211> LENGTH: 1353
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 78
caggtgcagc tggtggaatc aggcggcgga ctggtcaagc ctggcggtag cctgagactg      60
agctgcgctg ctagtggctt caccttctct agctacgtgg tgcactgggt cagacaggcc     120
cctggtaaag gcctggagtg ggtcggacgg attagactgg aaactcacgg ctacgccgcc     180
```

```
gagtacgccg ctagtgtgaa gggccggttc actatctcta gggacgactc taagaacacc    240
ctgtacctgc agatgaatag cctgaaaacc gaggacaccg ccgtctacta ctgcgctaga    300
gtggaacggt ctaagtcagg cttcgataac tggggtcagg caccctggt caccgtgtct     360 agcgctagca ctaagggccc aagtgtgttt cccctggccc ccagcagcaa gtctacttcc    420
ggcggaactg ctgccctggg ttgcctggtg aaggactact tccccgagcc cgtgacagtg    480
tcctggaact ctggggctct gacttccggc gtgcacacct tccccgccgt gctgcagagc    540
agcggcctgt acagcctgag cagcgtggtg acagtgccct ccagctctct gggaacccag    600
acctatatct gcaacgtgaa ccacaagccc agcaacacca aggtggacaa gagagtggag    660
cccaagagct gcgacaagac ccacacctgc ccccctgcc cagctccaga actgctggga    720
gggccttccg tgttcctgtt cccccccaag cccaaggaca ccctgatgat cagcaggacc    780
cccgaggtga cctgcgtggt ggtggacgtg tcccacgagg acccagaggt gaagttcaac    840
tggtacgtgg acggcgtgga ggtgcacaac gccaagacca gcccagaga ggagcagtac    900 aacagcacct acagggtggt gtccgtgctg accgtgctgc accaggactg gctgaacggc    960
aaagaataca gtgcaaagt ctccaacaag gccctgccag ccccaatcga aaagacaatc     1020
agcaaggcca agggccagcc acgggagccc caggtgtaca ccctgccccc cagccgggag    1080
gagatgacca agaaccaggt gtccctgacc tgtctggtga agggcttcta ccccagcgat    1140
atcgccgtgg agtgggagag caacggccag cccgagaaca actacaagac cacccccca    1200 gtgctggaca gcgacggcag cttcttcctg tacagcaagc tgaccgtgga caagtccagg    1260
tggcagcagg gcaacgtgtt cagctgcagc gtgatgcacg aggccctgca caaccactac    1320
acccagaagt ccctgagcct gagccccggc aag                                 1353

<210> SEQ ID NO 79
<211> LENGTH: 14
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 79

Thr Gly Ser Ser Ser Asn Ile Gly Ala Gly Tyr Ser Val His
1               5                   10

<210> SEQ ID NO 80
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 80

Gly Gln Ser Glu Arg Pro Ser
1               5

<210> SEQ ID NO 81
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

-continued

```
<400> SEQUENCE: 81

Gln Ser Trp Asp Ser Ser Gln Thr Leu Val Val
1               5                   10

<210> SEQ ID NO 82
<211> LENGTH: 10
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 82

Ser Ser Ser Asn Ile Gly Ala Gly Tyr Ser
1               5                   10

<210> SEQ ID NO 83
<211> LENGTH: 3
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 83

Gly Gln Ser
1

<210> SEQ ID NO 84
<211> LENGTH: 8
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 84

Trp Asp Ser Ser Gln Thr Leu Val
1               5

<210> SEQ ID NO 85
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Gln Ser Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
            20                  25                  30

Tyr Ser Val His Trp Tyr Gln Gln Leu Pro Gly Thr Ala Pro Lys Leu
        35                  40                  45

Leu Ile Tyr Gly Gln Ser Glu Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Trp Asp Ser Ser
```

```
                    85                  90                  95

Gln Thr Leu Val Val Phe Gly Gly Gly Thr Lys Leu Thr Val Leu
            100                 105                 110

<210> SEQ ID NO 86
<211> LENGTH: 333
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 86
cagtcagtcc tgactcagcc ccctagcgtc agcggcgctc ccggtcagag agtgactatt    60
agctgcaccg gctctagctc taatatcggc gctggctata gcgtgcactg gtatcagcag   120
ctgcccggca ccgcccctaa gctgctgatc tacggtcagt cagagcggcc tagcggcgtg   180
cccgataggt ttagcggctc taagtcaggc actagcgcta gtctggctat caccggcctg   240
caggctgagg acgaggccga ctactactgt cagtcctggg actctagtca gaccctggtg   300
gtgttcggcg gaggcactaa gctgaccgtg ctg                                333

<210> SEQ ID NO 87
<211> LENGTH: 217
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Gln Ser Val Leu Thr Gln Pro Pro Ser Val Ser Ala Pro Gly Gln
1               5                   10                  15

Arg Val Thr Ile Ser Cys Thr Gly Ser Ser Ser Asn Ile Gly Ala Gly
            20                  25                  30

Tyr Ser Val His Trp Tyr Gln Gln Leu Pro Gly Thr Ala Pro Lys Leu
        35                  40                  45

Leu Ile Tyr Gly Gln Ser Glu Arg Pro Ser Gly Val Pro Asp Arg Phe
    50                  55                  60

Ser Gly Ser Lys Ser Gly Thr Ser Ala Ser Leu Ala Ile Thr Gly Leu
65                  70                  75                  80

Gln Ala Glu Asp Glu Ala Asp Tyr Tyr Cys Gln Ser Trp Asp Ser Ser
                85                  90                  95

Gln Thr Leu Val Val Phe Gly Gly Gly Thr Lys Leu Thr Val Leu Gly
            100                 105                 110

Gln Pro Lys Ala Ala Pro Ser Val Thr Leu Phe Pro Pro Ser Ser Glu
        115                 120                 125

Glu Leu Gln Ala Asn Lys Ala Thr Leu Val Cys Leu Ile Ser Asp Phe
    130                 135                 140

Tyr Pro Gly Ala Val Thr Val Ala Trp Lys Ala Asp Ser Ser Pro Val
145                 150                 155                 160

Lys Ala Gly Val Glu Thr Thr Thr Pro Ser Lys Gln Ser Asn Asn Lys
                165                 170                 175

Tyr Ala Ala Ser Ser Tyr Leu Ser Leu Thr Pro Glu Gln Trp Lys Ser
            180                 185                 190

His Arg Ser Tyr Ser Cys Gln Val Thr His Glu Gly Ser Thr Val Glu
        195                 200                 205
```

Lys Thr Val Ala Pro Thr Glu Cys Ser
    210             215

<210> SEQ ID NO 88
<211> LENGTH: 651
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic polynucleotide"

<400> SEQUENCE: 88
cagtcagtcc tgactcagcc ccctagcgtc agcggcgctc ccggtcagag agtgactatt      60
agctgcaccg gctctagctc taatatcggc gctggctata gcgtgcactg gtatcagcag     120
ctgcccggca ccgcccctaa gctgctgatc tacggtcagt cagagcggcc tagcggcgtg     180
cccgataggt ttagcggctc taagtcaggc actagcgcta gtctggctat caccggcctg     240
caggctgagg acgaggccga ctactactgt cagtcctggg actctagtca gaccctggtg     300
gtgttcggcg gaggcactaa gctgaccgtg ctgggtcagc ctaaggctgc ccccagcgtg     360
accctgttcc cccccagcag cgaggagctg caggccaaca aggccaccct ggtgtgcctg     420
atcagcgact tctacccagg cgccgtgacc gtggcctgga aggccgacag cagccccgtg     480
aaggccggcg tggagaccac cacccccagc aagcagagca caacaagta cgccgccagc     540 agctacctga gcctgacccc cgagcagtgg aagagccaca ggtcctacag ctgccaggtg     600
acccacgagg gcagcaccgt ggaaaagacc gtggccccaa ccgagtgcag c              651

<210> SEQ ID NO 89
<211> LENGTH: 139
<212> TYPE: PRT
<213> ORGANISM: Homo sapiens

<400> SEQUENCE: 89

Ser Ala Ser Ser Arg Arg Gln Gln Ser Arg Asn Arg Ser Thr Gln
1               5                   10                  15

Ser Gln Asp Val Ala Arg Val Ser Ala Ser Asp Tyr Asn Ser Ser
                20                  25                  30

Glu Leu Lys Thr Ala Cys Arg Lys His Glu Leu Tyr Val Ser Phe Gln
            35                  40                  45

Asp Leu Gly Trp Gln Asp Trp Ile Ile Ala Pro Lys Gly Tyr Ala Ala
        50                  55                  60

Asn Tyr Cys Asp Gly Glu Cys Ser Phe Pro Leu Asn Ala His Met Asn
65                  70                  75                  80

Ala Thr Asn His Ala Ile Val Gln Thr Leu Val His Leu Met Asn Pro
                85                  90                  95

Glu Tyr Val Pro Lys Pro Cys Cys Ala Pro Thr Lys Leu Asn Ala Ile
            100                 105                 110

Ser Val Leu Tyr Phe Asp Asp Asn Ser Asn Val Ile Leu Lys Lys Tyr
        115                 120                 125

Arg Asn Met Val Val Arg Ala Cys Gly Cys His
    130                 135

<210> SEQ ID NO 90
<211> LENGTH: 139
<212> TYPE: PRT
<213> ORGANISM: Homo sapiens

<400> SEQUENCE: 90

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
            115                 120                 125

Arg Asn Met Val Val Arg Ala Cys Gly Cys His
        130                 135

<210> SEQ ID NO 91
<211> LENGTH: 138
<212> TYPE: PRT
<213> ORGANISM: Homo sapiens

<400> SEQUENCE: 91

Ala Ala Asn Lys Arg Lys Asn Gln Asn Arg Asn Lys Ser Ser Ser His
1               5                   10                  15

Gln Asp Ser Ser Arg Met Ser Ser Val Gly Asp Tyr Asn Thr Ser Glu
            20                  25                  30

Gln Lys Gln Ala Cys Lys Lys His Glu Leu Tyr Val Ser Phe Arg Asp
        35                  40                  45

Leu Gly Trp Gln Asp Trp Ile Ile Ala Pro Glu Gly Tyr Ala Ala Phe
    50                  55                  60

Tyr Cys Asp Gly Glu Cys Ser Phe Pro Leu Asn Ala His Met Asn Ala
65                  70                  75                  80

Thr Asn His Ala Ile Val Gln Thr Leu Val His Leu Met Phe Pro Asp
                85                  90                  95

His Val Pro Lys Pro Cys Cys Ala Pro Thr Lys Leu Asn Ala Ile Ser
            100                 105                 110

Val Leu Tyr Phe Asp Asp Ser Ser Asn Val Ile Leu Lys Lys Tyr Arg
            115                 120                 125

Asn Met Val Val Arg Ser Cys Gly Cys His
        130                 135

<210> SEQ ID NO 92
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 92

Gln Val Gln Leu Val Gln Ser Gly Ala Glu Val Lys Lys Pro Gly Ser
1               5                   10                  15

```
Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Asn Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Pro Phe Gly Asn Ala Met Asp Ile Trp Gly Gln Gly Thr
            100                 105                 110

Leu Val Thr Val Ser Ser
        115
```

<210> SEQ ID NO 93
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 93

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Tyr Ile Asn Pro Tyr Asn Asp Gly Thr Lys Tyr Asn Glu Asn Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Arg Pro Phe Gly Asn Ala Met Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
```

```
                        245                 250                 255
Val Thr Cys Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
290                 295                 300

Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
            325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
            355                 360                 365

Gly Phe Tyr Pro Ser Asp Ile Ala Val Glu Trp Glu Ser Asn Gly Gln
370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
            405                 410                 415

Glu Gly Asn Val Phe Ser Cys Ser Val Met His Glu Ala Leu His Asn
            420                 425                 430

His Tyr Thr Gln Lys Ser Leu Ser Leu Ser Leu Gly
            435                 440

<210> SEQ ID NO 94
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 94

Tyr Ile Asn Pro Tyr Asn Arg Gly Thr Lys Tyr Asn Glu Asn Phe Lys
1               5                   10                  15

<210> SEQ ID NO 95
<211> LENGTH: 118
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Tyr Ile Asn Pro Tyr Asn Arg Gly Thr Lys Tyr Asn Glu Asn Phe
    50                  55                  60

Lys Gly Arg Val Thr Ile Thr Ala Asp Glu Ser Thr Ser Thr Ala Tyr
65                  70                  75                  80
```

```
Met Glu Leu Ser Ser Leu Arg Ser Glu Asp Thr Ala Val Tyr Tyr Cys
                85                  90                  95

Ala Arg Arg Pro Phe Gly Asn Ala Met Asp Ile Trp Gly Gln Gly Thr
            100                 105                 110

Leu Val Thr Val Ser Ser
        115

<210> SEQ ID NO 96
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 96

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Ser Tyr
            20                  25                  30

Ala Met His Trp Val Arg Gln Ala Pro Gly Gln Gly Leu Glu Trp Met
        35                  40                  45

Gly Tyr Ile Asn Pro Tyr Asn Arg Gly Thr Lys Tyr Asn Glu Asn Phe
    50                  55                  60

Lys Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Arg Pro Phe Gly Asn Ala Met Asp Ile Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Lys Thr Tyr Thr Cys Asn Val Asp His Lys Pro Ser
        195                 200                 205

Asn Thr Lys Val Asp Lys Arg Val Glu Ser Lys Tyr Gly Pro Pro Cys
    210                 215                 220

Pro Pro Cys Pro Ala Pro Glu Ala Ala Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser Gln Glu Asp Pro Glu Val Gln
            260                 265                 270

Phe Asn Trp Tyr Val Asp Gly Val Glu Val His Asn Ala Lys Thr Lys
        275                 280                 285

Pro Arg Glu Glu Gln Phe Asn Ser Thr Tyr Arg Val Val Ser Val Leu
    290                 295                 300
```

```
Thr Val Leu His Gln Asp Trp Leu Asn Gly Lys Glu Tyr Lys Cys Lys
305                 310                 315                 320

Val Ser Asn Lys Gly Leu Pro Ser Ser Ile Glu Lys Thr Ile Ser Lys
                325                 330                 335

Ala Lys Gly Gln Pro Arg Glu Pro Gln Val Tyr Thr Leu Pro Pro Ser
            340                 345                 350

Gln Glu Glu Met Thr Lys Asn Gln Val Ser Leu Thr Cys Leu Val Lys
        355                 360                 365

Gly Phe Tyr Pro Ser Asp Ile Ala Val Glu Trp Glu Ser Asn Gly Gln
    370                 375                 380

Pro Glu Asn Asn Tyr Lys Thr Thr Pro Pro Val Leu Asp Ser Asp Gly
385                 390                 395                 400

Ser Phe Phe Leu Tyr Ser Arg Leu Thr Val Asp Lys Ser Arg Trp Gln
                405                 410                 415

Glu Gly Asn Val Phe Ser Cys Ser Val Met His Glu Ala Leu His Asn
                420                 425                 430

His Tyr Thr Gln Lys Ser Leu Ser Leu Ser Leu Gly
            435                 440

<210> SEQ ID NO 97
<211> LENGTH: 6
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic 6xHis tag"

<400> SEQUENCE: 97

His His His His His His
1               5

<210> SEQ ID NO 98
<211> LENGTH: 15
<212> TYPE: PRT
<213> ORGANISM: Homo sapiens

<400> SEQUENCE: 98

Gln Thr Leu Val His Leu Met Asn Pro Glu Tyr Val Pro Lys Pro
1               5                   10                  15

<210> SEQ ID NO 99
<211> LENGTH: 13
<212> TYPE: PRT
<213> ORGANISM: Homo sapiens

<400> SEQUENCE: 99

Val Ser Ser Ala Ser Asp Tyr Asn Ser Ser Glu Leu Lys
1               5                   10
```

METHODS FOR TREATING DISEASE USING INHIBITORS OF BONE MORPHOGENETIC PROTEIN 6 (BMP6)

CROSS REFERENCE TO RELATED APPLICATIONS

This application is a 371 U.S. national phase application of the International Application No. PCT/IB2017/053507, filed on Jun. 13, 2017, which claims priority to, and the benefit of, U.S. Patent Application No. 62/350,257, filed on Jun. 15, 2016, the contents of each of which are incorporated herein by reference in their entireties.

SEQUENCE LISTING

The instant application contains a Sequence Listing which has been submitted electronically in ASCII format and is hereby incorporated by reference in its entirety. Said ASCII copy, created on May 23, 2017, is named PAT057354-WO-PCT_SL.txt and is 82,879 bytes in size.

INTRODUCTION

The present invention relates to methods of treating anemia using inhibitors of bone morphogenetic protein 6 (BMP6).

BACKGROUND OF THE INVENTION

Anemia is prevalent in patients with chronic kidney disease (CKD) and is associated with lower quality of life and higher risk of adverse outcomes, including cardiovascular disease and death. Several modes of anemia management in patients with CKD involve the use of erythropoiesis-stimulating agents (ESA), supplemental oral and intravenous iron and blood transfusions. However, many patients do not respond adequately to these treatments or require higher doses of ESA and/or iron. High doses of iron may also cause toxicity associated with generation of oxygen radicals and allergic reactions. These treatments may lack efficacy because they do not fully address the underlying cause of the anemia, i.e., impaired iron absorption and iron mobilization from body stores.

Attempts to manage erythropoietin resistance are currently performed by the co-administration of high dose parenteral iron. However, most iron from intravenous preparations is first processed by macrophages, and its utilization for erythropoiesis is dependent on ferroportin-mediated iron export.

In many anemia patients, ferroportin-mediated iron export is suppressed by high levels of hepcidin. Additional evidence suggests that increased levels of hepcidin correlate with poor ESA responsiveness in hemodialysis. Hepcidin-lowering agents may therefore be an effective strategy for ameliorating ESA-refractory anemia in this patient population and in other forms of anemia of chronic disease (ACD) characterized by iron restriction.

Therefore, methods that decrease circulating hepcidin levels should enhance iron absorption, facilitate release of sequestered iron, and promote erythropoiesis in ESA-refractory anemia present in chronic kidney disease patients.

Despite current treatment options for treating diseases and disorders associated anemia, there remains a need for improved method s of treatment of anemia which are effective and well-tolerated.

SUMMARY OF THE INVENTION

Ferritin is an intracellular protein that is indicative of stored iron. Ferritin levels can be used as an indirect marker of the total amount of iron stored in the body. Without being bound by theory, it is believed that inhibitors of BMP6 may result the release of stored iron from cells, for example, from macrophages and/or enterocytes. Again, without being bound by theory, the present invention is based in part on the discovery that inhibitors of BMP6 may be effective in treating conditions associated with sequestered iron, e.g., anemia, in patients with high ferritin (e.g., pretreatment ferritin levels greater than 500 ng/mL), e.g., serum ferritin, levels, and hence, high stored iron.

In a first aspect, the invention pertains to a method of selectively:
a. inhibiting BMP6;
b. increasing serum iron levels, transferrin saturation (TAST), reticulocyte hemoglobin content (CHr), reticulocyte count, red blood cell count, hemoglobin, or hematocrit;
c. reducing the activity or level of Hepcidin;
d. treating anemia; or
e. increasing or maintaining hemoglobin level;
in a patient in need thereof, that includes selectively administering a therapeutically effective amount of a BMP6 antagonist to the patient on the basis of a biological sample from the patient having a ferritin level of ≤2000 ng/mL. In embodiments, the ferritin level is ≥500 ng/mL.

In another aspect, the invention pertains to a method of treating a patient having anemia with a BMP6 antagonist, including selectively administering a therapeutically effective amount of a BMP6 antagonist to the patient on the basis of a biological sample from the patient having a ferritin level of ≤2000 ng/mL. In embodiments, the ferritin level is ≥500 ng/mL.

In another aspect, the invention pertains to a method of selectively treating a patient having anemia with a BMP6 antagonist, including:
a) assaying a biological sample from the patient for ferritin level; and
b) thereafter, selectively administering to the patient a therapeutically effective amount of a BMP9 antagonist, wherein the ferritin level is ≤2000 ng/mL. In embodiments, the ferritin level is ≥500 ng/mL.

In another aspect, the invention pertains to a method of selectively treating a patient having anemia with a BMP6 antagonist, including:
a) assaying a biological sample from the patient for ferritin level;
b) thereafter, selecting the patient for treatment with the BMP6 antagonist on the basis of the biological sample from the patient having a ferritin level ≤2000 ng/mL; and
c) thereafter, administering a therapeutically effective amount of a BMP9 antagonist to the patient. In embodiments, the ferritin level is ≥500 ng/mL.

In another aspect, the invention pertains to a method of selectively:
a. inhibiting BMP6;
b. increasing serum iron levels, transferrin saturation (TAST), reticulocyte hemoglobin content (CHr), reticulocyte count, red blood cell count, hemoglobin, or hematocrit;
c. reducing the activity or level of Hepcidin;
d. treating anemia; or
e. increasing or maintaining hemoglobin level;

in a patient in need thereof, that includes selectively administering a therapeutically effective amount of a BMP6 antagonist to the patient on the basis of a biological sample from the patient having a ferritin level of ≥500 ng/mL.

In another aspect, the invention pertains to a method of treating a patient having anemia with a BMP6 antagonist, including selectively administering a therapeutically effective amount of a BMP6 antagonist to the patient on the basis of a biological sample from the patient having a ferritin level of ≥500 ng/mL.

In another aspect, the invention pertains to a method of selectively treating a patient having anemia with a BMP6 antagonist, including:
a) assaying a biological sample from the patient for ferritin level; and
b) thereafter, selectively administering to the patient a therapeutically effective amount of a BMP9 antagonist, wherein the ferritin level is 500 ng/mL.

In another aspect, the invention pertains to a method of selectively treating a patient having anemia with a BMP6 antagonist, including:
a) assaying a biological sample from the patient for ferritin level;
b) thereafter, selecting the patient for treatment with the BMP6 antagonist on the basis of the biological sample from the patient having a ferritin level 500 ng/mL; and
c) thereafter, administering a therapeutically effective amount of a BMP9 antagonist to the patient.

In embodiments, including in any of the aforementioned aspects, the ferritin level is ferritin protein level.

In embodiments, including in any of the aforementioned aspects, the step of assaying includes a technique selected from the group consisting of an immunoassay, immunohistochemistry, ELISA, flow cytometry, Western blot, HPLC, and mass spectrometry.

In another aspect, the invention pertains to a BMP6 antagonist for use in treating a patient having anemia, characterized in that a therapeutically effective amount of the BMP6 antagonist is to be administered to the patient on the basis of a biological sample from the patient having a ferritin level of ≤2000 ng/mL. In embodiments, the ferritin level is ≥500 ng/mL.

In another aspect, the invention pertains to a BMP6 antagonist for use in treating a patient having anemia, characterized in that a therapeutically effective amount of the BMP6 antagonist is to be administered to the patient on the basis of a biological sample from the patient having a ferritin level of ≥500 ng/mL.

In another aspect, the invention pertains to a BMP6 antagonist for use in treating a patient having anemia, characterized in that:
a) the patient is to be selected for treatment with the BMP6 antagonist on the basis of a biological sample from the patient having a ferritin level of ≤2000 ng/mL; and
b) thereafter, a therapeutically effective amount of the BMP6 antagonist s to be administered to the patient. In embodiments, the ferritin level is ≥500 ng/mL.

In another aspect, the invention pertains to a BMP6 antagonist for use in treating a patient having anemia, characterized in that:
a) the patient is to be selected for treatment with the BMP6 antagonist on the basis of a biological sample from the patient having a ferritin level of ≥500 ng/mL; and
b) thereafter, a therapeutically effective amount of the BMP6 antagonist is to be administered to the patient.

In another aspect, the invention pertains to a BMP6 antagonist for use in treating a patient having anemia, characterized in that:
a) a biological sample from the patient is to be assayed for ferritin; and
b) a therapeutically effective amount of the BMP6 antagonist is to be selectively administered to the patient on the basis of the biological sample from the patient having a ferritin level of ≤2000 ng/mL. In embodiments, the ferritin level is ≥500 ng/mL.

In another aspect, the invention pertains to a BMP6 antagonist for use in treating a patient having anemia, characterized in that:
a) a biological sample from the patient is to be assayed for ferritin; and
b) a therapeutically effective amount of the BMP6 antagonist is to be selectively administered to the patient on the basis of the biological sample from the patient having a ferritin level of ≤500 ng/mL.

In another aspect, the invention pertains to a BMP6 antagonist for use in treating a patient having anemia, characterized in that:
a) a biological sample from the patient is to be assayed for ferritin;
b) the patient is selected for treatment with the BMP6 antagonist on the basis of the biological sample from the patient having a ferritin level of ≤2000 ng/mL; and
c) a therapeutically effective amount of the BMP6 antagonist is to be selectively administered to the patient. In embodiments, the ferritin level is ≥500 ng/mL.

In another aspect, the invention pertains to a BMP6 antagonist for use in treating a patient having anemia, characterized in that:
a) a biological sample from the patient is to be assayed for ferritin;
b) the patient is selected for treatment with the BMP6 antagonist on the basis of the biological sample from the patient having a ferritin level of ≥500 ng/mL; and
c) a therapeutically effective amount of the BMP6 antagonist is to be selectively administered to the patient.

In another aspect, the invention pertains to method of predicting the likelihood that a patient having anemia will respond to treatment with a BMP6 antagonist, including assaying a biological sample from the patient for ferritin, wherein a ferritin level of ≤2000 ng/mL is indicative of an increased likelihood the patient will respond to treatment with the BMP6 antagonist. In embodiments, the ferritin level is ≥500 ng/mL.

In another aspect, the invention pertains to method of predicting the likelihood that a patient having anemia will respond to treatment with a BMP6 antagonist, including assaying a biological sample from the patient for ferritin, wherein a ferritin level of ≥500 ng/mL is indicative of an increased likelihood the patient will respond to treatment with the BMP6 antagonist.

In embodiments, including in embodiments of any of the aforementioned aspects and embodiments, the method or use further includes the step of obtaining the biological sample from the patient, wherein the step of obtaining is performed prior to the step of assaying.

In embodiments, including in embodiments of any of the aforementioned aspects and embodiments, the ferritin level is ferritin protein level.

In embodiments, including in embodiments of any of the aforementioned aspects and embodiments, the step of assaying includes a technique selected from the group consisting of an immunoassay, immunohistochemistry, ELISA, flow cytometry, Western blot, HPLC, and mass spectrometry.

In another aspect, the invention provides a method for producing a transmittable form of information for predicting the responsiveness of a patient having anemia to treatment with a BMP6 antagonist, including:
a) determining an increased likelihood of the patient responding to treatment with the BMP6 antagonist based on the presence of a ferritin level of ≤2000 ng/mL in a biological sample from the patient; and
b) recording the result of the determining step on a tangible or intangible media form for use in transmission. In embodiments, the ferritin level is ≥500 ng/mL.

In another aspect, the invention provides a method for producing a transmittable form of information for predicting the responsiveness of a patient having anemia to treatment with a BMP6 antagonist, including:
a) determining an increased likelihood of the patient responding to treatment with the BMP6 antagonist based on the presence of a ferritin level of ≥500 ng/mL in a biological sample from the patient; and
b) recording the result of the determining step on a tangible or intangible media form for use in transmission.

In embodiments, including in embodiments of any of the aforementioned aspects and embodiments, the patient has anemia. In embodiments, the anemia is anemia associated with chronic disease. In embodiments, the chronic disease is chronic kidney disease, cancer or inflammation.

In embodiments, including in embodiments of any of the aforementioned aspects and embodiments, the patient is being or has been treated with an erythropoiesis stimulating agent (ESA), for example, erythropoietin (EPO).

In embodiments, including in embodiments of any of the aforementioned aspects and embodiments, the anemia is EPO-hyporesponsive anemia.

In embodiments, including in embodiments of any of the aforementioned aspects and embodiments, the anemia is iron-restricted anemia, for example, functional iron-restricted anemia.

In embodiments, including in embodiments of any of the aforementioned aspects and embodiments, the patient is a chronic hemodialysis patient.

In embodiments, including in embodiments of any of the aforementioned aspects and embodiments, the method or use further includes reducing the patient's iron dose requirement, reducing the patient's EPO dose requirement, or reducing both the patient's iron dose requirement and the patient's EPO dose requirement, relative to said EPO dose requirement and/or iron dose requirement in the absence of treatment with the therapeutically effective amount of the BMP6 antagonist. In embodiments, including in embodiments of any of the aforementioned aspects and embodiments, the method or use further includes or results in a reduction in the patient's ESA resistance index (ERI).

In embodiments, including in embodiments of any of the aforementioned aspects and embodiments, the biological sample is synovial fluid, blood, serum, feces, plasma, urine, tear, saliva, cerebrospinal fluid, a leukocyte sample or a tissue sample.

In embodiments, including in embodiments of any of the aforementioned aspects and embodiments, the biological sample is serum or blood.

In embodiments, including in embodiments of any of the aforementioned aspects and embodiments, the biological sample is serum.

In embodiments, including in embodiments of any of the aforementioned aspects and embodiments, the BMP6 antagonist is a BMP6 binding molecule.

In embodiments, including in embodiments of any of the aforementioned aspects and embodiments, the BMP6 antagonist is an anti-BMP6 antibody or antigen-binding fragment thereof for example, as described in Table 1 or Table 14.

In embodiments, including in embodiments of any of the aforementioned aspects and embodiments, the anti-BMP6 antibody or antigen-binding fragment thereof includes:
(a) HCDR1, HCDR2, and HCDR3 sequences of SEQ ID NOs: 69, 70 and 71, respectively, and LCDR1, LCDR2, and LCDR3 sequences of SEQ ID NOs: 79, 80 and 81, respectively;
(b) HCDR1, HCDR2, and HCDR3 sequences of SEQ ID NOs: 72, 73 and 74, respectively, and LCDR1, LCDR2, and LCDR3 sequences of SEQ ID NOs: 82, 83 and 84, respectively;
(c) HCDR1, HCDR2, and HCDR3 sequences of SEQ ID NOs: 29, 30 and 31, respectively, and LCDR1, LCDR2, and LCDR3 sequences of SEQ NOs: 39, 40 and 41, respectively;
(d) HCDR1, HCDR2, and HCDR3 sequences of SEQ ID NOs: 32, 33 and 34, respectively, and LCDR1, LCDR2, and LCDR3 sequences of SEQ ID NOs: 42, 43 and 44, respectively;
(e) HCDR1, HCDR2, and HCDR3 sequences of SEQ ID NOs: 49, 50 and 51, respectively, and LCDR1, LCDR2, and LCDR3 sequences of SEQ ID NOs: 59, 60 and 61, respectively;
(f) HCDR1, HCDR2, and HCDR3 sequences of SEQ ID NOs: 52, 53 and 54, respectively, and LCDR1, LCDR2, and LCDR3 sequences of SEQ ID NOs: 62, 63 and 64, respectively;
(g) HCDR1, HCDR2, and HCDR3 sequences of SEQ ID NOs: 9, 10 and 11, respectively, and LCDR1, LCDR2, and LCDR3 sequences of SEQ ID NOs: 19, 20 and 21, respectively; or
(h) HCDR1, HCDR2, and HCDR3 sequences of SEQ ID NOs: 12, 13 and 14, respectively, and LCDR1, LCDR2, and LCDR3 sequences of SEQ ID NOs: 22, 23 and 24, respectively.

In embodiments, including in embodiments of any of the aforementioned aspects and embodiments, the anti-BMP6 antibody or antigen-binding fragment thereof includes:
(a) A VH sequence of SEQ ID NO: 75;
(b) A VH sequence of SEQ ID NO: 35;
(c) A VH sequence of SEQ ID NO: 55; or
(d) A VH sequence of SEQ ID NO: 15.

In embodiments, including in embodiments of any of the aforementioned aspects and embodiments, the anti-BMP6 antibody or antigen-binding fragment thereof includes:
(a) A VL sequence of SEQ ID NO: 85;
(b) A VL sequence of SEQ ID NO: 45;
(c) A VL sequence of SEQ ID NO: 65; or
(d) A VL sequence of SEQ ID NO: 25.

In embodiments, including in embodiments of any of the aforementioned aspects and embodiments, the anti-BMP6 antibody or antigen-binding fragment thereof includes:
(a) A VH sequence of SEQ ID NO: 75; and a VL sequence of SEQ ID NO: 85;
(b) A VH sequence of SEQ ID NO: 35; and a VL sequence of SEQ ID NO: 45;

(c) A VH sequence of SEQ ID NO: 55; and a VL sequence of SEQ ID NO: 65; or
(d) A VH sequence of SEQ ID NO: 15; and a VL sequence of SEQ ID NO: 25.

In embodiments, including in embodiments of any of the aforementioned aspects and embodiments, the anti-BMP6 antibody or antigen-binding fragment thereof includes:
(a) A heavy chain sequence of SEQ ID NO: 77;
(b) A heavy chain sequence of SEQ ID NO: 37;
(c) A heavy chain sequence of SEQ ID NO: 57; or
(d) A heavy chain sequence of SEQ NO: 17.

In embodiments, including in embodiments of any of the aforementioned aspects and embodiments, the anti-BMP6 antibody or antigen-binding fragment thereof includes:
(a) A light chain sequence of SEQ ID NO: 87;
(b) A light chain sequence of SEQ ID NO: 47;
(c) A light chain sequence of SEQ ID NO: 67; or
(d) A light chain sequence of SEQ ID NO: 27.

In embodiments, including in embodiments of any of the aforementioned aspects and embodiments, the anti-BMP6 antibody or antigen-binding fragment thereof includes:
(a) A heavy chain sequence of SEQ ID NO: 77; and a light chain sequence of SEQ ID NO: 87;
(b) A heavy chain sequence of SEQ ID NO: 37; and a light chain sequence of SEQ ID NO: 47;
(c) A heavy chain sequence of SEQ ID NO: 57; and a light chain sequence of SEQ ID NO: 67; or
(d) A heavy chain sequence of SEQ ID NO: 17; and a light chain sequence of SEQ ID NO: 27.

In embodiments, including in embodiments of any of the aforementioned aspects and embodiments, the anti-BMP6 antibody or antigen-binding fragment thereof binds human BMP6 with a KD of ≤1 nM.

In embodiments, including in embodiments of any of the aforementioned aspects and embodiments, the anti-BMP6 antibody or antigen-binding fragment thereof binds human BMP6 with a KD of ≤0.1 nM.

In embodiments, including in embodiments of any of the aforementioned aspects and embodiments, the anti-BMP6 antibody or antigen-binding fragment thereof has at least about 100-fold greater affinity for human BMP6 than human BMP7.

In embodiments, including in embodiments of any of the aforementioned aspects and embodiments, the anti-BMP6 antibody or antigen-binding fragment thereof has at least about 100-fold greater affinity for human BMP6 than human BMP2, human BMP5, or human BMP7.

In embodiments, including in embodiments of any of the aforementioned aspects and embodiments, the anti-BMP6 antibody or antigen-binding fragment thereof has at least about 500-fold greater affinity for human BMP6 than human BMP2, human BMP5, or human BMP7.

In embodiments, including in embodiments of any of the aforementioned aspects and embodiments, the anti-BMP6 antibody or antigen-binding fragment thereof has no detectable binding to human BMP2 and/or BMP7 in an ELISA.

In embodiments, including in embodiments of any of the aforementioned aspects and embodiments, the anti-BMP6 antibody or antigen-binding fragment thereof includes a scaffold selected from an IgM and an IgG.

In embodiments, including in embodiments of any of the aforementioned aspects and embodiments, the anti-BMP6 antibody or antigen-binding fragment thereof is an IgG selected from an IgG1, an IgG2, and IgG3 or an IgG4.

In embodiments, including in embodiments of any of the aforementioned aspects and embodiments, the anti-BMP6 antibody or antigen-binding fragment thereof is selected from the group consisting of: a monoclonal antibody, a chimeric antibody, a single chain antibody, a Fab and a scFv.

In embodiments, including in embodiments of any of the aforementioned aspects and embodiments, the anti-BMP6 antibody or antigen-binding fragment thereof is a component of an immunoconjugate.

In embodiments, including in embodiments of any of the aforementioned aspects and embodiments, the anti-BMP6 antibody or antigen-binding fragment thereof has altered effector function through mutation of the Fc region.

In embodiments, including in embodiments of any of the aforementioned aspects and embodiments, the anti-BMP6 antibody or antigen-binding fragment thereof binds to a human BMP6 epitope including, e.g., consisting of, the sequence (SEQ ID NO: 98)
QTLVHLMNPEYVPKP.

In embodiments, including in embodiments of any of the aforementioned aspects and embodiments, the antibody or antigen-binding fragment thereof is administered at a dose ranging from 0.001 mg/kg to 0.1 mg/kg.

In embodiments, including in embodiments of any of the aforementioned aspects and embodiments, the antibody or antigen-binding fragment thereof is administered at a dose ranging from 0.0063 to 0.1 mg/kg.

In embodiments, including in embodiments of any of the aforementioned aspects and embodiments, the antibody or antigen-binding fragment thereof is administered at a dose of 0.001 mg/kg, 0.0016 mg/kg, 0.0025 mg/kg, 0.0040 mg/kg, 0.0063 mg/kg, 0.01 mg/kg, 0.016 mg/kg, 0.025 mg/kg, 0.040 mg/kg, 0.063 mg/kg, or 0.1 mg/kg.

In embodiments, including in embodiments of any of the aforementioned aspects and embodiments, the antibody or antigen-binding fragment thereof is administered intravenously or subcutaneously.

In embodiments, including in embodiments of any of the aforementioned aspects and embodiments, the antibody or antigen-binding fragment thereof is administered intravenously.

In embodiments, including in embodiments of any of the aforementioned aspects and embodiments, the administration is by infusion over a period of about 30 to about 60 minutes.

In embodiments, including in embodiments of any of the aforementioned aspects and embodiments, the ferritin level is ≤1900 ng/mL, ≤1800 ng/mL, ≤1700 ng/mL, ≤1600 ng/mL, ≤1500 ng/mL, ≤1400 ng/mL, ≤1300 ng/mL, ≤1200 ng/mL, ≤1100 ng/mL, ≤1000 ng/mL, ≤900 ng/mL, ≤800 ng/mL, ≤700 ng/mL, ≤600 ng/mL, or ≤500 ng/mL.

In embodiments, including in embodiments of any of the aforementioned aspects and embodiments, the ferritin level is ≤1500 ng/mL. In embodiments, including in embodiments of any of the aforementioned aspects and embodiments, the ferritin level is ≤1000 ng/mL.

In embodiments, including in embodiments of any of the aforementioned aspects and embodiments, the ferritin level is ≥about 200 ng/mL, ≥about 250 ng/mL, ≥about 300 ng/mL, ≥about 350 ng/mL, ≥about 400 ng/mL, ≥about 450 ng/mL, ≥about 500 ng/mL, ≥about 600 ng/mL, ≥about 700 ng/mL, ≥about 800 ng/mL, ≥about 900 ng/mL, ≥about 1000 ng/mL, ≥about 1100 ng/mL, ≥about 1200 ng/mL, ≥about 1300 ng/mL, ≥about 1400 ng/mL, ≥about 1500 ng/mL, ≥about 1600 ng/mL, ≥about 1700 ng/mL, ≥about 1800 ng/mL, or ≥about 1900 ng/mL.

In embodiments, including in embodiments of any of the aforementioned aspects and embodiments, the ferritin level is ≥about 500 ng/mL, ≥about 600 ng/mL, ≥about 700 ng/mL, ≥about 800 ng/mL, ≥about 900 ng/mL, ≥about 1000 ng/mL, ≥about 1100 ng/mL, ≥about 1200 ng/mL, ≥about 1300 ng/mL, or ≥about 1400 ng/mL.

In embodiments, including in embodiments of any of the aforementioned aspects and embodiments, the ferritin level is ≥about 500 ng/mL.

Definitions

Unless defined otherwise, all technical and scientific terms used herein have the same meaning as commonly understood by those of ordinary skill in the art to which this invention pertains.

"BMP6", as used herein, means the protein Bone Morphogenetic Protein 6 (BMP6) or a gene or nucleic acid encoding BMP6. Hahn et al. 1992 Genomics 14: 759-62; Sauermann et al. 1993 J. Neurosci. Res. 33: 142-7; NCBI Gene ID: 654. BMP6 is also known as: BMP-6; VGR; VGR1; External IDs: OMIM: 112266 MGI: 88182; HomoloGene: 1300; GeneCards: BMP6 Gene. Orthologs: Species: Human: Entrez: 654; Ensembl: ENSG00000153162; UniProt: P22004; RefSeq (mRNA): NM_001718; RefSeq (protein): NP_001709; Location (UCSC): Chr 6: 7.73-7.88 Mb; Species: Mouse: Entrez: 12161; Ensembl: ENSMUSG00000039004; UniProt: P20722; RefSeq (mRNA): NM_907556; RefSeq (protein): NP_031582; Location (UCSC): Chr 13: 38.35-38.5 Mb. As described herein, an antibody antigen-binding fragment thereof which hinds to BMP6 binds to BMP6 protein.

"BMP2", as used herein, means the protein Bone Morphogenetic Protein 2 (BMP2) or a gene or nucleic acid encoding BMP2. BMP2 is also known as: BDA2; and BMP2A; External IDs OMIM: 112261 MGI: 88177 HomoloGene: 926 GeneCards: BMP2 Gene. Species: Human; Entrez: 650; Ensembl: ENSG00000125845; UniProt: P12643; RefSeq (mRNA): NM_001200; RetSeq (protein): NP_01191; Location (UCSC): Chr 20: 6.75-6.76 Mb. Species: Mouse; Entrez: 12156; Ensembl: ENSMUSG00000027358; UniProt: P21274; RefSeq (mRNA): NM_007553; RefSeq (protein): NP_031579; Location (UCSC): Chr 2: 133.55-133.56 Mb. As described herein, an antibody antigen-binding fragment thereof which binds to BMP2 binds to BMP2 protein.

"BMP5", as used herein, means the protein Bone Morphogenetic Protein 5 (BMP5) or a gene or nucleic acid encoding BMP5. BMP5 is also known as: MGC34244; External IDs OMIM: 112265 MGI: 88181 HomoloGene: 22412 GeneCards: BMP5 Gene. Species: Human; Entrez: 653; Ensembl: ENSG00000112175; UniProt: P22003; RefSeq (mRNA): NM_021073; RefSeq (protein): NP_066551; Location (UCSC): Chr 6: 55.62-55.74 Mb. Species: Mouse; Entrez: 12160; Ensembl: ENSMUSG00000032179; UniProt: P49003; RefSeq (mRNA): NM_007555; RefSeq (protein): NP_031581; Location (UCSC): Chr 9: 75.78-75.9 Mb. As described herein, an antibody antigen-binding fragment thereof which binds to BMP5 binds to BMP5 protein.

"BMP7", as used herein, means the protein Bone Morphogenetic Protein 7 (BMP7) or a gene or nucleic acid encoding BMP7. BMP7 is also known as: osteogenic protein-1; OP-1; External IDs OMIM: 112267 MGI: 103302 HomoloGene: 20410 GeneCards: BMP7 Gene. Species: Human; Entrez: 655; Ensembl: ENSG00000101144; UniProt: P18075; RefSeq (mRNA): NM_001719; RefSeq (protein): NP_001710; Location (UCSC): Chr 20: 55.74-55.84 Mb. Species: Mouse; Entrez: 12162; Ensembl: ENSMUSG00000008999; UniProt: P23359; RefSeq (mRNA): NM_007557; RefSeq (protein): NP_031583; Location (UCSC): Chr 2: 172.87-172.94 Mb. As described herein, an antibody antigen-binding fragment thereof which binds to BMP7 binds to BMP7 protein.

"Hepcidin" means the gene Hepcidin or the protein Hepcidin, a peptide hormone. Hepcidin is also known as: HAMP (Hepcidin anti-microbial protein or peptide); HEPC; HFE2B; LEAP1 (LEAP-1); PLTR; OMIM: 606464; HomoloGene: 81623; GeneCards: HAMP Gene; Entrez 57817; Ensembl ENSG00000105697; UniProt P81172; RefSeq (mRNA) NM_021175; RefSeq (protein) NP_066998; Location (UCSC) Chr 19: 35.77-35.78 Mb. Krause et al. FEBS Lett. 480: 147-150; and Pigeon et al. 2001 J. Biol. Chem. 276: 7811-9. See also: Ganz 2003 Blood 102: 783-8; Roy et al. 2005 Curr. Opin. Hemat. 12: 107-111; Fleming et al. 2006 Semin. Liver Dix. 25: 411-9; Park et al. 2001 J. Biol. Chem. 276: 7806-10; Majore et al. 2002 Haematologica 87: 221-2; Kluver et al. 2002 J. Pept. Res. 59: 241-8; Hunter et al. 2002 J. Biol. Chem. 277: 37597-603; Weinstein et al. 2003 Blood 100: 3776-81; Nemeth et al. 2003 Blood 101: 2461-3; Roetto et al. 2003 Nat. Genet. 33: 21-2; Strausberg et al. 2003 Proc. Natl. Acad. Sci USA 99: 16899-903; Gehrke et al. 2003 Blood 102: 371-6; Merryweather-Clarke et al. 2004 Human Mol. Genet, 12:2241-7; Clark et al. 2003 Genome Res. 13: 2265-70; Roetto et al. 2004 Blood 103: 2407-9; Jacolot et al. 2004 Blood 103: 2835-40; and Ota et al. 2004 Nat. Genet. 36: 40-45.

"BMP6 antagonist," as used herein refers to a molecule capable of antagonizing (e.g., reducing, inhibiting, decreasing, delaying) BMP6 function, expression and/or signalling (e.g., by blocking the binding of BMP6 to a BMP6 receptor). Non-limiting examples of BMP6 antagonists include BMP6 binding molecules and BMP6 receptor binding molecules. In some embodiments of the disclosed methods, regimens, kits, processes, uses and compositions, a BMP6 antagonist is employed.

"BMP6 binding molecule," as used herein, refers to any molecule capable of binding to the human BMP6 antigen either alone or associated with other molecules. The binding reaction may be shown by standard methods (qualitative assays) including, for example, a binding assay, competition assay or a bioassay for determining the inhibition of BMP6 binding to a BMP6 receptor or any kind of binding assays, with reference to a negative control test in which an antibody of unrelated specificity, but ideally of the same isotype is used. Non-limiting examples of BMP6 binding molecules include small molecules, BMP6 receptor decoys, and antibodies that bind to BMP6 as produced by B cells or hybridomas and chimeric, CDR-grafted or human antibodies or any fragment thereof, e.g., F(ab')2 and Fab fragments, as well as single chain or single domain antibodies. Preferably the BMP6 binding molecule antagonizes (e.g., reduces, inhibits, decreases, delays) BMP6 function, expression and/ or signalling. In some embodiments of the disclosed methods, regimens, kits, processes, uses and compositions, an BMP6 binding molecule is employed.

By "BMP6 receptor binding molecule" is meant any molecule capable of binding to a human BMP6 receptor either alone or associated with other molecules. The binding reaction may be shown by standard methods (qualitative assays) including, for example, a binding assay, competition assay or a bioassay for determining the inhibition of BMP6 receptor binding to BMP6 or any kind of binding assays, with reference to a negative control test in which an antibody of unrelated specificity, but ideally of the same isotype is used. Non-limiting examples of BMP6 receptor binding molecules include small molecules. BMP6 decoys, and antibodies to the BMP6 receptor as produced by B cells or hybridomas and chimeric, CDR-grafted or human antibodies or any fragment thereof, e.g., F(ab')2 and Fab fragments, as well as single chain or single domain antibodies. Preferably the BMP6 receptor binding molecule antagonizes (e.g., reduces, inhibits, decreases, delays) BMP6 function, expression and/or signaling. In some embodiments of the disclosed methods, regimens, kits, processes, uses and compositions, an BMP6 receptor binding molecule is employed.

"Anemia", as used herein, means a decrease in the number of red blood cells, or a decrease in the amount of hemoglobin or iron in the blood, with a decreased ability of the blood to carry oxygen.

"EPO resistance index" or "ERI", as used herein interchangeably, means the change in ESA, e.g., EPO, dose (Units per kg body weight) as a function of hemoglobin level. In embodiments, the ESA dose/hemoglobin level is measured weekly. In embodiments, the ESA dose/hemoglobin level is measured monthly. In embodiments, the ESA dose/hemoglobin level is compared over multiple measurement to arrive at the ERI.

Anemia can be diagnosed using any method known in the art, including, as a non-limiting example, in men based on a hemoglobin of less than about 130 to 140 g/L (13 to 14 g/dL) and in women, less than about 120 to 130 (12 to 13 g/dL). Janz et al. 2013 Emerg. Med. Pract. 15: 1-15; and Smith 2010 Am. J. Man. Care 16 Supp. S59-66.

As used herein, the terms "BMP6 antibody," "anti-human BMP6 antibody," "BMP6-binding antibody", "BMP6 antagonist antibody" and the like (and antigen-binding fragments thereof) include antibodies (and antigen-binding fragments thereof) which bind to the protein BMP6.

The terms "antibody", "antigen-binding fragment thereof", "antigen binding portion," and the like, as used herein, include whole antibodies and any antigen-binding fragment (i.e., "antigen-binding portion") or single chains thereof. A naturally occurring "antibody" is a glycoprotein comprising at least two heavy (H) chains and two light (L) chains inter-connected by disulfide bonds. Each heavy chain is comprised of a heavy chain variable region (abbreviated herein as VH) and a heavy chain constant region. The heavy chain constant region is comprised of three domains, CH1, CH2 and CH3. Each light chain is comprised of a light chain variable region (abbreviated herein as VL) and a light chain constant region. The light chain constant region is comprised of one domain, CL. The VH and VL regions can be further subdivided into regions of hypervariability, termed complementarly determining regions (CDR), interspersed with regions that are more conserved, termed framework regions (FR). Each VH and VL is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

The terms "antigen-binding fragment", "antigen-binding fragment thereof," "antigen binding portion" of an antibody, and the like, as used herein, refer to one or more fragments of an intact antibody that retain the ability to specifically bind to a given antigen (e.g., BMP6). Antigen binding functions of an antibody can be performed by fragments of an intact antibody. Examples of binding fragments encompassed within the term "antigen binding portion" of an antibody include a Fab fragment, a monovalent fragment consisting of the VL, VH, CL and CH1 domains; a F(ab)$_2$ fragment, a bivalent fragment comprising two Fab fragments linked by a disulfide bridge at the hinge region; an Fd fragment consisting of the VH and CH1 domains; an Fv fragment consisting of the VL and VH domains of a single arm of an antibody; a single domain antibody (dAb) fragment (Ward et al., 1989 Nature 341:544-546), which consists of a VH domain; and an isolated complementarity determining region (CDR).

Furthermore, although the two domains of the Fv fragment, VL and VH, are coded for by separate genes, they can be joined, using recombinant methods, by an artificial peptide linker that enables them to be made as a single protein chain in which the VL and VH regions pair to form monovalent molecules (known as single chain Fv (scFv); see, e.g., Bird et al., 1988 Science 242:423-426; and Huston et al., 1988 Proc. Natl. Acad. Sci. 85:5879-5883). Such single chain antibodies include one or more "antigen binding portions" of an antibody. These antibody fragments are obtained using conventional techniques known to those of skill in the art, and the fragments are screened for utility in the same manner as are intact antibodies.

Antigen binding portions can also be incorporated into single domain antibodies, maxibodies, minibodies, intrabodies, diabodies, triabodies, tetrabodies, v-NAR and bis-scFv (see, e.g., Hollinger and Hudson, 2005, Nature Biotechnology, 23, 9, 1126-1136). Antigen binding portions of antibodies can be grafted into scaffolds based on polypeptides such as Fibronectin type III (Fn3) (see U.S. Pat. No. 6,703,199, which describes fibronectin polypeptide monobodies).

Antigen binding portions can be incorporated into single chain molecules comprising a pair of tandem Fv segments (VH-CH1-VH-CH1) which, together with complementary light chain polypeptides, form a pair of antigen binding regions (Zapata et al., 1995 Protein Eng. 8 (10):1057-1062; and U.S. Pat. No. 5,641,870).

As used herein, the term "Affinity" refers to the strength of interaction between antibody and antigen at single antigenic sites. Within each antigenic site, the variable region of the antibody "arm" interacts through weak non-covalent forces with antigen at numerous sites; the more interactions, the stronger the affinity.

As used herein, the term "Avidity" refers to an informative measure of the overall stability or strength of the antibody-antigen complex. It is controlled by three major factors: antibody epitope affinity; the valency of both the antigen and antibody; and the structural arrangement of the interacting parts. Ultimately these factors define the specificity of the antibody, that is, the likelihood that the particular antibody is binding to a precise antigen epitope.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refer to compounds that have the same basic chemical structure as a naturally occurring amino acid, i.e., an alpha carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid.

Amino acid mimetics refers to chemical compounds that have a structure that is different from the general chemical structure of an amino acid, but that functions in a manner similar to a naturally occurring amino acid.

The term "binding specificity" as used herein refers to the ability of an individual antibody combining site to react with only one antigenic determinant. The combining site of the antibody is located in the Fab portion of the molecule and is constructed from the hypervariable regions of the heavy and light chains. Binding affinity of an antibody is the strength of the reaction between a single antigenic determinant and a single combining site on the antibody. It is the sum of the attractive and repulsive forces operating between the antigenic determinant and the combining site of the antibody.

Specific binding between two entities means a binding with an equilibrium constant (KA or $K_A$) of at least $1\times10^7$ $M^{-1}$, $10^8$ $M^{-1}$, $10^9$ $M^{-1}$, $10^{10}$ $M^{-1}$, or $10^{11}$ $M^{-1}$. The phrase "specifically (or selectively) binds" to an antibody (e.g., BMP6-binding antibody) refers to a binding reaction that is determinative of the presence of a cognate antigen (e.g., a human BMP6 protein) in a heterogeneous population of proteins and other biologics. In addition to the equilibrium constant (KA) noted above, an BMP6-binding antibody of the invention typically also has a dissociation rate constant (Kd or KD or $K_D$) of about $1\times10^{-2}$ $s^{-1}$, $1\times10^{-3}$ $s^{-1}$, or lower, and binds to BMP6 with an affinity that is at least two-fold greater than its affinity for binding to a non-specific antigen (e.g., BMP2, BMP5 or BMP7). The phrases "an antibody recognizing an antigen" and "an antibody specific for an antigen" are used interchangeably herein with the term "an antibody which binds specifically to an antigen".

Specific binding between two entities means a binding with an equilibrium constant (KA) (kon/koff) of at least $10^2M^{-1}$, at least $5\times10^2M^{-1}$, at least $10^3M^{-1}$, at least $5\times10^3M^{-1}$, at least $10^4M^{-1}$ at least $5\times10^4M^{-1}$, at least $10^5M^{-1}$, at least $5\times10^5M^{-1}$, at least $10^6M^{-1}$, at least $5\times10^6M^{-1}$, at least $10^7M^{-1}$, at least $5\times10^7M^{-1}$, at least $10^3M^{-1}$, at least $5\times10^8M^{-1}$, at least $10^9M^{-1}$, at least $5\times10^9M^{-1}$, at least $10^{10}M^{-1}$, at least $5\times10^{10}M^{-1}$, at least $10^{11}M^{-1}$, at least $5\times10^{11}M^{-1}$, at least $10^{12}M^{-1}$, at least $5\times10^{12}M^{-1}$, at least $10^{13}M^{-1}$, at least $5\times10^{13}M^{-1}$, at least $10^{14}M^{-1}$, at least $5\times10^{14}M^{-1}$, at least $10^{15}M^{-1}$, or at least $5\times10^{15}M^{-1}$.

The term "chimeric antibody" (or antigen-binding fragment thereof) is an antibody molecule (or antigen-binding fragment thereof) in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (h) the variable region, or a portion thereof, is altered, replaced or exchanged with a variable region having a different or altered antigen specificity. For example, a mouse antibody can be modified by replacing its constant region with the constant region from a human immunoglobulin. Due to the replacement with a human constant region, the chimeric antibody can retain its specificity in recognizing the antigen while having reduced antigenicity in human as compared to the original mouse antibody.

The term "conservatively modified variant" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid that encodes a polypeptide is implicit in each described sequence.

For polypeptide sequences, "conservatively modified variants" include individual substitutions, deletions or additions to a polypeptide sequence which result in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention. The following eight groups contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, Creighton, Proteins (1984)). In one embodiment, the term "conservative sequence modifications" are used to refer to amino acid modifications that do not significantly affect or alter the binding characteristics of the antibody containing the amino acid sequence.

The term "blocks" as used herein refers to stopping or preventing an interaction or a process, e.g., stopping ligand-dependent or ligand-independent signaling.

The term "recognize" as used herein refers to an antibody antigen-binding fragment thereof that finds and interacts (e.g., binds) with its conformational epitope.

The terms "cross-block", "cross-blocked", "cross-blocking", "compete", "cross compete" and related terms are used interchangeably herein to mean the ability of an antibody or other binding agent to interfere with the binding of other antibodies or binding agents to BMP6 in a standard competitive binding assay.

The ability or extent to which an antibody or other binding agent is able to interfere with the binding of another antibody or binding molecule to BMP6, and therefore whether it can be said to cross-block according to the invention, can be determined using standard competition binding assays. One suitable involves the use of the Biacore technology (e.g. by using the BIAcore 3000 instrument (Biacore, Uppsala, Sweden)), which can measure the extent of interactions using surface plasmon resonance technology. Another assay for measuring cross-blocking uses an ELISA-based approach.

The term "neutralizes" means that an antibody, upon binding to its target, reduces the activity, level or stability of the target; e.g., a BMP6 antibody, upon binding to BMP6 neutralizes BMP6 by at least partially reducing an activity, level or stability of BMP6, such as signaling or its role in hepcidin levels and anemia.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and nonconformational epitopes are distinguished in that the binding to the former but not the latter is lost in the presence of denaturing solvents.

The term "epitope" includes any protein determinant capable of specific binding to an immunoglobulin or otherwise interacting with a molecule. Epitopic determinants generally consist of chemically active surface groupings of molecules such as amino acids BMP6 or carbohydrate or sugar side chains and can have specific three-dimensional structural characteristics, as well as specific charge characteristics. An epitope may be "linear" or "conformational."

The term "linear epitope" refers to an epitope with all of the points of interaction between the protein and the interacting molecule (such as an antibody) occur linearly along the primary amino acid sequence of the protein (continuous). As used herein, the term "high affinity" for an IgG antibody refers to an antibody having a KD of $10^{-8}$ M or less, $10^{-9}$ M or less, or $10^{-10}$ M, or $10^{-11}$ M or less for a target antigen, e.g., BMP6. However, "high affinity" binding can vary for other antibody isotypes. For example, "high affinity" binding for an IgM isotype refers to an antibody having a KD of $10^{-7}$ M or less, or $10^{-8}$ M or less.

The term "human antibody" (or antigen-binding fragment thereof), as used herein, is intended to include antibodies (and antigen-binding fragments thereof) having variable regions in which both the framework and CDR regions are derived from sequences of human origin. Furthermore, if the antibody contains a constant region, the constant region also is derived from such human sequences, e.g., human germline sequences, or mutated versions of human germline sequences. The human antibodies and antigen-binding fragments thereof of the invention may include amino acid residues not encoded by human sequences (e.g., mutations introduced by random or site-specific mutagenesis in vitro or by somatic mutation in vivo).

The phrases "monoclonal antibody" or "monoclonal antibody composition" (or antigen-binding fragment thereof) as used herein refers to polypeptides, including antibodies, antibody fragments, bispecific antibodies, etc. that have substantially identical to amino acid sequence or are derived from the same genetic source. This term also includes preparations of antibody molecules of single molecular composition. A monoclonal antibody composition displays a single binding specificity and affinity for a particular epitope.

The term "human monoclonal antibody" (or antigen-binding fragment thereof) refers to antibodies (and antigen-binding fragments thereof) displaying a single binding specificity which have variable regions in which both the framework and CDR regions are derived from human sequences. In one embodiment, the human monoclonal antibodies are produced by a hybridoma which includes a B cell obtained from a transgenic nonhuman animal, e.g., a transgenic mouse, having a genome comprising a human heavy chain transgene and a light chain transgene fused to an immortalized cell.

The phrase "recombinant human antibody" (or antigen-binding fragment thereof), as used herein, includes all human antibodies (and antigen-binding fragments thereof) that are prepared, expressed, created or isolated by recombinant means, such as antibodies isolated from an animal a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In one embodiment, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

A "humanized" antibody (or antigen-binding fragment thereof), as used herein, is an antibody (or antigen-binding fragment thereof) that retains the reactivity of a non-human antibody while being less immunogenic in humans. This can be achieved, for instance, by retaining the non-human CDR regions and replacing the remaining parts of the antibody with their human counterparts (i.e., the constant region as well as the framework portions of the variable region). See, e.g., Morrison et al., Proc. Natl. Acad. Sci. USA, 81:6851-6855, 1984; Morrison and Oi, Adv. Immunol., 44:65-92, 1988; Verhoeyen et al., Science, 239:1534-1536, 1988; Padlan, Molec. Immun., 28:489-498, 1991; and Padlan, Molec. Immun., 31:169-217, 1994. Other examples of human engineering technology include, but is not limited to Xoma technology disclosed in U.S. Pat. No. 5,766,886.

The terms "identical" or percent "identity," in the context of two or more nucleic acids or polypeptide sequences, refer to two or more sequences or subsequences that are the same. Two sequences are "substantially identical" if two sequences have a specified percentage of amino acid residues or nucleotides that are the same (i.e., 60% identity, optionally 65%, 70%, 75%, 80%, 85%, 90%, 95%, or 99% identity over a specified region, or, when not specified, over the entire sequence), when compared and aligned for maximum correspondence over a comparison window, or designated region as measured using one of the following sequence comparison algorithms or by manual alignment and visual inspection. Optionally, the identity exists over a region that is at least about 50 nucleotides (or 10 amino acids) in length, or more preferably over a region that is 100 to 500 or 1000 or more nucleotides (or 20, 50, 200 or more amino acids) in length. Optionally, the identity exists over a region that is at least 50 nucleotides (or 10 amino acids) in length, or more preferably over a region that is 100 to 500 or 1000 or more nucleotides (or 20, 50, 200 or more amino acids) in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well known in the art. Optimal alignment of sequences for comparison can be conducted, e.g., by the local homology algorithm of Smith and Waterman (1970) Adv. Appl. Math. 2:482c, by the homology alignment algorithm of Needleman and Wunsch, J. Mol. Biol. 48:443, 1970, by the search for similarity method of Pearson and Lipman, Proc. Nat'l. Acad. Sci. USA 85:2444, 1988, by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Brent et al., Current Protocols in Molecular Biology, John Wiley & Sons. Inc. (ringbou ed., 2003)).

Two examples of algorithms that are suitable for determining percent sequence identity and sequence similarity are the BLAST and BLAST 2.0 algorithms, which are described in Altschul et al., Nuc. Acids Res. 25:3389-3402, 1977; and Altschul et al., J. Mol. Biol. 215:403-410, 1990, respectively. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score frills off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (N) of 11, an expectation (E) or 10, M=5, N=-4 and a comparison of both strands. For amino acid sequences, the BLASTP program uses as defaults a wordlength of 3, and expectation (E) of 10, and the BLOSUM62 scoring matrix (see Henikoff and Henikoff, Proc. Natl. Acad. Sci. USA 89:10915, 1989) alignments (B) of 50, expectation (E) of 10, M=5, N=-4, and a comparison of both strands.

The BLAST algorithm also performs a statistical analysis of the similarity between two sequences (see, e.g., Karlin and Altschul, Proc. Natl. Acad. Sci. USA 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

The percent identity between two amino acid sequences can also be determined using the algorithm of E. Meyers and W. Miller (Comput. Appl. Biosci., 4:11-17, 1988) which has been incorporated into the ALIGN program (version 2.0), using a PAM120 weight residue table, a gap length penalty of 12 and a gap penalty of 4. In addition, the percent identity between two amino acid sequences can be determined using the Needleman and Wunsch (J. Mol, Biol. 48:444-453, 1970) algorithm which has been incorporated into the GAP program in the GCG software package (available on the Internet at gcg.com), using either a Blossom 62 matrix or a PAM250 matrix, and a gap weight of 16, 14, 12, 10, 8, 6, or 4 and a length weight of 1, 2, 3, 4, 5, or 6.

Other than percentage of sequence identity noted above, another indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The term "isolated antibody" (or antigen-binding fragment thereof), as used herein, refers to an antibody (or antigen-binding fragment thereof) that is substantially free of other antibodies having different antigenic specificities (e.g., an isolated antibody that specifically binds BMP6 is substantially free of antibodies that specifically bind antigens other than BMP6). Moreover, an isolated antibody may be substantially free of other cellular material and/or chemicals.

The term "isotype" refers to the antibody class (e.g., IgM, IgE, IgG such as IgG1 or IgG4) that is provided by the heavy chain constant region genes. Isotype also includes modified versions of one of these classes, where modifications have been made to after the Fc function, for example, to enhance or reduce effector functions or binding to Fc receptors.

The term "Kassoc" or "Ka" or "KA" or "$K_A$," as used herein, is intended to refer to the association rate of a particular antibody-antigen interaction, whereas the term "Kdis" or "Kd," as used herein, is intended to refer to the dissociation rate of a particular antibody-antigen interaction. In one embodiment, the term "$K_D$", as used herein, is intended to refer to the dissociation constant, which is obtained from the ratio of Kd to Ka (i.e. Kd/Ka) and is expressed as a molar concentration (M). $K_D$ values for antibodies can be determined using methods well established in the art. A method for determining the $K_D$ of an antibody is by using surface plasmon resonance, or using a biosensor system such as a Biacore® system.

The terms "monoclonal antibody" (or antigen-binding fragment thereof) or "monoclonal antibody (or antigen-binding fragment thereof) composition" as used herein refer to a preparation of an antibody molecule (or antigen-binding fragment thereof) of single molecular composition. A monoclonal antibody composition displays a single binding specificity and affinity for a particular epitope.

The term "nucleic acid" is used herein interchangeably with the term "polynucleotide" and refers to deoxyribonucleotides or ribonucleotides and polymers thereof in either single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2-O-methyl ribonucleotides, peptide-nucleic acids (PNAs).

Unless otherwise indicated, a particular nucleic acid sequence also implicitly encompasses conservatively modified variants thereof (e.g., degenerate codon substitutions) and complementary sequences, as well as the sequence explicitly indicated. Specifically, as detailed below, degenerate codon substitutions may be achieved by generating sequences in which the third position of one or more selected (or all) codons is substituted with mixed-base and/or deoxyinosine residues (Batzer et al., Nucleic Acid Res. 19:5081, 1991; Ohtsuka et al., J. Biol. Chem. 260:2605-2608, 1985; and Rossolini et al., Mol. Cell. Probes 8:91-98, 1994).

The term "operably linked" refers to a functional relationship between two or more polynucleotide (e.g., DNA) segments. Typically, it refers to the functional relationship of a transcriptional regulatory sequence to a transcribed sequence. For example, a promoter or enhancer sequence is operably linked to a coding sequence if it stimulates or modulates the transcription of the coding sequence in an appropriate host cell or other expression system. Generally, promoter transcriptional regulatory sequences that are operably linked to a transcribed sequence are physically contiguous to the transcribed sequence, i.e., they are cis-acting. However, some transcriptional regulatory sequences, such as enhancers, need not be physically contiguous or located in close proximity to the coding sequences whose transcription they enhance.

As used herein, the term, "optimized" means that a nucleotide sequence has been altered to encode an amino acid sequence using codons that are preferred in the production cell or organism, generally a eukaryotic cell, for example, a cell of Pichia, a Chinese Hamster Ovary cell (CHO) or a human cell. The optimized nucleotide sequence is engineered to retain completely or as much as possible the amino acid sequence originally encoded by the starting nucleotide sequence, which is also known as the "parental" sequence. The optimized sequences herein have been engineered to have codons that are preferred in mammalian cells. However, optimized expression of these sequences in other eukaryotic cells or prokaryotic cells is also envisioned herein. The amino acid sequences encoded by optimized nucleotide sequences are also referred to as optimized.

The terms "polypeptide" and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer. Unless otherwise indicated, a particular polypeptide sequence also implicitly encompasses conservatively modified variants thereof.

The term "recombinant human antibody" (or antigen-binding fragment thereof), as used herein, includes all human antibodies (and antigen-binding fragments thereof) that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the human antibody, e.g., from a transfectoma, antibodies isolated from a recombinant, combinatorial human antibody library, and antibodies prepared, expressed, created or isolated by any other means that involve splicing of all or a portion of a human immunoglobulin gene, sequences to other DNA sequences. Such recombinant human antibodies have variable regions in which the framework and CDR regions are derived from human germline immunoglobulin sequences. In one embodiment, however, such recombinant human antibodies can be subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

The term "recombinant host cell" (or simply "host cell") refers to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "subject" includes human and non-human animals. Non-human animals include all vertebrates, e.g., mammals and non-mammals, such as non-human primates, sheep, dog, cow, chickens, amphibians, and reptiles. Except when noted, the terms "patient" or "subject" are used herein interchangeably.

The term "treating" includes the administration of compositions or antibodies to prevent or delay the onset of the symptoms, complications, or biochemical indicia of a disease (e.g., anemia), alleviating the symptoms or arresting or inhibiting further development of the disease, condition, or disorder. Treatment may be prophylactic (to prevent or delay the onset of the disease, or to prevent the manifestation of clinical or subclinical symptoms thereof) or therapeutic suppression or alleviation of symptoms after the manifestation of the disease.

The term "vector" is intended to refer to a polynucleotide molecule capable of transporting another polynucleotide to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "hematocrit" or "haematocrit", as used herein, is also known as a packed cell volume (PCV) or erythrocyte volume fraction (EVF) and is the volume (%) of red blood cells in blood. This is normally about 45% for men and about 50% for women. It is considered an integral part of a person's complete blood count results, along with hemoglobin concentration, white blood count, and platelet count. In one embodiment, anemia refers to an abnormally low hematocrit, as opposed to polycythemia, which is an abnormally high hematocrit.

The term "assaying" is used to refer to the act of identifying, screening, probing, testing measuring or determining, which act may be performed by any conventional means. For example, a sample may be assayed for the presence of a particular genetic or protein marker by using an ELISA assay, a Northern blot, imaging, serotyping, cellular typing, gene sequencing, phenotyping, haplotyping, immunohistochemistry, western blot, mass spectrometry, etc. The term "detecting" (and the like) means the act of extracting particular information from a given source, which may be direct or indirect. In some embodiments of the predictive methods disclosed herein, the presence or level of a given thing (e.g., level of protein, etc.) is detected in a biological sample indirectly, e.g., by querying a database. The terms "assaying" and "determining" contemplate a transformation of matter, e.g., a transformation of a biological sample, e.g., a blood sample or other tissue sample, from one state to another by means of subjecting that sample to physical testing.

The term "obtaining" means to procure, e.g., to acquire possession of in any way, e.g., by physical intervention (e.g., biopsy, blood draw) or non-physical intervention (e.g., transmittal of information via a server), etc.

The phrase "assaying a biological sample . . . " and the like, is used to mean that a sample may be tested (either directly or indirectly) for either the presence or level of a given marker (e.g., protein). It will be understood that, in a situation where the level of a substance denotes a probability, then the level of such substance may be used to guide a therapeutic decision. For example, one may determine the level of ferritin in a patient by assaying for its presence in by quantitative or relatively-quantitative means (e.g., levels relative to the levels in other samples). The disclosed methods involve, inter alia, determining the level of a particular marker, e.g., ferritin, in a patient.

As used herein, "selecting" and "selected" in reference to a patient is used to mean that a particular patient is specifically chosen from a larger group of patients on the basis of (due to) the particular patient having a predetermined criteria, e.g., the patient has a particular level of ferritin, e.g., as described herein. Similarly, "selectively treating" refers to providing treatment to a patient having a particular disease, where that patient is specifically chosen from a larger group of patients on the basis of the particular patient having a predetermined criteria, e.g., an anemia patient specifically chosen for treatment due to the patient having a particular ferritin level, e.g., as described herein. Similarly, "selectively administering" refers to administering a drug to a patient that is specifically chosen from a larger group of patients on the basis of (due to) the particular patient having a predetermined criteria, e.g., a particular genetic or other biological marker, e.g., a particular ferritin level, e.g., as described herein. By selecting, selectively treating and selectively administering, it is meant that a patient is delivered a personalized therapy based on the patient's particular biology, rather than being delivered a standard treatment regimen based solely on the patient having a particular disease. Selecting, in reference to a method of treatment as used herein, does not refer to fortuitous treatment of a patient that has a particular marker, but rather refers to the deliberate choice to administer a BMP6 antagonist to a patient based on the patient having a particular marker, e.g., a particular ferritin level, e.g., as described herein. Thus, selective treatment differs from standard treatment, which delivers a particular drug to all patients, regardless of their marker status.

As used herein, "predicting" indicates that the methods described herein provide information to enable a health care provider to determine the likelihood that an individual having a disease, e.g., anemia, will respond to or will respond more favorably to treatment with BMP6 binding molecule. It does not refer to the ability to predict response with 100% accuracy. Instead, the skilled artisan will understand that it refers to an increased probability.

As used herein. "likelihood" and "likely" is a measurement of how probable an event is to occur. It may be used interchangeably with "probability". Likelihood refers to a probability that is more than speculation, but less than certainty. Thus, an event is likely if a reasonable person using common sense, training or experience concludes that, given the circumstances, an event is probable. In some embodiments, once likelihood has been ascertained, the patient may be treated (or treatment continued, or treatment proceed with a dosage increase with the BMP6 binding molecule or the patient may not be treated (or treatment discontinued, or treatment proceed with a lowered dose) with the BMP6 binding molecule.

The phrase "increased likelihood" refers to an increase in the probability that an event will occur. For example, some methods herein allow prediction of whether a patient will display an increased likelihood of responding to treatment with a BMP6 binding molecule or an increased likelihood of responding better to treatment with a BMP6 binding molecule in comparison to a patient having the same or similar disease who does not have the marker (e.g., the level of ferritin as described herein).

DETAILED DESCRIPTION OF THE INVENTION

Figure 1A:
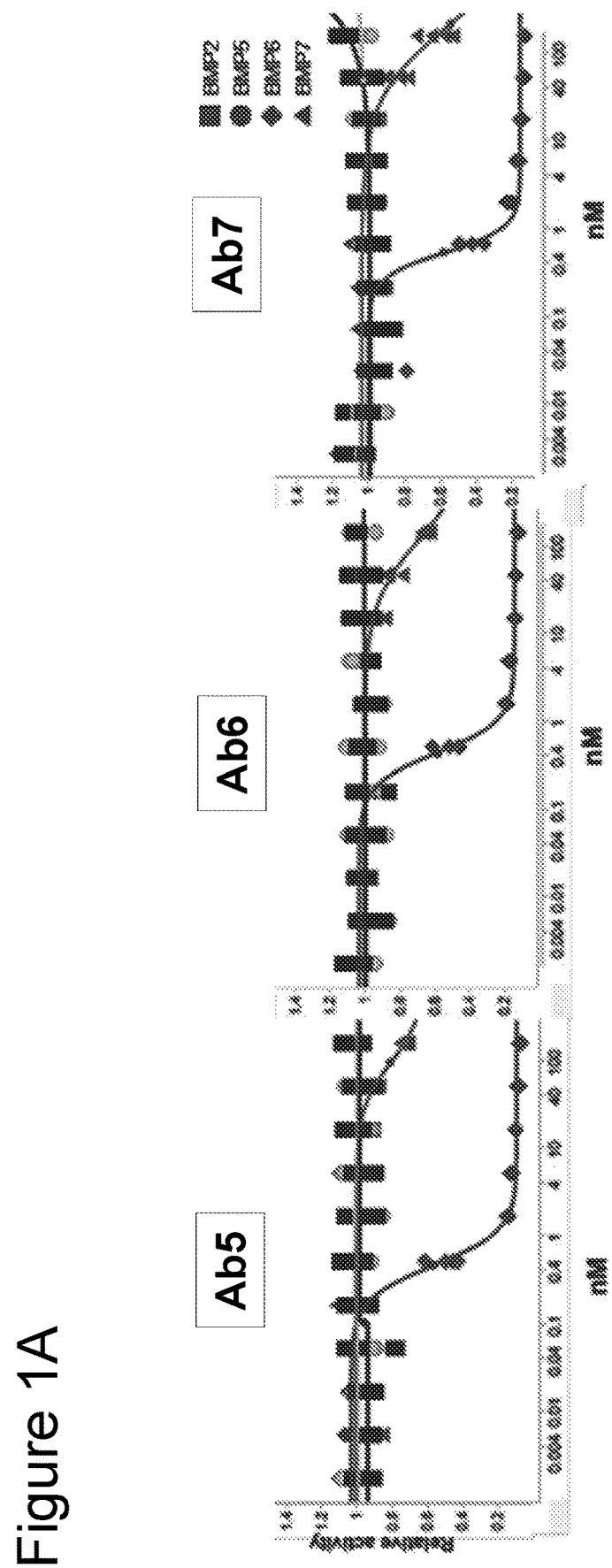
FIG. 1A shows inhibition of BMP activity by antagonist antibodies 5, 6 and 7 in reporter gene assay. Activity against BMP2, BLIPS, BMP6, and BMP7 is shown.

The present invention provides methods of treating conditions associated with reduced iron, e.g., anemia, with inhibitors of BMP6.

BMP6 Inhibitors

A wide variety of BMP6 antagonists can be used in the methods of the present invention, such as, for example, antibodies, fusion proteins, adnectins, aptamers, anticalins, lipocalins, nucleic acids (e.g., antisense molecules, such as RNA interfering agents and ribozymes), immunoconjugates (e.g., an antibody conjugated to a therapeutic agent), small molecules, fusion proteins, BMP6-derived peptidic compounds, and receptor-based antagonists (e.g. soluble BMP6 receptor domains).

Nucleic Acids/Antisense Molecules

In another embodiment, the BMP6 antagonist employed in the methods of the present invention is an antisense nucleic acid molecule that is complementary to a gene encoding BMP6, or to a portion of that gene, or a recombinant expression vector encoding the antisense nucleic acid molecule. As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

The use of antisense nucleic acids to down-modulate the expression of a particular protein in a cell is well known in the art (see e.g., Weintraub, H. et al., Antisense RNA as a molecular tool for genetic analysis, Reviews—Trends in Genetics, Vol. 1(1) 1986; Askart, F. K. and McDonnell, W. M. (1996) N. Eng. J. Med. 334:316-318; Bennett, M. R. and Schwartz, S. M. (1995) Circulation 92:1981-1993; Mercola, D. and Cohen, J. S. (1995) Cancer Gene Ther. 2:47-59; Rossi, J. J. (1995) Br. Med. Bull. 51:217-225; Wagner, R. W. (1994) Nature 372:333-335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3'untranslated region of the mRNA or a region bridging the coding region and an untranslated region (e.g., at the junction of the 5'untranslated region and the coding region). Furthermore, an antisense nucleic acid can be complementary in sequence to a regulators region of the gene encoding the mRNA, for instance a transcription initiation sequence or regulatory element. Preferably, an antisense nucleic acid is designed so as to be complementary to a region preceding or spanning the initiation codon on the coding strand/or in the 3' untranslated region of an mRNA.

Antisense nucleic acids can be designed according to the rules of Watson and Crick base pairing. The antisense nucleic acid molecule can be complementary to the entire coding region of BMP6 mRNA, but more preferably is an oligonucleotide which is antisense to only a portion of the coding or noncoding region of BMP6 mRNA. For example, the antisense oligonucleotide can be complementary to the region surrounding the translation start site of BMP6 mRNA. An antisense oligonucleotide can be, for example, about 5, 10, 15, 20, 25, 30, 35, 40, 45 or 50 nucleotides in length. An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine, 4-acetylcytosine, 5-(carboxyhydroxylmethypuracil, 5-carboxymethylaminomethyl-2-thiouridine, 5-carboxymethylaminotnethyluracil, dihydrouracil, beta-D-galactosylqueosine, inosine, N6-isopentenyladenine, methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation, RNA transcribed from the inserted nucleic acid will be if an antisense orientation to a target nucleic acid of interest, described further in the following subsection).

The antisense nucleic acid molecules that can be utilized in the methods of the present invention are typically administered to a subject or generated in situ such that they hybridize with or bind to cellular mRNA and/or genomic DNA encoding BMP6 to thereby inhibit expression by inhibiting transcription and/or translation. The hybridization can be by conventional nucleotide complementarity to form stable duplex, or, for example, in the case of an antisense nucleic acid molecule which binds to DNA duplexes, through specific interactions in the major groove of the double helix. An example of a route of administration of antisense nucleic acid molecules includes direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid in molecules to peptides or antibodies which bind to cell surface receptors or antigens. The antisense nucleic acid molecules can also be delivered to cells using vectors well known in the art and described in, for example, US20070111230 the entire contents of which are incorporated herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule employed by the methods of the present invention can include an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) Nucleic Acids. Res. 15:6625-6641). The antisense nucleic acid molecule can also comprise a 2'-o-methylribonucleotide (Inoue et al. (1987) Nucleic Acids Res. 15:6131-6148) or a chimeric RNA-DNA analogue (Inoue et al. (1987) FEBS Lett. 215:327-330).

In another embodiment, an antisense nucleic acid used in the methods of the present invention is a compound that mediates RNAi. RNA interfering agents include, but are not limited to, nucleic acid molecules including RNA molecules which are homologous to BMP6 or a fragment thereof, "short interfering RNA" (siRNA), "short hairpin" or "small hairpin RNA" (shRNA), and small molecules which interfere with or inhibit expression of a target gene by RNA interference (RNAi). RNA interference is a post-transcriptional, targeted gene-silencing technique that uses double-stranded RNA (dsRNA) to degrade messenger RNA (mRNA) containing the same sequence as the dsRNA (Sharp, P. A. and Zamore, P. D. 287, 2431-2432 (2000); Zamore, P. D. et al. Cell 101, 25-33 (2000). Tuschl, T. et al. Genes Dev. 13, 3191-3197 (1999)). The process occurs when an endogenous ribonuclease cleaves the longer dsRNA into shorter, 21- or 22-nucleotide-long RNAs, termed small interfering RNAs or siRNAs. The smaller RNA segments then mediate the degradation of the target mRNA. Kits for synthesis of RNAi are commercially available from, e.g., New England Biolabs and Ambion. In one embodiment one or more of the chemistries described above for use in antisense RNA can be employed.

In still another embodiment, an antisense nucleic acid is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach, 1988, Nature 334:585-591) can be used to catalytically cleave BMP6 mRNA transcripts to thereby inhibit translation of BMP6 mRNA.

Alternatively, gene expression can be inhibited by targeting nucleotide sequences complementary to the regulatory region of BMP6 (e.g., the promoter and/or enhancers) to form triple helical structures that prevent transcription of the BMP6 gene. See generally, Helene, C., 1991, Anticancer Drug Des. 6(6):569-84; Helene. C. et al., 1992, Ann. N.Y. Acad. Sci. 660:27-36; and Maher, L. J., 1992, Bioassays 14(12):807-15.

Fusion Proteins and BMP6-Derived Peptidic Compounds

In another embodiment, the BMP6 antagonist used in the methods of the present invention is a fusion protein or peptidic compound derived from the BMP6 amino acid sequence. In particular, the inhibitory compound comprises a fusion protein or a portion of BMP6 (or a mimetic thereof) that mediates interaction of BMP6 with a target molecule such that contact of BMP6 with this fusion protein or peptidic compound competitively inhibits the interaction of BMP6 with the target molecule. Such fusion proteins and peptidic compounds can be made using standard techniques known in the art. For example, peptidic compounds can be made by chemical synthesis using standard peptide synthesis techniques and then introduced into cells by a variety of means known in the art for introducing peptides into cells (e.g., liposome and the like).

The in vivo half-life of the fusion protein or peptidic compounds of the invention can be improved by making peptide modifications, such as the addition of N-linked glycosylation sites into the BMP6 peptidic compound, or conjugating the peptidic BMP6 compound to poly(ethylene glycol) (PEG; pegylation), e.g., via lysine-monopegylation. Such techniques have proven to be beneficial in prolonging the half-life of therapeutic protein drugs. It is expected that pegylation of the BMP6 polypeptides of the invention may result in similar pharmaceutical advantages.

In addition, pegylation can be achieved in any part of a polypeptide of the invention by the introduction of a nonnatural amino acid. Certain nonnatural amino acids can be introduced by the technology described in Deiters et al., J Am Chem Soc 125:11782-11783, 2003; Wang and Schultz, Science 301:964-967, 2003; Wang et al., Science 292:498-500, 2001; Zhang et al., Science 303:371-373, 2004 or in U.S. Pat. No. 7,083,970. Briefly, some of these expression systems involve site-directed mutagenesis to introduce a nonsense codon, such as an amber TAG, into the open reading frame encoding a polypeptide of the invention. Such expression vectors are then introduced into a host that can utilize a tRNA specific for the introduced nonsense codon and charged with the nonnatural amino acid of choice. Particular nonnatural amino acids that are beneficial for purpose of conjugating moieties to the polypeptides of the invention include those with acetylene and azido side chains. The BMP6 polypeptides containing these novel amino acids can then be pegylated at these chosen sites in the protein.

Receptor-Based Antagonist

In another embodiment, the BMP6 antagonist used in the methods of the present invention is a receptor-based antagonist. Receptor-based antagonists include soluble BMP6 receptors that bind BMP6 (or portions thereof), respectively, and disrupt BMP6 activity and/or function. In a particular embodiment, the receptor-based antagonist includes, but is not limited to, soluble hemojuvelin or BMP Type I or Type II receptor. Versions of soluble hemojuvelin include those described in patent application publication US2010/0136015.

BMP6 Antibodies and Antigen-Binding Fragments Thereof

The present invention provides, as BMP6 inhibitors useful in the methods and other embodiments and aspects of the invention described herein, antibodies and antigen-binding fragments thereof that specifically bind to human BMP6.

BMP6, a secreted BMP family growth factor ligand, has been identified as a critical endogenous regulator of hepatic expression of iron metabolism hormone hepcidin. Without being bound by any particular theory, this disclosure suggests a BMP6 antagonist antibody as a hepcidin-lowering therapy is expected to benefit patients with iron-restricted anemia by overcoming resistance to Erythropoiesis Stimulating Agent (ESA), which adds substantially to the morbidity of an underlying disease and is often a predictor of adverse outcome.

Examples of such anti-human BMP6 antibodies are Antibodies 3, 5, 6 and 7, whose sequences are listed in Table 1, and the anti-human BMP6 antibodies described in Table 14.

Figure 2:
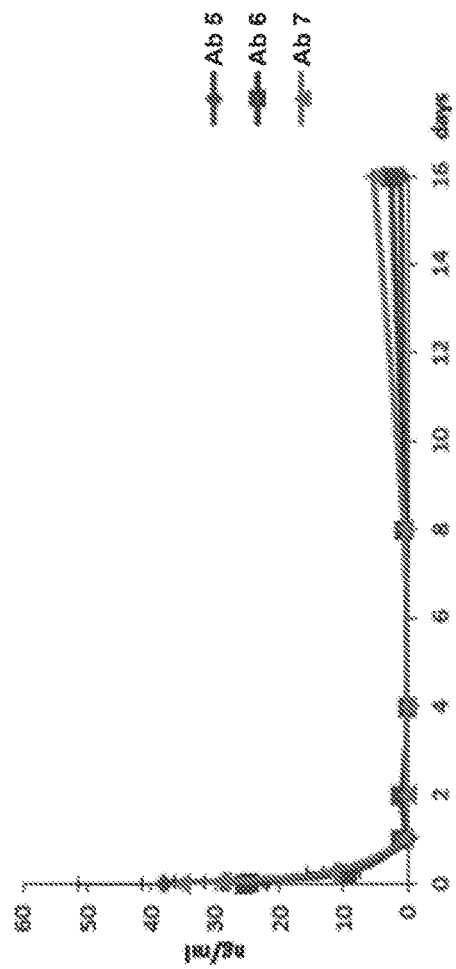
FIG. 2 shows the pharmacodynamics profiles of single dose rat triage PK study. Antibodies 5, 6 and 7 were used. Serum hepcidin and iron levels were measured at 1 hr, 6 hr, 1, 2, 4, 8, 16 days post dose (10 mg/kg, IV).
Figure 2:
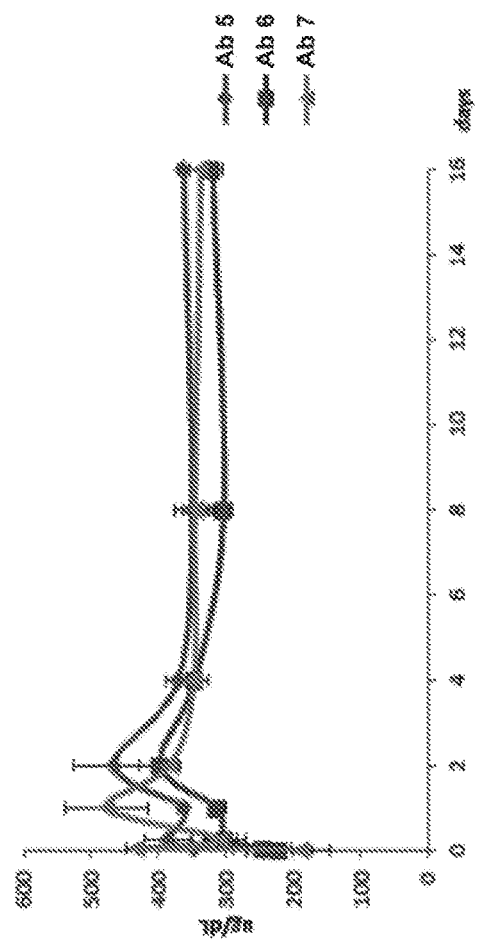

Antibodies 5, 6 and 7 all bind with high affinity for human BMP6, with high selectivity over human BMP7, human BMP5 and human BMP2 (see FIG. 1A). These antibodies also all demonstrate a decrease in serum hepcidin and an increase in serum iron in rats (see FIG. 2).

Additional examples of anti-human BMP6 antibodies are LY3113593 (see, e.g., clinical trial NCT02604160). Additional examples of anti-human BMP6 antibodies are described in PCT application publication number WO2014/099391, the contents of which are hereby incorporated by reference in their entirety. Particular anti-human BMP6 antibodies of WO2014/099391 include the antibodies described in Table 14.

TABLE 14

Examples of anti-human BMP6 antibodies

| Sequence Name | Sequence | SEQ ID NO: |
|---|---|---|
| Antibody 1 | | |
| LCDR1 | RSSENIYRNLA | 1 |
| LCDR2 | AATNLAD | 2 |
| LCDR3 | QGIWGTPLT | 3 |
| Light Chain Variable Region (aa) | DIQMTQSPSSLSASVGDRVTITCRSSENIYRNLAWY QQKPGKAPKLLIYAATNLADGVPSRFSGSGSGTDF TLTISSLQPEDFATYYCQGIWGTPLTFGGGIKVEIK | 4 |
| Light Chain (aa) | DIQMTQSPSSLSASVGDRVTITCRSSENIYRNLAWY QQKPGKAPKLLIYAATNLADGVPSRFSGSGSGTDF TLTISSLQPEDFATYYCQGIWGTPLTFGGGTKVEIK RTVAAPSVFIFPPSDEQLKSGTASVVCLLNNFYPRE AKVQWKVDNALQSGNSQESVTEQDSKDSTYSLSS TLTLSKADYEKHKVYACEVTHQGLSSPVTKSFNR GEC | 5 |
| HCDR1 | GYTFTSYAMH | 6 |
| HCDR2 | YINPYNDGTKYNENFK | 7 |
| HCDR3 | RPFGNAMDI | 8 |
| Heavy Chain Variable Region (aa) | QVQLVQSGAEVKKPGSSVKVSCKASGYTFTSYAM HWVRQAPGQGLEWMGYINPYNDGTKYNENFKGR VTITADESTSTAYMELSSLRSEDTAVYYCARRPFG NAMDIWGQGTLVTVSS | 92 |
| Heavy Chain (aa) | QVQLVQSGAEVKKPGSSVKVSCKASGYTFTSYAM HWVRQAPGQGLEWMGYINPYNDGTKYNENFKGR VTITADESTSTAYMELSSLRSEDTAVYYCARRPFG NAMDIWGQGTLVTVSSASTKGPSVFPLAPCSRSTS | 93 |

TABLE 14-continued

Examples of anti-human BMP6 antibodies

| Sequence Name | Sequence | SEQ ID NO: |
|---|---|---|
| | ESTAALGCLVKDYFPEPVTVSWNSGALTSGVHTFP AVLQSSGLYSLSSVVTVPSSSLGTKTYTCNVDHKP SNTKVDKRVESKYGPPCPPCPAPEAAGGPSVFLFPP KPKDTLMISRTPEVTCVVVDVSQEDPEVQFNWYV DGVEVHNAKTKPREEQFNSTYRVVSVLTVLHQD WLNGKEYKCKVSNKGLPSSIEKTISKAKGQPREPQ VYTLPPSQEEMTKNQVSLTCLVKGFYPSDIAVEWE SNGQPENNYKTTPPVLDSDGSFFLYSRLTVDKSRW QEGNVFSCSVMHEALHNHYTQKSLSLSLG | |

Antibody 2

| Sequence Name | Sequence | SEQ ID NO: |
|---|---|---|
| LCDR1 | RSSENIYRNLA | 1 |
| LCDR2 | AATNLAD | 2 |
| LCDR3 | QGIWGTPLT | 3 |
| Light Chain Variable Region (aa) | DIQMTQSPSSLSASVGDRVTITCRSSENIYRNLAWY QQKPGKAPKLLIYAATNLADGVPSRFSGSGSGTDF TLTISSLQPEDFATYYCQGIWGTPLTFGGGTKVEIK | 4 |
| Light Chain (aa) | DIQMTQSPSSLSASVGDRVTITCRSSENIYRNLAWY QQKPGKAPKLLIYAATNLADGVPSRFSGSGSGTDF TLTISSLQPEDFATYYCQGIWGTPLTFGGGTKVEIK RTVAAPSVFIFPPSDEQLKSGTASVVCLLNNFYPRE AKVQWKVDNALQSGNSQESVTEQDSKDSTYSLSS TLTLSKADYEKHKVYACEVTHQGLSSPVTKSFNR GEC | 5 |
| HCDR1 | GYTFTSYAMH | 6 |
| HCDR2 | YINPYNRGTKYNENFK | 94 |
| HCDR3 | RPFGNAMDI | |
| Heavy Chain Variable Region (aa) | QVQLVQSGAEVKKPGSSVKVSCKASGYTFTSYAM HWVRQAPGQGLEWMGYINPYNRGTKYNENFKGR VTITADESTSTAYMELSSLRSEDTAVYYCARRPFG NAMDIWGQGTLVTVSS | 95 |
| Heavy Chain (aa) | QVQLVQSGAEVKKPGSSVKVSCKASGYTFTSYAM HWVRQAPGQGLEWMGYINPYNRGTKYNENFKGR VTITADESTSTAYMELSSLRSEDTAVYYCARRPFG NAMDIWGQGTLVTVSSASTKGPSVFPLAPCSRSTS ESTAALGCLVKDYFPEPVTVSWNSGALTSGVHTFP AVLQSSGLYSLSSVVTVPSSSLGTKTYTCNVDHKP SNTKVDKRVESKYGPPCPPCPAPEAAGGPSVFLFPP KPKDTLMISRTPEVTCVVVDVSQEDPEVQFNWYV DGVEVHNAKTKPREEQFNSTYRVVSVLTVLHQD WLNGKEYKCKVSNKGLPSSIEKTISKAKGQPREPQ VYTLPPSQEEMTKNQVSLTCLVKGFYPSDIAVEWE SNGQPENNYKTTPPVLDSDGSFFLYSRLTVDKSRW QEGNVFSCSVMHEALHNHYTQKSLSLSLG | 96 |

To provide further evidence that targeting this pathway can confer improvement of functional endpoints, we tested the ability of BMP6-specific antibodies, Antibodies 5 to 7, to modulate serum biomarkers for iron metabolism in normal mice and rats, and to reverse ESA-resistant anemia in a mouse model of anemia of inflammation. We found that a single injection of animals with BMP6 antibody resulted in a sustained increase of serum iron levels, accompanied by potent suppression of circulating hepcidin. Furthermore, therapeutic treatment of mice subjected to inflammation-induced anemia significantly improved erythropoietic parameters in response to concurrent erythropoietin treatment.

In this disclosure, inhibition of BMP6 signaling in a mouse model of anemia of inflammation substantially improved iron-dependent red cell parameters.

The BMP6 antagonist antibodies disclosed herein represent a novel therapeutic approach to safely improve anemia with erythropoietin hypo-responsiveness. Without being bound by any particular theory, this disclosure suggests that this may occur through mobilization and availability of iron store to the demand from erythroid compartment.

Figure 1B:
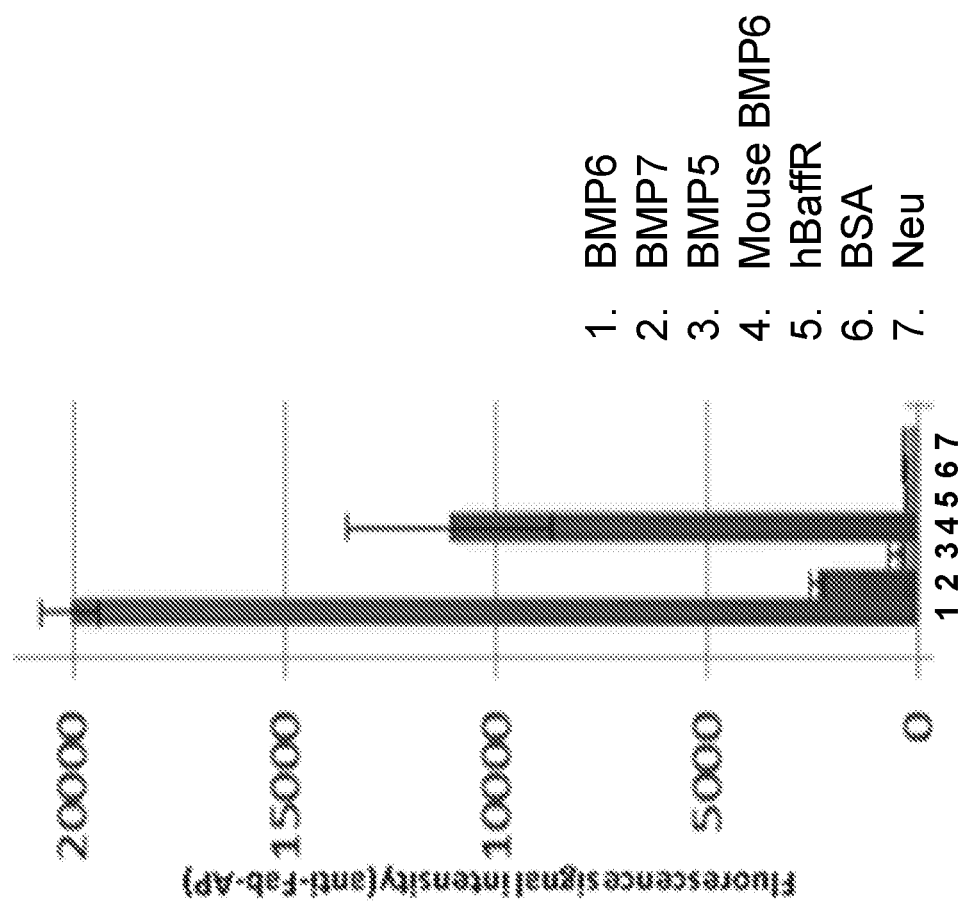
FIG. 1B shows an ELISA binding assay testing Antibody 7 binding to human BMP6, human BMP7, human BMP5, mouse BMP6, hBaffR, BSA and Neu. In this figure and various other figures, and elsewhere in the Specification, Ab 5=Antibody 5; Ab 6=Antibody 6; and Ab 7=Antibody 7.

In one embodiment, the present invention provides isolated antibodies or antigen-binding fragments thereof that bind with a 100-, 500- or 1000-fold higher affinity for human BMP6 protein, than to any of: human BMP5 or human BMP7 protein. Specificity to BMP6 without binding to BMP7 is important, as knock-out of BMP6 is not lethal to mice. However, knock-out mice for BMP7 die after birth with kidney, eye and bone defects. Individual knock-outs of either gene do not alter cardiogenesis, but a double knockout of BMP6 and BMP7 demonstrated several defects and delays in the heart; embryos died to cardiac insufficiency. BMP7 is important in preventing progression of chronic heart disease associated with fibrosis. Therefore, cross-reactivity of an anti-BMP6 antibody with BMP7 is not desirable. Antibodies provided herein are specific to BMP6 over BMP7; See, for example, Table 4A. FIG. 1B also shows evidence for binding specificity to human BMP6 over human BMP2, BMP5 and BMP7 proteins. In contrast, a commercially-available BMP6 antibody from R&D Systems, for example, was revealed to have strong cross-reactivity to BMP7 in a reporter gene assay, and to inhibit both BMP6 and BMP7.

Antibodies of the invention include, but are not limited to, the human monoclonal antibodies, isolated as described, in the Examples (see Section 6 below). Examples of such anti-human BMP6 antibodies are Antibodies 3, 5, 6 and 7, whose sequences are listed in Table 1.

Figure 5:
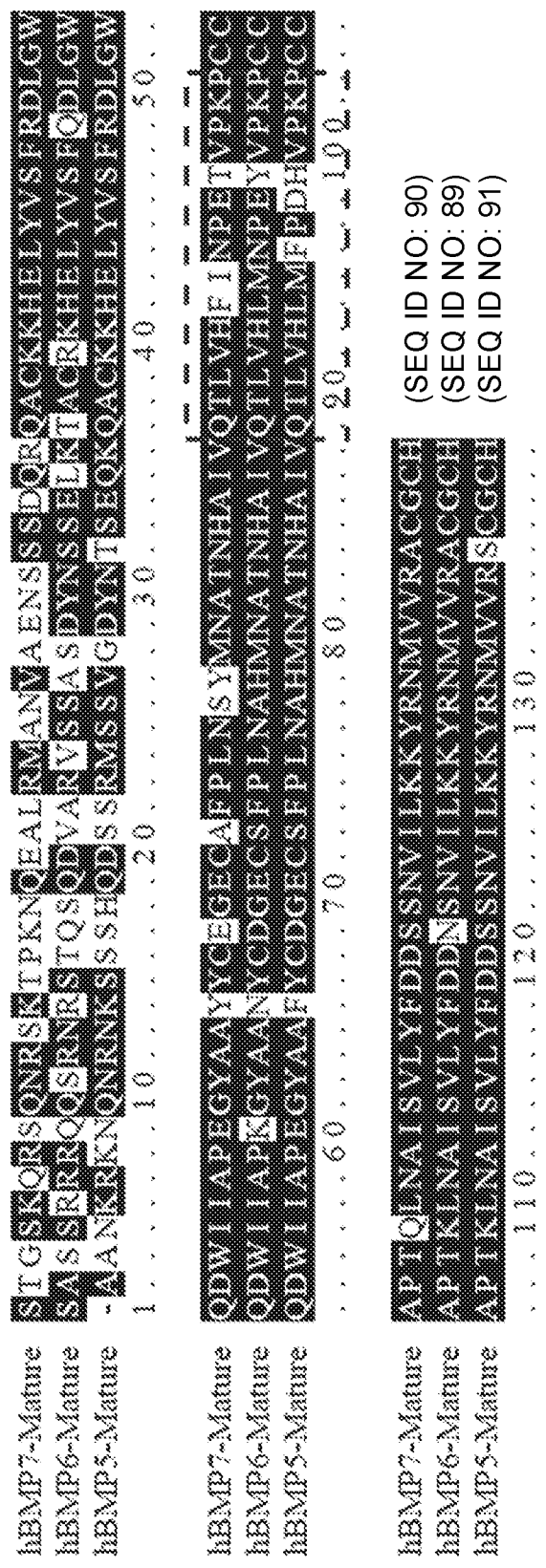
FIG. 5 shows linear epitope mapping by HDxMS (hydrogen/deuterium exchange coupled with mass spectometry). The epitope of BMP6 bound by Antibody 7 is shown (residues 88-102 of human BMP6 (QTLVHLMNPEYVPKP (SEQ ID NO: 98))). Using HDxMS, Antibody 676, a humanized version of a commercially available BMP6 antibody, was found to bind to an epitope consisting of residues 23-35 of human BMP6 (VSSASDYNSSELK (SEQ ID NO: 99)).

Matured antibody 7 is derived from NOV0442_VL (YGQ) Germlining/PTM removal, which is derived from parental IgG hit NOV0442 (VH3_3-15, V11_1e). Antibody 7 binds with high affinity for human BMP6 in an ELISA binding assay, with selectivity over human BMP7 of over 500-fold (i.e., an affinity to human BMP6 over 500-fold greater than to human BMP7). This antibody also has no detectable activity against human BMP2 or BMP5. The BMP6 peptide recognized by parental IgG NOV0442 and Antibody 7 is shown in FIG. 5. The peptide comprises amino acids QTLVHLMNPEYVPKP (SEQ ID NO: 98) of human BMP6. In contrast to IgG NOV0442 and Antibody 7, humanized mAb507 (R&D Systems) binds to the sequence VSSASDYNSSELK (SEQ ID NO: 99) of human BMP6. Thus, the epitope recognized by IgG NOV0442 and Antibody 7 represents a novel BMP6 epitope. Antibody 7 also inhibits BMP6 binding to receptors in vitro. Binding of BMP6 to BMPR1A is inhibited maximally 59%; binding to BMPR1B is inhibited maximally 85%; and binding to RGM-c is inhibited maximally 72%. A single 10 mg/kg treatment in rats led to sustained suppression of circulating hepcidin. The estimated minimum effective dose in mice is less than or equal to 0.1 mg/kg. Serum iron also showed an increase, and hepcidin showed a decrease after a single Antibody dose in monkeys of 3 mg/kg. In mice, wherein *Brucella abortus* antigen was used to simulate anemia, the treatment effect of Antibody 7 (2 mg/kg) is consistent with clinically significant erythropoietic response to chronic EPO therapy, with gradual hemoglobin increase of >2.0 g/dL from baseline.

In antibody 7, a potential post-translational modification site was removed by an N51Q mutation within LCDR2 to increase later product homogeneity. The antibody derived from the VH3/lambda1 framework was engineered in order to match the closest human germline sequence: in VH by a V40A mutation, in VL by D1Q, I2S mutations and introduction of amino acids Y49 and G50 to repair the framework in which these 2 residues were initially missing.

This work resulted in Antibody 7 (=NOV0958=NOV0806_VH[V40A]_VL[D1Q, I2S, Y49, G50, N51Q]).

Antibodies 3, 5, 6 and 7 all show high specificity for human BMP6 protein compared to human BMP2, BMP5 or BMP7 protein. The epitope of all these antibodies is predicted to be the same as they are all derived from a single parental Fab before affinity maturation. Antibody 3, for example, shares the same Fab clone with both antibodies 5 and 7 before affinity maturation of HCDR2. Antibody 5 is derived from NOV0442 (VH3_3-15, VI1_1e)→NOV0442_VL(YGQ)→(HCDR2 affinity maturation)→Antibody 5. Antibody 3 is derived from NOV0442 (VH3_3-15, VI1_1e)→NOV0442_VL(YGS)→(HCDR2 affinity maturation)→Antibody 3. Additional details regarding the generation of the antibodies described herein are provided in the Examples.

The present invention provides antibodies that specifically bind BMP6 (e.g., human BMP6 protein), said antibodies comprising a VH domain listed in Table 1 and/or Table 14. The present invention also provides antibodies that specifically bind to BMP6 protein, said antibodies comprising a VH CDR having an amino acid sequence of any one of the VH CDRs listed in Table 1 and/or Table 14. In particular, the invention provides antibodies that specifically bind to BMP6 protein, said antibodies comprising (or alternatively, consisting of) one, two, three, four, five or more VH CDRs having an amino acid sequence of any of the VH CDRs listed in Table 1 and/or Table 14.

The invention also provides antibodies and antigen-binding fragments thereof that specifically bind to BMP6, said antibodies or antigen-binding fragments thereof comprising (or alternatively, consisting of) a amino acid sequence listed in Table 1 and/or Table 14, wherein no more than about 10 amino acids in a framework sequence (for example, a sequence which is not a CDR) have been mutated (wherein a mutation is, as various non-limiting examples, an addition, substitution or deletion). The invention also provides antibodies and antigen-binding fragments thereof that specifically bind to BMP6, said antibodies or antigen-binding fragments thereof comprising alternatively, consisting of) a VH amino acid sequence listed in Table 1 and/or Table 14, wherein no more than 10 amino acids in a framework sequence (for example, a sequence which is not a CDR) have been mutated (wherein a mutation is, as various non-limiting examples, an addition, substitution or deletion).

The invention also provides antibodies and antigen-binding fragments thereof that specifically bind to BMP6, said antibodies or antigen-binding fragments thereof comprising (or alternatively, consisting of) a VH amino acid sequence listed in Table 1 and/or Table 14, wherein no more than about 20 amino acids in a framework sequence (for example, a sequence which is not a CDR) have been mutated (wherein a mutation is, as various non-limiting examples, an addition, substitution or deletion). The invention also provides antibodies and antigen-binding fragments thereof that specifically bind to BMP6, said antibodies or antigen-binding fragments thereof comprising (or alternatively, consisting of) a VH amino acid sequence listed in Table 1 and/or Table 14, wherein no more than 20 amino acids in a framework sequence (for example, a sequence which is not a CDR) have been mutated (wherein a mutation is, as various non-limiting examples, an addition, substitution or deletion).

The invention also provides antibodies and antigen-binding fragments thereof that specifically bind to BMP6, said antibodies or antigen-binding fragments thereof comprising (or alternatively, consisting of) a VL amino acid sequence listed in Table 1 and/or Table 14, wherein no more than about 10 amino acids in a framework sequence (for example, a sequence which is not a CDR) have been mutated (wherein a mutation is, as various non-limiting examples, an addition, substitution or deletion). The invention also provides antibodies and antigen-binding fragments thereof that specifically bind to BMP6, said antibodies or antigen-binding fragments thereof comprising (or alternatively, consisting of) a VL amino acid sequence listed in Table 1 and/or Table 14, wherein no more than 10 amino acids in a framework sequence (for example, a sequence which is not a CDR)

have been mutated (wherein a mutation is, as various non-limiting examples, an addition, substitution or deletion).

The invention also provides antibodies and antigen-binding fragments thereof that specifically bind to BMP6, said antibodies or antigen-binding fragments thereof comprising (or alternatively, consisting of) a VL amino acid sequence listed in Table 1 and/or Table 14, wherein no more than about 20 amino acids in a framework sequence (for example, a sequence which is not a CDR) have been mutated (wherein a mutation is, as various non-limiting examples, an addition, substitution or deletion). The invention also provides antibodies and antigen-binding fragments thereof that specifically bind to BMP6, said antibodies or antigen-binding fragments thereof comprising (or alternatively, consisting of) a VL amino acid sequence listed in Table 1 and/or Table 14, wherein no more than 20 amino acids in a framework sequence (for example, a sequence which is not a CDR) have been mutated (wherein a mutation is, as various non-limiting examples, an addition, substitution or deletion).

The present invention provides antibodies and antigen-binding fragments thereof that specifically bind to BMP6 protein, said antibodies or antigen-binding fragments thereof comprising a VL domain listed in Table 1 and/or Table 14. The present invention also provides antibodies and antigen-binding fragments thereof that specifically bind to BMP6 protein, said antibodies or antigen-binding fragments thereof comprising a VL CDR having an amino acid sequence of any one of the VL CDRs listed in Table 1 and/or Table 14. In particular, the invention provides antibodies and antigen-binding fragments thereof that specifically bind to BMP6 protein, said antibodies or antigen-binding fragments thereof comprising (or alternatively, consisting of) one, two, three or more VL CDRs having an amino acid sequence of any of the VL CDRs listed in Table 1 and/or Table 14.

Other antibodies and antigen-binding fragments thereof of the invention include amino acids that have been mutated, yet have at least 60, 70, 80, 90 or 95 percent identity in the CDR regions with the CDR regions depicted in the sequences described in Table 1 and/or Table 14, In one embodiment, it includes mutant amino acid sequences wherein no more than 1, 2, 3, 4 or 5 amino acids have been mutated in the CDR regions when compared with the CDR regions depicted in the sequence described in Table 1 and/or Table 14.

The present invention also provides nucleic acid sequences that encode VH, VL, the full length heavy chain, and the full length light chain of the antibodies and antigen-binding fragments thereof that specifically bind to BMP6 protein. Such nucleic acid sequences can be optimized for expression in mammalian cells (for example. Table 1 shows example nucleic acid sequences for the heavy chain and light chain of Antibodies 3, 5, 6 and 7).

TABLE 1

Examples of BMP6 Antibodies of the Present Invention

| | | | SEQ ID NO: |
|---|---|---|---|
| ANTIBODY 3 | | | |
| Kabat | HCDR1 | SYVVH | 9 |
| Kabat | HCDR2 | RIKDHKQGYTTAYAASVKG | 10 |
| Kabat | HCDR3 | VERSKSGFDN | 11 |
| Chothia | HCDR1 | GFTFSSY | 12 |
| Chothia | HCDR2 | KDHKQGYT | 13 |
| Chothia | HCDR3 | VERSKSGFDN | 14 |
| | VH | QVQLVESGGGLVKPGGSLRLSCAASGFT FSSYVVHWVRQAPGKGLEWVGRIKDHK QGYTTAYAASVKGRFTISRDDSKNTLYL QMNSLKTEDTAVYYCARVERSKSGFDN WGQGTLVTVSS | 15 |
| | DNA VH | CAGGTGCAATTGGTGGAAAGCGGCGGT GGCCTGGTGAAACCAGGCGGCAGCCTG CGCCTGAGCTGCGCCGCCTCCGGATTC ACCTTTTCTTCTTACGTTGTTCATTGGG TGCGCCAGGCCCCGGGCAAAGGTCTCG AGTGGGTGGGCCGTATCAAAGACCACA AACAGGGCTACACTACTGCTTATGCCG CCTCTGTGAAAGGCCGCTTTACCATTAG CCGCGATGATTCGAAAAACACCCTGTA TCTGCAAATGAACAGCCTGAAAACCGA AGATACGGCCGTGTATTATTGCGCGCG TGTTGAACGTTCTAAATCTGGTTTCGAT AACTGGGGCCAAGGCACCCTGGTGACT GTTAGCTCA | 16 |
| | Heavy Chain | QVQLVESGGGLVKPGGSLRLSCAASGFT FSSYVVHWVRQAPGKGLEWVGRIKDHK QGYTTAYAASVKGRFTISRDDSKNTLYL QMNSLKTEDTAVYYCARVERSKSGFDN WGQGTLVTVSSASTKGPSVFPLAPSSKST SGGTAALGCLVKDYFPEPVTVSWNSGAL TSGVHTFPAVLQSSGLYSLSSVVTVPSSSL | 17 |

TABLE 1-continued

Examples of BMP6 Antibodies of the Present Invention

| | | | SEQ ID NO: |
|---|---|---|---|
| | | GTQTYICNVNHKPSNTKVDKRVEPKSCD KTHTCPPCPAPELLGGPSVFLFPPKPKDTL MISRTPEVTCVVVDVSHEDPEVKFNWYV DGVEVHNAKTKPREEQYNSTYRVVSVLT VLHQDWLNGKEYKCKVSNKALPAPIEKT ISKAKGQPREPQVYTLPPSREEMTKNQVS LTCLVKGFYPSDIAVEWESNGQPENNYK TTPPVLDSDGSFFLYSKLTVDKSRWQQG NVFSCSVMHEALHNHYTQKSLSLSPGK | |
| | DNA Heavy Chain | CAGGTGCAATTGGTGGAAAGCGGCGGT GGCCTGGTGAAACCAGGCGGCAGCCTG CGCCTGAGCTGCGCCGCCTCCGGATTC ACCTTTTCTTCTTACGTTGTTCATTGGG TGCGCCAGGCCCCGGGCAAAGGTCTCG AGTGGGTGGGCCGTATCAAAGACCACA AACAGGGCTACACTACTGCTTATGCCG CCTCTGTGAAAGGCCGCTTTACCATTAG CCGCGATGATTCGAAAAACACCCTGTA TCTGCAAATGAACAGCCTGAAAACCGA AGATACGGCCGTGTATTATTGCGCGCG TGTTGAACGTTCTAAATCTGGTTTCGAT AACTGGGGCCAAGGCACCCTGGTGACT GTTAGCTCAGCCTCCACCAAGGGTCCA TCGGTCTTCCCCCTGGCACCCTCCTCCA AGAGCACCTCTGGGGGCACAGCGGCCC TGGGCTGCCTGGTCAAGGACTACTTCC CCGAACCGGTGACGGTGTCGTGGAACT CAGGCGCCCTGACCAGCGGCGTGCACA CCTTCCCGGCTGTCCTACAGTCCTCAGG ACTCTACTCCCTCAGCAGCGTGGTGAC CGTGCCCTCCAGCAGCTTGGGCACCCA GACCTACATCTGCAACGTGAATCACAA GCCCAGCAACACCAAGGTGGACAAGA GAGTTGAGCCCAAATCTTGTGACAAAA CTCACACATGCCCACCGTGCCCAGCAC CTGAACTCCTGGGGGGACCGTCAGTCT TCCTCTTCCCCCCAAAACCCAAGGACA CCCTCATGATCTCCCGGACCCCTGAGGT CACATGCGTGGTGGTGGACGTGAGCCA CGAAGACCCTGAGGTCAAGTTCAACTG GTACGTGGACGGCGTGGAGGTGCATAA TGCCAAGACAAAGCCGCGGGAGGAGC AGTACAACAGCACGTACCGGGTGGTCA GCGTCCTCACCGTCCTGCACCAGGACT GGCTGAATGGCAAGGAGTACAAGTGCA AGGTCTCCAACAAAGCCCTCCCAGCCC CCATCGAGAAAACCATCTCCAAAGCCA AAGGGCAGCCCCGAGAACCACAGGTGT ACACCCTGCCCCCATCCCGGGAGGAGA TGACCAAGAACCAGGTCAGCCTGACCT GCCTGGTCAAAGGCTTCTATCCCAGCG ACATCGCCGTGGAGTGGGAGAGCAATG GGCAGCCGGAGAACAACTACAAGACC ACGCCTCCCGTGCTGGACTCCGACGGC TCCTTCTTCCTCTACAGCAAGCTCACCG TGGACAAGAGCAGGTGGCAGCAGGGG AACGTCTTCTCATGCTCCGTGATGCATG AGGCTCTGCACAACCACTACACGCAGA AGAGCCTCTCCCTGTCTCCGGGTAAA | 18 |
| Kabat | LCDR1 | TGSSSNIGAGYSVH | 19 |
| Kabat | LCDR2 | GSSERPS | 20 |
| Kabat | LCDR3 | QSWDSSQTLVV | 21 |
| Chothia | LCDR1 | SSSNIGAGYS | 22 |
| Chothia | LCDR2 | GSS | 23 |
| Chothia | LCDR3 | WDSSQTLV | 24 |
| | VL | QSVLTQPPSVSGAPGQRVTISCTGSSSNIG AGYSVHWYQQLPGTAPKLLIYGSSERPS | 25 |

TABLE 1-continued

Examples of BMP6 Antibodies of the Present Invention

| | | | SEQ ID NO: |
|---|---|---|---|
| | | GVPDRFSGSKSGTSASLAITGLQAEDEAD YYCQSWDSSQTLVVFGGGTKLTVL | |
| | DNA VL | CAGAGCGTGCTGACCCAGCCGCCGAGC GTGAGCGGTGCACCGGGCCAGCGCGTG ACCATTAGCTGTACCGGCAGCAGCAGC AACATTGGTGCTGGTTACTCTGTGCATT GGTACCAGCAGCTGCCGGGCACGGCGC CGAAACTGCTGATCTATGGTAGCTCTG AACGCCCGAGCGGCGTGCCGGATCGCT TTAGCGGATCCAAAAGCGGCACCAGCG CCAGCCTGGCGATTACCGGCCTGCAAG CAGAAGACGAAGCGGATTATTACTGCC AGTCTTGGGACTCTTCTCAGACTCTGGT TGTGTTTGGCGGCGGCACGAAGTTAAC CGTCCTA | 26 |
| | Light Chain | QSVLTQPPSVSGAPGQRVTISCTGSSSNIG AGYSVHWYQQLPGTAPKLLIYGSSERPS GVPDRFSGSKSGTSASLAITGLQAEDEAD YYCQSWDSSQTLVVFGGGTKLTVLGQPK AAPSVTLFPPSSEELQANKATLVCLISDFY PGAVTVAWKADSSPVKAGVETTTPSKQS NNKYAASSYLSLTPEQWKSHRSYSCQVT HEGSTVEKTVAPTECS | 27 |
| | DNA Light Chain | CAGAGCGTGCTGACCCAGCCGCCGAGC GTGAGCGGTGCACCGGGCCAGCGCGTG ACCATTAGCTGTACCGGCAGCAGCAGC AACATTGGTGCTGGTTACTCTGTGCATT GGTACCAGCAGCTGCCGGGCACGGCGC CGAAACTGCTGATCTATGGTAGCTCTG AACGCCCGAGCGGCGTGCCGGATCGCT TTAGCGGATCCAAAAGCGGCACCAGCG CCAGCCTGGCGATTACCGGCCTGCAAG CAGAAGACGAAGCGGATTATTACTGCC AGTCTTGGGACTCTTCTCAGACTCTGGT TGTGTTTGGCGGCGGCACGAAGTTAAC CGTCCTAGGTCAGCCCAAGGCTGCCCC CTCGGTCACTCTGTTCCCGCCCTCCTCT GAGGAGCTTCAAGCCAACAAGGCCACA CTGGTGTGTCTCATAAGTGACTTCTACC CGGGAGCCGTGACAGTGGCCTGGAAGG CAGATAGCAGCCCCGTCAAGGCGGGAG TGGAGACCACCACACCCTCCAAACAAA GCAACAACAAGTACGCGGCCAGCAGCT ATCTGAGCCTGACGCCTGAGCAGTGGA AGTCCCACAGAAGCTACAGCTGCCAGG TCACGCATGAAGGGAGCACCGTGGAGA AGACAGTGGCCCCTACAGAATGTTCA | 28 |

ANTIBODY 5

| | | | |
|---|---|---|---|
| Kabat | HCDR1 | SYVVH | 29 |
| Kabat | HCDR2 | RIKRESSSYTTMYAAPVKG | 30 |
| Kabat | HCDR3 | VERSKSGFDN | 31 |
| Chothia | HCDR1 | GFTFSSY | 32 |
| Chothia | HCDR2 | KRESSSYT | 33 |
| Chothia | HCDR3 | VERSKSGFDN | 34 |
| | VH | QVQLVESGGGLVKPGGSLRLSCAASGFT FSSYVVHWVRQAPGKGLEWVGRIKRESS SYTTMYAAPVKGRFTISRDDSKNTLYLQ MNSLKTEDTAVYYCARVERSKSGFDNW GQGTLVTVSS | 35 |
| | DNA VH | CAGGTGCAGCTGGTGGAATCAGGCGGC GGACTGGTCAAGCCTGGCGGTAGCCTG AGACTGAGCTGCGCTGCTAGTGGCTTC ACCTTCTCTAGCTACGTGGTGCACTGGG | 36 |

TABLE 1-continued

Examples of BMP6 Antibodies of the Present Invention

| | | SEQ ID NO: |
|---|---|---|
| | TCAGACAGGCCCCTGGTAAAGGCCTGG<br>AGTGGGTCGGACGGATTAAGAGAGAGT<br>CCTCTAGCTACACTACTATGTACGCCGC<br>TCCCGTGAAGGGCCGGTTCACTATCTCT<br>AGGGACGACTCTAAGAACACCCTGTAC<br>CTGCAGATGAATAGCCTGAAAACCGAG<br>GACACCGCCGTCTACTACTGCGCTAGA<br>GTGGAACGGTCTAAGTCAGGCTTCGAT<br>AACTGGGGTCAGGGCACCCTGGTCACC<br>GTGTCTAGC | |
| Heavy Chain | QVQLVESGGGLVKPGGSLRLSCAASGFT<br>FSSYVVHWVRQAPGKGLEWVGRIKRESS<br>SYTTMYAAPVKGRFTISRDDSKNTLYLQ<br>MNSLKTEDTAVYYCARVERSKSGFDNW<br>GQGTLVTVSSASTKGPSVFPLAPSSKSTS<br>GGTAALGCLVKDYFPEPVTVSWNSGALT<br>SGVHTFPAVLQSSGLYSLSSVVTVPSSSL<br>GTQTYICNVNHKPSNTKVDKRVEPKSCD<br>KTHTCPPCPAPELLGGPSVFLFPPKPKDTL<br>MISRTPEVTCVVVDVSHEDPEVKFNWYV<br>DGVEVHNAKTKPREEQYNSTYRVVSVLT<br>VLHQDWLNGKEYKCKVSNKALPAPIEKT<br>ISKAKGQPREPQVYTLPPSREEMTKNQVS<br>LTCLVKGFYPSDIAVEWESNGQPENNYK<br>TTPPVLDSDGSFFLYSKLTVDKSRWQQG<br>NVFSCSVMHEALHNHYTQKSLSLSPGK | 37 |
| DNA Heavy Chain | CAGGTGCAGCTGGTGGAATCAGGCGGC<br>GGACTGGTCAAGCCTGGCGGTAGCCTG<br>AGACTGAGCTGCGCTGCTAGTGGCTTC<br>ACCTTCTCTAGCTACGTGGTGCACTGGG<br>TCAGACAGGCCCCTGGTAAAGGCCTGG<br>AGTGGGTCGGACGGATTAAGAGAGAGT<br>CCTCTAGCTACACTACTATGTACGCCGC<br>TCCCGTGAAGGGCCGGTTCACTATCTCT<br>AGGGACGACTCTAAGAACACCCTGTAC<br>CTGCAGATGAATAGCCTGAAAACCGAG<br>GACACCGCCGTCTACTACTGCGCTAGA<br>GTGGAACGGTCTAAGTCAGGCTTCGAT<br>AACTGGGGTCAGGGCACCCTGGTCACC<br>GTGTCTAGCGCTAGCACTAAGGGCCCA<br>AGTGTGTTTCCCCTGGCCCCCAGCAGC<br>AAGTCTACTTCCGGCGGAACTGCTGCC<br>CTGGGTTGCCTGGTGAAGGACTACTTC<br>CCCGAGCCCGTGACAGTGTCCTGGAAC<br>TCTGGGGCTCTGACTTCCGGCGTGCAC<br>ACCTTCCCCGCCGTGCTGCAGAGCAGC<br>GGCCTGTACAGCCTGAGCAGCGTGGTG<br>ACAGTGCCCTCCAGCTCTCTGGGAACC<br>CAGACCTATATCTGCAACGTGAACCAC<br>AAGCCCAGCAACACCAAGGTGGACAA<br>GAGAGTGGAGCCCAAGAGCTGCGACA<br>AGACCCACACCTGCCCCCCCTGCCCAG<br>CTCCAGAACTGCTGGGAGGGCCTTCCG<br>TGTTCCTGTTCCCCCCAAGCCCAAGGA<br>CACCCTGATGATCAGCAGGACCCCCGA<br>GGTGACCTGCGTGGTGGTGGACGTGTC<br>CCACGAGGACCCAGAGGTGAAGTTCAA<br>CTGGTACGTGGACGGCGTGGAGGTGCA<br>CAACGCCAAGACCAAGCCCAGAGAGG<br>AGCAGTACAACAGCACCTACAGGGTGG<br>TGTCCGTGCTGACCGTGCTGCACCAGG<br>ACTGGCTGAACGGCAAAGAATACAAGT<br>GCAAAGTCTCCAACAAGGCCCTGCCAG<br>CCCCAATCGAAAAGACAATCAGCAAGG<br>CCAAGGGCCAGCCACGGGAGCCCCAGG<br>TGTACACCCTGCCCCCCAGCCGGGAGG<br>AGATGACCAAGAACCAGGTGTCCCTGA<br>CCTGTCTGGTGAAGGGCTTCTACCCCA<br>GCGATATCGCCGTGGAGTGGGAGAGCA<br>ACGGCCAGCCCGAGAACAACTACAAGA<br>CCACCCCCCCAGTGCTGGACAGCGACG<br>GCAGCTTCTTCCTGTACAGCAAGCTGA<br>CCGTGGACAAGTCCAGGTGGCAGCAGG | 38 |

TABLE 1-continued

Examples of BMP6 Antibodies of the Present Invention

| | | | SEQ ID NO: |
|---|---|---|---|
| | | GCAACGTGTTCAGCTGCAGCGTGATGC ACGAGGCCCTGCACAACCACTACACCC AGAAGTCCCTGAGCCTGAGCCCCGGCA AG | |
| Kabat | LCDR1 | TGSSSNIGAGYSVH | 39 |
| Kabat | LCDR2 | GQSERPS | 40 |
| Kabat | LCDR3 | QSWDSSQTLVV | 41 |
| Chothia | LCDR1 | SSSNIGAGYS | 42 |
| Chothia | LCDR2 | GQS | 43 |
| Chothia | LCDR3 | WDSSQTLV | 44 |
| | VL | QSVLTQPPSVSGAPGQRVTISCTGSSSNIG AGYSVHWYQQLPGTAPKLLIYGQSERPS GVPDRFSGSKSGTSASLAITGLQAEDEAD YYCQSWDSSQTLVVFGGGTKLTVL | 45 |
| | DNA VL | CAGTCAGTCCTGACTCAGCCCCCTAGC GTCAGCGGCGCTCCCGGTCAGAGAGTG ACTATTAGCTGCACCGGCTCTAGCTCTA ATATCGGCGCTGGCTATAGCGTGCACT GGTATCAGCAGCTGCCCGGCACCGCCC CTAAGCTGCTGATCTACGGTCAGTCAG AGCGGCCTAGCGGCGTGCCCGATAGGT TTAGCGGCTCTAAGTCAGGCACTAGCG CTAGTCTGGCTATCACCGGCCTGCAGG CTGAGGACGAGGCCGACTACTACTGTC AGTCCTGGGACTCTAGTCAGACCCTGG TGGTGTTCGGCGGAGGCACTAAGCTGA CCGTGCTG | 46 |
| | Light Chain | QSVLTQPPSVSGAPGQRVTISCTGSSSNIG AGYSVHWYQQLPGTAPKLLIYGQSERPS GVPDRFSGSKSGTSASLAITGLQAEDEAD YYCQSWDSSQTLVVFGGGTKLTVLGQPK AAPSVTLFPPSSEELQANKATLVCLISDFY PGAVTVAWKADSSPVKAGVETTTPSKQS NNKYAASSYLSLTPEQWKSHRSYSCQVT HEGSTVEKTVAPTECS | 47 |
| | DNA Light Chain | CAGTCAGTCCTGACTCAGCCCCCTAGC GTCAGCGGCGCTCCCGGTCAGAGAGTG ACTATTAGCTGCACCGGCTCTAGCTCTA ATATCGGCGCTGGCTATAGCGTGCACT GGTATCAGCAGCTGCCCGGCACCGCCC CTAAGCTGCTGATCTACGGTCAGTCAG AGCGGCCTAGCGGCGTGCCCGATAGGT TTAGCGGCTCTAAGTCAGGCACTAGCG CTAGTCTGGCTATCACCGGCCTGCAGG CTGAGGACGAGGCCGACTACTACTGTC AGTCCTGGGACTCTAGTCAGACCCTGG TGGTGTTCGGCGGAGGCACTAAGCTGA CCGTGCTGGGTCAGCCTAAGGCTGCCC CCAGCGTGACCCTGTTCCCCCCCAGCA GCGAGGAGCTGCAGGCCAACAAGGCC ACCCTGGTGTGCCTGATCAGCGACTTCT ACCCAGGCGCCGTGACCGTGGCCTGGA AGGCCGACAGCAGCCCCGTGAAGGCCG GCGTGGAGACCACCACCCCCAGCAAGC AGAGCAACAACAAGTACGCCGCCAGCA GCTACCTGAGCCTGACCCCCGAGCAGT GGAAGAGCCACAGGTCCTACAGCTGCC AGGTGACCCACGAGGGCAGCACCGTGG AAAAGACCGTGGCCCCAACCGAGTGCA GC | 48 |

TABLE 1-continued

Examples of BMP6 Antibodies of the Present Invention

| | | | SEQ ID NO: |
|---|---|---|---|
| | | ANTIBODY 6 | |
| Kabat | HCDR1 | SYVVH | 49 |
| Kabat | HCDR2 | RTRHSDMGYATSYAAPVKG | 50 |
| Kabat | HCDR3 | VERSKSGFDN | 51 |
| Chothia | HCDR1 | GFTFSSY | 52 |
| Chothia | HCDR2 | RHSDMGYA | 53 |
| Chothia | HCDR3 | VERSKSGFDN | 54 |
| | VH | QVQLVESGGGLVKPGGSLRLSCAASGFTFSSYVVHWVRQAPGKGLEWVGRTRHSDMGYATSYAAPVKGRFTISRDDSKNTLYLQMNSLKTEDTAVYYCARVERSKSGFDNWGQGTLVTVSS | 55 |
| | DNA VH | CAGGTGCAGCTGGTGGAATCAGGCGGCGGACTGGTCAAGCCTGGCGGTAGCCTGAGACTGAGCTGCGCTGCTAGTGGCTTCACCTTCTCTAGCTACGTGGTGCACTGGGTCAGACAGGCCCCTGGTAAAGGCCTGGAGTGGGTCGGACGGACTAGACACTCAGATATGGGCTACGCTACTAGCTACGCCGCTCCCGTGAAGGGCCGGTTCACTATCTCTAGGGACGACTCTAAGAACACCCTGTACCTGCAGATGAATAGCCTGAAAACCGAGGACACCGCCGTCTACTACTGCGCTAGAGTGGAACGGTCTAAGTCAGGCTTCGATAACTGGGGTCAGGGCACCCTGGTCACCGTGTCTAGC | 56 |
| | Heavy Chain | QVQLVESGGGLVKPGGSLRLSCAASGFTFSSYVVHWVRQAPGKGLEWVGRTRHSDMGYATSYAAPVKGRFTISRDDSKNTLYLQMNSLKTEDTAVYYCARVERSKSGFDNWGQGTLVTVSSASTKGPSVFPLAPSSKSTSGGTAALGCLVKDYFPEPVTVSWNSGALTSGVHTFPAVLQSSGLYSLSSVVTVPSSSLGTQTYICNVNHKPSNTKVDKRVEPKSCDKTHTCPPCPAPELLGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPAPIEKTISKAKGQPREPQVYTLPPSREEMTKNQVSLTCLVKGFYPSDIAVEWESNGQPENNYKTTPPVLDSDGSFFLYSKLTVDKSRWQQGNVFSCSVMHEALHNHYTQKSLSLSPGK | 57 |
| | DNA Heavy Chain | CAGGTGCAGCTGGTGGAATCAGGCGGCGGACTGGTCAAGCCTGGCGGTAGCCTGAGACTGAGCTGCGCTGCTAGTGGCTTCACCTTCTCTAGCTACGTGGTGCACTGGGTCAGACAGGCCCCTGGTAAAGGCCTGGAGTGGGTCGGACGGACTAGACACTCAGATATGGGCTACGCTACTAGCTACGCCGCTCCCGTGAAGGGCCGGTTCACTATCTCTAGGGACGACTCTAAGAACACCCTGTACCTGCAGATGAATAGCCTGAAAACCGAGGACACCGCCGTCTACTACTGCGCTAGAGTGGAACGGTCTAAGTCAGGCTTCGATAACTGGGGTCAGGGCACCCTGGTCACCGTGTCTAGCGCTAGCACTAAGGGCCCAAGTGTGTTTCCCCTGGCCCCAGCAGCAAGTCTACTTCCGGCGGAACTGCTGCCCTGGGTTGCTGGTGAAGGACTACTTCCCCGAGCCCGTGACAGTGTCCTGGAACTCTGGGGCTCTGACTTCCGGCGTGCACACCTTCCCCGCCGTGCTGCAGAGCAGCGGCCTGTACAGCCTGAGCAGCGTGGTGACAGTGCCCTCCAGCTCTCTGGGAACC | 58 |

TABLE 1-continued

Examples of BMP6 Antibodies of the Present Invention

| | | | SEQ ID NO: |
|---|---|---|---|
| | | CAGACCTATATCTGCAACGTGAACCAC AAGCCCAGCAACACCAAGGTGGACAA GAGAGTGGAGCCCAAGAGCTGCGACA AGACCCACACCTGCCCCCCTGCCCAG CTCCAGAACTGCTGGGAGGGCCTTCCG TGTTCCTGTTCCCCCCAAGCCCAAGGA CACCCTGATGATCAGCAGGACCCCCGA GGTGACCTGCGTGGTGGTGGACGTGTC CCACGAGGACCCAGAGGTGAAGTTCAA CTGGTACGTGGACGGCGTGGAGGTGCA CAACGCCAAGACCAAGCCCAGAGAGG AGCAGTACAACAGCACCTACAGGGTGG TGTCCGTGCTGACCGTGCTGCACCAGG ACTGGCTGAACGGCAAAGAATACAAGT GCAAAGTCTCCAACAAGGCCCTGCCAG CCCCAATCGAAAAGACAATCAGCAAGG CCAAGGGCCAGCCACGGGAGCCCCAGG TGTACACCCTGCCCCCAGCCGGGAGG AGATGACCAAGAACCAGGTGTCCCTGA CCTGTCTGGTGAAGGGCTTCTACCCCA GCGATATCGCCGTGGAGTGGGAGAGCA ACGGCCAGCCCGAGAACAACTACAAGA CCACCCCCCAGTGCTGGACAGCGACG GCAGCTTCTTCCTGTACAGCAAGCTGA CCGTGGACAAGTCCAGGTGGCAGCAGG GCAACGTGTTCAGCTGCAGCGTGATGC ACGAGGCCCTGCACAACCACTACACCC AGAAGTCCCTGAGCCTGAGCCCCGGCA AG | |
| Kabat | LCDR1 | TGSSSNIGAGYSVH | 59 |
| Kabat | LCDR2 | GQSERPS | 60 |
| Kabat | LCDR3 | QSWDSSQTLVV | 61 |
| Chothia | LCDRI | SSSNIGAGYS | 62 |
| Chothia | LCDR2 | GQS | 63 |
| Chothia | LCDR3 | WDSSQTLV | 64 |
| | VL | QSVLTQPPSVSGAPGQRVTISCTGSSSNIG AGYSVHWYQQLPGTAPKLLIYGQSERPS GVPDRFSGSKSGTSASLAITGLQAEDEAD YYCQSWDSSQTLVVFGGGTKLTVL | 65 |
| | DNA VL | CAGTCAGTCCTGACTCAGCCCCCTAGC GTCAGCGGCGCTCCCGGTCAGAGAGTG ACTATTAGCTGCACCGGCTCTAGCTCTA ATATCGGCGCTGGCTATAGCGTGCACT GGTATCAGCAGCTGCCCGGCACCGCCC CTAAGCTGCTGATCTACGGTCAGTCAG AGCGGCCTAGCGGCGTGCCCGATAGGT TTAGCGGCTCTAAGTCAGGCACTAGCG CTAGTCTGGCTATCACCGGCCTGCAGG CTGAGGACGAGGCCGACTACTACTGTC AGTCCTGGGACTCTAGTCAGACCCTGG TGGTGTTCGGCGGAGGCACTAAGCTGA CCGTGCTG | 66 |
| | Light Chain | QSVLTQPPSVSGAPGQRVITSCTGSSSNIG AGYSVHWYQQLPGTAPKLLIYGQSERPS GVPDRFSGSKSGTSASLAITGLQAEDEAD YYCQSWDSSQTLVVFGGGTKLTVLGQPK AAPSVTLFPPSSEELQANKATLVCLISDFY PGAVTVAWKADSSPVKAGVETTTPSKQS NNKYAASSYLSLTPEQWKSHRSYSCQVT HEGSTVEKTVAPTECS | 67 |
| | DNA Light Chain | CAGTCAGTCCTGACTCAGCCCCCTAGC GTCAGCGGCGCTCCCGGTCAGAGAGTG ACTATTAGCTGCACCGGCTCTAGCTCTA ATATCGGCGCTGGCTATAGCGTGCACT GGTATCAGCAGCTGCCCGGCACCGCCC | 68 |

TABLE 1-continued

Examples of BMP6 Antibodies of the Present Invention

| | | | SEQ ID NO: |
|---|---|---|---|
| | | CTAAGCTGCTGATCTACGGTCAGTCAG AGCGGCCTAGCGGCGTGCCCGATAGGT TTAGCGGCTCTAAGTCAGGCACTAGCG CTAGTCTGGCTATCACCGGCCTGCAGG CTGAGGACGAGGCCGACTACTACTGTC AGTCCTGGGACTCTAGTCAGACCCTGG TGGTGTTCGGCGGAGGCACTAAGCTGA CCGTGCTGGGTCAGCCTAAGGCTGCCC CCAGCGTGACCCTGTTCCCCCCCAGCA GCGAGGAGCTGCAGGCCAACAAGGCC ACCCTGGTGTGCCTGATCAGCGACTTCT ACCCAGGCGCCGTGACCGTGGCCTGGA AGGCCGACAGCAGCCCCGTGAAGGCCG GCGTGGAGACCACCACCCCCAGCAAGC AGAGCAACAACAAGTACGCCGCCAGCA GCTACCTGAGCCTGACCCCCGAGCAGT GGAAGAGCCACAGGTCCTACAGCTGCC AGGTGACCCACGAGGGCAGCACCGTGG AAAAGACCGTGGCCCCAACCGAGTGCA GC | |
| | ANTIBODY 7 | | |
| Kabat | HCDR1 | SYVVH | 69 |
| Kabat | HCDR2 | RIRLETHGYAAEYAASVKG | 70 |
| Kabat | HCDR3 | VERSKSGFDN | 71 |
| Chothia | HCDR1 | GFTFSSY | 72 |
| Chothia | HCDR2 | RLETHGYA | 73 |
| Chothia | HCDR3 | VERSKSGFDN | 74 |
| | VH | QVQLVESGGGLVKPGGSLRLSCAASGFT FSSYVVHWVRQAPGKGLEWVGRIRLETH GYAAEYAASVKGRFTISRDDSKNTLYLQ MNSLKTEDTAVYYCARVERSKSGFDNW GQGTLVTVSS | 75 |
| | DNA VH | CAGGTGCAGCTGGTGGAATCAGGCGGC GGACTGGTCAAGCCTGGCGGTAGCCTG AGACTGAGCTGCGCTGCTAGTGGTTC ACCTTCTCTAGCTACGTGGTGCACTGGG TCAGACAGGCCCCTGGTAAAGGCCTGG AGTGGGTCGGACGGATTAGACTGGAAA CTCACGGCTACGCCGCCGAGTACGCCG CTAGTGTGAAGGGCCGGTTCACTATCT CTAGGGACGACTCTAAGAACACCCTGT ACCTGCAGATGAATAGCCTGAAAACCG AGGACACCGCCGTCTACTACTGCGCTA GAGTGGAACGGTCTAAGTCAGGCTTCG ATAACTGGGGTCAGGGCACCCTGGTCA CCGTGTCTAGC | 76 |
| | Heavy Chain | QVQLVESGGGLVKPGGSLRLSCAASGFT FSSYVVHWVRQAPGKGLEWVGRIRLETH GYAAEYAASVKGRFTISRDDSKNTLYLQ MNSLKTEDTAVYYCARVERSKSGFDNW GQGTLVTVSSASTKGPSVFPLAPSSKSTS GGTAALGCLVKDYFPEPVTVSWNSGALT SGVHTFPAVLQSSGLYSLSSVVTVSSSL GTQTYICNVNHKPSNTKVDKRVEPKSCD KTHTCPPCPAPELLGGPSVFLFPPKPKDTL MISRTPEVTCVVVDVSHEDPEVKFNWYV DGVEVHNAKTKPREEQYNSTYRVVSVLT VLHQDWLNGKEYKCKVSNKALPAPIEKT ISKAKGQPREPQVYTLPPSREEMTKNQVS LTCLVKGFYPSDIAVEWESNGQPENNYK TTPPVLDSDGSFFLYSKLTVDKSRWQQG NVFSCSVMHEALHNHYTQKSLSLSPGK | 77 |

TABLE 1-continued

Examples of BMP6 Antibodies of the Present Invention

| | | | SEQ ID NO: |
|---|---|---|---|
| | DNA Heavy Chain | CAGGTGCAGCTGGTGGAATCAGGCGGC GGACTGGTCAAGCCTGGCGGTAGCCTG AGACTGAGCTGCGCTGCTAGTGGCTTC ACCTTCTCTAGCTACGTGGTGCACTGGG TCAGACAGGCCCCTGGTAAAGGCCTGG AGTGGGTCGGACGGATTAGACTGGAAA CTCACGGCTACGCCGCCGAGTACGCCG CTAGTGTGAAGGGCCGGTTCACTATCT CTAGGGACGACTCTAAGAACACCCTGT ACCTGCAGATGAATAGCCTGAAAACCG AGGACACCGCCGTCTACTACTGCGCTA GAGTGGAACGGTCTAAGTCAGGCTTCG ATAACTGGGGTCAGGGCACCCTGGTCA CCGTGTCTAGCGCTAGCACTAAGGGCC CAAGTGTGTTTCCCCTGGCCCCCAGCA GCAAGTCTACTTCCGGCGGAACTGCTG CCCTGGGTTGCCTGGTGAAGGACTACT TCCCCGAGCCCGTGACAGTGTCCTGGA ACTCTGGGGCTCTGACTTCCGGCGTGC ACACCTTCCCCGCCGTGCTGCAGAGCA GCGGCCTGTACAGCCTGAGCAGCGTGG TGACAGTGCCCTCCAGCTCTCTGGGAA CCCAGACCTATATCTGCAACGTGAACC ACAAGCCCAGCAACACCAAGGTGGACA AGAGAGTGGAGCCCAAGAGCTGCGAC AAGACCCACACCTGCCCCCCCTGCCCA GCTCCAGAACTGCTGGGAGGGCCTTCC GTGTTCCTGTTCCCCCCCAAGCCCAAGG ACACCCTGATGATCAGCAGGACCCCCG AGGTGACCTGCGTGGTGGTGGACGTGT CCCACGAGGACCCAGAGGTGAAGTTCA ACTGGTACGTGGACGGCGTGGAGGTGC ACAACGCCAAGACCAAGCCCAGAGAG GAGCAGTACAACAGCACCTACAGGGTG GTGTCCGTGCTGACCGTGCTGCACCAG GACTGGCTGAACGGCAAGAATACAAG TGCAAAGTCTCCAACAAGGCCCTGCCA GCCCCAATCGAAAAGACAATCAGCAAG GCCAAGGGCCAGCCACGGGAGCCCCAG GTGTACACCCTGCCCCCCAGCCGGGAG GAGATGACCAAGAACCAGGTGTCCCTG ACCTGTCTGGTGAAGGGCTTCTACCCC AGCGATATCGCCGTGGAGTGGGAGAGC AACGGCCAGCCCGAGAACAACTACAAG ACCACCCCCCCAGTGCTGGACAGCGAC GGCAGCTTCTTCCTGTACAGCAAGCTG ACCGTGGACAAGTCCAGGTGGCAGCAG GGCAACGTGTTCAGCTGCAGCGTGATG CACGAGGCCCTGCACAACCACTACACC CAGAAGTCCCTGAGCCTGAGCCCCGGC AAG | 78 |
| Kabat | LCDR1 | TGSSSNIGAGYSVH | 79 |
| Kabat | LCDR2 | GQSERPS | 80 |
| Kabat | LCDR3 | QSWDSSQTLVV | 81 |
| Chothia | LCDR1 | SSSNIGAGYS | 82 |
| Chothia | LCDR2 | GQS | 83 |
| Chothia | LCDR3 | WDSSQTLV | 84 |
| | VL | QSVLTQPPSVSGAPGQRVTISCTGSSSNIG AGYSVHWYQQLPGTAPKLLIYGQSERPS GVPDRFSGSKSGTSASLAITGLQAEDEAD YYCQSWDSSQTLVVFGGGTKLTVL | 85 |
| | DNA VL | CAGTCAGTCCTGACTCAGCCCCCTAGC GTCAGCGGCGCTCCCGGTCAGAGAGTG ACTATTAGCTGCACCGGCTCTAGCTCTA ATATCGGCGCTGGCTATAGCGTGCACT GGTATCAGCAGCTGCCCGGCACCGCCC | 86 |

TABLE 1-continued

Examples of BMP6 Antibodies of the Present Invention

| | | SEQ ID NO: |
|---|---|---|
| | CTAAGCTGCTGATCTACGGTCAGTCAG AGCGGCCTAGCGGCGTGCCCGATAGGT TTAGCGGCTCTAAGTCAGGCACTAGCG CTAGTCTGGCTATCACCGGCCTGCAGG CTGAGGACGAGGCCGACTACTACTGTC AGTCCTGGGACTCTAGTCAGACCCTGG TGGTGTTCGGCGGAGGCACTAAGCTGA CCGTGCTG | |
| Light Chain | QSVLTQPPSVSGAPGQRVTISCTGSSSNIG AGYSVHWYQQLPGTAPKLLIYGQSERPS GVPDRFSGSKSGTSASLAITGLQAEDEAD YYCQSWDSSQTLVVFGGGTKLTVLGQPK AAPSVTLFPPSSEELQANKATLVCLISDFY PGAVTVAWKADSSPVKAGVETTTPSKQS NNKYAASSYLSLTPEQWKSHRSYSCQVT HEGSTVEKTVAPTECS | 87 |
| DNA Light Chain | CAGTCAGTCCTGACTCAGCCCCCTAGC GTCAGCGGCGCTCCCGGTCAGAGAGTG ACTATTAGCTGCACCGGCTCTAGCTCTA ATATCGGCGCTGGCTATAGCGTGCACT GGTATCAGCAGCTGCCCGGCACCGCCC CTAAGCTGCTGATCTACGGTCAGTCAG AGCGGCCTAGCGGCGTGCCCGATAGGT TTAGCGGCTCTAAGTCAGGCACTAGCG CTAGTCTGGCTATCACCGGCCTGCAGG CTGAGGACGAGGCCGACTACTACTGTC AGTCCTGGGACTCTAGTCAGACCCTGG TGGTGTTCGGCGGAGGCACTAAGCTGA CCGTGCTGGGTCAGCCTAAGGCTGCCC CCAGCGTGACCCTGTTCCCCCCCAGCA GCGAGGAGCTGCAGGCCAACAAGGCC ACCCTGGTGTGCCTGATCAGCGACTTCT ACCCCAGGCGCCGTGACCGTGGCCTGGA AGGCCGACAGCAGCCCCGTGAAGGCCG GCGTGGAGACCACCACCCCCAGCAAGC AGAGCAACAACAAGTACGCCGCCAGCA GCTACCTGAGCCTGACCCCCGAGCAGT GGAAGAGCCACAGGTCCTACAGCTGCC AGGTGACCCACGAGGGCAGCACCGTGG AAAAGACCGTGGCCCCAACCGAGTGCA GC | 88 |

Other antibodies and antigen-binding fragments thereof of the invention include those wherein the amino acids or nucleic acids encoding the amino acids have been mutated, yet have at least 60, 70, 80, 90 or 95 percent identity to the sequences described in Table 1 and/or Table 14. In one embodiment, it include mutant amino acid sequences wherein no more than 1, 2, 3, 4 or 5 amino acids have been mutated in the variable regions when compared with the variable regions depicted in the sequence described in Table 1 and/or Table 14, while retaining substantially the same therapeutic activity.

In another specific embodiment, the present invention provides an isolated antibody or antigen-binding fragment thereof, which binds human BMP6 and comprises the HCDR1, HCDR2, and HCDR3 sequences of SEQ ID NOs: 9, 10 and 11, respectively, and the LCDR1, LCDR2, and LCDR3 sequences of SEQ ID NOs: 19, 20 and 21, respectively.

In another specific embodiment, the present invention provides an isolated antibody or antigen-binding fragment thereof, which binds human BMP6 and comprises the HCDR1, HCDR2, and HCDR3 sequences of SEQ ID NOs: 12, 13 and 14, respectively, and the LCDR1, LCDR2, and LCDR3 sequences of SEQ ID NOs: 22, 23 and 24, respectively.

In another specific embodiment, the present invention provides an isolated antibody or antigen-binding fragment thereof, which binds human BMP6 and comprises the HCDR1, HCDR2, and HCDR3 sequences of SEQ ID NOs: 29, 30 and 31, respectively, and the LCDR1, LCDR2, and LCDR3 sequences of SEQ ID NOs: 39, 40 and 41, respectively.

In another specific embodiment, the present invention provides an isolated antibody or antigen-binding fragment thereof, which binds human BMP6 and comprises the HCDR1, HCDR2, and HCDR3 sequences of SEQ ID NOs: 32, 33 and 34, respectively, and the LCDR1, LCDR2, and LCDR3 sequences of SEQ ID NOs: 42, 43 and 44, respectively.

In another specific embodiment, the present invention provides an isolated antibody or antigen-binding fragment thereof, which binds human BMP6 and comprises the HCDR1, HCDR2, and HCDR3 sequences of SEQ ID NOs: 49, 50 and 51, respectively, and the LCDR1, LCDR2, and LCDR3 sequences of SEQ ID NOs: 59, 60 and 61, respectively.

In another specific embodiment, the present invention provides an isolated antibody or antigen-binding fragment thereof, which binds human BMP6 and comprises the HCDR1, HCDR2, and HCDR3 sequences of SEQ ID NOs: 52, 53 and 54, respectively, and the LCDR1, LCDR2, and LCDR3 sequences of SEQ ID NOs: 62, 63 and 64, respectively.

In another specific embodiment, the present invention provides an isolated antibody or antigen-binding fragment thereof, which binds human BMP6 and comprises the HCDR1, HCDR2, and HCDR3 sequences of SEQ ID NOs: 69, 70 and 71, respectively, and the LCDR1, LCDR2, and LCDR3 sequences of SEQ ID NOs: 79, 80 and 81, respectively.

In another specific embodiment, the present invention provides an isolated antibody or antigen-binding fragment thereof, which binds human BMP6 and comprises the HCDR1, HCDR2, and HCDR3 sequences of SEQ NOs: 72, 73 and 74, respectively, and the LCDR1, LCDR2, and LCDR3 sequences of SEQ ID NOs: 82, 83 and 84, respectively.

Since each of these antibodies can bind to BMP6, the VH, VL, full length light chain, and full length heavy chain sequences (amino acid sequences and the nucleotide sequences encoding the amino acid sequences) can be "mixed and matched" to create other BMP6-binding antibodies and antigen-binding fragments thereof of the invention. Such "mixed and matched" BMP6-binding antibodies can be tested using the binding assays known in the art (e.g., ELISAs, and other assays described in the Example section). When these chains are mixed and matched, a VH sequence from a particular VH/VL pairing should be replaced with a structurally similar VH sequence. Likewise a full length heavy chain sequence from a particular full length heavy chain/full length light chain pairing should be replaced with a structurally similar full length heavy chain sequence. Likewise, a VL sequence from a particular VH/VL pairing should be replaced with a structurally similar VL sequence. Likewise a full length light chain sequence from a particular full length heavy chain/full length light chain pairing should be replaced with a structurally similar full length light chain sequence.

In another aspect, the present invention provides BMP6-binding antibodies that comprise the heavy chain and light chain CDR1s, CDR2s and CDR3s as described in Table 1 and/or Table 14, or combinations thereof. The CDR regions are delineated using the Kabat system (Kabat et al. 1991 Sequences of Proteins of Immunological Interest, Fifth Edition, U.S. Department of Health and Human Services, NIH Publication No. 91-3242), or using the Chothia system [Chothia et al. 1987 J. Mol. Biol. 196: 901-917; and Al-Lazikani et al. 1997 J. Mol. Biol. 273: 927-948].

Given that each of these antibodies can bind to BMP6 and that antigen-binding specificity is provided primarily by the CDR1, 2 and 3 regions, the VH CDR1, 2 and 3 sequences and VL CDR1, 2 and 3 sequences can be "mixed and matched" (i.e., CDRs from different antibodies can be mixed and match, although each antibody must contain a VH CDR1, 2 and 3 and a VL CDR1, 2 and 3 to create other BMP6-binding binding molecules of the invention, Such "mixed and matched" BMP6-binding antibodies can be tested using the binding assays known in the art and those described in the Examples (e.g., ELISAs). When VH CDR sequences are mixed and matched, the CDR1, CDR2 and/or CDR3 sequence from a particular VH sequence should be replaced with a structurally similar CDR sequence(s). Likewise, when VL CDR sequences are mixed and matched, the CDR1, CDR2 and/or CDR3 sequence from a particular VL sequence should be replaced with a structurally similar CDR sequence(s). It will be readily apparent to the ordinarily skilled artisan that novel VH and VL sequences can be created by mutating one or more VH and/or VL CDR region sequences with structurally similar sequences from the CDR sequences shown herein for monoclonal antibodies of the present invention.

Accordingly, the present invention provides an isolated monoclonal antibody or antigen binding region thereof comprising a heavy chain variable region CDR1 comprising an amino acid sequence selected from any of SEQ ID NOs: 29, 49, 69, 12, 32, 52, 72, or 9; a heavy chain variable region CDR2 comprising an amino acid sequence selected from any of SEQ ID NOs: 10, 30, 50, 70, 13, 33, 53, or 73; a heavy chain variable region CDR3 comprising an amino acid sequence selected from any of SEQ ID NOs: 11, 31, 51, 71, 14, 34, 54, or 74; a light chain variable region CDR1 comprising an amino acid sequence selected from any of SEQ ID NOs: 19, 39, 59, 79, 22, 42, 62, or 82; a light chain variable region CDR2 comprising an amino acid sequence selected from any of SEQ ID NOs: 20, 40, 60, 80, 23, 43, 63, or 83; and a light chain variable region CDR3 comprising an amino acid sequence selected from any of SEQ ID NOs: 21, 41, 61, 81, 24, 44, 64, or 84; wherein the antibody specifically binds BMP6.

In one embodiment, an antibody that specifically binds to BMP6 is an antibody that is described in Table 1 and/or Table 14.

As used herein, a human antibody comprises heavy or light chain variable regions or full length heavy or light chains that are the product of or "derived from" a particular germline sequence if the variable regions or full length chains of the antibody are obtained from a system that uses human germline immunoglobulin genes. Such systems include immunizing a transgenic mouse carrying human immunoglobulin genes with the antigen of interest or screening a human immunoglobulin gene library displayed on phage with the antigen of interest. A human antibody that is "the product of" or "derived from" a human germline immunoglobulin sequence can be identified as such by comparing the amino acid sequence of the human antibody to the amino acid sequences of human germline immunoglobulins and selecting the human germline immunoglobulin sequence that is closest in sequence (i.e., greatest % identity) to the sequence of the human antibody. A human antibody that is "the product of" or "derived from" a particular human germline immunoglobulin sequence may contain amino acid differences as compared to the germline sequence, due to, for example, naturally occurring somatic mutations or intentional introduction of site-directed mutations. However, in the VH or VL framework regions, a selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody may be at least 60%, 70%, 80%, 90%, or at least 95%, or even at least 96%, 97%, 98%, or 99% identical in amino acid sequence to the amino acid sequence encoded by the germline immunoglobulin gene. Typically, a recombinant human antibody will display no more than 10 amino acid differences from the amino acid sequence encoded by the human germline immunoglobulin gene in the VH or VL framework regions. In certain cases, the human antibody may display no more than 5, or even no more than 4, 3, 2, or 1 amino acid difference from the amino acid sequence encoded by the germline immunoglobulin gene.

BMP Family Members and Hepcidin

In one embodiment, the invention provides an antibody or binding fragment thereof that specifically binds to BMP6 is an antibody. In one embodiment, the antibody or binding fragment thereof is described in Table 1 and/or Table 14. In one embodiment, the antibody or binding fragment thereof specifically binds to BMP6 but not to other BMP proteins (such as BMP2, BMP5 or BMP7). BMP6, a secreted BMP family growth factor ligand, is a 30 kDa disulfide-linked homodimer in its mature active form. The protein is a member of the TGF-Beta superfamily. Bone morphogenetic proteins are known for their ability to induce the growth of bone and cartilage. BMP6 is able to induce all osteogenic markers in mesenchymal stem cells.

The bone morphogenetic proteins (BMPs) are a family of secreted signaling molecules that can induce ectopic bone growth. BMPs are part of the transforming growth factor-beta (TGF-Beta) superfamily. BMPs were originally identified by an ability of demineralized bone extract to induce endochondral osteogenesis in vivo in an extraskeletal site. Based on its expression early in embryogenesis, the BMP encoded by this gene has a proposed role in early development. In addition, the fact that this BMP is closely related to BMP5 and BMP7 has led to speculation of possible bone inductive activity. An additional function of BMP6 has been identified as described in Nature Genetics April; 41 [4]:386-8.

Mice with a knock-out of BMP6 are viable and fertile, and show normal bone and cartilage development.

BMP6 is the key regulator of hepcidin, the small peptide secreted by the liver which is the major regulator of iron metabolism in mammals. Hepcidin controls both the amount of dietary iron absorbed in the duodenum and iron released by reticuloendothelial cells. Hepcidin is upregulated by a variety of stimuli, including inflammation and iron overload, and downregulated by anemia, hypoxia, and iron deficiency.

Without being bound by any particular theory, this disclosure suggests that a BMP6 antagonist antibody as a hepcidin-lowering therapy is expected to benefit patients with iron-restricted anemia by overcoming resistance to Erythropoiesis Stimulating Agent (ESA), which adds substantially to the morbidity of an underlying disease and is often a predictor of adverse outcome. Through its interaction with BMPR1 and BMPR2 receptors, it induces receptors dimerization and transcription of hepcidin. BMP6 also binds to HJV co-receptor in liver and muscle cells.

Thus, BMP6 is known to increase expression of hepcidin. Hepcidin is known to be a key hormone involved in iron homeostasis. High hepcidin levels are associated with iron restricted erythropoiesis in ACD.

WO 2010/056981 disclosed that administration to mice of an antibody to BMP6 decreased hepcidin and increased iron.

BMP6 is further described in the art, e.g.: Hahn et al. 1992 Genomics 14: 759-62; Sauermann et al. 1993 J. Neurosci. Res. 33: 142; Celeste et al. 1991 Proc. Natl. Acad. Sci. USA 87: 9843; Schluesener et al. 1995 Atherosclerosis 113: 153; Gitelman et al. 1994 J. Cell Biol. 126: 1595; Barnes et al. 1997 W. J. Urol. 13: 337; and Hamdy et al. 1997 Cancer Res. 57: 4427.

BMP2, like other bone morphogenetic proteins, plays an important role in the development of bone and cartilage. It is involved in the hedgehog pathway, TGF-Beta signaling pathway, and in cytokine-cytokine receptor interaction. It is also involved in cardiac cell differentiation and epithelial to mesenchymal transition. BMP2 has many essential roles, as noted by Kishimoto et al. 1997 Dev. 124: 4457; Ma et al. 2005 Dev. 132: 5601; Wang et al. Bone 48: 524; and Rosen 2009 Cyt. Growth Fact. Rev. 20: 475. It is thus preferable for a BMP6 antibody to not bind to BMP2.

BMP2 is further described in, inter alia: Sampath et al. 1990 J. Biol. Chem. 265: 13198; Chen et al. 2004 Growth Factors 22: 233; Marie et al. 2002 Histol. Histopath. 17: 877; Nickel et al. 2001 J. Bone Joint Surg. 83-A Supp. 1: S7-14; Kirsch et al. 2000 FEBS Lett. 468: 215; Kirsch et al. 2000 EMBO J. 19: 3314; Gilboa et al. 2000 Mol. Biol. Cell 11: 1023.

BMP5 is also a member of the TGF-Beta superfamily. Like other BMPs, it is known for its ability to induce bone and cartilage development. BMP5 is expressed in the trabecular meshwork and optic nerve head and may have a role in development and normal function. It is also expressed in lung and liver.

Additional information on BMP5 is known in the art, e.g., Hahn et al, 1992 Genomics 14: 759; Beck et al. 2003 BMC Neurosci. 2: 12; Celeste et al. 1991 Proc. Natl. Acad. Sci. USA 87: 9843; and Sakaue et al. 1996 Biochem. Biophys. Res. Comm. 221: 768.

BMP7 is also a member of the TGF-Beta superfamily. Like other members of the BMP family of proteins, it plays a key role in the transformation of mesenchymal cells into bone and cartilage. It induces the phosphorylation of SMAD1 and SMAD5, which in turn induce transcription of numerous osteogenic genes.

As noted above, mice with a knock-out of BMP6 are viable and fertile, and show normal bone and cartilage development. However, knock-out mice for BMP7 die after birth with kidney, eye and bone defects. Individual knock-outs of either gene do not alter cardiogenesis, but a double knock-out of BMP6 and BMP7 demonstrated several defects and delays in the heart; embryos died to cardiac insufficiency. BMP7 is important in preventing progression of chronic heart disease associated with fibrosis, Therefore, cross-reactivity of an anti-BMP6 antibody with BMP7 is not desirable.

Additional information related to BMP7 is provided in the art, e.g., Hahn et al. 1992 Genomics 14: 759; Chen et al. 2004 Growth Factors 22: 233; Itoh et al. 2001 EMBO J. 20: 4132; Zeisberg et al. 2003 Am. J. Physiol. Renal Physiol. 285: F1060; Kallui et al. 2009 J. Clin. Invest. 119: 1420; and Wang et al. 2001 J. Am. Soc. Neph. 12: 2392.

Hepcidin is a peptide hormone also known as RAMP (Hepcidin anti-microbial protein or peptide).

A recent gene duplication event in mouse evolution has led to the presence of two similar hepcidin genes in mice, Hepcidin1 and Hepcidin2. Ilyin et al. 2003 FEBS Lett. 542: 22-26. Mouse hepcidin2 lacks several conserved residues found in mammalian hepcidins. Lou et al. 2004 Blood 103: 2816-2821.

The Hepcidin gene product is involved in the maintenance of iron homeostasis, and it is necessary for the regulation of iron storage in macrophages, and for intestinal iron absorption. These peptides exhibit antimicrobial activity.

The preproprotein (or preprohormone or preprohepcidin) (84 aa) and proprotein (or prohormone or prohepcidin) (60 aa) are processed into mature peptides of 20, 22 and 25 amino acids. The 25-aa peptide is secreted mainly by the liver and is considered the "master regulator" of iron metabolism. The 20- and 22-aa metabolites exist in the urine. The N-terminal region of Hepcidin is required for function; deletion of the 5 N-terminal amino acids results in loss of function.

The active Hepcidin peptides are rich in cysteines, which form intramolecular bonds that stabilize their beta sheet structures.

Hepcidin is mainly synthesized in the liver, with smaller amounts found to be synthesized in other tissues. Bekri et al, 2006 Gastroent. 131: 788-96.

The 25-aa Hepcidin peptide is secreted mainly by the liver and is considered the "master regulator" of iron metabolism. Hepcidin inhibits iron transport by binding to the iron export channel ferroportin, which is located on the basolateral surface of gut enterocytes and the plasma membrane of reticuloendothelial cells (macrophages). By inhibiting ferroportin, hepcidin prevents enterocytes of the intestines from secreting iron into the hepatic portal system, thereby functionally reducing iron absorption. The iron release from macrophages is also prevented by ferroportin inhibition; therefore, the hepcidin maintains iron homeostasis. Hepcidin activity is also partially responsible for iron sequestration seen in anemia of chronic inflammation such as inflammatory bowel disease, chronic heart failure, carcinomas, rheumatoid arthritis and renal failure.

Mutations in the hepcidin gene cause hemochromatosis type 2B, also known as juvenile hemochromatosis, a disease caused by severe iron overload that results in cardiomyopathy, cirrhosis, and endocrine failure. The majority of juvenile hemochromatosis cases are due to mutations in hemojuvelin, a regulator of hepcidin production.

Genetically modified mice engineered to overexpress hepcidin die shortly after birth with severe iron deficiency, suggesting a central and not redundant role in iron regulation. The first evidence that linked hepcidin to anemia of inflammation came when researchers examined tissues from two patients with liver tumors with a severe microcytic, anemia that did not respond to iron supplements. The tumor tissue overproduced hepcidin, and removing the tumors surgically cured the anemia.

There are many diseases wherein failure to adequately absorb iron contributes to iron deficiency and iron deficiency anemia. The treatment will depend on the hepcidin levels, as oral treatment will likely be ineffective if hepcidin is blocking enteral absorption.

In one embodiment, administration of the antibody or binding fragment thereof to BMP6 reduces the activity and/or level of Hepcidin and is thus useful in a treatment for anemia. In one embodiment, the invention pertains to a method of reducing the activity or level of Hepcidin in a patient in need thereof, the method comprising the step of administering to the patient an antibody or antigen-binding fragment thereof to BMP6. In one embodiment, the activity or level of Hepcidin is reduced by at least 50%.

Inhibitors to Hepcidin, such as BMP6 antibodies, can be used to treat a Hepcidin-related disease. This includes any disease associated with Hepcidin and/or a mutation and/or an over-expression of a wild-type and/or mutant Hepcidin, and/or diseases wherein disease progression is enhanced by or prognosis worsened by the presence of Hepcidin and/or a mutation and/or an over-expression of wild-type and/or mutant Hepcidin, and/or reduced renal elimination of hepcidin via the urine. Non-limiting examples of Hepcidin-related diseases include: anemia, iron-deficient erythropoiesis, hypoferremia, impaired dietary iron uptake, iron sequestration, anemia of inflammation (AI), atherosclerosis, diabetes, and multiple neurodegenerative disorders such as Alzheimer's disease, Parkinson's disease and Friedrich's ataxia, heart failure, chronic kidney disease, cardiorenal-anemia syndrome, infection, blood loss, hemolysis, vitamin B12 or folate deficiency, hyperparathyroidism, hemoglobinopathies and malignancies, cancer, AIDS, surgery, stunted growth, and/or hair loss. In one embodiment, the subject is a dialysis patient. In one embodiment, the Hepcidin-related disease is anemia and the subject is a dialysis patient. The prevalence of iron and ESA-refractory anemia is high in chronic hemodialysis population.

Anemia includes, inter alia, anemia of chronic disease (ACD), anemia of chronic kidney disease (CKD), anemia of cancer, erythropoiesis stimulating agent (ESA) resistant anemia, and/or iron-restricted anemia.

Anemia of CKD is a common and early complication of chronic kidney disease. Anemia of cancer is caused by hematological malignancies and some solid tumors. As defined herein, this term also includes chemotherapy-induced anemia, which is anemia caused by chemotherapeutic agents. Anemia in chronic kidney diseases can worsen diabetic neuropathy, cardiovascular disease, retinopathy and other problems. Cancer-related anemia is associated with increased risk of death.

Some chronic diseases such as cancer, kidney disease and autoimmune disorders can lead to anemia. Overactive inflammatory cytokines can cause dysregulation of iron homeostasis, reduction of erythropoiesis, and a decrease in the life span of red blood cells. Some treatments for anemia include administration of an ESA, erythropoietin, iron (as a dietary supplement) or a blood transfusion.

Hepcidin is a key hormone involved in iron homeostasis. High levels of hepcidin have been associated with iron restricted erythropoiesis in ACD. BMP6 is known to increase expression of hepcidin.

Various types of antibodies and antigen-binding fragments thereof to BMP6 are described below.

Homologous Antibodies

In yet another embodiment, the present invention provides an antibody or an antigen-binding fragment thereof comprising amino acid sequences that are homologous to the sequences described in Table 1 and/or Table 14, and said antibody binds to BMP6, and retains the desired functional properties of those antibodies described in Table 1 and/or Table 14.

For example, the invention provides an isolated monoclonal antibody (or a functional antigen-binding fragment thereof) comprising a heavy chain variable region and a light chain variable region, wherein the heavy chain variable region comprises an amino acid sequence that is at least 80%, at least 90%, or at least 95% identical to an amino acid sequence selected from the group consisting of SEQ NOs: 16; 36; 56; or 76; the light chain variable region comprises an amino acid sequence that is at least 80%, at least 90%, or at least 95% identical to an amino acid sequence selected from the group consisting of SEQ ID NOs: 26; 46; 66; or 86; the antibody specifically binds to BMP6 protein, and the antibody can inhibit red blood cell lysis in a hemolytic assay, wherein a hemolytic assay is known in the art. In a specific example, such antibodies have an $IC_{50}$ value in a hemolytic assay of 20-200 pM when using human BMP6-depleted serum that is reconstituted with 100 pM human BMP6.

In one embodiment, the VH and/or VL amino acid sequences may be 50%, 60%, 70%, 80%, 90%, 95%, 96%, 97%, 98% or 99% identical to the sequences set forth in Table 1 and/or Table 14. In one embodiment, the VH and/or VL amino acid sequences may be identical except an amino acid substitution in no more than 1, 2, 3, 4 or 5 amino acid position. An antibody having VH and VL regions having high (i.e., 80% or greater) identity to the VH and VL regions of those described in Table 1 and/or Table 14 can be obtained by mutagenesis (e.g., site-directed or PCR-mediated mutagenesis) of nucleic acid molecules encoding SEQ ID NOs: 16; 36; 56; or 76; and 26; 46; 66; or 86 respectively, followed by testing of the encoded altered antibody for retained function using the functional assays described herein.

In one embodiment, the full length heavy chain and/or full length light chain amino acid sequences may be 50% 60%, 70%. 80%, 90%, 95%, 96%, 97%, 98% or 99% identical to the sequences set forth in Table 1 and/or Table 14. An antibody having a full length heavy chain and full length light chain having high (i.e., 80% or greater) identity to the full length heavy chains of any of SEQ ID NOs: 18; 38; 58; or 78 and full length light chains of any of SEQ ID NOs: 28; 48; 68 or 88 respectively, can be obtained by mutagenesis (e.g., site-directed or PCR-mediated mutagenesis) of nucleic acid molecules encoding such polypeptides respectively, followed by testing of the encoded altered antibody for retained function using the functional assays described herein.

In one embodiment, the full length heavy chain and/or full length light chain nucleotide sequences may be 60%, 70%, 80%, 90%, 95%, 96%, 97%, 98% or 99% identical to the sequences set forth in Table 1 and/or Table 14.

In one embodiment, the variable regions of heavy chain and/or light chain nucleotide sequences may be 60%, 70%, 80%, 90%, 95%, 96%, 97%, 98% or 99% identical to the sequences set forth in Table 1 and/or Table 14.

As used herein, the percent identity between the two sequences is a function of the number of identical positions shared by the sequences (i.e., % identity equals number of identical positions/total number of positions X 100), taking into account the number of gaps, and the length of each gap, which need to be introduced for optimal alignment of the two sequences. The comparison of sequences and determination of percent identity between two sequences can be accomplished using a mathematical algorithm, as described in the non-limiting examples below. Additionally or alternatively, the protein sequences of the present invention can further be used as a "query sequence" to perform a search against public databases to, for example, identify related sequences. For example, such searches can be performed using the BLAST program (version 2.0) of Altschul, et al., 1990 J. Mol. Biol. 215:403-10.

Antibodies with Conservative Modifications

In one embodiment, an antibody of the invention has a heavy chain variable region comprising CDR1, CDR2, and CDR3 sequences and a light chain variable region comprising CDR1, CDR2, and CDR3 sequences, wherein one or more of these CDR sequences have specified amino acid sequences based on the antibodies described herein or conservative modifications thereof, and wherein the antibodies retain the desired functional properties of the BMP6-binding antibodies and antigen-binding fragments thereof of the invention. Accordingly, the invention provides an isolated monoclonal antibody, or a functional antigen-binding fragment thereof, consisting of a heavy chain variable region comprising CDR1, CDR2, and CDR3 sequences and a light chain variable region comprising CDR1, CDR2, and CDR3 sequences, wherein: a heavy chain variable region CDR1 comprising an amino acid sequence selected from any of SEQ ID NOs: 29, 49, 69, 12, 32, 52, 72, or 9 or conservative variants thereof; a heavy chain variable region CDR2 comprising an amino acid sequence selected from any of SEQ ID NOs: 10, 30, 50, 70, 13, 33, 53, or 73 or conservative variants thereof; a heavy chain variable region CDR3 comprising an amino acid sequence selected from any of SEQ ID NOs: 11, 31, 51, 71, 14, 34, 54, or 74 or conservative variants thereof a light chain variable region CDR1 comprising an amino acid sequence selected from any of SEQ ID NOs: 19, 39, 59, 79, 22, 42, 62, or 82 or conservative variants thereof; a light chain variable region CDR2 comprising an amino acid sequence selected from any of SEQ ID NOs: 20, 40, 60, 80, 23, 43, 63, or 83 or conservative variants thereof; and a light chain variable region CDR3 comprising an amino acid sequence selected from any of SEQ ID NOs: 21, 41, 61, 81, 24, 44, 64, or 84 or conservative variants thereof; the antibody or the antigen-binding fragment thereof specifically binds to BMP6, and inhibits red blood cell lysis in a hemolytic assay.

In one embodiment, an antibody of the invention optimized for expression in a mammalian cell has a full length heavy chain sequence and a full length light chain sequence, wherein one or more of these sequences have specified amino acid sequences based on the antibodies described herein or conservative modifications thereof, and wherein the antibodies retain the desired functional properties of the BMP6-binding antibodies and antigen-binding fragments thereof of the invention. Accordingly, the invention provides an isolated monoclonal antibody optimized for expression in a mammalian cell consisting of a full length heavy chain and a full length light chain wherein: the full length heavy chain has amino acid sequences selected from the group of SEQ ID NOs: 18; 38; 58; or 78, and conservative modifications thereof; and the full length light chain has amino acid sequences selected from the group of SEQ ID NOs: 28; 48; 68 or 88, and conservative modifications thereof the antibody specifically binds to BMP6; and the antibody inhibits red blood cell lysis in a hemolytic assay as described herein. In a specific embodiment, such antibodies have an $IC_{50}$ value in a hemolytic assay of 20-200 pM when using human BMP6-depleted serum that is reconstituted with 100 pM human BMP6.

Antibodies that Bind to the Same Epitope

The present invention provides antibodies that bind to the same epitope as do the BMP6-binding antibodies listed in Table 1 and/or Table 14. The epitope bound by Antibody 7 is shown in FIG. 5. Additional antibodies can therefore be identified based on their ability to cross-compete (e.g., to competitively inhibit the binding of, in a statistically significant manner with other antibodies and antigen-binding fragments thereof of the invention in BMP6 binding assays. The ability of a test antibody to inhibit the binding of antibodies and antigen-binding fragments thereof of the present invention to BMP6 protein demonstrates that the test antibody can compete with that antibody for binding to BMP6; such an antibody may, according to non-limiting theory, bind to the same or a related (e.g., a structurally similar or spatially proximal) epitope on the BMP6 as the antibody with which it competes. In a certain embodiment, the antibody that binds to the same epitope on BMP6 as the antibodies and antigen-binding fragments thereof of the present invention is a human monoclonal antibody. Such human monoclonal antibodies can be prepared and isolated as described herein.

Once a desired epitope on an antigen is determined, it is possible to generate antibodies to that epitope, e.g., using the techniques described in the present invention. Alternatively, during the discovery process, the generation and characterization of antibodies may elucidate information about desirable epitopes. From this information, it is then possible to competitively screen antibodies for binding to the same epitope. An approach to achieve this is to conduct cross-competition studies to find antibodies that competitively bind with one another, e.g., the antibodies compete for binding to the antigen. A high throughput process tier "binning" antibodies based upon their cross-competition is described in International Patent Application No. WO 2003/48731. As will be appreciated by one of skill in the art, practically anything to which an antibody can specifically bind could be an epitope. An epitope can comprises those residues to which the antibody binds.

Generally, antibodies specific for a particular target antigen will preferentially recognize an epitope on the target antigen in a complex mixture of proteins and/or macromolecules.

Regions of a given polypeptide that include an epitope can be identified using any number of epitope mapping techniques, well known in the art. See, e.g., Epitope Mapping Protocols in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al., (1984) Proc. Natl. Acad. Sci. USA 8:3998-4002; Geysen et al., (1985) Proc. Natl. Acad. Sci. USA 82:78-182; Geysen et al., (1986) Mol. Immunol. 23:709-715. Similarly, conformational epitopes are readily identified by determining spatial conformation of amino acids BMP6 such as by, e.g., hydrogen/deuterium exchange, x-ray crystallography and two-dimensional nuclear magnetic resonance. See, e.g., Epitope Mapping Protocols, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., (1981) Proc. Natl. Acad. Sci USA 78:3824-3828; for determining antigenicity profiles, and the Kyte-Doolittle technique, Kyte et al., (1982) J. Mol. Biol. 157:105-132; for hydropathy plots.

Engineered and Modified Antibodies

An antibody of the invention further can be prepared using an antibody having one or more of the VH and/or VL sequences shown herein as starting material to engineer a modified antibody, which modified antibody may have altered properties from the starting antibody. An antibody can be engineered by modifying one or more residues within one or both variable regions (i.e., VH and/or VL), for example within one or more CDR regions and/or within one or more framework regions. Additionally or alternatively, an antibody can be engineered by modifying residues within the constant region(s), for example to alter the effector function(s) of the antibody.

One type of variable region engineering that can be performed is CDR grafting. Antibodies interact with target antigens predominantly through amino acid residues that are located in the six heavy and light chain complementarity determining regions (CDRs). For this reason, the amino acid sequences within CDRs are more diverse between individual antibodies than sequences outside of CDRs. Because CDR sequences are responsible for most antibody-antigen interactions, it is possible to express recombinant antibodies that mimic the properties of specific naturally occurring antibodies by constructing expression vectors that include CDR sequences from the specific naturally occurring antibody grafted onto framework sequences from a different antibody with different properties (see, Riechmann, L. et al., 1998 Nature 332:323-327; Jones, P. et al., 1986 Nature 321:522-525; Queen, C. et al., 1989 Proc. Natl. Acad., U.S.A. 86:10029-10033; U.S. Pat. No. 5,225,539 to Winter, and U.S. Pat. Nos. 5,530,101; 5,585,089; 5,693,762 and 6,180,370 to Queen et al.) Such framework sequences can be obtained from public DNA databases or published references that include germline antibody gene sequences. For example, germline DNA sequences for human heavy and light chain variable region genes can be found in the "VBase" human germline sequence database (available on the Internet at mrc-cpe.cam.ac.uk/vbase), as well as in Kabat, E. A., et al., 1991 Sequences of Proteins of Immunological Interest, Fifth Edition, U.S. Department of Health and Human Services, NIH Publication No. 91-3242; Tomlinson, I. M., et al., 1992 J. fol. Biol. 227:776-798; and Cox, J. P. L. et al., 1994 Eur. J Immunol. 24:827-836; the contents of each of which are expressly incorporated herein by reference.

An example of framework sequences for use in the antibodies and antigen-binding fragments thereof of the invention are those that are structurally similar to the framework sequences used by selected antibodies and antigen-binding fragments thereof of the invention, e.g., consensus sequences and/or framework sequences used by monoclonal antibodies of the invention. The VH CDR1, 2 and 3 sequences, and the VL CDR1, 2 and 3 sequences, can be grafted onto framework regions that have the identical sequence as that found in the germline immunoglobulin gene from which the framework sequence derive, or the CDR sequences can be grafted onto framework regions that contain one or more mutations as compared to the germline sequences. For example, it has been found that in certain instances it is beneficial to mutate residues within the framework regions to maintain or enhance the antigen binding ability of the antibody (see e.g., U.S. Pat. Nos. 5,530,101; 5,585,089; 5,693,762 and 6,180,370 to Queen et al).

Another type of variable region modification is to mutate amino acid residues within the VH and/or VL CDR1, CDR2 and/or CDR3 regions to thereby improve one or more binding properties (e.g., affinity) of the antibody of interest, known as "affinity maturation." Site-directed mutagenesis or PCR-mediated mutagenesis can be performed to introduce the mutation(s) and the effect on antibody binding, or other functional property of interest, can be evaluated in in vitro or in vivo assays as described herein and provided in the Examples. Conservative modifications (as discussed above) can be introduced. The mutations may be amino acid substitutions, additions or deletions. Moreover, typically no more than one, two, three, four or five residues within a CDR region are altered.

Grafting Antigen-Binding Domains into Alternative Frameworks or Scaffolds

A wide variety of antibody/immunoglobulin frameworks or scaffolds can be employed so long as the resulting polypeptide includes at least one binding region which specifically binds to BMP6. Such frameworks or scaffolds include the 5 main idiotypes of human immunoglobulins, antigen-binding fragments thereof, and include immunoglobulins of other animal species, preferably having humanized aspects. Single heavy-chain antibodies such as those identified in camelids are of particular interest in this regard. Novel frameworks, scaffolds and fragments continue to be discovered and developed by those skilled in the art.

In one aspect, the invention pertains to a method of generating non-immunoglobulin based antibodies using non-immunoglobulin scaffolds onto which CDRs of the invention can be grafted. Known or future non-immunoglobulin frameworks and scaffolds may be employed, as long as they comprise a binding region specific for the target BMP6 protein. Known non-immunoglobulin frameworks or scaffolds include, but are not limited to, fibronectin (Compound Therapeutics, Inc., Waltham, Mass.), ankyrin (Molecular Partners AG, Zurich, Switzerland), domain antibodies (Domantis, Ltd., Cambridge, Mass., and Ablynx nv, Zwijnaarde, Belgium), lipocalin (Pieris Proteolab AG, Freising, Germany), small modular immuno-pharmaceuticals (Trubion Pharmaceuticals Inc., Seattle, Wash.), maxybodies (Avidia, Inc., Mountain View, Calif.), Protein A (Affibody AG, Sweden), and affilin (gamma-crystallin or ubiquitin) (SciI. Proteins GmbH, Halle, Germany).

The fibronectin scaffolds are based on fibronectin type III domain (e.g., the tenth module of the fibronectin type III (10 Fn3 domain)). The fibronectin type III domain has 7 or 8 beta strands which are distributed between two beta sheets, which themselves pack against each other to form the core of the protein, and further containing loops (analogous to CDRs) which connect the beta strands to each other and are solvent exposed. There are at least three such loops at each edge of the beta sheet sandwich, where the edge is the boundary of the protein perpendicular to the direction of the beta strands (see U.S. Pat. No. 6,818,418). These fibronectin-based scaffolds are not an immunoglobulin, although the overall fold is closely related to that of the smallest functional antibody fragment, the variable region of the heavy chain, which comprises the entire antigen recognition unit in camel and llama IgG. Because of this structure, the non-immunoglobulin antibody mimics antigen binding properties that are similar in nature and affinity for those of antibodies. These scaffolds can be used in a loop randomization and shuffling strategy in vitro that is similar to the process of affinity maturation of antibodies in vivo. These fibronectin-based molecules can be used as scaffolds where the loop regions of the molecule can be replaced with CDRs of the invention using standard cloning techniques.

The ankyrin technology is based on using proteins with ankyrin derived repeat modules as scaffolds for bearing variable regions which can be used for binding to different targets. The ankyrin repeat module is a 33 amino acid polypeptide consisting of two anti-parallel alpha-helices and a beta-turn. Binding of the variable regions is mostly optimized by using ribosome display.

Avimers are derived from natural A-domain containing protein such as LRP-1. These domains are used by nature for protein-protein interactions and in human over 250 proteins are structurally based on A-domains. Avimers consist of a number of different "A-domain" monomers (2-10) linked via amino acid linkers. Avimers can be created that can bind to the target antigen using the methodology described in, for example, U.S. Patent Application Publication Nos. 20040175756; 20050053973; 20050048512; and 20060008844.

Affibody affinity ligands are small, simple proteins composed of a three-helix bundle based on the scaffold of one of the IgG-binding domains of Protein A. Protein A is a surface protein from the bacterium *Staphylococcus aureus*. This scaffold domain consists of 58 amino acids, 13 of which are randomized to generate affibody libraries with a large number of ligand variants (See e.g., U.S. Pat. No. 5,831,012). Affibody molecules mimic antibodies, they have a molecular weight of 6 kDa, compared to the molecular weight of antibodies, which is 150 kDa. In spite of its small size, the binding site of affibody molecules is similar to that of an antibody.

Anticalins are products developed by the company Pieris ProteoLab AG. They are derived from lipocalins, a widespread group of small and robust proteins that are usually involved in the physiological transport or storage of chemically sensitive or insoluble compounds. Several natural lipocalins occur in human tissues or body liquids. The protein architecture is reminiscent of immunoglobulins, with hypervariable loops on top of a rigid framework. However, in contrast with antibodies or their recombinant fragments, lipocalins are composed of a single polypeptide chain with 160 to 180 amino acid residues, being just marginally bigger than a single immunoglobulin domain. The set of four loops, which makes up the binding pocket, shows pronounced structural plasticity and tolerates a variety of side chains. The binding site can thus be reshaped in a proprietary process in order to recognize prescribed target molecules of different shape with high affinity and specificity. One protein of lipocalin family, the bilin-binding protein (BBP) of Pieris Brassicae has been used to develop anticalins by mutagenizing the set of four loops. One example of a patent application describing anticalins is in PCT Publication No. WO 199916873.

Affilin molecules are small non-immunoglobulin proteins which are designed for specific affinities towards proteins and small molecules. New affilin molecules can be very quickly selected from two libraries, each of which is based on a different human derived scaffold protein. Affilin molecules do not show any structural homology to immunoglobulin proteins. Currently, two affilin scaffolds are employed, one of which is gamma crystalline, a human structural eye lens protein and the other is "ubiquitin" superfamily proteins. Both human scaffolds are very small, show high temperature stability and are almost resistant to pH changes and denaturing agents. This high stability is mainly due to the expanded beta sheet structure of the proteins. Examples of gamma crystalline derived proteins are described in WO200104144 and examples of "ubiquitin-like" proteins are described in WO2004106368. Protein epitope mimetics (PEM) are medium-sized, cyclic, peptide-like molecules (MW 1-2 kDa) mimicking beta-hairpin secondary structures of proteins, the major secondary structure involved in protein-protein interactions.

The human BMP6-binding antibodies can be generated using methods that are known in the art. For example, the humaneering technology used to converting non-human antibodies into engineered human antibodies. U.S. Patent Publication No. 20050008625 describes an in vivo method for replacing a nonhuman antibody variable region with a human variable region in an antibody while maintaining the same or providing better binding characteristics relative to that of the nonhuman antibody. The method relies on epitope guided replacement of variable regions of a non-human reference antibody with a fully human antibody. The resulting human antibody is generally unrelated structurally to the reference nonhuman antibody, but binds to the same epitope on the same antigen as the reference antibody. Briefly, the serial epitope-guided complementarity replacement approach is enabled by setting up a competition in cells between a "competitor" and a library of diverse hybrids of the reference antibody ("lest antibodies") for binding to limiting amounts of antigen in the presence of a reporter system which responds to the binding of test antibody to antigen. The competitor can be the reference antibody or derivative thereof such as a single-chain Fv fragment. The competitor can also be a natural or artificial ligand of the antigen which binds to the same epitope as the reference antibody. The only requirements of the competitor are that it binds to the same epitope as the reference antibody, and that it competes with the reference antibody for antigen binding. The test antibodies have one antigen-binding V-region in common from the nonhuman reference antibody, and the other V-region selected at random from a diverse source such as a repertoire library of human antibodies. The common V-region from the reference antibody serves as a guide, positioning the test antibodies on the same epitope on the antigen, and in the same orientation, so that selection is biased toward the highest antigen-binding fidelity to the reference antibody.

Many types of reporter system can be used to detect desired interactions between test antibodies and antigen. For example, complementing reporter fragments may be linked to antigen and test antibody, respectively, so that reporter activation by fragment complementation only occurs when the test antibody binds to the antigen. When the test antibody- and antigen-reporter fragment fusions are co-expressed with a competitor, reporter activation becomes dependent on the ability of the test antibody to compete with the competitor, which is proportional to the affinity of the test antibody for the antigen. Other reporter systems that can be used include the reactivator of an auto-inhibited reporter reactivation system (RAIR) as disclosed in U.S. patent application Ser. No. 10/208,730 (Publication No. 20030198971), or competitive activation system disclosed in U.S. patent application Ser. No. 10/076,845 (Publication No, 20030157579).

With the serial epitope-guided complementarity replacement system, selection is made to identify cells expresses a single test antibody along with the competitor, antigen, and reporter components. In these cells, each test antibody competes one-on-one with the competitor for binding to a limiting amount of antigen. Activity of the reporter is proportional to the amount of antigen bound to the test antibody, which in turn is proportional to the affinity of the test antibody for the antigen and the stability of the test antibody. Test antibodies are initially selected on the basis of their activity relative to that of the reference antibody when expressed as the test antibody. The result of the first round of selection is a set of "hybrid" antibodies, each of which is comprised of the same non-human V-region from the reference antibody and a human V-region from the library, and each of which binds to the same epitope on the antigen as the reference antibody. One of more of the hybrid antibodies selected in the first round will have an affinity for the antigen comparable to or higher than that of the reference antibody.

In the second V-region replacement step, the human V-regions selected in the first step are used as guide for the selection of human replacements for the remaining non-human reference antibody V-region with a diverse library of cognate human V-regions. The hybrid antibodies selected in the first round may also be used as competitors for the second round of selection. The result of the second round of selection is a set of fully human antibodies which differ structurally from the reference antibody, but which compete with the reference antibody for binding to the same antigen. Some of the selected human antibodies bind to the same epitope on the same antigen as the reference antibody. Among these selected human antibodies, one or more binds to the same epitope with an affinity which is comparable to or higher than that of the reference antibody.

Using one of the mouse or chimeric BMP6-binding antibodies described above as the reference antibody, this method can be readily employed to generate human antibodies that bind to human BMP6 with the same binding specificity and the same or better binding affinity. In addition, such human BMP6-binding antibodies can also be commercially obtained from companies which customarily produce human antibodies, e.g., KaloBios, Inc. (Mountain View, Calif.).

Camelid Antibodies

Antibody proteins obtained from members of the camel and dromedary (*Camelus bactrianus* and *Calelus dromaderius*) family including new world members such as llama species (*Lama paccos, Lama glama* and *Lama vicugna*) have been characterized with respect to size, structural complexity and antigenicity for human subjects. Certain IgG antibodies from this family of mammals as found in nature lack light chains, and are thus structurally distinct from the typical four chain quaternary structure having two heavy and two light chains, for antibodies from other animals. See PCT/EP93/02214 (WO 94/04678 published 3 Mar. 1994).

A region of the camelid antibody which is the small single variable domain identified as VHH can be obtained by genetic engineering to yield a small protein having high affinity for a target, resulting in a low molecular weight antibody-derived protein known as a "camelid nanobody". See U.S. Pat. No. 5,759,808 issued Jun. 2, 1998; see also Stijlemans, B. et al., 2004 J Biol Chem 279: 1256-1261; Dumoulin, M. et al., 2003 Nature 424: 783-788; Pleschherger, M. et al. 2003 Bioconjugate Chem. 14: 440-448; Cortez-Retamozo, V. et al. 2002 Int J Cancer 89: 456-62; and Lauwereys, M. et al. 1998 EMBO J 17: 3512-3520. Engineered libraries of camelid antibodies and antibody fragments are commercially available, for example, from Ablynx, Ghent, Belgium. As with other antibodies and antigen-binding fragments thereof of non-human origin, an amino acid sequence of a camelid antibody can be altered recombinantly to obtain a sequence that more closely resembles a human sequence, i.e., the nanobody can be "humanized". Thus the natural low antigenicity of camelid antibodies to humans can be further reduced.

The camelid nanobody has a molecular weight approximately one-tenth that of a human IgG molecule, and the protein has a physical diameter of only a few nanometers. One consequence of the small size is the ability of camelid nanobodies to bind to antigenic sites that are functionally invisible to larger antibody proteins, i.e., camelid nanobodies are useful as reagents detect antigens that are otherwise cryptic using classical immunological techniques, and as possible therapeutic agents. Thus yet another consequence of small size is that a camelid nanobody can inhibit as a result of binding to a specific site in a groove or narrow cleft of a target protein, and hence can serve in a capacity that more closely resembles the function of a classical low molecular weight drug than that of a classical antibody.

The low molecular weight and compact size further result in camelid nanobodies being extremely thermostable, stable to extreme pH and to proteolytic digestion, and poorly antigenic. Another consequence is that camelid nanobodies readily move from the circulatory system into tissues, and even cross the blood-brain barrier and can treat disorders that affect nervous tissue. Nanobodies can further facilitated drug transport across the blood brain barrier. See U.S. patent application 20040161738 published Aug. 19, 2004. These features combined with the low antigenicity to humans indicate great therapeutic potential. Further, these molecules can be fully expressed in prokaryotic cells such as *E. coli* and are expressed as fusion proteins with bacteriophage and are functional.

Accordingly, a feature of the present invention is a camelid antibody or nanobody having high affinity for BMP6. In one embodiment herein, the camelid antibody or nanobody is naturally produced in the camelid animal, is produced by the camelid following immunization with BMP6 or a peptide fragment thereof, using techniques described herein for other antibodies. Alternatively, the BMP6-binding camelid nanobody is engineered, i.e., produced by selection for example from a library of phage displaying appropriately mutagenized camelid nanobody proteins using panning procedures with BMP6 as a target as described in the examples herein. Engineered nanobodies can further be customized by genetic engineering to have a half life in a recipient subject of from 45 minutes to two weeks. In a specific embodiment, the camelid antibody or nanobody is obtained by grafting the CDRs sequences of the heavy or light chain of the human antibodies of the invention into nanobody or single domain antibody framework sequences, as described for example in PCT/EP93/02214.

Bispecific Molecules and Multivalent Antibodies

In another aspect, the present invention features bispecific or multispecific molecules comprising an BMP6-binding antibody, or a fragment thereof, of the invention. An antibody of the invention, or antigen-binding regions thereof, can be derivatized or linked to another functional molecule, e.g., another peptide or protein (e.g., another antibody or ligand for a receptor) to generate a bispecific molecule that binds to at least two different binding sites or target molecules. The antibody of the invention may in fact be derivatized or linked to more than one other functional molecule to generate multi-specific molecules that bind to more than two different binding sites and/or target molecules; such multi-specific molecules are also intended to be encompassed by the term "bispecific molecule" as used herein. To create a bispecific molecule of the invention, an antibody of the invention can be functionally linked (e.g., by chemical coupling, genetic fusion, noncovalent association or otherwise) to one or more other binding molecules, such as another antibody, antibody fragment, peptide or binding mimetic, such that a bispecific molecule results.

Accordingly, the present invention includes bispecific molecules comprising at least one first binding specificity for BMP6 and a second binding specificity for a second target epitope. For example, the second target epitope is another epitope of BMP6 different from the first target epitope.

Additionally, for the invention in which the bispecific molecule is multi-specific, the molecule can further include a third binding specificity, in addition to the first and second target epitope.

In one embodiment, the bispecific molecules of the invention comprise as a binding specificity at least one antibody, or an antibody fragment thereof, including, e.g., an Fab, Fab', F(ab')2, Fv, or a single chain Fv. The antibody may also be a light chain or heavy chain dimer, or any minimal fragment thereof such as a Fv or a single chain construct as described in Ladner et al. U.S. Pat. No. 4,946,778.

Diabodies are bivalent, bispecific molecules in which VH and VL domains are expressed on a single polypeptide chain, connected by a linker that is too short to allow for pairing between the two domains on the same chain. The VH and VL domains pair with complementary domains of another chain, thereby creating two antigen binding sites (see e.g., Holliger et al., 1993 Proc. Natl. Acad. Sci. USA 90:6444-6448; Poijak et al., 1994 Structure 2:1121-1123). Diabodies can be produced by expressing two polypeptide chains with either the structure VHA-VLB and VHB-VLA (VH-VL configuration), or VLA-VHB and VLB-VHA (VL-VH configuration) within the same cell. Most of them can be expressed in soluble form in bacteria. Single chain diabodies (scDb) are produced by connecting the two diabody-forming polypeptide chains with linker of approximately 15 amino acid residues (see Holliger and Winter, 1997 Cancer Immunol. Immunother., 45 (3-4):128-30; Wu et al., 1996 Immunotechnology, 2 (1):21-36). scDb can be expressed in bacteria in soluble, active monomeric form (see Holliger and Winter, 1997 Cancer Immunol. Immunother., 45 (34): 128-30; Wu et al., 1996 Immunotechnology, 2 (1):21-36; Pluckthun and Pack, 1997 Immunotechnology, 3 (2): 83-105; Ridgway et al., 1996 Protein Eng., 9 (7):617-21). A diabody can be fused to Fc to generate a "di-diabody" (see Lu et al., 2004 J. Biol. Chem., 279 (4):2856-65).

Other antibodies which can be employed in the bispecific molecules of the invention are murine, chimeric and humanized monoclonal antibodies.

The bispecific molecules of the present invention can be prepared by conjugating the constituent binding specificities, using methods known in the art. For example, each binding specificity of the bispecific molecule can be generated separately and then conjugated to one another. When the binding specificities are proteins or peptides, a variety of coupling or cross-linking agents can be used for covalent conjugation. Examples of cross-linking agents include protein A, carbodiimide, N-succinimidyl-5-acetyl-thioacetate (SATA), 5,5'-dithiobis (2-nitrobenzoic acid) (DTNB), o-phenylenedimaleimide (oPDM), N-succinimidyl-3-(2-pyridyldithio)propionate (SPDP), and sulfosuccinimidyl 4-(N-maleimidomethyl)cyclohexane-1-carboxylate (sulfo-SMCC) (see e.g., Karpovsky et al., 1984 J. Exp. Med. 160:1686; Liu, M A et al., 1985 Proc. Natl. Acad. Sci. USA 82:8648). Other methods include those described in Paulus, 1985 Behring Ins. Mitt. No. 78, 118-132; Brennan et al., 1985 Science 229:81-83), and Glennie et al., 1987 J. Immunol. 139: 2367-2375). Conjugating agents are SATA and sulfo-SMCC, both available from Pierce Chemical Co. (Rockford, Ill.).

When the binding specificities are antibodies, they can be conjugated by sulfhydryl bonding of the C-terminus hinge regions of the two heavy chains. In a particularly embodiment, the hinge region is modified to contain an odd number of sulfhydryl residues, for example one, prior to conjugation.

Alternatively, both binding specificities can be encoded in the same vector and expressed and assembled in the same host cell. This method is particularly useful where the bispecific molecule is a mAb X mAb, mAb X Fab, Fab X F(ab')2 or ligand X Fab fusion protein. A bispecific molecule of the invention can be a single chain molecule comprising one single chain antibody and a binding determinant, or a single chain bispecific molecule comprising two binding determinants. Bispecific molecules may comprise at least two single chain molecules. Methods for preparing bispecific molecules are described for example in U.S. Pat. Nos. 5,260,203; 5,455,030; 4,881,175; 5,132,405; 5,091,513; 5,476,786; 5,013,653; 5,258,498; and 5,482,858.

Binding of the bispecific molecules to their specific targets can be confirmed by, for example, enzyme-linked immunosorbent assay (ELISA), radioimmunoassay (REA), FACS analysis, bioassay (e.g., growth inhibition), or Western Blot assay. Each of these assays generally detects the presence of protein-antibody complexes of particular interest by employing a labeled reagent (e.g., an antibody) specific for the complex of interest.

In another aspect, the present invention provides multivalent compounds comprising at least two identical or different antigen-binding portions of the antibodies and antigen-binding fragments thereof of the invention binding to BMP6. The antigen-binding portions can be linked together via protein fusion or covalent or non covalent linkage. Alternatively, methods of linkage has been described for the bispecific molecules. Tetravalent compounds can be obtained for example by cross-linking antibodies and antigen-binding fragments thereof of the invention with an antibody or antigen-binding fragment that binds to the constant regions of the antibodies and antigen-binding fragments thereof of the invention, for example the Fc or hinge region.

Trimerizing domain are described for example in Borean patent EP 1 012 280B1. Pentamerizing modules are described for example in PCT/EP97/05897.

Antibodies with Extended Half Life

The present invention provides for antibodies that specifically bind to BMP6 which have an extended half-life in vivo.

Many factors may affect a protein's half life in vivo. For examples, kidney filtration, metabolism in the liver, degradation by proteolytic enzymes (proteases), and immunogenic responses (e.g., protein neutralization by antibodies and uptake by macrophages and dentritic cells). A variety of strategies can be used to extend the half life of the antibodies and antigen-binding fragments thereof of the present invention. For example, by chemical linkage to polyethyleneglycol (PEG), reCODE PEG, antibody scaffold, polysialic acid (PSA), hydroxyethyl starch (HES), albumin-binding ligands, and carbohydrate shields; by genetic fusion to proteins binding to serum proteins, such as albumin, IgG, FcRn, and transferring; by coupling (genetically or chemically) to other binding moieties that bind to serum proteins, such as nanobodies, Fabs, DARPins, avimers, affibodies, and anticalins; by genetic fusion to rPEG, albumin, domain of albumin, albumin-binding proteins, and Fc; or by incorporation into nancarriers, slow release formulations, or medical devices.

To prolong the serum circulation of antibodies in vivo, inert polymer molecules such as high molecular weight PEG can be attached to the antibodies or a fragment thereof with or without a multifunctional linker either through site-specific conjugation of the PEG to the N- or C-terminus of the antibodies or via epsilon-amino groups present on lysine residues. To pegylate an antibody, the antibody, antigen-binding fragment thereof, typically is reacted with polyethylene glycol (PEG), such as a reactive ester or aldehyde derivative of PEG, under conditions in which one or more PEG groups become attached to the antibody or antibody fragment. The pegylation can be carried out by an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10)alkoxy- or aryloxy-polyethylene glycol or polyethylene glycol-maleimide. In one embodiment, the antibody to be pegylated is an aglycosylated antibody. Linear or branched polymer derivatization that results in minimal loss of biological activity will be used. The degree of conjugation can be closely monitored by SDS-PAGE and mass spectrometry to ensure proper conjugation of PEG molecules to the antibodies. Unreacted PEG can be separated from antibody-PEG conjugates by size-exclusion or by ion-exchange chromatography. PEG-derivatized antibodies can be tested for binding activity as well as for in vivo efficacy using methods well-known to those of skill in the art, for example, by immunoassays described herein. Methods for pegylating proteins are known in the art and can be applied to the antibodies and antigen-binding fragments thereof of the invention. See for example, EP 0 154 316 by Nishimura et al. and EP 0 401 384 by Ishikawa et al.

Other modified pegylation technologies include reconstituting chemically orthogonal directed engineering technology (ReCODE PEG), which incorporates chemically specified side chains into biosynthetic proteins via a reconstituted system that includes tRNA synthetase and tRNA. This technology enables incorporation of more than 30 new amino acids into biosynthetic proteins in E. coli, yeast, and mammalian cells. The tRNA incorporates a normative amino acid any place an amber codon is positioned, converting the amber from a stop codon to one that signals incorporation of the chemically specified amino acid.

Recombinant pegylation technology (rPEG) can also be used for serum halflife extension. This technology involves genetically fusing a 300-600 amino acid unstructured protein tail to an existing pharmaceutical protein. Because the apparent molecular weight of such an unstructured protein chain is about 15-fold larger than its actual molecular weight, the serum halflife of the protein is greatly increased. In contrast to traditional PEGylation, which requires chemical conjugation and repurification, the manufacturing process is greatly simplified and the product is homogeneous.

Polysialytion is another technology, which uses the natural polymer polysialic acid (PSA) to prolong the active life and improve the stability of therapeutic peptides and proteins. PSA is a polymer of sialic acid (a sugar). When used for protein and therapeutic peptide drug delivery, polysialic acid provides a protective microenvironment on conjugation. This increases the active life of the therapeutic protein in the circulation and prevents it from being recognized by the immune system. The PSA polymer is naturally found in the human body. It was adopted by certain bacteria which evolved over millions of years to coat their walls with it. These naturally polysialylated bacteria were then able, by virtue of molecular mimicry, to foil the body's defense system. PSA, nature's ultimate stealth technology, can be easily produced from such bacteria in large quantities and with predetermined physical characteristics. Bacterial PSA is completely non-immunogenic, even when coupled to proteins, as it is chemically identical to PSA in the human body.

Another technology include the use of hydroxyethyl starch ("HES") derivatives linked to antibodies. HES is a modified natural polymer derived from waxy maize starch and can be metabolized by the body's enzymes. HES solutions are usually administered to substitute deficient blood volume and to improve the rheological properties of the blood. Hesylation of an antibody enables the prolongation of the circulation half-life by increasing the stability of the molecule, as well as by reducing renal clearance, resulting in an increased biological activity. By varying different parameters, such as the molecular weight of HES, a wide range of HES antibody conjugates can be customized.

Antibodies having an increased half-life in vivo can also be generated introducing one or more amino acid modifications (i.e., substitutions, insertions or deletions) into an IgG constant domain, or FcRn binding fragment thereof (preferably a Fc or hinge Fc domain fragment). See, e.g., International Publication No. WO 98/23289; International Publication No. WO 97/34631; and U.S. Pat. No. 6,277,375. Further, antibodies can be conjugated to albumin in order to make the antibody or antibody fragment more stable in vivo or have a longer half life in vivo. The techniques are well-known in the art, see, e.g., International Publication Nos. WO 93/15199, WO 93/15200, and WO 01/77137; and European Patent No. EP 413,622.

The strategies for increasing half life is especially useful in nanobodies, fibronectin-based binders, and other antibodies or proteins for which increased in vivo half life is desired.

Antibody Conjugates

The present invention provides antibodies or antigen-binding fragments thereof that specifically bind to BMP6 recombinantly fused or chemically conjugated (including both covalent and non-covalent conjugations) to a heterologous protein or polypeptide (or antigen-binding fragment thereof, preferably to a polypeptide of at least 10, at least 20, at least 30, at least 40, at least 50, at least 60, at least 70, at least 80, at least 90 or at least 100 amino acids) to generate fusion proteins. In particular, the invention provides fusion proteins comprising an antigen-binding fragment of an antibody described herein (e.g., a Fab fragment, Fd fragment, Fv fragment, F(ab)$_2$ fragment, a VH domain, a VH CDR, a VL domain or a VL CDR) and a heterologous protein, polypeptide, or peptide. Methods for fusing or conjugating proteins, polypeptides, or peptides to an antibody or an antibody fragment are known in the art. See, e.g., U.S. Pat. Nos. 5,336,603, 5,622,929, 5,359,046, 5,349,053, 5,447,851, and 5,112,946; European Patent Nos. EP 307,434 and EP 367, 166; International Publication Nos. WO 96/04388 and WO 91/06570; Ashkenazi et al., 1991, Proc. Natl. Acad. Sci. USA 88: 10535-10539; Zheng et al., 1995, J. Immunol. 154:5590-5600; and Vil et al., 1992, Proc. Natl. Acad. Sci. USA 89:11337-11341.

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of antibodies and antigen-binding fragments thereof of the invention (e.g., antibodies and antigen-binding fragments thereof with higher affinities and lower dissociation rates). See, generally, U.S. Pat. Nos. 5,605,793, 5,811, 238, 5,830,721, 5,834,252, and 5,837,458; Patten et al., 1997, Curr. Opinion Biotechnol. 8:724-33; Harayama, 1998, Trends Biotechnol. 16 (2):76-82; Hansson, et al., 1999, J. Mol. Biol. 287:265-76; and Lorenzo and Blasco, 1998, Biotechniques 24 (2):308-313 (each of these patents and publications are hereby incorporated by reference in its entirety). Antibodies and antigen-binding fragments thereof, or the encoded antibodies and antigen-binding fragments thereof, may be altered by being subjected to random mutagenesis by error-prone PCR, random nucleotide insertion or other methods prior to recombination. A polynucleotide encoding an antibody antigen-binding fragment thereof that specifically binds to BMP6 may be recombined with one or more components, motifs, sections, parts, domains, fragments, etc. of one or more heterologous molecules.

Moreover, the antibodies and antigen-binding fragments thereof can be fused to marker sequences, such as a peptide to facilitate purification. In one embodiment, the marker amino acid sequence is a hexa-histidine peptide (SEQ ID NO: 97), such as the tag provided in a pQE vector (QIAGEN, Inc., 9259 Eton Avenue, Chatsworth, Calif., 91311), among others, many of which are commercially available. As described in Gentz et al., 1989, Proc. Natl. Acad. Sci. USA 86:821-824, for instance, hexa-histidine (SEQ ID NO: 97) provides for convenient purification of the fusion protein. Other peptide tags useful for purification include, but are not limited to, the hemagglutinin ("HA") tag, which corresponds to an epitope derived from the influenza hemagglutinin protein (Wilson et al., 1984, Cell 37:767), and the "flag" tag.

In one embodiment, antibodies and antigen-binding fragments thereof of the present invention antigen-binding fragments thereof conjugated to a diagnostic or detectable agent. Such antibodies can be useful for monitoring or prognosing the onset, development, progression and/or severity of a disease or disorder as part of a clinical testing procedure, such as determining the efficacy of a particular therapy. Such diagnosis and detection can accomplished by coupling the antibody to detectable substances including, but not limited to, various enzymes, such as, but not limited to, horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliferone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as, but not limited to, iodine (131I, 125I, 123I, and 121I), carbon (14C), sulfur (35S), tritium (3H), indium (115In, 113In, 112In, and 111In), technetium (99Tc), thallium (201Ti), gallium (68Ga, 67Ga), palladium (103Pd), molybdenum (99Mo), xenon (133Xe), fluorine (18F), 153Sm, 177Lu, 159Gd, 149 Pm, 140La, 175Yb, 166Ho, 90Y, 47Sc, 186Re, 188Re, 142Pr, 105Rh, 97Ru, 68Ge, 57Co, 65Zn, 85Sr, 32P, 153Gd, 169Yb, 51Cr, 54Mn, 75Se, 113Sn, and 117Tin; and positron emitting metals using various positron emission tomographies, and nonradioactive paramagnetic metal ions.

The present invention further encompasses uses of antibodies and antigen-binding fragments thereof conjugated to a therapeutic moiety. An antibody antigen-binding fragment thereof may be conjugated to a therapeutic moiety such as a cytotoxin, e.g., a cytostatic or cytocidal agent, a therapeutic agent or a radioactive metal ion, e.g., alpha-emitters. A cytotoxin or cytotoxic agent includes any agent that is detrimental to cells.

Further, an antibody antigen-binding fragment thereof may be conjugated to a therapeutic moiety or drug moiety that modifies a given biological response. Therapeutic moieties or drug moieties are not to be construed as limited to classical chemical therapeutic agents. For example, the drug moiety may be a protein, peptide, or polypeptide possessing a desired biological activity. Such proteins may include, for example, a toxin such as abrin, ricin A, *Pseudomonas* exotoxin, cholera toxin, or diphtheria toxin; a protein such as tumor necrosis factor, alpha-interferon, beta-interferon, nerve growth factor, platelet derived growth factor, tissue plasminogen activator, an apoptotic agent, an anti-angiogenic agent; or, a biological response modifier such as, for example, a lymphokine.

Moreover, an antibody can be conjugated to therapeutic moieties such as a radioactive metal ion, such as alpha-emitters such as 213Bi or macrocyclic chelators useful for conjugating radiometal ions, including but not limited to, 131In, 131LU, 131Y, 131Ho, 131Sm, to polypeptides. In one embodiment, the macrocyclic chelator is 1,4,7,10-tetraazacyclododecane-N,N',N",N'"-tetraacetic acid (DOTA) which can be attached to the antibody via a linker molecule. Such linker molecules are commonly known in the art and described in Denardo et al., 1998, Clin Cancer Res. 4 (10):2483-90; Peterson et al., 1999, Bioconjug. Chem. 10 (4):553-7; and Zimmerman et al., 1999, Nucl. Med. Biol. 26 (8):943-50, each incorporated by reference in their entireties.

Techniques for conjugating therapeutic moieties to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies 84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., 1982, Immunol. Rev. 62:119-58.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Methods of Producing Antibodies of the Invention
Nucleic Acids Encoding the Antibodies The invention provides substantially purified nucleic acid molecules which encode polypeptides comprising segments or domains of the BMP6-binding antibody chains described above. Some of the nucleic acids of the invention comprise the nucleotide sequence encoding the heavy chain variable region shown in any of SEQ NOs: 16; 36; 56; or 76, and/or the nucleotide sequence encoding the light chain variable region shown in any of SEQ ID NOs: 26; 46; 66; or 86. In a specific embodiment, the nucleic acid molecules are those identified in Table 1. Some other nucleic acid molecules of the invention comprise nucleotide sequences that are substantially identical (e.g., at least 65, 80%, 95%, or 99%) to the nucleotide sequences of those identified in Table 1. When expressed from appropriate expression vectors, polypeptides encoded by these polynucleotides are capable of exhibiting BMP6 antigen binding capacity.

Also provided in the invention are polynucleotides which encode at least one CDR region and usually all three CDR regions from the heavy or light chain of the BMP6-binding antibody set forth in Table 1 and/or Table 14. Some other polynucleotides encode all or substantially all of the variable region sequence of the heavy chain and/or the light chain of the BMP6-binding antibody set forth in Table 1 and/or Table 14. Because of the degeneracy of the code, a variety of nucleic acid sequences will encode each of the immunoglobulin amino acid sequences.

The nucleic acid molecules of the invention can encode both a variable region and a constant region of the antibody. Some of nucleic acid sequences of the invention comprise nucleotides encoding a mature heavy chain variable region sequence that is substantially identical (e.g., at least 80%, 90%, or 99%) to the mature heavy chain variable region sequence set forth in any of SEQ ID NOs: 16; 36; 56; or 76. Some other nucleic acid sequences comprising nucleotide encoding a mature light chain variable region sequence that is substantially identical at least 80%, 90%, or 99%) to the mature light chain variable region sequence set forth in any of SEQ ID NOs: 26; 46; 66; or 86.

The polynucleotide sequences can be produced by de novo solid-phase DNA synthesis or by PCR mutagenesis of an existing sequence (e.g., sequences as described in the Examples below) encoding an BMP6-binding antibody or its binding fragment. Direct chemical synthesis of nucleic acids can be accomplished by methods known in the art, such as the phosphodiester method of Narang et al., 1979, Meth. Enzymol. 68:90; the phosphodiester method of Brown et al., Meth. Enzymol. 68:109, 1979; the diethylphosphoramidite method of Beaucage et al., Tetra. Lett., 22:1859, 1981; and the solid support method of U.S. Pat. No. 4,458,066. Introducing mutations to a polynucleotide sequence by PCR can be performed as described in, e.g., PCR Technology: Principles and Applications for DNA Amplification, H. A. Erlich (Ed.), Freeman Press, NY, N.Y., 1992; PCR Protocols: A Guide to Methods and Applications, Innis et al. (Ed.), Academic Press, San Diego, Calif., 1990; Mattila et al., Nucleic Acids Res. 19:967, 1991; and Eckert et al., PCR Methods and Applications 1:17, 1991.

Also provided in the invention are expression vectors and host cells for producing the BMP6-binding antibodies described above. Various expression vectors can be employed to express the polynucleotides encoding the BMP6-binding antibody chains or binding fragments. Both viral-based and nonviral expression vectors can be used to produce the antibodies in a mammalian host cell. Nonviral vectors and systems include plasmids, episomal vectors, typically with an expression cassette for expressing a protein or RNA, and human artificial chromosomes (see, e.g., Harrington et al., Nat Genet. 15:345, 1997). For example, nonviral vectors useful for expression of the BMP6-binding polynucleotides and polypeptides in mammalian (e.g., human) cells include pThioHis A, B & C, pcDNA3.1/His, pEBVHis A, B & C, (Invitrogen, San Diego, Calif.), MPSV vectors, and numerous other vectors known in the art for expressing other proteins. Useful viral vectors include vectors based on retroviruses, adenoviruses, adenoassociated viruses, herpes viruses, vectors based on SV40, papilloma virus, HBP Epstein Barr virus, vaccinia virus vectors and Semliki Forest virus (SFV). See, Brent et al., supra; Smith, Annu. Rev. Microbiol. 49:807, 1995; and Rosenfeld et al., Cell 68:143, 1992.

The choice of expression vector depends on the intended host cells in which the vector is to be expressed. Typically, the expression vectors contain a promoter and other regulatory sequences (e.g., enhancers) that are operably linked to the polynucleotides encoding an BMP6-binding antibody chain antigen-binding fragment. In one embodiment, an inducible promoter is employed to prevent expression of inserted sequences except under inducing conditions. Inducible promoters include, e.g., arabinose, lacZ, metallothionein promoter or a heat shock promoter. Cultures of transformed organisms can be expanded under noninducing conditions without biasing the population for coding sequences whose expression products are better tolerated by the host cells. In addition to promoters, other regulatory elements may also be required or desired for efficient expression of an BMP6-binding antibody chain antigen-binding fragment. These elements typically include an ATG initiation codon and adjacent ribosome binding site or other sequences. In addition, the efficiency of expression may be enhanced by the inclusion of enhancers appropriate to the cell system in use see, e.g., Scharf et al., Results Probl. Cell Differ. 20:125, 1994; and Bittner et al., Meth. Enzymol., 153:516, 1987). For example, the SV40 enhancer or CMV enhancer may be used to increase expression in mammalian host cells.

The expression vectors may also provide a secretion signal sequence position to form a fusion protein with polypeptides encoded by inserted BMP6-binding antibody sequences. More often, the inserted BMP6-binding antibody sequences are linked to a signal sequences before inclusion in the vector. Vectors to be used to receive sequences encoding BMP6-binding antibody light and heavy chain variable domains sometimes also encode constant regions or parts thereof. Such vectors allow expression of the variable regions as fusion proteins with the constant regions thereby leading to production of intact antibodies and antigen-binding fragments thereof. Typically, such constant regions are human.

The host cells for harboring and expressing the BMP6-binding antibody chains can be either prokaryotic or eukaryotic. *E. coli* is one prokaryotic host useful for cloning and expressing the polynucleotides of the present invention. Other microbial hosts suitable for use include bacilli, such as *Bacillus subtilis*, and other enterobacteriaceae, such as *Salmonella, Serratia*, and various *Pseudomonas* species. In these prokaryotic hosts, one can also make expression vectors, which typically contain expression control sequences compatible with the host cell (e.g., an origin of replication). In addition, any number of a variety of well-known promoters will be present, such as the lactose promoter system, a tryptophan (trp) promoter system, a beta-lactamase promoter system, or a promoter system from phage lambda. The promoters typically control expression, optionally with an operator sequence, and have ribosome binding site sequences and the like, for initiating and completing transcription and translation. Other microbes, such as yeast, can also be employed to express BMP6-binding polypeptides of the invention. Insect cells in combination with baculovirus vectors can also be used.

In one embodiment, mammalian host cells are used to express and produce the BMP6-binding polypeptides of the present invention. For example, they can be either a hybridoma cell line expressing endogenous immunoglobulin genes (e.g., the 1D6.C9 myeloma hybridoma clone as described in the Examples) or a mammalian cell line harboring an exogenous expression vector (e.g., the SP2/0 myeloma cells exemplified below). These include any normal mortal or normal or abnormal immortal animal or human cell. For example, a number of suitable host cell lines capable of secreting intact immunoglobulins have been developed including the CHO cell lines, various Cos cell lines, HeLa cells, myeloma cell lines, transformed B-cells and hybridomas. The use of mammalian tissue cell culture to express polypeptides is discussed generally in, e.g., Winnacker, FROM GENES TO CLONES, VCH Publishers, N.Y., N.Y., 1987. Expression vectors for mammalian host cells can include expression control sequences, such as an origin of replication, a promoter, and an enhancer (see, e.g., Queen, et al., Immunol. Rev. 89:49-68, 1986), and necessary processing information sites, such as ribosome binding sites, RNA splice sites, polyadenylation sites, and transcriptional terminator sequences. These expression vectors usually contain promoters derived from mammalian genes or from mammalian viruses. Suitable promoters may be constitutive, cell type-specific, stage-specific, and/or modulatable or regulatable. Useful promoters include, but are not limited to, the metallothionein promoter, the constitutive adenovirus major late promoter, the dexamethasone-inducible MMTV promoter, the SV40 promoter, the MRP polIII promoter, the constitutive MPSV promoter, the tetracycline-inducible CMV promoter (such as the human immediate-early CMV promoter), the constitutive CMV promoter, and promoter-enhancer combinations known in the art.

Methods for introducing expression vectors containing the polynucleotide sequences of interest vary depending on the type of cellular host. For example, calcium chloride transfection is commonly utilized for prokaryotic cells, whereas calcium phosphate treatment or electroporation may be used for other cellular hosts. (See generally Sambrook, et al., supra). Other methods include, e.g., electroporation, calcium phosphate treatment, liposome-mediated transformation, injection and microinjection, ballistic methods, virosomes, immunoliposomes, polycation:nucleic acid conjugates, naked DNA, artificial virions, fusion to the herpes virus structural protein VP22 (Elliot and O'Hare, Cell 88:223, 1997), agent-enhanced uptake of DNA, and ex vivo transduction. For long-term, high-yield production of recombinant proteins, stable expression will often be desired. For example, cell lines which stably express BMP6-binding antibody chains or binding fragments can be prepared using expression vectors of the invention which contain viral origins of replication or endogenous expression elements and a selectable marker gene. Following the introduction of the vector, cells may be allowed to grow for 1-2 days in an enriched media before they are switched to selective media. The purpose of the selectable marker is to confer resistance to selection, and its presence allows growth of cells which successfully express the introduced sequences in selective media. Resistant, stably transfected cells can be proliferated using tissue culture techniques appropriate to the cell type.

Generation of Monoclonal Antibodies of the Invention

Monoclonal antibodies (mAbs) can be produced by a variety of techniques, including conventional monoclonal antibody methodology e.g., the standard somatic cell hybridization technique of Kohler and Milstein, 1975 Nature 256: 495. Many techniques for producing monoclonal antibody can be employed e.g., viral or oncogenic transformation of B lymphocytes.

An animal system for preparing hybridomas is the murine system. Hybridoma production in the mouse is a well established procedure. Immunization protocols and techniques for isolation of immunized splenocytes for fusion are known in the art. Fusion partners (e.g., murine myeloma cells) and fusion procedures are also known. Chimeric or humanized antibodies and antigen-binding fragments thereof of the present invention can be prepared based on the sequence of a murine monoclonal antibody prepared as described above. DNA encoding the heavy and light chain immunoglobulins can be obtained from the murine hybridoma of interest and engineered to contain non-murine (e.g., human) immunoglobulin sequences using standard molecular biology techniques. For example, to create a chimeric antibody, the murine variable regions can be linked to human constant regions using methods known in the art (see e.g., U.S. Pat. No. 4,816,567 to Cabilly et al.). To create a humanized antibody, the murine CDR regions can be inserted into a human framework using methods known in the art. See e.g., U.S. Pat. No. 5,225,539 to Winter, and U.S. Pat. Nos. 5,530,101, 5,585,089, 5,693,762 and 6,180,370 to Queen et al.

In a certain embodiment, the antibodies of the invention are human monoclonal antibodies. Such human monoclonal antibodies directed against BMP6 can be generated using transgenic or transchromosomic mice carrying parts of the human immune system rather than the mouse system. These transgenic and transchromosomic mice include mice referred to herein as HuMAb mice and KM mice, respectively, and are collectively referred to herein as "human Ig mice." The HuMAb Mouse® (Medarex, Inc.) contains human immunoglobulin gene miniloci that encode un-rearranged human heavy (mu and gamma) and kappa light chain immunoglobulin sequences, together with targeted mutations that inactivate the endogenous mu and kappa chain loci (see e.g., Lonberg, et al., 1994 Nature 368 (6474): 856-859). Accordingly, the mice exhibit reduced expression of mouse IgM or K, and in response to immunization, the introduced human heavy and light chain transgenes undergo class switching and somatic mutation to generate high affinity human IgG-kappa monoclonal (Lonberg, N. et al., 1994 supra; reviewed in Lonberg, N., 1994 Handbook of Experimental Pharmacology 113:49-101; Lonberg, N. and Huszar, D., 1995 Intern. Rev. Immunol. 13: 65-93, and Harding, F. and Lonberg, N., 1995 Ann. N.Y. Acad. Sci. 764:536-546). The preparation and use of HuMAb mice, and the genomic modifications carried by such mice, is further described in Taylor, L. et al., 1992 Nucleic Acids Research 20:6287-6295: Chen. J. et al., 1993 International Immunology 5: 647-656; Tuaillon et al., 1993 Proc. Natl. Acad. Sci. USA 94:3720-3724; Choi et al., 1993 Nature Genetics 4:117-123; Chen, J. et al., 1993 EMBO J. 12: 821-830; Tuaillon et al., 1994 J. Immunol. 152:2912-2920; Taylor, L. et al., 1994 International Immunology 579-591; and Fishwild, D. et al., 1996 Nature Biotechnology 14: 845-851, the contents of all of which are hereby specifically incorporated by reference in their entirety. See further, U.S. Pat. Nos. 5,545,806; 5,569, 825; 5,625,126; 5,633,425; 5,789,650; 5,877,397; 5,661, 016; 5,814,318; 5,874,299; and 5,770,429; all to Lonberg and Kay; U.S. Pat. No. 5,545,807 to Surani et al.; PCT Publication Nos. WO 92103918, WO 93/12227, WO 94/25585, WO 97/13852, WO 98/24884 and WO 99/45962, all to Lonberg and Kay; and PCT Publication No. WO 01/14424 to Korman et al.

In another embodiment, human antibodies of the invention can be raised using a mouse that carries human immunoglobulin sequences on transgenes and transchomosomes such as a mouse that carries a human heavy chain transgene and a human light chain transchromosome. Such mice, referred to herein as "KM mice", are described in detail in PCT Publication WO 02/43478 to Ishida et al.

Still further, alternative transgenic animal systems expressing human immunoglobulin genes are available in the art and can be used to raise BMP6-binding antibodies and antigen-binding fragments thereof of the invention. For example, an alternative transgenic system referred to as the Xenomouse (Abgenix, Inc.) can be used. Such mice are described in, e.g., U.S. Pat. Nos. 5,939,598; 6,075,181; 6,114,598; 6,150,584 and 6,162,963 to Kucherlapati et al.

Moreover, alternative transchromosomic animal systems expressing human immunoglobulin genes are available in the art and can be used to raise BMP6-binding antibodies of the invention. For example, mice carrying both a human heavy chain transchromosome and a human light chain transchromosome, referred to as "TC mice" can be used; such mice are described in Tomizuka et al., 2000 Proc. Natl. Acad. Sci. USA 97:722-727. Furthermore, cows carrying human heavy and light chain transchromosomes have been described in the art (Kuroiwa et al., 2002 Nature Biotechnology 20:889-894) and can be used to raise BMP6-binding antibodies of the invention.

Human monoclonal antibodies of the invention can also be prepared using phage display methods for screening libraries of human immunoglobulin genes. Such phage display methods for isolating human antibodies are established in the art or described in the examples below. See for example: U.S. Pat. Nos. 5,223,409; 5,403,484; and 5,571, 698 to Ladner et al; U.S. Pat. Nos. 5,427,908 and 5,580,717 to Dower et al; U.S. Pat. Nos. 5,969,108 and 6,172,197 to McCafferty et al; and U.S. Pat. Nos. 5,885,793; 6,521,404; 6,544,731; 6,555,313; 6,582,915 and 6,593,081 to Griffiths et al.

Human monoclonal antibodies of the invention can also be prepared using SCID mice into which human immune cells have been reconstituted such that a human antibody response can be generated upon immunization. Such mice are described in, for example, U.S. Pat. Nos. 5,476,996 and 5,698,767 to Wilson et al.

Framework or Fc Engineering

Engineered antibodies and antigen-binding fragments thereof of the invention include those in which modifications have been made to framework residues within VH and/or VL, e.g. to improve the properties of the antibody. Typically such framework modifications are made to decrease the immunogenicity of the antibody. For example, one approach is to "backmutate" one or more framework residues to the corresponding germline sequence. More specifically, an antibody that has undergone somatic mutation may contain framework residues that differ from the germline sequence from which the antibody is derived. Such residues can be identified by comparing the antibody framework sequences to the germline sequences from which the antibody is derived. To return the framework region sequences to their germline configuration, the somatic mutations can be "backmutated" to the germline sequence by, for example, site-directed mutagenesis. Such "backmutated" antibodies are also intended to be encompassed by the invention.

Another type of framework modification involves mutating one or more residues within the framework region, or even within one or more CDR regions, to remove T cell-epitopes to thereby reduce the potential immunogenicity of the antibody. This approach is also referred to as "deimmunization" and is described in further detail in U.S. Patent Publication No. 20030153043 by Carr et al.

In addition or alternative to modifications made within the framework or CDR regions, antibodies of the invention may be engineered to include modifications within the Fc region, typically to alter one or more functional properties of the antibody, such as serum half-life, complement fixation, Fc receptor binding, and/or antigen-dependent cellular cytotoxicity. Furthermore, an antibody of the invention may be chemically modified (e.g., one or more chemical moieties can be attached to the antibody) or be modified to alter its glycosylation, again to alter one or more functional properties of the antibody. Each of these embodiments is described in further detail below. The numbering of residues in the Fc region is that of the EU index of Kabat.

In one embodiment, the hinge region of CH1 is modified such that the number of cysteine residues in the hinge region is altered, e.g., increased or decreased. This approach is described further in U.S. Pat. No. 5,677,425 by Bodmer et al. The number of cysteine residues in the hinge region of CH1 is altered to, for example, facilitate assembly of the light and heavy chains or to increase or decrease the stability of the antibody.

In another embodiment, the Fc hinge region of an antibody is mutated to decrease the biological half-life of the antibody. More specifically, one or more amino acid mutations are introduced into the CH2-CH3 domain interface region of the Fc-hinge fragment such that the antibody has impaired Staphylococcyl protein A (SpA) binding relative to native Fc-hinge domain SpA binding. This approach is described in further detail in U.S. Pat. No. 6,165,745 by Ward et al.

In another embodiment, the antibody is modified to increase its biological half-life. Various approaches are possible. For example, one or more of the following mutations can be introduced: T252L, T254S, T256F, as described in U.S. Pat. No. 6,277,375 to Ward. Alternatively, to increase the biological half life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022 by Presta et al.

In one embodiment, the Fc region is altered by replacing at least one amino acid residue with a different amino acid residue to alter the effector functions of the antibody. For example, one or more amino acids can be replaced with a different amino acid residue such that the antibody has an altered affinity for an effector ligand but retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260, both by Winter et al.

In another embodiment, one or more amino acids selected from amino acid residues can be replaced with a different amino acid residue such that the antibody has altered C1q binding and/or reduced or abolished complement dependent cytotoxicity (CDC). This approach is described in further detail in U.S. Pat. No. 6,194,551 by Idusogie et al.

In another embodiment, one or more amino acid residues are altered to thereby alter the ability of the antibody to fix complement. This approach is described further in PCT Publication WO 94/29351 by Bodmer et al.

In yet another embodiment, the Fc region is modified to increase the ability of the antibody to mediate antibody dependent cellular cytotoxicity (ADCC) and/or to increase the affinity of the antibody for an Fc-gamma receptor by modifying one or more amino acids. This approach is described further in PCT Publication WO 00/42072 by Presta. Moreover, the binding sites on human IgG1 for Fc-gamma RI, Fc-gamma RII, Fc-gamma RIII and FcRn have been mapped and variants with improved binding have been described (see Shields, R. L. et al., 2001 J. Biol. Chen. 276:6591-6604).

In still another embodiment, the glycosylation of an antibody is modified. For example, an aglycoslated antibody can be made (i.e., the antibody lacks glycosylation). Glycosylation can be altered to, for example, increase the affinity of the antibody for "antigen". Such carbohydrate modifications can be accomplished by, for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen. Such an approach is described in further detail in U.S. Pat. Nos. 5,714,350 and 6,350,861 by Co et al.

Additionally or alternatively, an antibody can be made that has an altered type of glycosylation, such as a hypofucosylated antibody having reduced amounts of fucosyl residues or an antibody having increased bisecting GlcNac structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. For example, EP 1,176,195 by Hang et al. describes a cell line with a functionally disrupted FUT8 gene, which encodes a fucosyl transferase, such that antibodies expressed in such a cell line exhibit hypofucosylation. PCT Publication WO 03/035835 by Presta describes a variant CHO cell line, LecI3 cells, with reduced ability to attach fucose to Asn (297)-linked carbohydrates, also resulting in hypofucosylation of antibodies expressed in that host cell (see also Shields, R. L. et al., 2002 J. Biol. Chem. 277:26733-26740). PCT Publication WO 99/54342 by Umana et al. describes cell lines engineered to express glycoprotein-modifying glycosyl transferases (e.g., beta (1,4)-N acetylglucosaminyltransferase III (GnTIII)) such that antibodies expressed in the engineered cell lines exhibit increased bisecting GlcNac structures which results in increased ADCC activity of the antibodies (see also Umana et al., 1999 Nat. Biotech. 17:176-180).

Methods of Engineering Altered Antibodies

As discussed above, the BMP6-binding antibodies having VH and VL sequences or full length heavy and light chain sequences shown herein can be used to create new BMP6-binding antibodies by modifying full length heavy chain and/or light chain sequences, VH and/or VL sequences, or the constant region(s) attached thereto. Thus, in another aspect of the invention, the structural features of BMP6-binding antibody of the invention are used to create structurally related BMP6-binding antibodies that retain at least one functional property of the antibodies and antigen-binding fragments thereof of the invention, such as binding to human BMP6 and also inhibiting one or more functional properties of BMP6 (e.g., inhibit red blood cell lysis in a hemolytic assay).

For example, one or more CDR regions of the antibodies and antigen-binding fragments thereof of the present invention, or mutations thereof, can be combined recombinantly with known framework regions and/or other CDRs to create additional, recombinantly-engineered, BMP6-binding antibodies and antigen-binding fragments thereof of the invention, as discussed above. Other types of modifications include those described in the previous section. The starting material for the engineering method is one or more of the VH and/or VL sequences provided herein, or one or more CDR regions thereof. To create the engineered antibody, it is not necessary to actually prepare (i.e., express as a protein) an antibody having one or more of the VH and/or VL sequences provided herein, or one or more CDR regions thereof. Rather, the information contained in the sequence(s) is used as the starting material to create a "second generation" sequence(s) derived from the original sequence(s) and then the "second generation" sequence(s) is prepared and expressed as a protein.

The altered antibody sequence can also be prepared by screening antibody libraries having fixed CDR3 sequences or minimal essential binding determinants as described in US20050255552 and diversity on CDR1 and CDR2 sequences. The screening can be performed according to any screening technology appropriate for screening antibodies from antibody libraries, such as phage display technology.

Standard molecular biology techniques can be used to prepare and express the altered antibody sequence. The antibody encoded by the altered antibody sequence(s) is one that retains one, some or all of the functional properties of the BMP6-binding antibodies described herein, which functional properties include, but are not limited to, specifically binding to human BMP6 protein; and the antibody inhibit red blood cell lysis in a hemolytic assay.

The functional properties of the altered antibodies can be assessed using standard assays available in the art and/or described herein, such as those set forth in the Examples (e.g., ELISAs).

In one embodiment of the methods of engineering antibodies and antigen-binding fragments thereof of the invention, mutations can be introduced randomly or selectively along all or part of an BMP6-binding antibody coding sequence and the resulting modified BMP6-binding antibodies can be screened for binding activity and/or other functional properties as described herein. Mutational methods have been described in the art. For example, PCT Publication WO 02/092780 by Short describes methods for creating and screening antibody mutations using saturation mutagenesis, synthetic ligation assembly, or a combination thereof. Alternatively, PCT Publication WO 03/074679 by Lazar et al. describes methods of using computational screening methods to optimize physiochemical properties of antibodies.

Characterization of the Antibodies of the Invention

The antibodies and antigen-binding fragments thereof of the invention can be characterized by various functional assays. For example, they can be characterized by their ability to inhibit BMP6.

The ability of an antibody to bind to BMP6 can be detected by labelling the antibody of interest directly, or the antibody may be unlabelled and binding detected indirectly using various sandwich assay formats known in the art.

In one embodiment, the BMP6-binding antibodies and antigen-binding fragments thereof of the invention block or compete with binding of a reference BMP6-binding antibody to BMP6 polypeptide. These can be fully human BMP6-binding antibodies described above. They can also be other mouse, chimeric or humanized BMP6-binding antibodies which bind to the same epitope as the reference antibody. The capacity to block or compete with the reference antibody binding indicates that BMP6-binding antibody wider test binds to the same or similar epitope as that defined by the reference antibody, or to an epitope which is sufficiently proximal to the epitope bound by the reference BMP6-binding antibody. Such antibodies are especially likely to share the advantageous properties identified for the reference antibody. The capacity to block or compete with the reference antibody may be determined by, e.g., a competition binding assay. With a competition binding assay, the antibody under test is examined for ability to inhibit specific binding of the reference antibody to a common antigen, such as BMP6 polypeptide. A test antibody competes with the reference antibody for specific binding to the antigen if an excess of the test antibody substantially inhibits binding of the reference antibody. Substantial inhibition means that the test antibody reduces specific binding of the reference antibody usually by at least 10%, 25%, 50%, 75%, or 90%.

There are a number of known competition binding assays that can be used to assess competition of an antibody with a reference antibody for binding to a particular protein, in this case, BMP6. These include, e.g., solid phase direct or indirect radioimmunoassay (RIA), solid phase direct or indirect enzyme immunoassay (EIA), sandwich competition assay (see Stahli et al., Methods in Enzymology 9:242-253, 1983); solid phase direct biotin-avidin EIA (see Kirkland et al., J. Immunol. 137:3614-3619, 1986); solid phase direct labeled assay, solid phase direct labeled sandwich assay (see Harlow & Lane, supra); solid phase direct label RIA using I-125 label (see Morel et al., Molec. Immunol. 25:7-15, 1988); solid phase direct biotin-avidin EIA (Cheung et al., Virology 176:546-552, 1990); and direct labeled RIA (Moldenhauer et al., Scand. J. Immunol. 32:77-82, 1990). Typically, such an assay involves the use of purified antigen bound to a solid surface or cells bearing either of these, an unlabelled test BMP6-binding antibody and a labelled reference antibody. Competitive inhibition is measured by determining the amount of label bound to the solid surface or cells in the presence of the test antibody. Usually the test antibody is present in excess. Antibodies identified by competition assay (competing antibodies) include antibodies binding to the same epitope as the reference antibody and antibodies binding to an adjacent epitope sufficiently proximal to the epitope bound by the reference antibody for steric hindrance to occur.

To determine if the selected BMP6-binding monoclonal antibodies bind to unique epitopes, each antibody can be biotinylated using commercially available reagents (e.g., reagents from Pierce, Rockford, Ill.). Competition studies using unlabeled monoclonal antibodies and biotinylated monoclonal antibodies can be performed using BMP6 polypeptide coated-ELISA plates. Biotinylated MAb binding can be detected with a strep-avidin-alkaline phosphatase probe. To determine the isotype of a purified BMP6-binding antibody, isotype ELISAs can be performed. For example, wells of microtiter plates can be coated with 1 □g/ml of anti-human IgG overnight at 4 degrees C. After blocking with 1% BSA, the plates are reacted with 1 □g/ml or less of the monoclonal BMP6-binding antibody or purified isotype controls, at ambient temperature for one to two hours. The wells can then be reacted with either human IgG1 or human IgM-specific alkaline phosphatase-conjugated probes. Plates are then developed and analyzed so that the isotype of the purified antibody can be determined.

To demonstrate binding of monoclonal BMP6-binding antibodies to live cells expressing BMP6 polypeptide, flow cytometry can be used. Briefly, cell lines expressing BMP6 (grown under standard growth conditions) can be mixed with various concentrations of BMP6-binding antibody in PBS containing 0.1% BSA and 10% fetal calf serum, and incubated at 37 degrees C. for 1 hour. After washing, the cells are reacted with Fluorescein-labeled anti-human IgG antibody under the same conditions as the primary antibody staining. The samples can be analyzed by FACScan instrument using light and side scatter properties to gate on single cells. An alternative assay using fluorescence microscopy may be used (in addition to or instead of) the flow cytometry assay. Cells can be stained exactly as described above and examined by fluorescence microscopy. This method allows visualization of individual cells, but may have diminished sensitivity depending on the density of the antigen. BMP6-binding antibodies and antigen-binding fragments thereof of the invention can be further tested for reactivity with BMP6 polypeptide or antigenic fragment by Western blotting. Briefly, purified BMP6 polypeptides or fusion proteins, or cell extracts from cells expressing BMP6 can be prepared and subjected to sodium dodecyl sulfate polyacrylamide gel electrophoresis. After electrophoresis, the separated antigens are transferred to nitrocellulose membranes, blocked with 10% fetal calf serum, and probed with the monoclonal antibodies to be tested. Human IgG binding can be detected using anti-human IgG alkaline phosphatase and developed with BCIP/NBT substrate tablets (Sigma Chem. Co., St. Louis, Mo.).

Examples of functional assays are also described in the Example section below.

Prophylactic and Therapeutic Uses

The present invention provides methods of treating a disease or disorder associated with increased BMP6 activity by administering to a subject in need thereof an effective amount of the antibodies and antigen-binding fragments thereof of the invention. In a specific embodiment, the present invention provides a method of treating anemia by administering to a subject in need thereof an effective amount of the antibodies and antigen-binding fragments thereof of the invention.

The antibodies and antigen-binding fragments thereof of the invention can be used, inter alia to prevent progression of anemia. It can also be used in combination with other therapies for the treatment of anemia patients.

In one embodiment, the present invention provides methods of treating a BMP6 related disease or disorder by administering to a subject in need thereof an effective amount of the antibodies and antigen-binding fragments thereof of the invention. Examples of known BMP6 related diseases or disorders include: anemia, including, as non-limiting examples: anemia of chronic disease (ACD), anemia of (e.g., associated with) chronic kidney disease (CKD), anemia of cancer, anemia of inflammation, erythropoiesis stimulating agent (ESA) resistant anemia (for example erythropoietin (EPO) resistant anemia, ESA hyporesponsive anemia (for example, EPO hyporesponsive anemia), functional iron-deficiency anemia, and/or iron-restricted anemia.

In a specific embodiment, the present invention provides methods of treating a BMP6 related disease or disorder by administering to a subject in need thereof an effective amount of the antibodies and antigen-binding fragments thereof of the invention, wherein said disease or disorder is anemia. In an embodiment the anemia is anemia of chronic disease. In an embodiment the chronic disease is chronic kidney disease. In an embodiment the chronic disease is cancer. In an embodiment the chronic disease is inflammation. In an embodiment the anemia (e.g., the anemia of chronic disease) is ESA (for example, EPO)-resistant anemia. In an embodiment the anemia (e.g., the anemia of chronic disease) is ESA (for example, EPO)-hyporesponsive anemia. In an embodiment, the anemia (e.g., the anemia of chronic disease) is iron-restricted anemia. In embodiments, including in any of the above embodiments, the subject is a chronic hemodialysis (HD) subject. In embodiments, including in any of the above embodiments, the subject has renal disease, for example, end-stage renal disease.

In a specific embodiment, the present invention provides methods of treating a BMP6 related disease or disorder by administering to a subject in need thereof an effective amount of an antibody and antigen-binding fragment thereof of the invention, wherein said disease or disorder is functional iron deficiency anemia. In an embodiment, the subject is an ESA (for example, EPO) treated chronic hemodialysis patients. In an embodiment, the subject is an ESA (for example, EPO) treated chronic hemodialysis patient with chronic kidney disease.

In a specific embodiment, the present invention provides methods of treating anemia by administering to a subject in need thereof an effective amount of a composition comprising an antibody of the present invention. In a specific embodiment, the present invention provides methods of treating anemia by administering to a subject in need thereof an effective amount of a composition comprising an antibody of the present invention. In an embodiment the anemia is anemia of chronic kidney disease. In an embodiment the anemia is ESA (for example, EPO)-resistant anemia. In an embodiment the anemia is ESA (for example, EPO)-hyporesponsive anemia. In an embodiment, the anemia is iron-restricted anemia. In an embodiment, the anemia is anemia associated with kidney disease, for example, chronic kidney disease. In embodiments, including in any of the above embodiments, the subject is a chronic hemodialysis (HD) subject. In embodiments, including in any of the above embodiments, the subject has renal disease, for example, end-stage renal disease.

In a specific embodiment, the present invention provides methods of treating a BMP6 related disease or disorder by administering to a subject in need thereof an effective amount of a composition comprising an antibody of the present invention, wherein said disease or disorder is functional iron deficiency anemia. In an embodiment, the subject is an ESA (for example, EPO) treated chronic hemodialysis patients. In an embodiment, the subject is an ESA (for example, EPO) treated chronic hemodialysis patient with chronic kidney disease.

In a specific embodiment, the present invention provides methods of treating anemia.

In a specific embodiment, the present invention provides a method for reducing a subject's ESA (for example, EPO) dosing needs by administering to a subject in need thereof an effective amount of an antibody or antigen-binding fragment thereof of the invention. In an embodiment the anemia is anemia of chronic disease. In an embodiment the chronic disease is chronic kidney disease. In an embodiment the chronic disease is cancer. In an embodiment the chronic disease is inflammation. In an embodiment the anemia (e.g., the anemia of chronic disease) is ESA (for example, EPO)-resistant anemia. In an embodiment the anemia (e.g., the anemia of chronic disease) is ESA (for example, EPO)-hyporesponsive anemia. In an embodiment, the anemia (e.g., the anemia of chronic disease) is iron-restricted anemia. In embodiments, including in any of the above embodiments, the subject is a chronic hemodialysis (HD) subject. In embodiments, including in any of the above embodiments, the subject has renal disease, for example, end-stage renal disease. In embodiments, the methods and use of the invention result in a decrease in a patients ESA resistance index (ERI).

In a specific embodiment, the present invention provides methods of reducing s subject's ESA (for example, EPO) dosing needs by administering to a subject in need thereof an effective amount of an antibody or antigen-binding fragment thereof of the invention, wherein said subject has functional iron deficiency anemia. In an embodiment, the subject is an ESA (for example, EPO) treated chronic hemodialysis patient. In an embodiment, the subject is an ESA (for example, EPO) treated chronic hemodialysis patient with chronic kidney disease.

In a specific embodiment, the present invention provides a method for reducing a subject's ESA (for example, EPO) dosing needs by administering to a subject in need thereof an effective amount of a composition comprising an antibody of the present invention. In an embodiment, the subject has anemia. In an embodiment the anemia is anemia of chronic disease. In an embodiment the chronic disease is chronic kidney disease. In an embodiment the chronic disease is cancer. In an embodiment the chronic disease is inflammation. In an embodiment the anemia (e.g., the anemia of chronic disease) is ESA (for example, EPO)-resistant anemia. In an embodiment the anemia (e.g., the anemia of chronic disease) is ESA (for example, EPO)-hyporesponsive anemia. In an embodiment, the anemia (e.g., the anemia of chronic disease) is iron-restricted anemia. In embodiments, including in any of the above embodiments, the subject is a chronic hemodialysis (HD) subject. In embodiments, including in any of the above embodiments, the subject has renal disease, for example, end-stage renal disease.

In a specific embodiment, the present invention provides methods of reducing s subject's ESA (for example, EPO) dosing needs by administering to a subject in need thereof an effective amount of a composition comprising an antibody of the present invention, wherein said subject has functional iron deficiency anemia. In an embodiment, the subject is an ESA (for example, EPO) treated chronic hemodialysis patient. In an embodiment, the subject is an ESA (for example, EPO) treated chronic hemodialysis patient with chronic kidney disease.

In a specific embodiment, the present invention provides a method for reducing a subject's iron (for example, IV iron) dosing needs by administering to a subject in need thereof an effective amount of the antibodies and antigen-binding fragments thereof of the invention. In an embodiment, the subject has anemia. In an embodiment the anemia is anemia of chronic disease. In an embodiment the chronic disease is chronic kidney disease. In an embodiment the chronic disease is cancer. In an embodiment the chronic disease is inflammation. In an embodiment the anemia (e.g., the anemia of chronic disease) is ESA (for example, EPO)-resistant anemia. In an embodiment the anemia (e.g., the anemia of chronic disease) is ESA (for example, EPO)-hyporesponsive anemia. In an embodiment, the anemia (e.g., the anemia of chronic disease) is iron-restricted anemia. In embodiments, including in any of the above embodiments, the subject is a chronic hemodialysis (HD) subject. In embodiments, including in any of the above embodiments, the subject has renal disease, for example, end-stage renal disease.

In a specific embodiment, the present invention provides methods of reducing s subject's iron (for example, IV iron) dosing needs by administering to a subject in need thereof an effective amount of the antibodies and antigen-binding fragments thereof of the invention, wherein said subject has functional iron deficiency anemia. In an embodiment, the subject is an ESA (for example, EPO) treated chronic hemodialysis patient. In an embodiment, the subject is an ESA (for example, EPO) treated chronic hemodialysis patient with chronic kidney disease.

In a specific embodiment, the present invention provides a method for reducing a subject's iron (for example, IV iron) dosing needs by administering to a subject in need thereof an effective amount of a composition comprising an antibody of the present invention. In an embodiment, the subject has anemia. In an embodiment the anemia is anemia of chronic disease. In an embodiment the chronic disease is chronic kidney disease. In an embodiment the chronic disease is cancer. In an embodiment the chronic disease is inflammation. In an embodiment the anemia (e.g., the anemia of chronic disease) is ESA (for example, EPO)-resistant anemia. In an embodiment the anemia (e.g., the anemia of chronic disease) is ESA (for example, EPO)-hyporesponsive anemia. In an embodiment, the anemia (e.g., the anemia of chronic disease) is iron-restricted anemia. In embodiments, including in any of the above embodiments, the subject is a chronic hemodialysis (HD) subject. In embodiments, including in any of the above embodiments, the subject has renal disease, for example, end-stage renal disease.

In a specific embodiment, the present invention provides methods of reducing s subject's iron (for example, IV iron) dosing needs by administering to a subject in need thereof an effective amount of a composition comprising an antibody of the present invention, wherein said subject has functional iron deficiency anemia. In an embodiment, the subject is an ESA (for example, EPO) treated chronic hemodialysis patient. In an embodiment, the subject is an ESA (for example, EPO) treated chronic hemodialysis patient with chronic kidney disease.

In a specific embodiment, the invention provides a method for reducing a subject's iron (for example, IV iron) dosing needs and reducing a subject's ESA (for example, EPO) dosing needs, comprising administering the antibody or antigen binding fragment of the invention or a composition comprising said antibody or antigen binding fragment.

In an embodiment the anemia is anemia of chronic disease. In an embodiment the chronic disease is chronic kidney disease. In an embodiment the chronic disease is cancer. In an embodiment, the subject has anemia. In an embodiment the chronic disease is inflammation. In an embodiment the anemia (e.g., the anemia of chronic disease) is ESA (for example, EPO)-resistant anemia. In an embodiment the anemia (e.g., the anemia of chronic disease) is ESA (for example, EPO)-hyporesponsive anemia. In an embodiment, the anemia (e.g., the anemia of chronic disease) is iron-restricted anemia. In embodiments, including in any of the above embodiments, the subject is a chronic hemodialysis (HD) subject. In embodiments, including in any of the above embodiments, the subject has renal disease, for example, end-stage renal disease.

In an embodiment, present invention provides methods of mobilizing sequestered iron by administering to a subject in need thereof an effective amount of the antibodies and antigen-binding fragments thereof of the invention.

In an embodiment, present invention provides methods of mobilizing sequestered iron by administering to a subject in need thereof an effective amount of a composition comprising an antibody of the present invention.

In an embodiment, the present invention provides a method for improving (for example, increasing) the level of hemoglobin in a subject with anemia, while reducing the need for dosing with erythropoietin and/or iron (e.g., IV iron), said method comprising administering to a subject in need thereof an antibody or antigen binding fragment thereof of the invention. In an embodiment, the anemia is anemia associated with chronic disease. In an embodiment, the improving the level of hemoglobin comprises improving the level to a level as specified by a clinical practice guideline, for example, Kidney Disease: Improving Global Outcomes (KDIGO) Anemia Work Group. KDIGO Clinical Practice Guideline for Anemia in Chronic Kidney Disease. Kidney inter., Suppl. 2012; 2: 279-335, the contents of which are hereby incorporated by reference in their entirety. In an embodiment, the improving the level of hemoglobin comprises improving the level of hemoglobin to at least about 11.0 g/dL, e.g., to from about 11.0 g/dL to about 12.5 g/dL. In an embodiment, the improving the level of hemoglobin comprises improving the level of hemoglobin to at least 11.0 g/dL, e.g., to from 11.0 g/dL to 12.5 g/dL.

In an embodiment, the present invention provides a method for improving (for example, increasing) the level of hemoglobin in a subject with anemia, while reducing the need for dosing with erythropoietin and/or iron e.g., IV iron), said method comprising administering to a subject in need thereof a composition comprising an antibody of the invention. In an embodiment, the anemia is anemia associated with chronic disease. In an embodiment, the improving the level of hemoglobin comprises improving the level to a level as specified by a clinical practice guideline, for example, Kidney Disease: Improving Global Outcomes (KDIGO) Anemia Work Group. KDIGO Clinical Practice Guideline for Anemia in Chronic Kidney Disease. Kidney inter., Suppl. 2012; 2: 279-335, the contents of which are hereby incorporated by reference in its entirety. In an embodiment, the improving the level of hemoglobin comprises improving the level of hemoglobin to at least about 11.0 g/dL, e.g., to from about 11.0 g/dL to about 12.5 g/dL. In an embodiment, the improving the level of hemoglobin comprises improving the level of hemoglobin to at least 11.0 g/dL, e.g., to from 11.0 g/dL to 12.5 g/dL.

In an embodiment, the present invention provides a method for maintaining the level of hemoglobin in a subject with anemia, while reducing the need for dosing with erythropoietin and/or iron (e.g., IV iron), said method comprising administering to a subject in need thereof an antibody or antigen binding fragment thereof of the invention. In an embodiment, the anemia is anemia associated with chronic disease. In an embodiment, the improving the level of hemoglobin comprises improving the level to a level as specified by a clinical practice guideline, for example, Kidney Disease: Improving Global Outcomes (KDIGO) Anemia Work Group. KDIGO Clinical Practice Guideline for Anemia in Chronic Kidney Disease, Kidney inter., Suppl. 2012; 2: 279-335, the contents of which are hereby incorporated by reference in its entirety. In an embodiment, the improving the level of hemoglobin comprises improving the level of hemoglobin to at least about 11.0 g/dL, e.g., to from about 11.0 g/dL to about 12.5 g/dL. In an embodiment, the improving the level of hemoglobin comprises improving the level of hemoglobin to at least 11.0 g/dL, e.g., to from 11.0 g/dL to 12.5 g/dL.

In an embodiment, the present invention provides a method for maintaining the level of hemoglobin in a subject with anemia, while reducing the need for dosing with erythropoietin and/or iron (e.g., IV iron), said method comprising administering to a subject in need thereof a composition comprising an antibody of the invention. In an embodiment, the anemia is anemia associated with chronic disease. In an embodiment, the improving the level of hemoglobin comprises improving the level to a level as specified by a clinical practice guideline, for example, Kidney Disease: Improving Global Outcomes (KDIGO) Anemia Work Group. KDIGO Clinical Practice Guideline for Anemia in Chronic Kidney Disease. Kidney inter., Suppl. 2012; 2: 279-335, the contents of which are hereby incorporated by reference in its entirety. In an embodiment, the improving the level of hemoglobin comprises improving the level of hemoglobin to at least about 11.0 g/dL, e.g., to from about 11.0 g/dL to about 12.5 g/dL. In an embodiment, the improving the level of hemoglobin comprises improving the level of hemoglobin to at least 11.0 g/dL, e.g., to from 11.0 g/dL, to 12.5 g/dL.

In one embodiment, the isolated antibody or antigen-binding fragment thereof described in Table 1 and/or Table 14 can be administered to a patient in need thereof in conjunction with a therapeutic method or procedure, such as described herein or known in the art. Such a method or procedure includes, as non-limiting examples: administration of a therapeutically effective amount of ESA (for example, EPO), erythropoietin, or iron, and blood transfusion. Treatment is typically continued at intervals for a period of a week, a month, three months, six months or a year. In some patients, treatment is administered for up to the rest of a patient's life.

When the therapeutic agents of the present invention are administered together with another agent, the two can be administered sequentially in either order or simultaneously. In some aspects, an antibody of the present invention is administered to a subject who is also receiving therapy with a second agent or method (e.g., ESA, erythropoietin, iron, blood transfusion). In other aspects, the binding molecule is administered in conjunction with surgical treatments.

Suitable agents for combination treatment with BMP6-binding antibodies include agents known in the art that inhibit or reduce the expression, level, stability and/or activity of BMP6. Such agents include antibodies, siRNAs, and small molecules to BMP6.

Various antibodies to BMP6 are known in the art, including, inter alia, those described in:
Andriopoulos et al. 2009 Nat. Genet. 41: 482-487;
Arndt et al. 2010 Gastroent. 138: 372-382;
Barnes et al. 1995 World J. Urol, 13: 337-343;
Camaschella et al. 2009 Nat. Genet. 41: 386-388;
Celement et al. 1999 Int. J. Cancer 80: 250-256;
Corradini et al. 2011 Hepatol. 54: 273-284;
Crews et al. 2010 J. Neuro. 30: 12252-12262;
Dai et al. 2005 Cancer Res. 65: 8274;
Darby et al. 2007 J. Pathol. 214: 394-404;
Hadziahmetovic et al. 2011 179: 335-348;
Hamdy et al. 1997 Cancer Res. 57: 4427;
Haudenschild et al. 2004 Cancer Res. 64: 8276;
Hee et al. 2008 J. Orth. Res. 27: 162-168;
Herrera et al. 2009 BMC Cell Biol. 10: 20;
Inagaki et al. 2005 Endocrin. 147: 2681-2689;
Jung et al. 2008 Stem Cells 26: 2042-2051;
Kaiser et al. 1998 J. Invest. Derm. 111: 1145-1152;
Kautz et al. 2011 Haematol. 96: 199-203;
Khalaf et al. 2012 Eur. J. Endocrin, 168: 437-444;
Kochanowska et al. 2002 Exp. Biol. Med. 227: 57-62;
Li et al. 2006 Int. J. Med. Sci. 3: 97-105;
Meynard et al. 2011 Blood 118: 747-756;
Pederson et al. 2008 Proc. Natl. Acad. Sci. USA 105: 20764-69;
Plant et al. 2002 J. Bone Min. Res. 17: 782-790;
Schluesener et al. 1994 Atheroscl. 113: 153-156;
Schluesener et al. 2004 GLIA 12: 161-164;
Shi et al. 2009 Fert. Steril. 92: 1794-1798;
Varley et al. 1996 Exp. Neur. 140: 84-94;
Wang et al. 2007 Mol. Cell. Neurosci. 34: 653-661; and
Zhang et al. 2006 Neurosci. 138: 47-53;
U.S. Pat. No. 8,795,665; and
WO 2010/056981;

Additional antibodies to BMP6 are known in the art; many are commercially available.

Various siRNAs to BMP6 are known in the art, including, inter alia, those described in:
He et al. 2003 Cell. Signal. 25: 1372-1378;
Ikeda et al. 2012 PLoS 0040465;
Kautz et al. 2008 Blood 112: 1503;
Mi et al. 2011 J. Cancer Res. Clin. Oncol. 137: 245;
Xia et al. 2007 J. Biol. Chem. 282: 18129-18140;
Xia et al. 2008 Blood 111: 5195; and
Yang et al. 2009 Int. J. Bioch. Cell Biol. 41: 853-861.

Additional inhibitors of BMP6 are known. Any of these can be used in combination with any antibody or antigen-binding fragment thereof disclosed herein.

A combination therapy regimen may be additive, or it may produce synergistic results (e.g., reductions in BMP6 activity more than expected for the combined use of the two agents). In one embodiment, the present invention provide a combination therapy for preventing and/or treating anemia or another BMP6 related disease as described above with BMP6-binding antibody of the invention and an anti-anemia agent or method, such as ESA, erythropoietin, iron, or blood transfusion.

Diagnostic Uses

In one aspect, the invention encompasses diagnostic assays for determining BMP6 and/or nucleic acid expression as well as BMP6 function, in the context of a biological sample (e.g., blood, serum, cells, tissue) or from individual is afflicted with a disease or disorder, or is at risk of developing a disorder associated with anemia. Diagnostic assays, such as competitive assays rely on the ability of a labelled analogue (the "tracer") to compete with the test sample analyte for a limited number of binding sites on a common binding partner. The binding partner generally is insolubilized before or after the competition and then the tracer and analyte bound to the binding partner are separated from the unbound tracer and analyte. This separation is accomplished by decanting (where the binding partner was preinsolubilized) or by centrifuging (where the binding partner was precipitated after the competitive reaction). The amount of test sample analyte is inversely proportional to the amount of bound tracer as measured by the amount of marker substance. Dose-response curves with known amounts of analyte are prepared and compared with the test results in order to quantitatively determine the amount of analyte present in the test sample. These assays are called ELISA systems when enzymes are used as the detectable markers. In an assay of this form, competitive binding between antibodies and BMP6-binding antibodies results in the bound BMP6, preferably the BMP6 epitopes of the invention, being a measure of antibodies in the serum sample, most particularly, neutralising antibodies in the serum sample.

A significant advantage of the assay is that measurement is made of neutralising antibodies directly (i.e., those which interfere with binding of BMP6, specifically, epitopes). Such an assay, particularly in the form of an ELISA test has considerable applications in the clinical environment and in routine blood screening. In the clinical diagnosis or monitoring of patients with disorders associated with anemia, the detection of BMP6 proteins in comparison to the levels in a corresponding biological sample from a normal subject is indicative of a patient with disorders associated with anemia.

In vivo diagnostic or imaging is described in US2006/0067935. Briefly, these methods generally comprise administering or introducing to a patient a diagnostically effective amount of BMP6 binding molecule that is operatively attached to a marker or label that is detectable by non-invasive methods. The antibody-marker conjugate is allowed sufficient time to localize and bind to BMP6. The patient is then exposed to a detection device to identify the detectable marker, thus forming an image of the location of the BMP6 binding molecules in the tissue of a patient. The presence of BMP6 binding antibody or an antigen-binding fragment thereof is detected by determining whether an antibody-marker binds to a component of the tissue. Detection of an increased level in BMP6 proteins or a combination of protein in comparison to a normal individual without anemia is indicative of a predisposition for and/or on set of disorders associated with anemia. These aspects of the invention are also for use in tissue imaging methods and combined diagnostic and treatment methods.

The invention also pertains to the field of predictive medicine in which diagnostic assays, prognostic assays, pharmacogenomics, and monitoring clinical trials are used for prognostic (predictive) purposes to thereby treat an individual prophylactically.

The invention also provides for prognostic (or predictive) assays for determining whether an individual is at risk of developing a disorder associated with dysregulation of BMP6 pathway activity. For example, mutations in BMP6 gene can be assayed in a biological sample. Such assays can be used for prognostic or predictive purpose to thereby prophylactically treat an individual prior to the onset of a disorder characterized by or associated with BMP6, nucleic acid expression or activity.

Another aspect of the invention provides methods for determining BMP6 nucleic acid expression or BMP6 activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.)

Yet another aspect of the invention provides a method of monitoring the influence of agents (e.g., drugs) on the expression or activity of BMP6 in clinical trials.

Pharmaceutical Compositions

The invention provides pharmaceutical compositions comprising the BMP6-binding antibody or binding fragment thereof formulated together with a pharmaceutically acceptable carrier. The compositions can additionally contain one or more other therapeutical agents that are suitable for treating or preventing a BMP6-associated disease (e.g., anemia). Pharmaceutically carriers enhance or stabilize the composition, or to facilitate preparation of the composition. Pharmaceutically acceptable carriers include solvents, dispersion media, coatings, antibacterial and antifungal agents, isotonic and absorption delaying agents, and the like that are physiologically compatible.

A pharmaceutical composition of the present invention can be administered by a variety of methods known in the art. The route and/or mode of administration vary depending upon the desired results. Administration can be intravenous, intramuscular, intraperitoneal, or subcutaneous, or administered proximal to the site of the target. The pharmaceutically acceptable carrier should be suitable for intravenous, intramuscular, subcutaneous, parenteral, spinal or epidermal administration (e.g., by injection or infusion). Depending on the route of administration, the active compound, i.e., antibody, bispecific and multispecific molecule, may be coated in a material to protect the compound from the action of acids and other natural conditions that may inactivate the compound.

The composition should be sterile and fluid. Proper fluidity can be maintained, for example, by use of coating such as lecithin, by maintenance of required particle size in the case of dispersion and by use of surfactants. In many cases, it is preferable to include isotonic agents, for example, sugars, polyalcohols such as mannitol or sorbitol, and sodium chloride in the composition. Long-term absorption of the injectable compositions can be brought about by including in the composition an agent which delays absorption, for example, aluminum monostearate or gelatin. Pharmaceutical compositions of the invention can be prepared in accordance with methods well known and routinely practiced in the art. See, e.g., Remington: The Science and Practice of Pharmacy, Mack Publishing Co., 20th ed., 2000; and Sustained and Controlled Release Drug Delivery Systems, J. R. Robinson, ed., Marcel Dekker, Inc., New York, 1978. Pharmaceutical compositions are preferably manufactured under GMP conditions. Typically, a therapeutically effective dose or efficacious dose of the BMP6-binding antibody is employed in the pharmaceutical compositions of the invention. The BMP6-binding antibodies are formulated into pharmaceutically acceptable dosage forms by conventional methods known to those of skill in the art. Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A physician or veterinarian can start doses of the antibodies and antigen-binding fragments thereof of the invention employed in the pharmaceutical composition at levels lower than that required to achieve the desired therapeutic effect and gradually increase the dosage until the desired effect is achieved. In general, effective doses of the compositions of the present invention, for the treatment of an allergic inflammatory disorder described herein vary depending upon many different factors, including means of administration, target site, physiological state of the patient, whether the patient is human or an animal, other medications administered, and whether treatment is prophylactic or therapeutic. Treatment dosages need to be titrated to optimize safety and efficacy. For systemic administration with an antibody, the dosage ranges from about 0.0001 to 100 mg/kg, and more usually 0.001 to 15 mg/kg, of the host body weight. An exemplary treatment regime entails systemic administration (e.g., intravenous or subcutaneous) once, or alternatively, more than once on a dosing schedule (e.g., repeat dosing), for example, once per every two weeks, once every three weeks, or once a month or once every 3 to 6 months. For intravitreal administration with an antibody, the dosage ranges from about 0.0001 to about 10 mg. An exemplary treatment regime entails systemic administration once per every two weeks, once every three weeks, or once a month or once every 3 to 6 months.

Antibody is usually administered on multiple occasions. Intervals between single dosages can be weekly, monthly or yearly. Intervals can also be irregular as indicated by measuring blood levels of BMP6-binding antibody in the patient. In some methods of systemic administration, dosage is adjusted to achieve a plasma antibody concentration of 1-1000 □g/ml and in some methods 25-500 □g/ml. Alternatively, antibody can be administered as a sustained release formulation, in which case less frequent administration is required. Dosage and frequency vary depending on the half-life of the antibody in the patient. In general, humanized antibodies show longer half life than that of chimeric antibodies and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

In a specific embodiment the composition comprising the antibody or antigen binding fragment of the invention is administered at a dose (antibody or antigen-binding fragment thereof) of between 0.001 mg/kg and 0.1 mg/kg. In a specific embodiment the composition comprising the antibody or antigen binding fragment of the invention is administered at a dose of between about 0.001 mg/kg and about 0.1 mg/kg. In a specific embodiment the composition comprising the antibody or antigen binding fragment of the invention is administered at a dose of 0.001 mg/kg, 0.0016 mg/kg, 0.0025 mg/kg, 0.0040 mg/kg, 0.0063 mg/kg, 0.01 mg/kg, 0.016 mg/kg, 0.025 mg/kg, 0.040 mg/kg, 0.063 mg/kg, or 0.1 mg/kg. In a specific embodiment the composition comprising the antibody or antigen binding fragment of the invention is administered at a dose of about 0.001 mg/kg, about 0.0016 mg/kg, about 0.0025 mg/kg, about 0.0040 mg/kg, about 0.0063 mg/kg, about 0.01 mg/kg, about 0.016 mg/kg, about 0.025 mg/kg, about 0.040 mg/kg, about 0.063 mg/kg, or about 0.1 mg/kg. In an embodiment, the composition comprising the antibody or antigen binding fragment of the invention is administered, including, for example, at any of the doses recited above, intravenously. In embodiments, the intravenous administration is an intravenous infusion. In embodiments, the infusion takes place over 30-60 minutes. In embodiments, the infusion takes place over about 30-60 minutes.

Level of Ferritin

The disclosed methods may involve the determination of the level of ferritin from a biological sample, e.g., blood or serum, and in embodiments, patients, e.g., patients having a disease described herein, e.g., anemia, are selected for treatment with a BMP6 antagonist (e.g., as described herein, e.g., a BMP6 antibody, e.g., Antibody 7, e.g., as described in Table 1) or are predicted to have a response to BMP6 antagonist therapy based on the level of ferritin.

In embodiments, the level of ferritin, e.g., the level of ferritin predictive of response (e.g., increased response) to treatment with BMP6 is ≤about 1500 ng/mL. In embodiments, the level of ferritin, e.g., the level of ferritin predictive of response (e.g., increased response) to treatment with BMP6 is ≤1500 ng/mL. In embodiments, the level of ferritin is <1500 ng/mL. In embodiments, the level of ferritin is ≤about 2000 ng/mL. In embodiments, the level of ferritin is ≤2000 ng/mL. In embodiments, the level of ferritin is <about 2000 ng/mL.

In embodiments, the level of ferritin, e.g., the level of ferritin predictive of response (e.g., increased response) to treatment with BMP6 is ≤about 1450 ng/mL, e.g., ≤about 1400 ng/mL, ≤about 1350 ng/mL, ≤about 1300 ng/mL, ≤about 1250 ng/mL, ≤about 1200 ng/mL, ≤about 1150 ng/mL, ≤about 1100 ng/mL, ≤about 1050 ng/mL, or ≤about 1000 ng/mL, etc.

In embodiments, the level of ferritin, e.g., the level of ferritin predictive of response (e.g., increased response) to treatment with BMP6 is ≥about 200 ng/mL, e.g., ≥about 250 ng/mL, ≥about 300 ng/mL, ≥about 350 ng/mL, ≥about 400 ng/mL, ≥about 450 ng/mL, ≥about 500 ng/mL, ≥about 550 ng/mL, ≥about 600 ng/mL, ≥about 650 ng/mL, ≥about 700 ng/mL, ≥about 750 ng/mL, ≥about 800 ng/mL, ≥about 850 ng/mL, ≥about 900 ng/mL, ≥about 950 ng/mL, ≥about 1000 ng/mL, or ≥about 1500 ng/mL, etc. In embodiments, the level of ferritin is between any of the levels recited above and about 2000 ng/mL.

In embodiments, the level of ferritin, e.g., the level of ferritin predictive of response (e.g., increased response) to treatment with BMP6 is ≥about 500 ng/mL, ≥about 550 ng/mL, ≥about 600 ng/mL, ≥about 650 ng/mL, ≥about 700 ng/mL, ≥about 750 ng/mL, ≥about 800 ng/mL, ≥about 850 ng/mL, ≥about 900 ng/mL, ≥about 950 ng/mL, ≥about 1000 ng/mL, or ≥about 1500 ng/mL, etc. In embodiments, the level of ferritin is between any of the levels recited above and about 2000 ng/mL. In embodiments, the level of ferritin, e.g., the level of ferritin predictive of response (e.g., increased response) to treatment with BMP6 is ≥about 500 ng/mL. In embodiments, the level of ferritin is between about 500 ng/mL, and about 2000 ng/mL. In embodiments, the level of ferritin is between about 500 ng/mL, and about 1000 ng/mL. In embodiments, the level of ferritin is between about 500 ng/mL and about 1500 ng/mL.

In embodiments, the level of ferritin, e.g., the level of ferritin predictive of response (e.g., increased response) to treatment with BMP6 is between about 200 ng/mL and about 1500 ng/mL. In embodiments, the level of ferritin, e.g., the level of ferritin predictive of response (e.g., increased response) to treatment with BMP6 is between about 300 ng/mL and about 1500 ng/mL. In embodiments, the level of ferritin, e.g., the level of ferritin predictive of response (e.g., increased response) to treatment with BMP6 is between about 400 ng/mL and about 1500 ng/mL. In embodiments, the level of ferritin, e.g., the level of ferritin predictive of response (e.g., increased response) to treatment with BMP6 is between about 500 ng/mL and about 1500 ng/mL. In embodiments, the level of ferritin, e.g., the level of ferritin predictive of response (e.g., increased response) to treatment with BMP6 is between about 600 ng/mL, and about 1500 ng/mL. In embodiments, the level of ferritin, e.g., the level of ferritin predictive of response (e.g., increased response) to treatment with BMP6 is between about 700 ng/mL and about 1500 ng/mL. In embodiments, the level of ferritin, e.g., the level of ferritin predictive of response (e.g., increased response) to treatment with BMP6 is between about 800 ng/mL and about 1500 ng/mL. In embodiments, the level of ferritin, e.g., the level of ferritin predictive of response (e.g., increased response) to treatment with BMP6 is between about 900 ng/mL and about 1500 ng/mL. In embodiments, the level of ferritin, e.g., the level of ferritin predictive of response (e.g., increased response) to treatment with BMP6 is between about 1000 and about 1500 ng/mL. In embodiments, the level of ferritin, e.g., the level of ferritin predictive of response (e.g., increased response) to treatment with BMP6 is between about 1100 ng/mL and about 1500 ng/mL. In embodiments, the level of ferritin, e.g., the level of ferritin predictive of response increased response) to treatment with BMP6 is between about 1200 ng/mL, and about 1500 ng/mL. In embodiments, the level of ferritin, e.g., the level of ferritin predictive of response (e.g., increased response) to treatment with BMP6 is between about 1300 ng/mL and about 1500 ng/mL. In embodiments, the level of ferritin, e.g., the level of ferritin predictive of response (e.g., increased response) to treatment with BMP6 is between about 1400 ng/mL and about 1500 ng/mL.

In embodiments, the level of ferritin, e.g., the level of ferritin predictive of response (e.g., increased response) to treatment with BMP6 is between about 200 ng/mL and about 1600 ng/mL. In embodiments, the level of ferritin, e.g., the level of ferritin predictive of response (e.g., increased response) to treatment with BMP6 is between about 300 ng/mL and about 1600 ng/mL. In embodiments, the level of ferritin, e.g., the level of ferritin predictive of response (e.g., increased response) to treatment with BMP6 is between about 400 ng/mL and about 1600 ng/mL. In embodiments, the level of ferritin, e.g., the level of ferritin predictive of response (e.g., increased response) to treatment with BMP6 is between about 500 ng/mL and about 1600 ng/mL. In embodiments, the level of ferritin, e.g., the level of ferritin predictive of response (e.g., increased response) to treatment with BMP6 is between about 600 ng/mL, and about 1600 ng/mL. In embodiments, the level of ferritin, e.g., the level of ferritin predictive of response (e.g., increased response) to treatment with BMP6 is between about 700 ng/mL and about 1600 ng/mL. In embodiments, the level of ferritin, e.g., the level of ferritin predictive of response (e.g., increased response) to treatment with BMP6 is between about 800 ng/mL and about 1600 ng/mL. In embodiments, the level of ferritin, e.g., the level of ferritin predictive of response (e.g., increased response) to treatment with BMP6 is between about 900 ng/mL and about 1600 ng/mL. In embodiments, the level of ferritin, e.g., the level of ferritin predictive of response (e.g., increased response) to treatment with BMP6 is between about 1000 ng/mL and about 1600 ng/mL. In embodiments, the level of ferritin, e.g., the level of ferritin predictive of response (e.g., increased response) to treatment with BMP6 is between about 1100 ng/mL and about 1600 ng/mL. In embodiments, the level of ferritin, e.g., the level of ferritin predictive of response (e.g., increased response) to treatment with BMP6 is between about 1200 ng/mL, and about 1600 ng/mL. In embodiments, the level of ferritin, e.g., the level of ferritin predictive of response (e.g., increased response) to treatment with BMP6 is between about 1300 ng/mL and about 1600 ng/mL. In embodiments, the level of ferritin, the level of ferritin predictive of response (e.g., increased response) to treatment with BMP6 is between about 1400 ng/mL and about 1600 ng/mL. In embodiments, the level of ferritin, e.g., the level of ferritin predictive of response (e.g., increased response) to treatment with BMP6 is between about 1500 ng/mL and about 1600 ng/mL.

In embodiments, the level of ferritin, e.g., the level of ferritin predictive of response (e.g., increased response) to treatment with BMP6 is between about 200 ng/mL and about 1700 ng/mL. In embodiments, the level of ferritin, e.g., the level of ferritin predictive of response (e.g., increased response) to treatment with BMP6 is between about 300 ng/mL and about 1700 ng/mL. In embodiments, the level of ferritin, e.g., the level of ferritin predictive of response (e.g., increased response) to treatment with BMP6 is between about 400 ng/mL and about 1700 ng/mL. In embodiments, the level of ferritin, e.g., the level of ferritin predictive of response (e.g., increased response) to treatment with BMP6 is between about 500 ng/mL and about 1700 ng/mL. In embodiments, the level of ferritin, e.g., the level of ferritin predictive of response (e.g., increased response) to treatment with BMP6 is between about 600 ng/mL and about 1700 ng/mL. In embodiments, the level of ferritin, e.g., the level of ferritin predictive of response (e.g., increased response) to treatment with BMP6 is between about 700 ng/mL and about 1700 ng/mL. In embodiments, the level of ferritin, e.g., the level of ferritin predictive of response (e.g., increased response) to treatment with BMP6 is between about 800 ng/mL and about 1700 ng/mL. In embodiments, the level of ferritin, e.g., the level of ferritin predictive of response (e.g., increased response) to treatment with BMP6 is between about 900 ng/mL and about 1700 ng/mL. In embodiments, the level of ferritin, e.g., the level of ferritin predictive of response (e.g., increased response) to treatment with BMP6 is between about 1000 ng/mL and about 1700 ng/mL. In embodiments, the level of ferritin, e.g., the level of ferritin predictive of response (e.g., increased response) to treatment with BMP6 is between about 1100 ng/mL and about 1700 ng/mL. In embodiments, the level of ferritin, e.g., the level of ferritin predictive of response (e.g., increased response) to treatment with BMP6 is between about 1200 ng/mL and about 1700 ng/mL. In embodiments, the level of ferritin, e.g., the level of ferritin predictive of response (e.g., increased response) to treatment with BMP6 is between about 1300 ng/mL and about 1700 ng/mL. In embodiments, the level of ferritin, the level of ferritin predictive of response (e.g., increased response) to treatment with BMP6 is between about 1400 ng/mL and about 1700 ng/mL. In embodiments, the level of ferritin, e.g., the level of ferritin predictive of response (e.g., increased response) to treatment with BMP6 is between about 1500 ng/mL and about 1700 ng/mL. In embodiments, the level of ferritin, e.g., the level of ferritin predictive of response (e.g., increased response) to treatment with BMP6 is between about 1600 ng/mL and about 1700 ng/mL.

In embodiments, the level of ferritin, e.g., the level of ferritin predictive of response (e.g., increased response) to treatment with BMP6 is between about 200 ng/mL and about 1800 ng/mL. In embodiments, the level of ferritin, e.g., the level of ferritin predictive of response (e.g., increased response) to treatment with BMP6 is between about 300 ng/mL and about 1800 ng/mL. In embodiments, the level of ferritin, e.g., the level of ferritin predictive of response (e.g., increased response) to treatment with BMP6 is between about 400 ng/mL and about 1800 ng/mL. In embodiments, the level of ferritin, e.g., the level of ferritin predictive of response increased response) to treatment with BMP6 is between about 500 ng/mL and about 1800 ng/mL. In embodiments, the level of ferritin, e.g., the level of ferritin predictive of response (e.g., increased response) to treatment with BMP6 is between about 600 ng/mL and about 1800 ng/mL. In embodiments, the level of ferritin, e.g., the level of ferritin predictive of response (e.g., increased response) to treatment with BMP6 is between about 700 ng/mL and about 1800 ng/mL. In embodiments, the level of ferritin, e.g., the level of ferritin predictive of response (e.g., increased response) to treatment with BMP6 is between about 800 ng/mL and about 1800 ng/mL. In embodiments, the level of ferritin, e.g., the level of ferritin predictive of response (e.g., increased response) to treatment with BMP6 is between about 900 ng/mL and about 1800 ng/mL. In embodiments, the level of ferritin, e.g., the level of ferritin predictive of response (e.g., increased response) to treatment with BMP6 is between about 1000 ng/mL and about 1800 ng/mL. In embodiments, the level of ferritin, e.g., the level of ferritin predictive of response (e.g., increased response) to treatment with BMP6 is between about 1100 ng/mL and about 1800 ng/mL. In embodiments, the level of ferritin, e.g., the level of ferritin predictive of response (e.g., increased response) to treatment with BMP6 is between about 1200 ng/mL, and about 1800 ng/mL. In embodiments, the level of ferritin, e.g., the level of ferritin predictive of response (e.g., increased response) to treatment with BMP6 is between about 1300 ng/mL and about 1800 ng/mL. In embodiments, the level of ferritin, e.g., the level of ferritin predictive of response (e.g., increased response) to treatment with BMP6 is between about 1400 ng/mL and about 1800 ng/mL. In embodiments, the level of ferritin, e.g., the level of ferritin predictive of response (e.g., increased response) to treatment with BMP6 is between about 1500 ng/mL and about 1800 ng/mL. In embodiments, the level of ferritin, e.g., the level of ferritin predictive of response (e.g., increased response) to treatment with BMP6 is between about 1600 ng/mL and about 1800 ng/mL. In embodiments, the level of ferritin, e.g., the level of ferritin predictive of response (e.g., increased response) to treatment with BMP6 is between about 1700 ng/mL and about 1800 ng/mL.

In embodiments, the level of ferritin, e.g., the level of ferritin predictive of response (e.g., increased response) to treatment with BMP6 is between about 200 ng/mL and about 1900 ng/mL. In embodiments, the level of ferritin, e.g., the level of ferritin predictive of response (e.g., increased response) to treatment with BMP6 is between about 300 ng/mL and about 1900 ng/mL. In embodiments, the level of ferritin, e.g., the level of ferritin predictive of response (e.g., increased response) to treatment with BMP6 is between about 400 ng/mL and about 1900 ng/mL. In embodiments, the level of ferritin, e.g., the level of ferritin predictive of response (e.g., increased response) to treatment with BMP6 is between about 500 ng/mL and about 1900 ng/mL. In embodiments, the level of ferritin, e.g., the level of ferritin predictive of response (e.g., increased response) to treatment with BMP6 is between about 600 ng/mL and about 1900 ng/mL. In embodiments, the level of ferritin, e.g., the level of ferritin predictive of response (e.g., increased response) to treatment with BMP6 is between about 700 ng/mL and about 1900 ng/mL. In embodiments, the level of ferritin, e.g., the level of ferritin predictive of response (e.g., increased response) to treatment with BMP6 is between about 800 ng/mL and about 1900 ng/mL. In embodiments, the level of ferritin, e.g., the level of ferritin predictive of response (e.g., increased response) to treatment with BMP6 is between about 900 ng/mL and about 1900 ng/mL. In embodiments, the level of ferritin, e.g., the level of ferritin predictive of response (e.g., increased response) to treatment with BMP6 is between about 1000 ng/mL and about 1900 ng/mL. In embodiments, the level of ferritin, e.g., the level of ferritin predictive of response (e.g., increased response) to treatment with BMP6 is between about 1100 ng/mL and about 1900 ng/mL. In embodiments, the level of ferritin, e.g., the level of ferritin predictive of response (e.g., increased response) to treatment with BMP6 is between about 1200 ng/mL and about 1900 ng/mL. In embodiments, the level of ferritin, e.g., the level of ferritin predictive of response (e.g., increased response) to treatment with BMP6 is between about 1300 ng/mL and about 1900 ng/mL. In embodiments, the level of ferritin, e.g., the level of ferritin predictive of response (e.g., increased response) to treatment with BMP6 is between about 1400 ng/mL and about 1900 ng/mL. In embodiments, the level of ferritin, e.g., the level of ferritin predictive of response (e.g., increased response) to treatment with BMP6 is between about 1500 ng/mL and about 1900 ng/mL. In embodiments, the level of ferritin, e.g., the level of ferritin predictive of response (e.g., increased response) to treatment with BMP6 is between about 1600 ng/mL and about 1900 ng/mL. In embodiments, the level of ferritin, e.g., the level of ferritin predictive of response (e.g., increased response) to treatment with BMP6 is between about 1700 ng/mL and about 1900 ng/mL. In embodiments, the level of ferritin, e.g., the level of ferritin predictive of response (e.g., increased response) to treatment with BMP6 is between about 1800 ng/mL and about 1900 ng/mL.

In embodiments, the level of ferritin, e.g., the level of ferritin predictive of response (e.g., increased response) to treatment with BMP6 is between about 200 ng/mL and about 2000 ng/mL. In embodiments, the level of ferritin, e.g., the level of ferritin predictive of response (e.g., increased response) to treatment with BMP6 is between about 300 ng/mL and about 2000 ng/mL. In embodiments, the level of ferritin, e.g., the level of ferritin predictive of response (e.g., increased response) to treatment with BMP6 is between about 400 ng/mL and about 2000 ng/mL. In embodiments, the level of ferritin, e.g., the level of ferritin predictive of response (e.g., increased response) to treatment with BMP6 is between about 500 ng/mL and about 2000 ng/mL. In embodiments, the level of ferritin, e.g., the level of ferritin predictive of response (e.g., increased response) to treatment with BMP6 is between about 600 ng/mL and about 2000 ng/mL. In embodiments, the level of ferritin, e.g., the level of ferritin predictive of response (e.g., increased response) to treatment with BMP6 is between about 700 ng/mL and about 2000 ng/mL. In embodiments, the level of terrain, e.g., the level of ferritin predictive of response (e.g., increased response) to treatment with BMP6 is between about 800 ng/mL and about 2000 ng/mL. In embodiments, the level of ferritin, e.g., the level of ferritin predictive of response (e.g., increased response) to treatment with BMP6 is between about 900 ng/mL and about 2000 ng/mL. In embodiments, the level of ferritin, e.g., the level of ferritin predictive of response (e.g., increased response) to treatment with BMP6 is between about 1000 ng/mL and about 2000 ng/mL. In embodiments, the level of ferritin, e.g., the level of ferritin predictive of response (e.g., increased response) to treatment with BMP6 is between about 1100 ng/mL and about 2000 ng/mL. In embodiments, the level of terrain, e.g., the level of terrain predictive of response (e.g., increased response) to treatment with BMP6 is between about 1200 ng/mL and about 2000 ng/mL. In embodiments, the level of ferritin, e.g., the level of ferritin predictive of response (e.g., increased response) to treatment with BMP6 is between about 1300 ng/mL and about 2000 ng/mL. In embodiments, the level of ferritin, e.g., the level of ferritin predictive of response (e.g., increased response) to treatment with BMP6 is between about 1400 ng/mL and about 2000 ng/mL. In embodiments, the level of ferritin, e.g., the level of ferritin predictive of response (e.g., increased response) to treatment with BMP6 is between about 1500 ng/mL and about 2000 ng/mL. In embodiments, the level of ferritin, e.g., the level of ferritin predictive of response (e.g., increased response) to treatment with BMP6 is between about 1600 ng/mL and about 2000 ng/mL. In embodiments, the level of ferritin, e.g., the level of ferritin predictive of response (e.g., increased response) to treatment with BMP6 is between about 1700 ng/mL and about 2000 ng/mL. In embodiments, the level of terrain, e.g., the level of terrain predictive of response (e.g., increased response) to treatment with BMP6 is between about 1800 ng/mL and about 2000 ng/mL. In embodiments, the level of terrain, e.g., the level of terrain predictive of response (e.g., increased response) to treatment with BMP6 is between about 1900 ng/mL and about 2000 ng/mL.

In embodiments, the level of ferritin, e.g., the level of ferritin predictive of response (e.g., increased response) to treatment with BMP6 is between 200 ng/mL and 1500 ng/mL. In embodiments, the level of ferritin, e.g., the level of ferritin predictive of response (e.g., increased response) to treatment with BMP6 is between 300 ng/mL and 1500 ng/mL. In embodiments, the level of ferritin, e.g., the level of ferritin predictive of response (e.g., increased response) to treatment with BMP6 is between 400 ng/mL and 1500 ng/mL. In embodiments, the level of ferritin, e.g., the level of ferritin predictive of response (e.g., increased response) to treatment with BMP6 is between 500 ng/mL and 1500 ng/mL. In embodiments, the level of ferritin, e.g., the level of ferritin predictive of response (e.g., increased response) to treatment with BMP6 is between 600 ng/mL and 1500 ng/mL. In embodiments, the level of ferritin, e.g., the level of ferritin predictive of response increased response) to treatment with BMP6 is between 700 ng/mL and 1500 ng/mL. In embodiments, the level of ferritin, e.g., the level of ferritin predictive of response (e.g., increased response) to treatment with BMP6 is between 800 ng/mL and 1500 ng/mL. In embodiments, the level of ferritin, e.g., the level of ferritin predictive of response (e.g., increased response) to treatment with BMP6 is between 900 ng/mL and 1500 ng/mL. In embodiments, the level of ferritin, e.g., the level of ferritin predictive of response (e.g., increased response) to treatment with BMP6 is between 1000 ng/mL and 1500 ng/mL. In embodiments, the level of ferritin, e.g., the level of ferritin predictive of response (e.g., increased response) to treatment with BMP6 is between 1100 ng/mL and 1500 ng/mL. In embodiments, the level of ferritin, e.g., the level of ferritin predictive of response (e.g., increased response) to treatment with BMP6 is between 1200 ng/mL and 1500 ng/mL. In embodiments, the level of ferritin, e.g., the level of ferritin predictive of response (e.g., increased response) to treatment with BMP6 is between 1300 ng/mL and 1500 ng/mL. In embodiments, the level of ferritin, e.g., the level of ferritin predictive of response (e.g., increased response) to treatment with BMP6 is between 1400 ng/mL and 1500 ng/mL. In preferred embodiments, all ranges are inclusive of the recited endpoint values.

In embodiments, the level of ferritin, e.g., the level of ferritin predictive of response (e.g., increased response) to treatment with BMP6 is between 200 ng/mL and 1600 ng/mL. In embodiments, the level of ferritin, e.g., the level of ferritin predictive of response (e.g., increased response) to treatment with BMP6 is between 300 ng/mL and 1600 ng/mL. In embodiments, the level of ferritin, e.g., the level of ferritin predictive of response (e.g., increased response) to treatment with BMP6 is between 400 ng/mL and 1600 ng/mL. In embodiments, the level of ferritin, e.g., the level of ferritin predictive of response (e.g., increased response) to treatment with BMP6 is between 500 ng/mL and 1600 ng/mL. In embodiments, the level of ferritin, e.g., the level of ferritin predictive of response (e.g., increased response) to treatment with BMP6 is between 600 ng/mL and 1600 ng/mL. In embodiments, the level of ferritin, e.g., the level of ferritin predictive of response (e.g., increased response) to treatment with BMP6 is between 700 ng/mL and 1600 ng/mL. In embodiments, the level of ferritin, e.g., the level of ferritin predictive of response (e.g., increased response) to treatment with BMP6 is between 800 ng/mL and 1600 ng/mL. In embodiments, the level of ferritin, e.g., the level of ferritin predictive of response (e.g., increased response) to treatment with BMP6 is between 900 ng/mL and 1600 ng/mL. In embodiments, the level of ferritin, e.g., the level of ferritin predictive of response (e.g., increased response) to treatment with BMP6 is between 1000 ng/mL and 1600 ng/mL. In embodiments, the level of ferritin, e.g., the level of ferritin predictive of response (e.g., increased response) to treatment with BMP6 is between 1100 ng/mL and 1600 ng/mL. In embodiments, the level of ferritin, e.g., the level of ferritin predictive of response (e.g., increased response) to treatment with BMP6 is between 1200 ng/mL and 1600 ng/mL. In embodiments, the level of ferritin, e.g., the level of ferritin predictive of response (e.g., increased response) to treatment with BMP6 is between 1300 ng/mL and 1600 ng/mL. In embodiments, the level of ferritin, e.g., the level of ferritin predictive of response (e.g., increased response) treatment with BMP6 is between 1400 ng/mL and 1600 ng/mL. In embodiments, the level of ferritin, e.g., the level of ferritin predictive of response (e.g., increased response) to treatment with BMP6 is between 1500 ng/mL and 1600 ng/mL. In preferred embodiments, all ranges are inclusive of the recited endpoint values.

In embodiments, the level of ferritin, e.g., the level of ferritin predictive of response (e.g., increased response) to treatment with BMP6 is between 200 ng/mL and 1700 ng/mL. In embodiments, the level of ferritin, e.g., the level of ferritin predictive of response (e.g., increased response) to treatment with BMP6 is between 300 ng/mL and 1700 ng/mL. In embodiments, the level of ferritin, e.g., the level of ferritin predictive of response (e.g., increased response) to treatment with BMP6 is between 400 ng/mL and 1700 ng/mL. In embodiments, the level of ferritin, e.g., the level of ferritin predictive of response (e.g., increased response) to treatment with BMP6 is between 500 ng/mL and 1700 ng/mL. In embodiments, the level of ferritin, e.g., the level of ferritin predictive of response (e.g., increased response) to treatment with BMP6 is between 600 ng/mL and 1700 ng/mL. In embodiments, the level of ferritin, e.g., the level of ferritin predictive of response (e.g., increased response) to treatment with BMP6 is between 700 ng/mL and 1700 ng/mL. In embodiments, the level of ferritin, e.g., the level of ferritin predictive of response (e.g., increased response) to treatment with BMP6 is between 800 ng/mL and 1700 ng/mL. In embodiments, the level of ferritin, e.g., the level of ferritin predictive of response (e.g., increased response) to treatment with BMP6 is between 900 ng/mL and 1700 ng/mL. In embodiments, the level of ferritin, e.g., the level of ferritin predictive of response (e.g., increased response) to treatment with BMP6 is between 1000 ng/mL and 1700 ng/mL. In embodiments, the level of ferritin, e.g., the level of ferritin predictive of response (e.g., increased response) to treatment with BMP6 is between 1100 ng/mL and 1700 ng/mL. In embodiments, the level of ferritin, e.g., the level of ferritin predictive of response (e.g., increased response) to treatment with BMP6 is between 1200 ng/mL and 1700 ng/mL. In embodiments, the level of ferritin, e.g., the level of ferritin predictive of response (e.g., increased response) to treatment with BMP6 is between 1300 ng/mL and 1700 ng/mL. In embodiments, the level of ferritin, e.g., the level of ferritin predictive of response (e.g., increased response) to treatment with BMP6 is between 1400 ng/mL and 1700 ng/mL. In embodiments, the level of ferritin, e.g., the level of ferritin predictive of response (e.g., increased response) to treatment with BMP6 is between 1500 ng/mL and 1700 ng/mL. In embodiments, the level of ferritin, the level of ferritin predictive of response (e.g., increased response) to treatment with BMP6 is between 1600 ng/mL and 1700 ng/mL. In preferred embodiments, all ranges are inclusive of the recited endpoint values.

In embodiments, the level of ferritin, e.g., the level of ferritin predictive of response (e.g., increased response) to treatment with BMP6 is between 200 ng/mL and 1800 ng/mL. In embodiments, the level of ferritin, e.g., the level of ferritin predictive of response (e.g., increased response) to treatment with BMP6 is between 300 ng/mL and 1800 ng/mL. In embodiments, the level of ferritin, the level of ferritin predictive of response (e.g., increased response) to treatment with BMP6 is between 400 ng/mL and 1800 ng/mL. In embodiments, the level of ferritin, e.g., the level of ferritin predictive of response (e.g., increased response) to treatment with BMP6 is between 500 ng/mL and 1800 ng/mL. In embodiments, the level of ferritin, e.g., the level of ferritin predictive of response (e.g., increased response) to treatment with BMP6 is between 600 ng/mL and 1800 ng/mL. In embodiments, the level of ferritin, e.g., the level of ferritin predictive of response (e.g., increased response) to treatment with BMP6 is between 700 ng/mL and 1800 ng/mL. In embodiments, the level of ferritin, e.g., the level of ferritin predictive of response (e.g., increased response) to treatment with BMP6 is between 800 ng/mL and 1800 ng/mL. In embodiments, the level of ferritin, e.g., the level of ferritin predictive of response (e.g., increased response) to treatment with BMP6 is between 900 ng/mL and 1800 ng/mL. In embodiments, the level of ferritin, e.g., the level of ferritin predictive of response (e.g., increased response) to treatment with BMP6 is between 1000 ng/mL and 1800 ng/mL. In embodiments, the level of ferritin, e.g., the level of ferritin predictive of response (e.g., increased response) to treatment with BMP6 is between 1100 ng/mL and 1800 ng/mL. In embodiments, the level of ferritin, e.g., the level of ferritin predictive of response increased response) to treatment with BMP6 is between 1200 ng/mL and 1800 ng/mL. In embodiments, the level of ferritin, e.g., the level of ferritin predictive of response (e.g., increased response) to treatment with BMP6 is between 1300 ng/mL and 1800 ng/mL. In embodiments, the level of ferritin, e.g., the level of ferritin predictive of response (e.g., increased response) to treatment with BMP6 is between 1400 ng/mL and 1800 ng/mL. In embodiments, the level of ferritin, e.g., the level of ferritin predictive of response (e.g., increased response) to treatment with BMP6 is between 1500 ng/mL and 1800 ng/mL. In embodiments, the level of ferritin, e.g., the level of ferritin predictive of response (e.g., increased response) to treatment with BMP6 is between 1600 ng/mL and 1800 ng/mL. In embodiments, the level of ferritin, e.g., the level of ferritin predictive of response (e.g., increased response) to treatment with BMP6 is between 1700 ng/mL and 1800 ng/mL. In preferred embodiments, all ranges are inclusive of the recited endpoint values.

In embodiments, the level of ferritin, e.g., the level of ferritin predictive of response (e.g., increased response) to treatment with BMP6 is between 200 ng/mL and 1900 ng/mL. In embodiments, the level of ferritin, e.g., the level of ferritin predictive of response (e.g., increased response) to treatment with BMP6 is between 300 ng/mL and 1900 ng/mL. In embodiments, the level of ferritin, e.g., the level of ferritin predictive of response (e.g., increased response) to treatment with BMP6 is between 400 ng/mL and 1900 ng/mL. In embodiments, the level of ferritin, e.g., the level of ferritin predictive of response (e.g., increased response) to treatment with BMP6 is between 500 ng/mL and 1900 ng/mL. In embodiments, the level of ferritin, e.g., the level of ferritin predictive of response (e.g., increased response) to treatment: with BMP6 is between 600 ng/mL and 1900 ng/mL. In embodiments, the level of ferritin, e.g., the level of ferritin predictive of response (e.g., increased response) to treatment with BMP6 is between 700 ng/mL and 1900 ng/mL. In embodiments, the level of ferritin, e.g., the level of ferritin predictive of response (e.g., increased response) to treatment with BMP6 is between 800 ng/mL and 1900 ng/mL. In embodiments, the level of ferritin, the level of ferritin predictive of response (e.g., increased response) to treatment with BMP6 is between 900 ng/mL and 1900 ng/mL. In embodiments, the level of ferritin, e.g., the level of ferritin predictive of response (e.g., increased response) to treatment with BMP6 is between 1000 ng/mL and 1900 ng/mL. In embodiments, the level of ferritin, e.g., the level of ferritin predictive of response (e.g., increased response) to treatment with BMP6 is between 1100 ng/mL and 1900 ng/mL. In embodiments, the level of ferritin, e.g., the level of ferritin predictive of response (e.g., increased response) to treatment with BMP6 is between 1200 ng/mL and 1900 ng/mL. In embodiments, the level of ferritin, e.g., the level of ferritin predictive of response (e.g., increased response) to treatment with BMP6 is between 1300 ng/mL and 1900 ng/mL. In embodiments, the level of ferritin, e.g., the level of ferritin predictive of response (e.g., increased response) to treatment with BMP6 is between 1400 ng/mL and 1900 ng/mL. In embodiments, the level of ferritin, e.g., the level of ferritin predictive of response (e.g., increased response) to treatment with BMP6 is between 1500 ng/mL and 1900 ng/mL. In embodiments, the level of ferritin, e.g., the level of ferritin predictive of response (e.g., increased response) to treatment with BMP6 is between 1600 ng/mL and 1900 ng/mL. In embodiments, the level of ferritin, e.g., the level of ferritin predictive of response (e.g., increased response) to treatment with BMP6 is between 1700 ng/mL and 1900 ng/mL. In embodiments, the level of ferritin, e.g., the level of ferritin predictive of response (e.g., increased response) to treatment with BMP6 is between 1800 ng/mL and 1900 ng/mL. In preferred embodiments, all ranges are inclusive of the recited endpoint values.

In embodiments, the level of ferritin, e.g., the level of ferritin predictive of response (e.g., increased response) to treatment with BMP6 is between 200 ng/mL and 2000 ng/mL. In embodiments, the level of ferritin, e.g., the level of ferritin predictive of response (e.g., increased response) to treatment with BMP6 is between 300 ng/mL and 2000 ng/mL. In embodiments, the level of ferritin, e.g., the level of ferritin predictive of response (e.g., increased response) to treatment with BMP6 is between 400 ng/mL and 2000 ng/mL. In embodiments, the level of ferritin, e.g., the level of ferritin predictive of response (e.g., increased response) to treatment with BMP6 is between 500 ng/mL and 2000 ng/mL. In embodiments, the level of ferritin, e.g., the level of ferritin predictive of response (e.g., increased response) to treatment with BMP6 is between 600 ng/mL and 2000 ng/mL. In embodiments, the level of ferritin, e.g., the level of ferritin predictive of response (e.g., increased response) to treatment with BMP6 is between 700 ng/mL and 2000 ng/mL. In embodiments, the level of ferritin, e.g., the level of ferritin predictive of response (e.g., increased response) to treatment with BMP6 is between 800 ng/mL and 2000 ng/mL. In embodiments, the level of ferritin, e.g., the level of ferritin predictive of response (e.g., increased response) to treatment with BMP6 is between 900 ng/mL and 2000 ng/mL. In embodiments, the level of ferritin, e.g., the level of ferritin predictive of response (e.g., increased response) to treatment with BMP6 is between 1000 ng/mL and 2000 ng/mL. In embodiments, the level of ferritin, e.g., the level of ferritin predictive of response (e.g., increased response) to treatment with BMP6 is between 1100 ng/mL and 2000 ng/mL. In embodiments, the level of ferritin, e.g., the level of ferritin predictive of response (e.g., increased response) to treatment with BMP6 is between 1200 ng/mL and 2000 ng/mL. In embodiments, the level of ferritin, e.g., the level of ferritin predictive of response (e.g., increased response) to treatment with BMP6 is between 1300 ng/mL and 2000 ng/mL. In embodiments, the level of ferritin, e.g., the level of ferritin predictive of response (e.g., increased response) to treatment with BMP6 is between 1400 ng/mL and 2000 ng/mL. In embodiments, the level of ferritin, e.g., the level of ferritin predictive of response (e.g., increased response) to treatment with BMP6 is between 1500 ng/mL and 2000 ng/mL. In embodiments, the level of ferritin, e.g., the level of ferritin predictive of response (e.g., increased response) to treatment with BMP6 is between 1600 ng/mL and 2000 ng/mL. In embodiments, the level of ferritin, e.g., the level of ferritin predictive of response (e.g., increased response) to treatment with BMP6 is between 1700 ng/mL and 2000 ng/mL. In embodiments, the level of ferritin, e.g., the level of ferritin predictive of response (e.g., increased response) to treatment with BMP6 is between 1800 ng/mL and 2000 ng/mL. In preferred embodiments, all ranges are inclusive of the recited endpoint values.

In embodiments, the levels of ferritin described above are measured from a biological sample selected from blood and serum. In embodiments, the levels of ferritin described above are measured from serum.

Techniques for Assaying, Diagnostic Methods and Methods of Producing Transmittable Form of Information The disclosed methods are useful for the treatment, prevention, or amelioration of diseases associated with low iron levels, e.g., diseases described herein, e.g., anemia, as well as predicting the likelihood of a disease patient's response to treatment with a BMP6 antagonist, e.g., Antibody 7 (e.g., as described in Table 1). These methods employ, inter alia, determining whether a patient has a particular level of ferritin, e.g., as described herein, in a sample from the patient. A biological sample from the patient may be assayed for the level of ferritin by any applicable conventional means.

Numerous biological samples may be used to identify the presence the marker, e.g., proteins, the level of expression of genes or proteins, and the activity of a protein, e.g., blood, synovial fluid, buffy coat, serum, plasma, lymph, feces, urine, tear, saliva, cerebrospinal fluid, buccal swabs, sputum, or tissue. Various sources within a biological sample may be used in the disclosed methods, e.g., one may assay a biological sample, e.g., blood or serum, from the patient for the level of ferritin. We have determined that the level of ferritin may be a useful biomarker in determining or predicting response to therapy with a BMP9 antagonist. Accordingly, a skilled artisan will understand that one may identify whether a subject has a given level of ferritin by assaying a biological sample, e.g., blood or serum, from the patient for the level of ferritin. In preferred embodiments, patient serum is analyzed to determine whether a subject has a particular level of ferritin. In other preferred embodiments, patient blood is analyzed to determine whether a subject has a particular level of ferritin.

As described herein, the invention is based in part on the conclusion that the level of ferritin may be useful to predict improved response to BMP6 antagonism (e.g., Antibody 7, as described in Table 1) for anemia or other disease described herein. Detection of ferritin can be performed using any known method in the art including, but not limited, to immunocytochemical staining, ELISA, flow cytometry, Western blot, spectrophotometry, HPLC, and mass spectrometry. One method for detecting polypeptide products in a sample is by means of a probe that is a binding protein capable of interacting specifically with a marker protein (e.g., an antibody capable of binding ferritin protein). Preferably, labeled antibodies, binding portions thereof, or other binding partners can be used. The antibodies can be monoclonal or polyclonal in origin, or may be biosynthetically produced. The binding partners may also be naturally occurring molecules or synthetically produced. The amount of complexed proteins is determined using standard protein detection methodologies described in the art. A detailed review of immunological assay design, theory and protocols can be found in numerous texts in the art, including Practical Immunology, Butt, W. R., ed., Marcel Dekker, New York, 1984. A variety of assays are available for detecting proteins with labeled antibodies. Direct labels include fluorescent or luminescent tags, metals, dyes, radionucleides, and the like, attached to the antibody. Indirect labels include various enzymes well known in the art, such as alkaline phosphatase, hydrogen peroxidase and the like. In a one-step assay, polypeptide products, if present, are immobilized and incubated with a labeled antibody. The labeled antibody binds to the immobilized target molecule. After washing to remove unbound molecules, the sample is assayed for the label.

The use of immobilized antibodies specific for the proteins or polypeptides is also contemplated by the present disclosure. The antibodies can be immobilized onto a variety of solid supports, such as magnetic or chromatographic matrix particles, the surface of an assay place (such as microtiter wells), pieces of a solid substrate material (such as plastic, nylon, paper), and the like. An assay strip can be prepared by coating the antibody or a plurality of antibodies in an array on solid support. This strip can then be dipped into the test sample and then processed quickly through washes and detection steps to generate a measurable signal, such as a colored spot.

In a two-step assay, immobilized marker (e.g., ferritin) may be incubated with an unlabeled antibody. The unlabeled antibody complex, if present, is then bound to a second, labeled antibody that is specific for the unlabeled antibody. The sample is washed and assayed for the presence of the label. The choice of marker used to label the antibodies will vary depending upon the application. However, the choice of the marker is readily determinable to one skilled in the art. The antibodies may be labeled with a radioactive atom, an enzyme, a chromophoric or fluorescent moiety, or a colorimetric tag. The choice of tagging label also will depend on the detection limitations desired. Enzyme assays (ELISAs) typically allow detection of a colored product formed by interaction of the enzyme-tagged complex with an enzyme substrate. Some examples of radioactive atoms include 32P, 125I, 3H, and 14P. Some examples of enzymes include horseradish peroxidase, alkaline phosphatase, beta-galactosidase, and glucose-6-phosphate dehydrogenase. Some examples of chromophoric moieties include fluorescein and rhodamine. The antibodies may be conjugated to these labels by methods known in the art. For example, enzymes and chromophoric molecules may be conjugated to the antibodies by means of coupling agents, such as dialdehydes, carbodiimides, dimaleimides, and the like. Alternatively, conjugation may occur through a ligand-receptor pair. Some suitable ligand-receptor pairs include, for example, biotin-avidin or -streptavidin, and antibody-antigen.

In one aspect, the present disclosure contemplates the use of a sandwich technique for detecting polypeptide products in biological samples. The technique requires two antibodies capable of binding the protein of interest: e.g., one immobilized onto a solid support and one free in solution, but labeled with some easily detectable chemical compound. Examples of chemical labels that may be used for the second antibody include but are not limited to radioisotopes, fluorescent compounds, and enzymes or other molecules which generate colored or electrochemically active products when exposed to a reactant or enzyme substrate. When samples containing polypeptide products are placed in this system, the polypeptide products hinds to both the immobilized antibody and the labeled antibody. The result is a "sandwich" immune complex on the support's surface. The complexed protein is detected by washing away nonbound sample components and excess labeled antibody, and measuring the amount of labeled antibody complexed to protein on the support's surface. The sandwich immunoassay is highly specific and very sensitive, provided that labels with good limits of detection are used.

Preferably, the presence of polypeptide products in a sample is detected by radioimmunoassays or enzyme-linked immunoassays, competitive binding enzyme-linked immunoassays, dot blot, Western blot, chromatography, preferably high performance liquid chromatography (HPLC), or other assays known in the art. Specific immunological binding of the antibody to the protein or polypeptide can be detected directly or indirectly.

Dot blotting is routinely practiced by the skilled artisan to detect a desired protein using an antibody as a probe (Promega Protocols and Applications Guide, Second Edition, 1991, Page 263, Promega Corporation). Samples are applied to a membrane using a dot blot apparatus. A labeled probe is incubated with the membrane, and the presence of the protein is detected.

Western blot analysis is well known to the skilled artisan (Sambrook et al., Molecular Cloning, A Laboratory Manual, 1989, Vol. 3, Chapter 18, Cold Spring Harbor Laboratory). In Western blot, the sample is separated by SDS-PAGE. The gel is transferred to a membrane. The membrane is incubated with labeled antibody for detection of the desired protein.

The assays described above involve steps such as but not limited to, immunoblotting, immunodiffusion, immunoelectrophoresis, or immunoprecipitation. In some embodiments, an automatic analyzer is used to determine the presence and/or level of ferritin.

The level of ferritin activity may be assayed by various methods disclosed in the art, e.g., via the methods set forth in Kochan et al. (2011) Proc Natl Acad Sci USA. 108(19): 7745-50.

For comparative purposes, the level of ferritin expression, ferritin protein, or ferritin activity from a patient may be compared to the level of ferritin expression, ferritin protein, or ferritin activity from a control. The control may be a reference level of ferritin expression, ferritin protein, or ferritin activity derived from subjects (e.g., anemia patients) known to respond well to treatment with a BMP6 antagonist (e.g., Antibody 7, described in Table 1) or subjects known to respond poorly to treatment with a BMP6 antagonist (e.g., Antibody 7, described in Table 1), as the case may be. A control level of expression may be derived from biological samples from reference subjects (i.e., anemia patients known to respond well to treatment with a BMP6 antagonist (e.g., Antibody 7, described in Table 1) or subjects known to respond poorly to treatment with a BMP6 antagonist (e.g., Antibody 7, described in Table 1)), or may simply be a numerical standard (e.g., mean, median, range, [+/−standard deviation]) previously derived from reference subjects. In some embodiments the control is a reference level of ferritin expression, ferritin protein, or ferritin activity derived from a subject known to respond poorly to treatment with a BMP6 antagonist and the level of ferritin expression, ferritin protein, or ferritin activity (as the case may be) from the patient is compared to this control. In other embodiments, the control is a reference level of ferritin expression, ferritin protein, or ferritin activity derived from a subject known to respond well to treatment with a BMP6 antagonist and the level of ferritin expression, ferritin protein, or ferritin activity from the patient to be treated is compared to this control, wherein a similar (e.g., statistically similar) level of ferritin expression, ferritin protein, or ferritin activity in the patient (relative to a control) provides an indication that the patient will have an increased likelihood of responding to treatment with the BMP6 antagonist Antibody 7, described in Table 7).

In performing any of the methods described herein that require determining the presence or level of ferritin expression, ferritin protein, or ferritin activity, such determination may be made by consulting a data repository that contains sufficient information on the patient's composition to determine whether the patient has the marker level of marker) of interest. Preferably, the data repository lists the marker and level of marker of interest in the individual. The data repository could include the individual's patient records, a medical data card, a file (e.g., a flat ASCII file) accessible by a computer or other electronic or non-electronic media on which appropriate information or genetic data can be stored. As used herein, a medical data card is a portable storage device such as a magnetic data card, a smart card, which has an on-board processing unit and which is sold by vendors such as Siemens of Munich Germany, or a flash-memory card. If the data repository is a file accessible by a computer; such files may be located on various media, including: a server, a client, a hard disk, a CD, a DVD, a personal digital assistant such as a smart phone, Palm Pilot, a tape recorder, a zip disk, the computer's internal ROM (read-only-memory) or the internet or worldwide web. Other media for the storage of files accessible by a computer will be obvious to one skilled in the art.

Typically, once levels of ferritin expression, ferritin protein, or ferritin activity is determined, physicians or genetic counselors or patients or other researchers may be informed of the result. Specifically the result can be cast in a transmittable form of information that can be communicated or transmitted to other researchers or physicians or genetic counselors or patients. Such a form can vary and can be tangible or intangible. The result in the individual tested can be embodied in descriptive statements, diagrams, photographs, charts, images or any other visual forms. For example, images of gel electrophoresis or capture assays can be used in explaining the results. Statements regarding levels of ferritin expression, ferritin protein, or ferritin activity are also useful in indicating the testing results. These statements and visual forms can be recorded on a tangible media such as papers, computer readable media such as floppy disks, compact disks, etc., or on an intangible media, e.g., an electronic media in the form of email or website on internet or intranet. In addition, the result can also be recorded in a sound form and transmitted through any suitable media, e.g., analog or digital cable lines, fiber optic cables, etc., via telephone, facsimile, wireless mobile phone, internet phone and the like. All such forms (tangible and intangible) would constitute a "transmittable form of information". Thus, the information and data on a test result can be produced anywhere in the world and transmitted to a different location. The test result in a transmittable form thus can be imported into the U.S. Accordingly, the present disclosure also encompasses a method for producing a transmittable form of information containing levels of ferritin expression, ferritin protein, or ferritin activity in an individual. This form of information is useful for predicting the responsiveness of a patient having a disease described herein, e.g., anemia, with a BMP6 antagonist, for selecting a course of treatment based upon that information, and for selectively treating a patient based upon that information.

Disclosed herein are methods of predicting the likelihood that a patient with levels of ferritin protein will respond (e.g., respond with enhanced efficacy, e.g., relative to a general population of patients suffering from the same or similar disease) to treatment with a BMP6 antagonist, comprising detecting the level of ferritin in a biological sample from the patient, wherein a level of ferritin described herein, e.g., 1500 ng/mL, is indicative of an increased likelihood that the patient will respond to treatment with the BMP6 antagonist.

In some embodiments, the method further comprises the step of obtaining the biological sample from the patient, wherein the step of obtaining is performed prior to the step of assaying.

In some embodiments, the biological sample is selected from the group consisting of synovial fluid, blood, serum, feces, plasma, urine, tear, saliva, cerebrospinal fluid, a leukocyte sample and a tissue sample. In some embodiments, the biological sample is blood or serum.

In some embodiments, the presence and/or level of ferritin expression, ferritin protein, or ferritin activity is detected by a technique selected from the group consisting of immunoassays, immunohistochemistry, ELISA, flow cytometry, Western blot, HPLC, and mass spectrometry.

In some embodiments of the disclosed methods and uses, the BMP6 antagonist is a BMP6 binding molecule or a BMP6 receptor binding molecule. In some embodiments, the BMP6 binding molecule or BMP6 receptor binding molecule is a BMP6 binding molecule. In some embodiments, the BMP6 binding molecule is a BMP6 antibody or antigen-binding portion thereof.

In some embodiments of the disclosed methods and uses, the BMP6 antibody is Antibody 7, as described in Table 1.

Methods of Treatment and Uses of BMP6 Antagonists

The disclosed methods allow clinicians to provide a personalized therapy for patients suffering from a disease described herein, e.g., anemia patients, i.e., they allow determination of whether to selectively treat the patient with a BMP6 antagonist (e.g., Antibody 7, e.g., as described in Table 1). In this way, a clinician can maximize the benefit and minimize the risk of BMP6 antagonism in the entire population of patients afflicted with a disease described herein, e.g., anemia. It will be understood that BMP6 antagonists, e.g., BMP6 binding molecules (e.g., BMP6 antibody or antigen-binding portion thereof, e.g., Antibody 7, e.g., as described in Table 1) or BMP6 receptor binding molecules (e.g., BMP6 receptor antibody or antigen-binding portion thereof) are useful for the treatment, prevention, or amelioration of a disease described herein, e.g., anemia (e.g., signs and symptoms, etc.) as disclosed herein, particularly in patients that have a level of ferritin described herein.

EXAMPLES

The following examples are provided to further illustrate the invention but not to limit its scope. Other variants of the invention will be readily apparent to one of ordinary skill in the art and are encompassed by the appended claims.

Example 1

In Vitro and In Vivo Activity, and PK/PD of Anti-BMP6 Antibodies Materials

Test compounds were Antibodies 5, 6 and 7 (Table 8), at a concentration of ~8 mg/ml in 50 mM citrate buffer, pH 7.0, 150 mM NaCl and diluted in PBS before animal administration. Male C56BL/6 mice or Sprague Dawley rats were used (Table 9).

TABLE 8

Properties of BMP6 antagonist antibodies

| Antibody ID | Framework | KD(nM) BMP6 | IC50(ug/ml) BMP6 reporter |
|---|---|---|---|
| ANTIBODY 5 | VH3_15, Vl1 | 0.1 | 0.06 |
| ANTIBODY 6 | VH3_15, Vl1 | <0.1 | 0.08 |
| ANTIBODY 7 | VH3_15, Vl1 | 0.1 | 0.07 |

TABLE 9

Animal characteristics

| Species | Strain | Category | Vendor | Gender | Age |
|---|---|---|---|---|---|
| Mouse (Mus musculus) | C57BL/6 | wild-type | Jackson Laboratory, Bar Harbor, ME | Male | 8-9 Weeks |
| Rat (Rattus norvegicu) | Sprague Dawley | wild-type | Charles River Laboratory, Wilmington, MA | Male | 8-12 weeks |

For BMP reporter gene assays, a lentiviral vector was constructed containing BMP responsive element BRE in the promoter [Korchynskyi et al, 2002. J. Biol. Chem. 277: 4882-91] driving firefly luciferase derived from pGL4-BRE2-Luc2. The lentiviral vector was used to stably transfect HEP3B hepatoma cell line. The cell line was maintained in EMEM with 10% fetal bovine serum, 1% Penicillin/streptomycin, and 5 ug/ml Blasticidin. Recombinant human BMP proteins were purchased from R&D Systems.

Brucella abortus Ring Test Antigen (strain 1119-3) in 60 ml bottles were purchased from U.S. Department of Agriculture, Animal and Plant Health Inspection Service, National Veterinary Services Laboratories, Ames, Iowa. Brucellosis ring test antigen contains a suspension of killed, stained B. abortus strain 1119-3 cells in phenolized buffer. The concentration of each 60 mL bottle is approximately $10^9$ particles/ml. A $5 \times 10^9$ stock is washed and prepared in the following manner. First, 60 ml bottles are removed from refrigerator and mix completely. 500 ml of BA is then transferred into 500 mL centrifuge bottle. These are then centrifuges at 10,000 rpm for 15 minutes using an ultracentrifuge. The supernatant is removed and re-suspend in 100 mL PBS, resulting a $5\times10^9$ particles/ml stock, which was aliquoted and frozen at −80° C.

Animal Maintenance Conditions

Animals were socially housed in micro-isolator solid-bottom cages during the acclimation and study periods. Animals were kept under a standard light cycle as follows: 12 hours dark, 12 hours light (lights on: 6:30 AM, lights off: 6:30 PM) with room temperature 21-23° C. and humidity 30-70%. During the acclimation and study periods, animals were given access to rodent diets and water ad libitum (ad lib).

Experimental Conditions

Determination of the Antibody Activity in BMP Reporter Gene Assay

In a typical assay, $0.6\times10^4$ BRE-Luc2 HEP3B cells were seeded on 384-well plates in 25 ul of basic culture medium except that serum was reduced to 2%. On the next day antibodies diluted in PBS were added, following by the addition of BMP6 to a final concentration of 10 ng/ml. The volume was brought to 50 ul with EMEM media without any serum, making final serum concentration 1%. As counter assays, activation with BMP2/4/7 was done in parallel. BrighGlo assay (Promega) was performed 24 hours post-antibody addition according to manufacturer's instruction, using an Envision plate reader (PerkinElmer). Data were calculated as percent of inhibition for each antibody compared to full reporter activation by a control antibody.

Single Dose Antibody Pharmacokinetics Study in Rat

The rat PK triaging study is not intended to determine classical PK parameters with a defined statistical certainty, but rather to provide an estimate of the serum half-life for the test antibody. 3 animals were injected with a single IV dose of the antibody.

For mouse dose-response PK/PD study, animals were divided into in 2 separate cohorts of equal numbers. Each cohort includes both vehicle- and compound-treated mice. One cohort was subjected for analyses on day 2, 4 whereas the second cohort was analyzed on day 6, 8 after antibody injection. The reason for the separation of cohorts is to reduce the need for serial bleeding so that the impact on serum iron parameters is kept minimal. The animal groups are shown in Table 10.

TABLE 10

| Design, animal allocation and test article doses | | | | |
|---|---|---|---|---|
| Experiment | Group | Number | Dose (mg/kg, IV) | Frequency |
| Mouse PK/PD | Control hIgG | 5 | 0.5 | Once |
| | 0.05 mpk ANTIBODY 6 | 5 | 0.05 | Once |
| | 0.1 mpk ANTIBODY 6 | 5 | 0.1 | Once |
| | 0.5 mpk ANTIBODY 6 | 5 | 0.5 | Once |
| Mouse BA anemia | Sham (No BA) | 6 | 0 | 0 |
| | BA, EPO + control hIgG | 6 | 2 | Once |
| | BA, EPO + ANTIBODY 5 | 6 | 2 | Once |
| | BA, EPO + ANTIBODY 6 | 7 | 2 | Once |
| | BA, EPO + ANTIBODY 7 | 6 | 2 | Once |

Establishment of Anemia of Inflammation in Mice and Therapeutic Treatment $5\times10^8$ BA particles for injection are prepared in the following manner (example for 10 mice). Starting concentration needs to be $2.5\times10^9$ particles/ml since 200 μl/mouse will be injected. Dilute stock 2-fold using PBS. For example, 10 mice times 0.200 μl=2 ml+20% overage=2.2 mL of $2.5\times10^9$ particles ml needed. 1.1 ml BA stock+1.1 mL PBS. BA administration 1 to 8 days before ESA treatment was shown to result in a blunted HGB response 6 to 7 days later.

C57BL/6 mice were injected with BA ($3\times10^8$ particles/mouse) and serum IL6 levels were measured 5 hours later by ELISA (KMC0061, Life Technologies) to determine the inflammatory response. Animals with a IL6 concentration lower than the 95% confidence interval of the mean for all BA-treated animals were excluded from the study, resulting in fewer than 5-6 mice in some groups. This exclusion process was carried out to lessen the possibility of false-positive results produced by including animals that did not have sufficient inflammation to blunt ESA response. After the exclusion process, mice were injected IV with the antibodies as indicated on day 6, and EPO (100 g/kg subcutaneous darbepoetin alfa, Amgen) was administered at 100 mg/kg on day 7 relative to BA treatment. Response to ESA and antibody therapy was measured 6 days later.

Analyses of Pharmacokinetics, Pharmacodynamics, and Efficacy Endpoints For mouse and rat PK/PD studies, serum samples were collected at indicated time points post antibody injection. Aliquots of the sera were used to determine circulating antibody concentration through automated high-throughput immunoassay system (Gyros) with biotinylated anti-human IgG as primary capture antibody. A second serum aliquot of each sample was used for quantitative colorimetric iron assay (Quntichrom, DIFE-250, Bioassay Systems). A third aliquot was processed for LC-MS quantitation of the rat or mouse hepcidin-25 peptide, following a modified procedure described earlier. Li et al. 2009. J. Pharm. Tox. Meth. 59: 171-80.

For BA-induced anemia and antibody treatment study, a final bleed in EDTA-coated BD Microtainer tubes were obtained at termination through cardiac puncture. The whole blood was used for Complete Blood Count analyses on an XT-2000iV hematology analyzer. Efficacy endpoints include HGB, HCT RETA, and RET-HE.

Statistical Analyses

One-way analysis of variance (ANOVA) followed by Bonferroni's post hoc test was carried out to analyze group differences (with $p<0.05$ considered significant) in hematology parameters. Data are reported as means±SEM.

Results

Biological Activity of BMP6 Antagonist Antibodies in Cellular BMP-Dependent Transcriptional Assays All three BMP6 antagonist antibodies 5, 6 and 7 fully inhibit the bioactivity of recombinant human BMP6-induced BMP reporter (BRE-luc) activity in human hepatoma cell line Hep3B (IC50=0.4 nM against 0.3 nM rhBMP6) and therefore is active at a 1:1 Ag/mAb molar ratio or better. The antibodies demonstrated good selectivity over the related BMP family proteins including BMP2, 5, and 7, with a window of 500 fold or more. See FIG. 1.

Snapshot Pharmacokinetics and Pharmacodynamics Profiles of BMP6 Antagonist Antibodies in Rat Single dose triage pharmacokinetics study in Sprague Dawley rats was performed for BMP6 antibodies 5, 6 and 7, through IV injection via jugular vein catheter at 10 mg/kg body weight. Comparing the total antibody concentration-time relationship (particularly $t_{1/2}$, MRT) in serum of the three antibodies with a standard profile suggested characteristics consistent with a typical human IgG (see FIG. 2 and Table 11). There is no evidence of target-mediated drug disposition. At this dose, all BMP6 antibodies suppressed serum hepcidin to below detection levels by day 1 post injection. The sustained strong suppression of hepcidin expression was still evident by day 16, suggesting a long duration of activity. Correspondingly, a transient peak rise in circulating iron concentration was observed on day 2 after antibody injection and the levels remain elevated by day 16.

Serum antibody concentration was measured overtime after a single antibody injection. Samples were collected at 1 hr, 6 hr, 1, 2, 4, 8, 16, 28 days post dose (10 mg/kg, IV).

TABLE 11

Key parameters in single dose rat triage PK study

| Parameters | ANTIBODY 5 | ANTIBODY 6 | ANTIBODY 7 |
|---|---|---|---|
| $T_{1/2}$ (days) | 9.1 | 7.8 | 9.2 |
| $C_{max}$ (ug/ml) | 140.7 | 189.0 | 146.2 |
| Mean resident time (days) | 8.6 | 7.0 | 6.9 |

Figure 9:
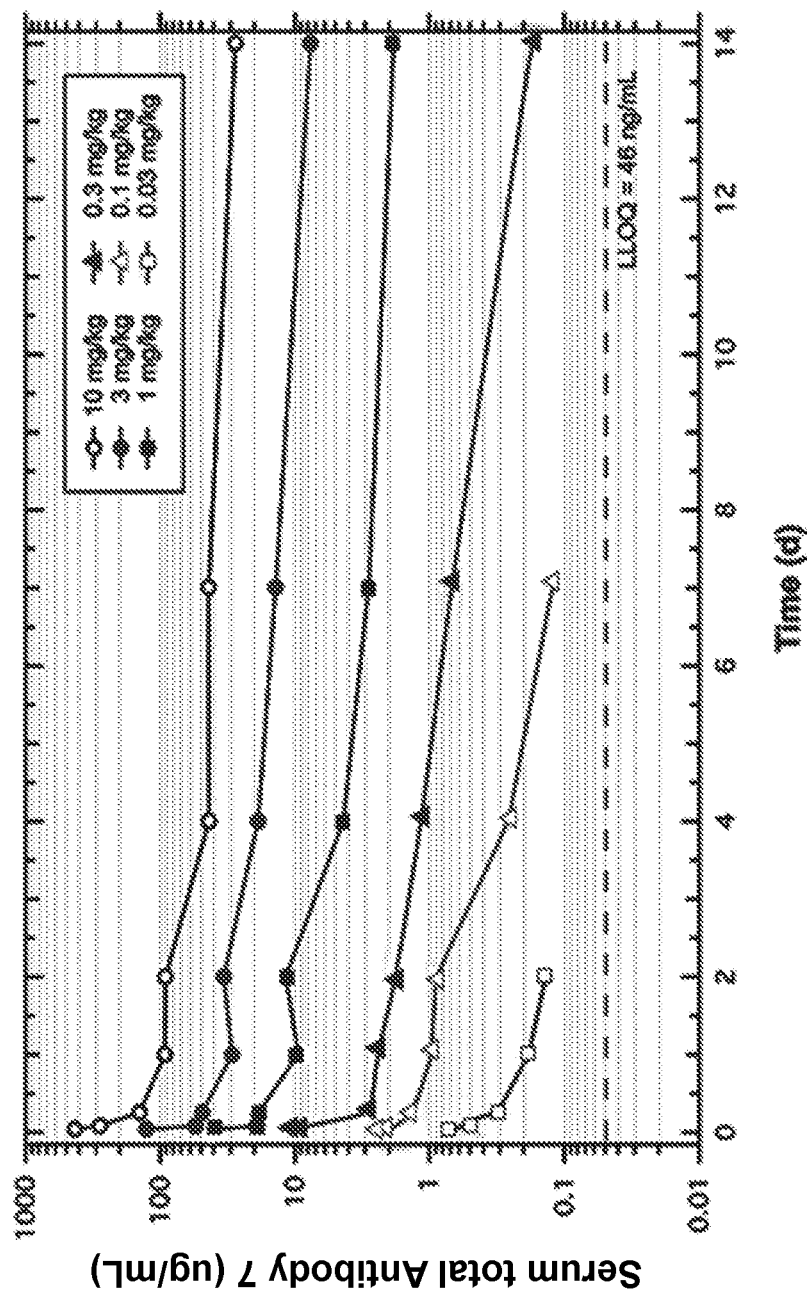
FIG. 9 shows pharmacokinetics profiles of single dose Antibody 7 in male rats.
Figure 10:
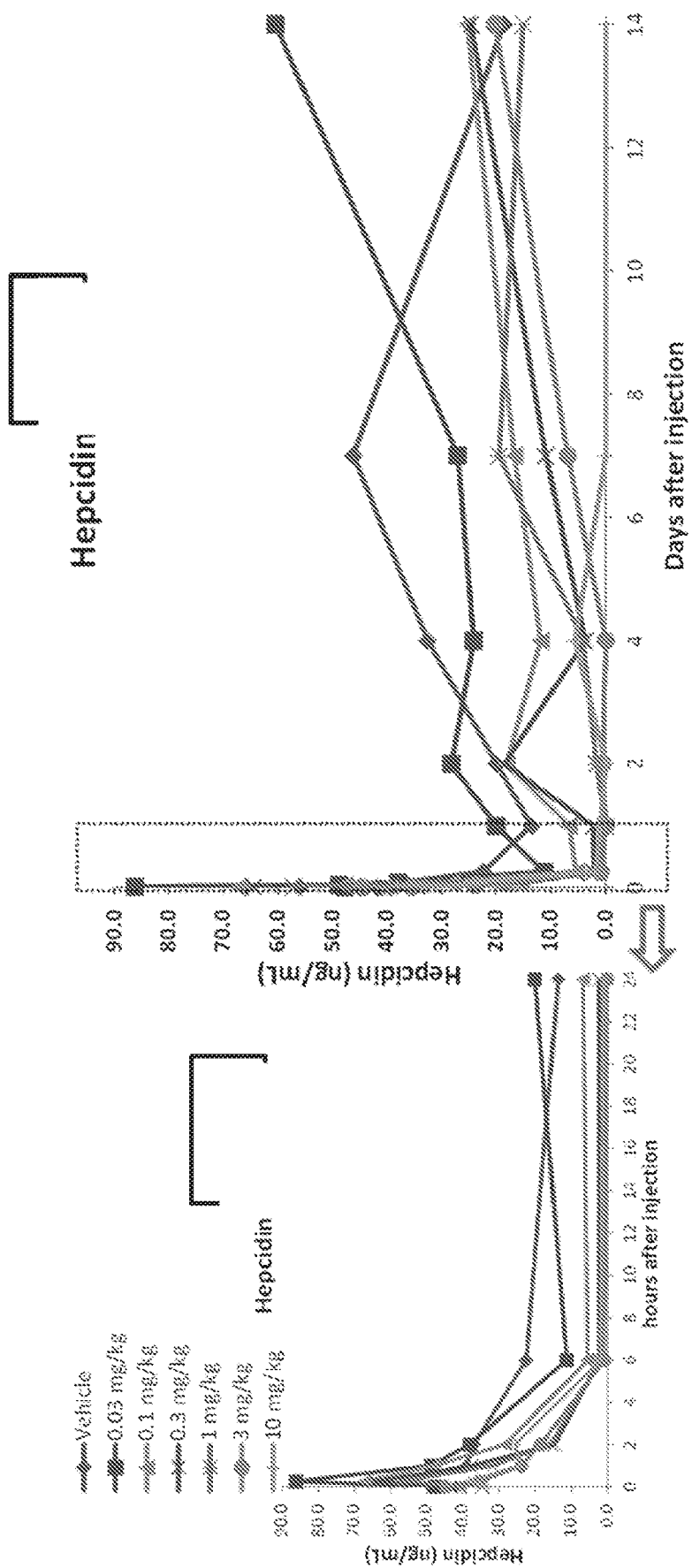
FIG. 10 shows dose-dependent effects of Antibody 7 on serum biomarkers of iron metabolism in rats. Shown is the quantitative analysis of serum hepcidin concentration after a single Antibody 7 or control (vehicle) injection at the indicated dose. Left panel shows an expanded view of the effects in the first 24 hours after administration.

As well, total serum concentration of Antibody 7 (both free and BMP6-bound) was measured in rats and cynomolgus monkeys following a single IV injection of Antibody 7 (in rats, at doses of 10, 3, 1, 0.3, 0.1 and 0.03 mg/kg; in monkey at 3 mg/kg) at the indicated times by ELISA with an LLOQ of 46 ng/mL (dotted line) rats and a LLOQ of 0.2 ug/mL (dotted line) in monkey. The results are shown in FIGS. 9 (rat) and 12 (monkey).

Dose-Dependent Response in Serum Iron Parameters After BMP6 Antibody Treatment in Mice and Cynomolgus Monkey To further define dose-dependent response of iron metabolism to BMP6 antibody treatment, naive C57BL/6 mice were injected with increasing dose of Antibody 6, ranging from 0.02 to 0.5 mg/kg, as indicated. Antibody 6 was chosen as representative of the 3 antibodies since they share similar framework, rodent PK profile and in vitro activities. A single dose of 0.5 or 0.1 mg/kg significantly suppressed serum hepcidin and accordingly increased serum iron concentration 2 days after treatment. However, only at 0.5 mg/kg, was a strong sustained effect on iron metabolism observed up to 8 days post injection. See FIG. 3. These results suggest dose-dependent, saturable target neutralization can be readily achieved using potent BMP6 antagonist antibodies.

Figure 3:
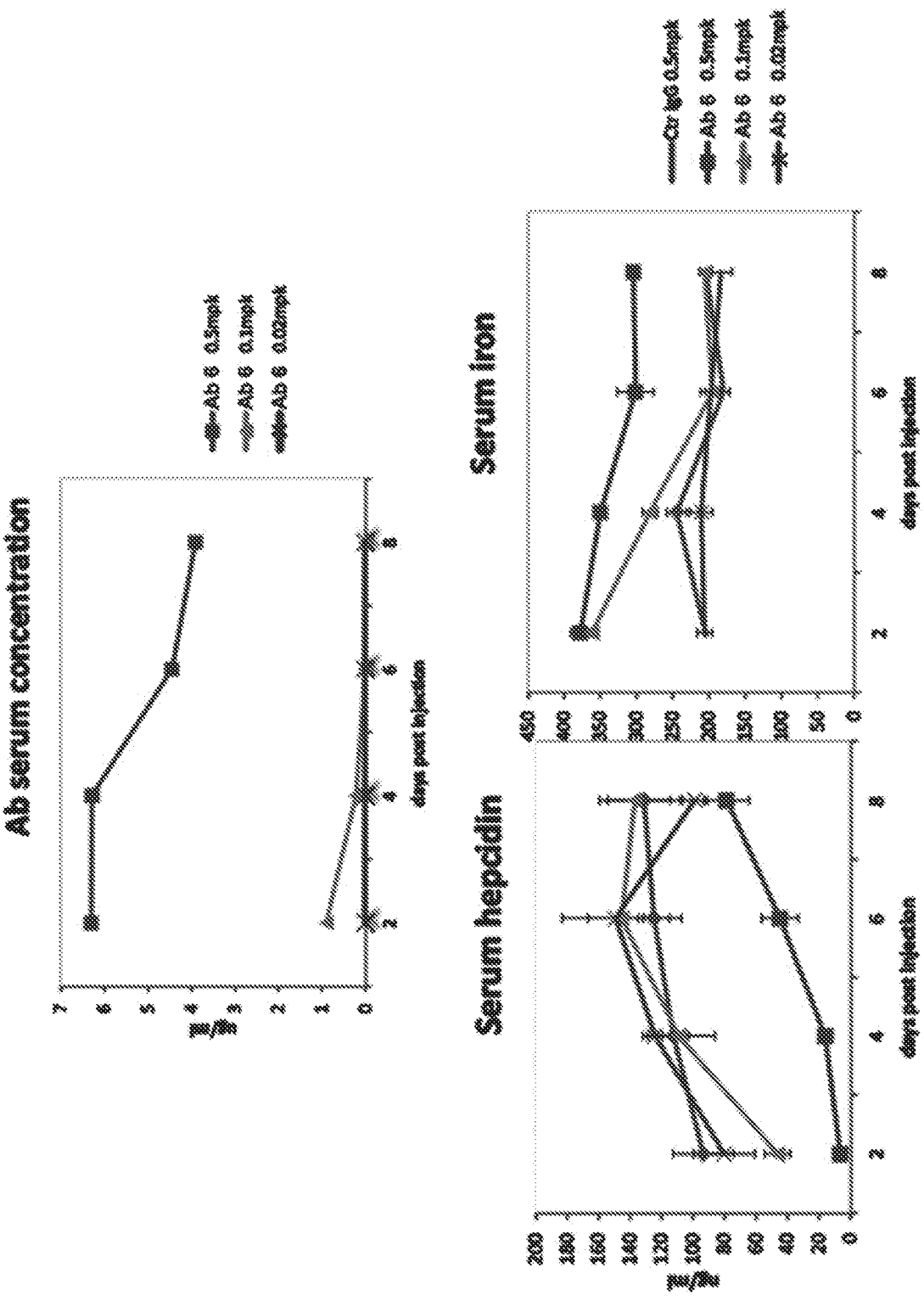
FIG. 3 shows dose-dependent effects of a BMP6 antibody on serum biomarkers of iron metabolism, Top: Serum hIgG concentration over time following a single IV injection of Antibody 6 at the indicated doses. Bottom: Left panel is quantitative analysis of serum hepcidin concentration after a single Antibody 6 or control human IgG injection, whereas right panel is serum iron concentration.

See FIG. 3, Dose-dependent effects of a BMP6 antibody on serum biomarkers of iron metabolism Top: Serum hIgG concentration over time following a single IV injection of Antibody 6 at the indicated doses. Bottom: Left panel is quantitative analysis of serum hepcidin concentration after a single Antibody 6 or control human IgG injection, whereas right panel is serum iron concentration.

Figure 11:
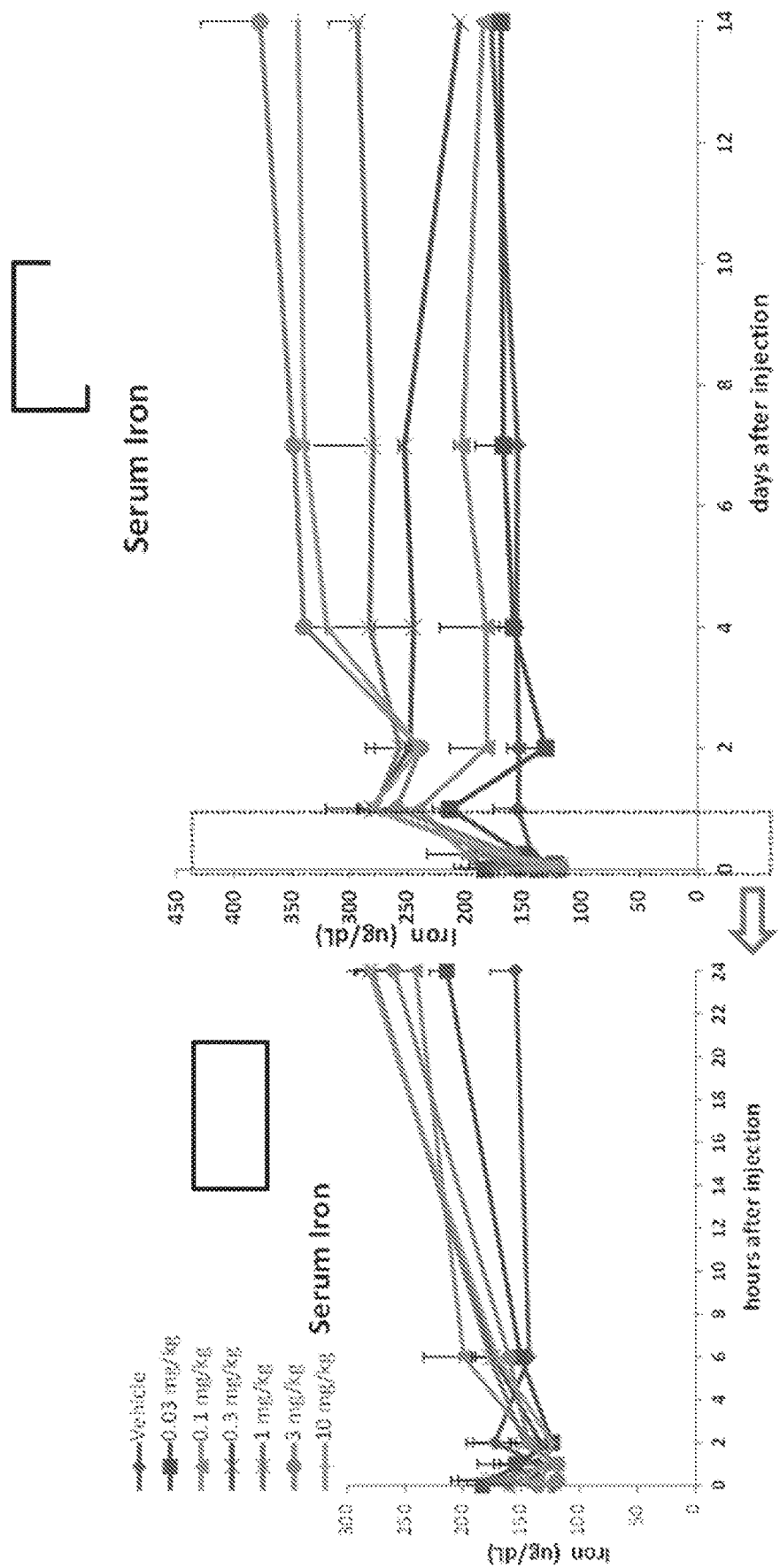
FIG. 11 shows dependent effects of Antibody 7 on serum iron in rats. Shown is the quantitative analysis of serum iron concentration after a single Antibody 7 or control (vehicle) injection at the indicated dose. Left panel shows an expanded view of the effects in the first 24 hours after administration.
Figure 12:
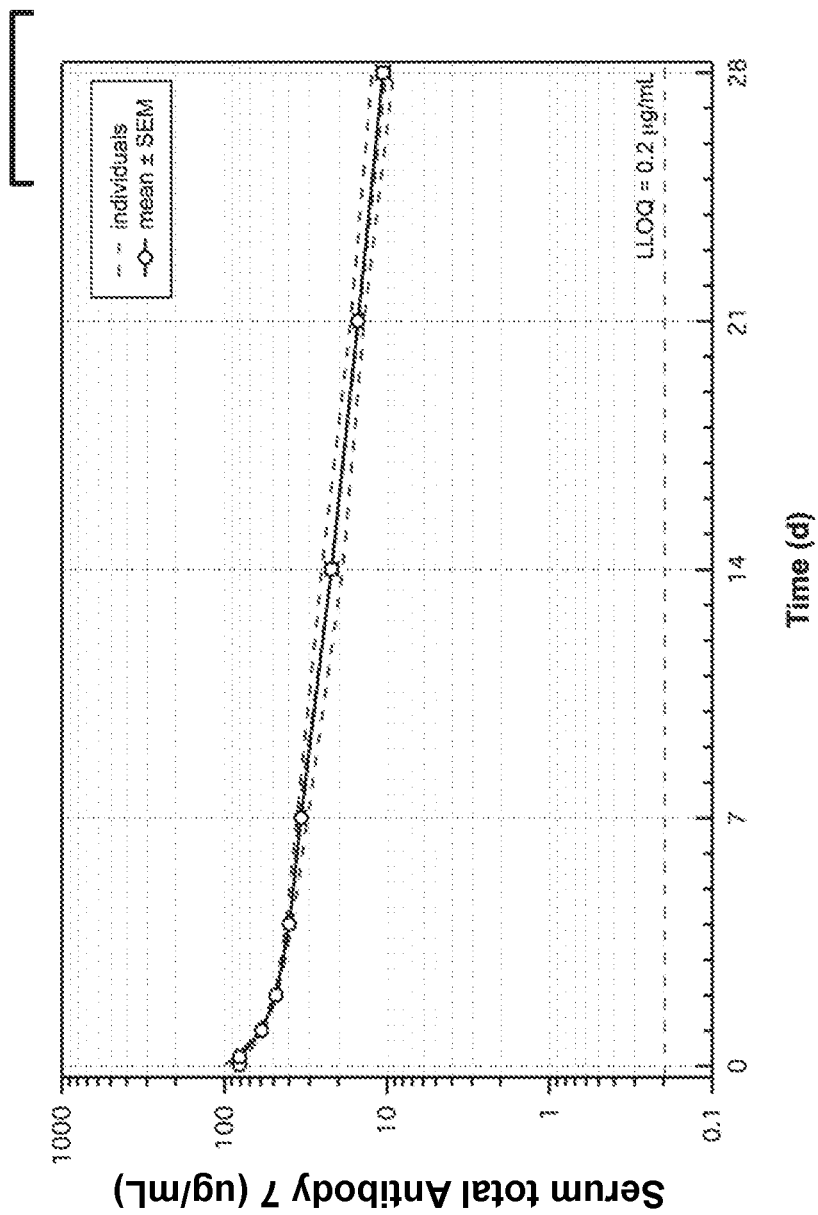
FIG. 12 shows the concentration-time profile of single dose IV injection of Antibody 7 (3 mg/kg) in cynomolgus monkeys. Plotted is total Antibody 7 concentration (both free and BMP6-bound).

Similar experiments were performed with Antibody 7. Dose- and time-dependent suppression of circulating serum hepcidin by Antibody 7 was tested in male Sprague-Dawley rats. Serum samples were collected at 0.25, 1, 2, 6 hr, and 1, 2, 4, 7 and 14 d post-dose after a single dose of Antibody 7 was administered by IV injection at a dose ranging from 0.03 mg/kg to 10 mg/kg. Serum hepcidin levels were measured by LC/MS with a LLOQ 9 ng/mL. In the same animals, serum iron levels were also measured. The results are reported in FIG. 11.

These results indicate that the anti-BMP6 antibodies of the present invention are able to cause a dose-dependent increase in serum iron. The effects were robust and persisted for at least 2 weeks after antibody administration.

Figure 13:
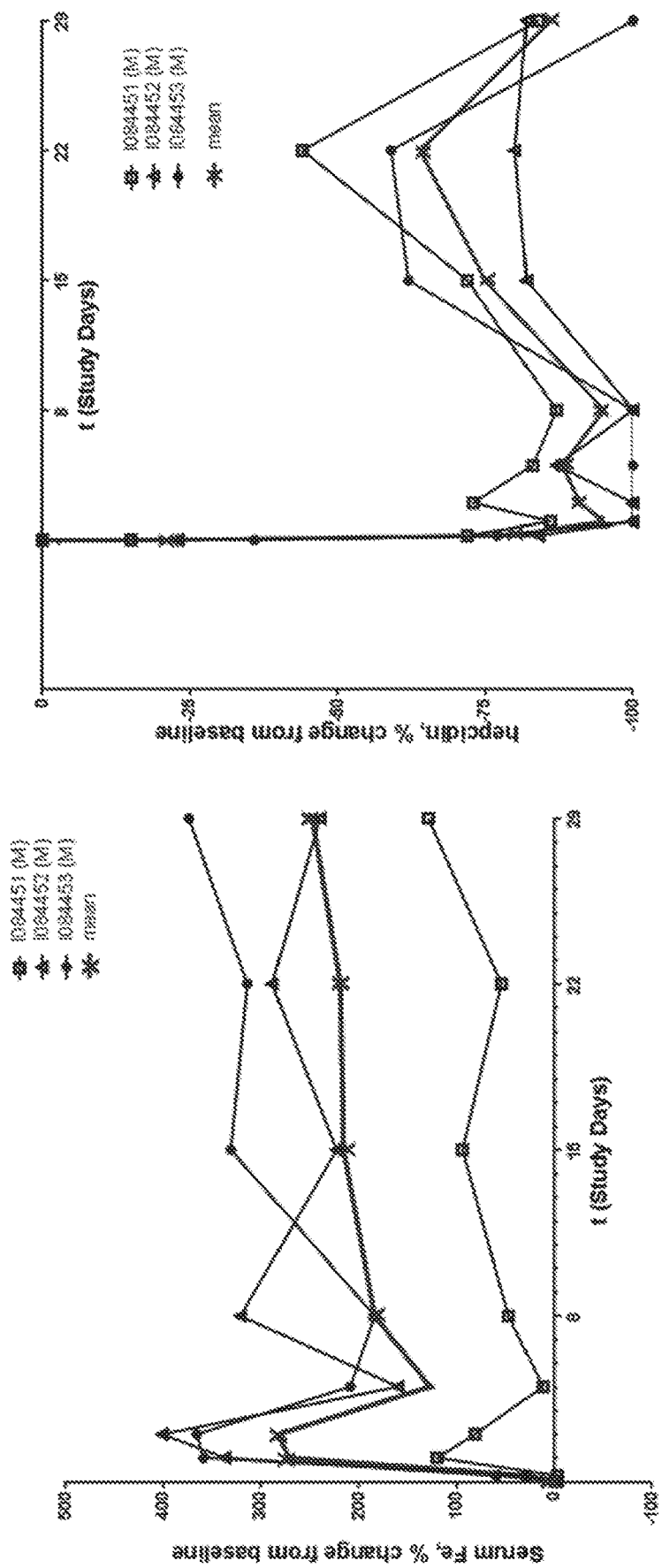
FIG. 13 shows serum hepcidin and Fe concentration in male cynomolgus monkeys after a single intravenous injection of Antibody 7 at a dose of 3 mg/kg. Data from three different monkeys is shown, together with the mean.

The effects on serum iron parameters in response to anti-BMP6 antibody was also tested in cynomolgus monkey. Male Cynomolgus monkeys were given a single intravenous injection of Antibody 7 at a dose of 3 mg/kg. At indicated days post injection, serum samples were collected and analyzed for total serum iron (Fe) and hepcidin concentration. The results are shown in FIG. 13. Data from 3 individual animals are presented (plotted against the pre-dose baseline levels). Mean values are indicated by the "x" line. An increase in serum iron and suppression of serum hepcidin were observed 24 hr after antibody administration and the effects remained (relative to pre-dose levels) through the end of the 28-day study. These results indicate that the BMP6 antibodies of the invention potently induce hepcidin expression and reduce circulating iron concentration in non-human primates.

Effect of BMP6 Antibodies on Red Cell Parameters in Inflammation-Driven, ESA-Resistant Anemia in Mice Experiments were performed to evaluate the therapeutic utility of the anti-BMP6 antibodies in a mouse model of anemia of inflammation. See FIG. 4. Mice treated with abortus antigen (BA) developed anemia 6 days later. Anemic animals were treated with anti-BMP6 plus antibody recombinant erythropoietin (EPO) initiated at one day apart, and the effect of antibody therapy on anemia progression was monitored at day 13 relative to BA. HGB and HCT values decreased between onset of treatment and day 13, which was resistant to EPO treatment alone. Combined BMP6 antibody and EPO treatment effectively restored EPO response and significant raised HGB and HCT levels. This effect was associated with a concomitant stimulation of erythropoietin activity, as reflected by persistent increase in RETA, as well as restored reticulocyte hemoglobin content, suggesting a correction of heme synthesis due to functional iron deficiency in the erythropoiesis compartment.

Figure 4:
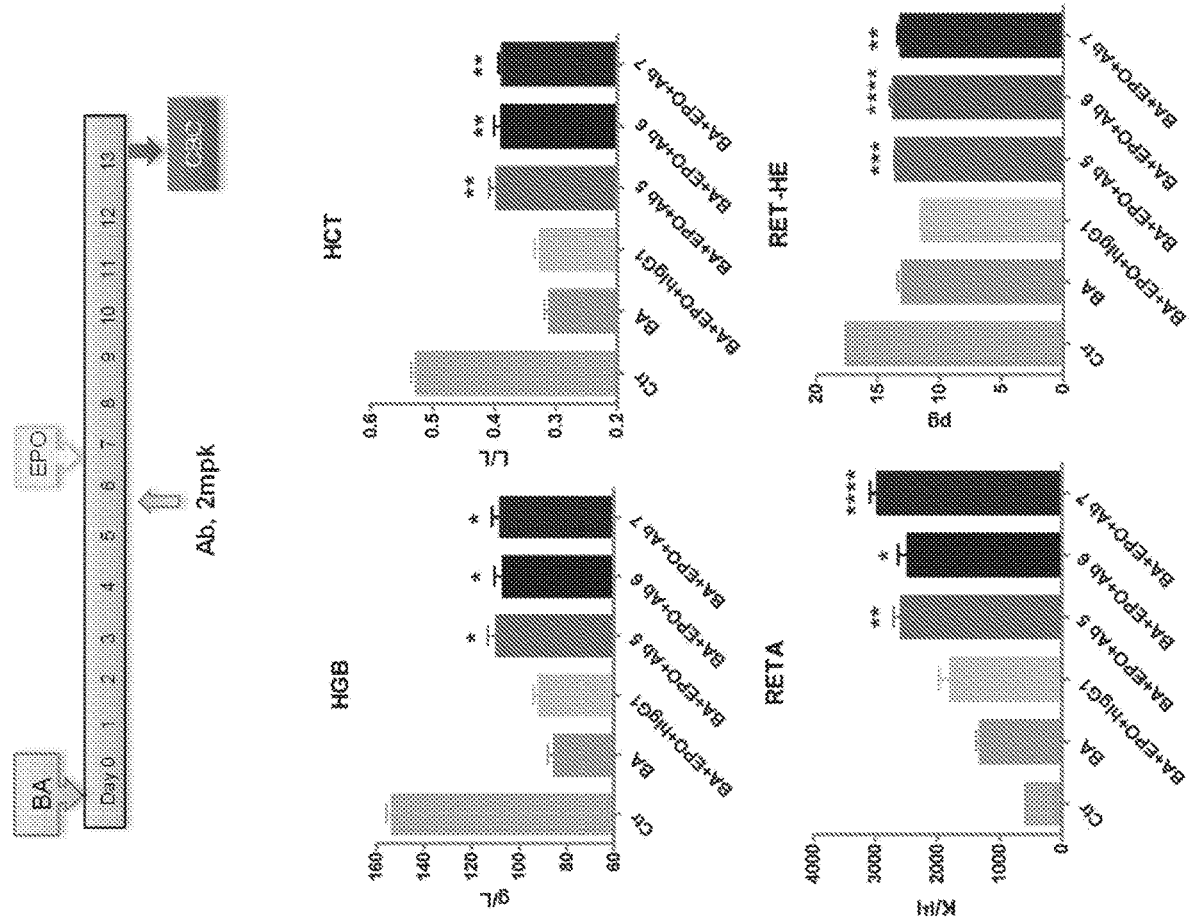
FIG. 4 shows therapeutic treatment of BMP6 Antibody in an ESA-resistant anemia of inflammation mouse model. Top: Experimental scheme of BA-induced ESA-resistant anemia of inflammation model. Bottom: Erythropoiesis parameters at 13 days after BA treatment. HGB: hemoglobin; HCT: hematocrit; RETA: reticulocyte count; RET-HE: Reticulocyte hemoglobin equivalent. *$p<0.05$, $p<0.01$, *$p<0.001$, ****$p<0.0001$ versus BA+EPO+hIgG1.

See FIG. 4, therapeutic treatment of BMP6 Antibody in an ESA-resistant anemia of inflammation mouse model. Top: Experimental scheme of BA-induced ESA-resistant anemia of inflammation model. Bottom: Erythropoiesis parameters at 13 days after BA treatment. HGB: hemoglobin; HCT: hematocrit; RETA: reticulocyte count; RET-HE: Reticulocyte hemoglobin equivalent.

$*p<0.05$, $p<0.01$, $*p<0.001$, $****p<0.0001$ versus BA+EPO+hIgG1

Example 2

Clinical Plan for Testing of BMP6 Antibodies in Humans

Clinical Trial Plan: Assessment of therapy using antibodies or antigen-binding fragments thereof that bind human BMP6.

Patients with end-stage renal disease (ESRD) produce little, if any erythropoietin (EPO) and generally require periodic administration of exogenous EPO and intravenous (IV) infusions of iron to enable EPO-induced synthesis of Hgb. Up to one third of chronic hemodialysis (HD) patients do not respond adequately to EPO, owing primarily to intracellular sequestration of iron. Hepcidin is primarily cleared by the kidney, but removal by dialysis is insufficient. Therefore, chronic HD patients tend to have significantly elevated hepcidin levels, which block mobilization of iron for erythropoiesis. IV iron therapy is no longer effective or recommended once body iron stores reach a critical level (indicated by high serum ferritin levels). Current guidelines recommend against giving IV iron to anemic dialysis patients with high ferritin levels, and these patients may therefore receive even higher EPO doses, with the potential associated risk of EPO hypo-responsive anemia (Kidney Disease Improving Global Outcomes (KDIGO) Anemia Work Group 2012). EPO hypo-responsive anemia imparts a significantly increased risk of all-cause mortality related to both anemia and higher EPO dose in hemodialysis (Kilpatrick et al 2008, Lopez-Gomez et al 2008, Fukuma et al 2012) and peritoneal dialysis patients (Suttorp et al 2013). The isolated antibodies or antigen-binding fragments thereof that bind human BMP6 of the present disclosure may benefit chronic kidney disease patients with iron-restricted anemia by improving hemoglobin (Hgb) levels while simultaneously reducing EPO and IV iron dosing needs. A lower EPO resistance index (ratio of EPO dose vs. Hgb level) is correlated with a lower mortality risk.

In summary, the goal of therapy using the isolated antibodies or antigen-binding fragments thereof that bind human BMP6 of the present disclosure is to mobilize sequestered iron, which may then reduce EPO and iron dose needs and improve Hgb levels, all of which is expected to improve patient outcomes. This is a first-in-human, single dose study of therapy using isolated antibodies or antigen-binding fragments thereof that bind human BMP6. This study will assess safety, tolerability, pharmacokinetics, pharmacodynamics and efficacy in a chronic hemodialysis patient population. The purpose of this study is to evaluate whether therapy using isolated antibodies or antigen-binding fragments thereof that bind human BMP6 warrants further clinical development in anemia associated with chronic kidney disease.

Investigational Plan
Study Design

This is a first-in-human, two-part, single-dose, non-confirmatory study of an isolated antibody or antigen-binding fragment thereof that binds human BMP6 to assess safety, tolerability, PK, PD and efficacy in a chronic hemodialysis patient population. Part 1 is a first-in-human, single-dose, open-label dose-finding study. Part 2 is a randomized, double-blind, placebo-controlled, single-dose study that will compare two dose levels of an isolated antibody or antigen-binding fragment thereof that binds human BMP6.

Safety assessments will include physical examinations, ECGs, vital signs, standard clinical laboratory evaluations (hematology, blood chemistry, serum iron indices) adverse event and serious adverse event monitoring.

Part 1

The aims of Part 1 are (a) to evaluate single-dose safety, PK, PD, and tolerability, and (b) to determine the minimum PAD of an isolated antibody or antigen-binding fragment thereof that binds human BMP6, defined as the lowest dose tested in Part 1 that results in an increase in Hgb (median change from baseline ~0.5 g/dL) at 29 days post-dose.

Figure 6:
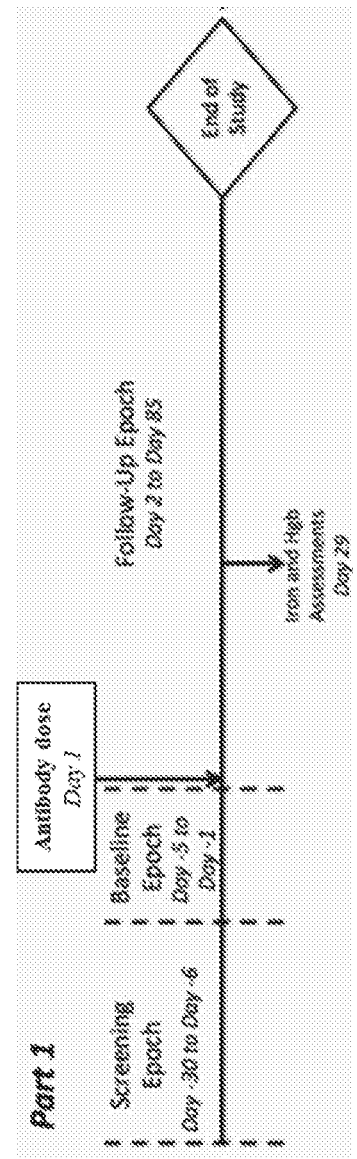
FIG. 6 shows the protocol for Part 1 of the clinical program to investigate the safety and efficacy of BMP6 antibodies.

During Part 1, a screening visit will take place, where the patient's eligibility to enter the study will be determined (FIG. 6). Eligible patients will be admitted to the study site and re-evaluated for eligibility criteria during the baseline visit. All baseline safety evaluation results must be available and reviewed prior to dosing.

FIG. 6 provides and overview of the study design for Part 1. Patients will be asked to arrive at the study site on Day 1, directly following their routine dialysis visit. Patients will then receive an infusion of an antibody or antigen-binding fragment thereof that binds human BMP6 (exact dose will be dependent on cohort). If possible, dosing should preferably take place on a dialysis day prior to two inter-dialysis days (e.g. Friday or Saturday), and will occur following that day's dialysis session. However, if not possible, then dosing may occur on a dialysis day not preceding two inter-dialysis days. Following dosing, the first two patients in Part 1 will be domiciled for at least 48 hours for safety and PK/PD assessments. Patients will return to the study site at Days 4 and 6 for PK/PD assessments, and then weekly for a total of 29 days for PK assessments, and a total of 12 weeks for safety assessment, with an end-of-study visit at approximately Day 85. Study visits, including all laboratory tests other than post-dialysis PK assessments, should take place before the patients scheduled dialysis visit.

Part 1 will be initiated with a dose that is predicted to be not pharmacologically active. The dose will be adjusted for each subsequent Part 1 cohort, based on each cohorts median change in Hgb following a single dose of an isolated antibody or antigen-binding fragment thereof that binds human BMP6 and transferrin saturation (TSAT) level as discussed in the Statistical Considerations section and shown in FIG. 7. The aim of this decision tree is to identify the minimum feasible dose that induces iron mobilization (as indicated by transferrin saturation (TSAT) levels >50% observed in at least 4 patients in the 6-patient cohort at one week post-dose) and increases Hgb. If iron is mobilized but Hgb does not increase by at least 0.5 g/dL at 29 days post-dose, then the clinical data will be analyzed to assess potential confounding factors (e.g. blood loss due to excessive non-study phlebotomy). The applicable Investigators and representative(s) from the Sponsor will review each cohort's adverse events and will assess these events in the context of (a) known medical issues associated with chronic renal failure and (b) an nonclinical toxicology findings. Subsequent cohorts will not be dosed until the Investigators and Sponsor indicate that it is safe to proceed.

Figure 7:
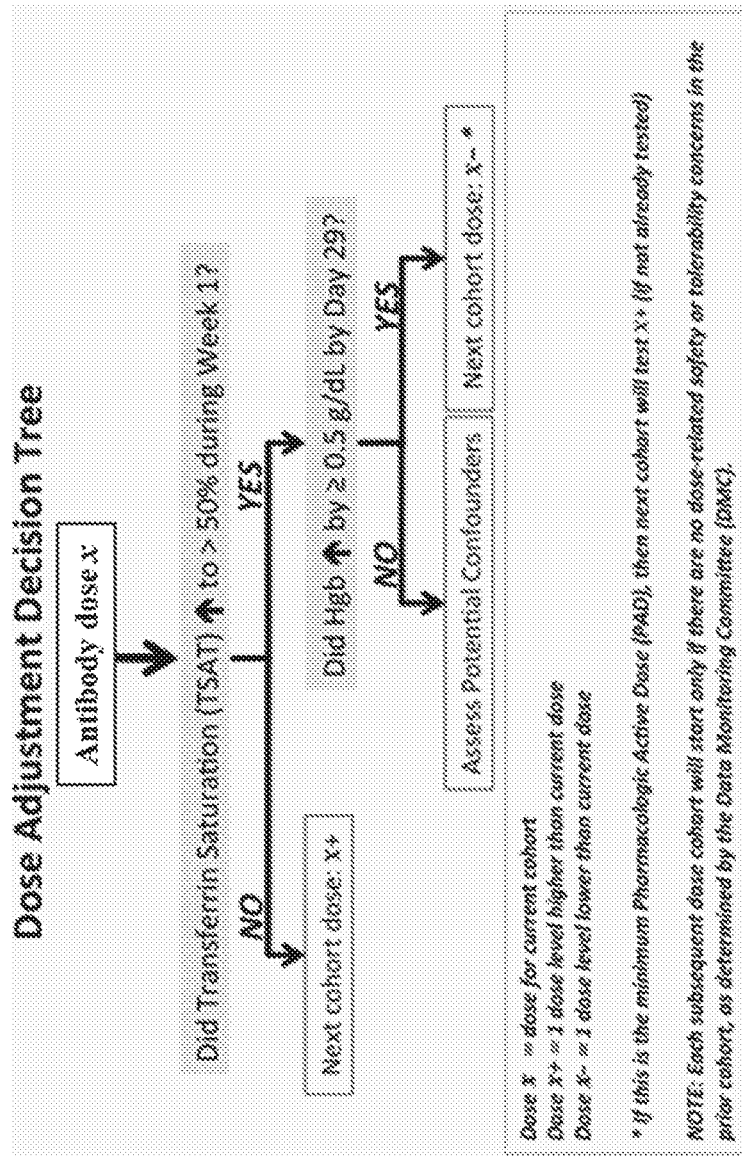
FIG. 7 shows the dose adjustment decision tree for the clinical program to investigate the safety and efficacy of BMP6 antibodies.

FIG. 7 provides the algorithm for adjustment of doses in Part 1. Blood work including Hgb measurements will occur pre-dialysis. The starting dose will be 0.01 mg/kg. In Part 1, patients will be assigned to one of up to 6 open label dose cohorts of up to 6 patients each. The minimum PAD of an isolated antibody or antigen-binding fragment thereof that binds human BMP6, as defined above, will be the lower dose arm selected for Part 2. The dose for each subsequent cohort may be adjusted higher or lower, as shown in FIG. 7. If the lowest feasible dose (0.001 mg/kg) results in a median increase in Hgb of ≥0.5 g/dL, it will be the minimum PAD and the lower dose selected for Part 2 and the next highest dose evaluated in Part 1 will be the higher dose arm for Part 2. If the highest dose (0.1 mg/kg) evaluated in Part 1 is the minimum PAD, Part 2 will proceed with 2 arms only: placebo and minimum PAD. In the event that additional dose cohorts are needed in Part 1, these cohorts will be added as described in herein.

Each Part 1 cohort will include 6 patients. The first 2 patients in the first cohort of Part 1 will be dosed at least 7 days apart. Timing of subsequent Part 1 cohort patient doses will occur as is feasible for the respective site's schedule and support resources. All Part 1 patients will be followed for 12 weeks following the dose.

Part 2

Figure 8:
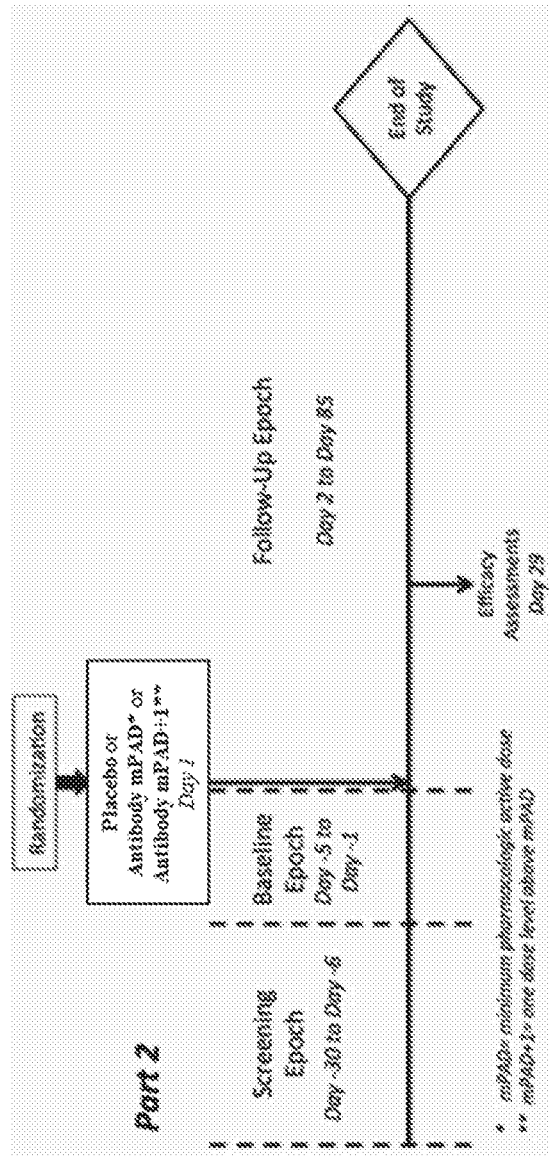
FIG. 8 shows the protocol for Part 2 of the clinical program to investigate the safety and efficacy of BMP6 antibodies.

The aims of Part 2 are (a) to evaluate safety, PK, PD, and tolerability and (b) to determine efficacy based on Hgb changes in response to single dose of an antibody that binds human BMP6 vs. placebo. Part 2 will include up to three arms: Up to two Ab dose arms and a placebo arm (FIG. 8). The two Ab dose arms will be derived from data generated in Part 1. Part 2 will include approximately 60 patients with a randomization of 1:1:1 to the three arms. If, in Part 1, the minimum PAD is also the highest dose (0.1 mg/kg) evaluated, then Part 2 will have only two arms: minimum PAD and placebo. In this case, 40 patients will be randomized to the two arms with a randomization ratio of 1:1. Sample size of Part 2 may be adjusted based on the variability of the change from baseline in Hgb in Part 1.

FIG. 8 provides a study design for Part 2. During Part 2, a screening visit will take place, where patient's eligibility to enter the study will be determined. Eligible patients will be re-evaluated as per eligibility criteria during the baseline visit. All baseline safety evaluation results must be available and reviewed prior to dosing.

Patients will be asked to arrive at the study site on Day 1, directly following, their routine dialysis visit. Patients will then receive either an infusion of Ab or placebo, as determined by randomization assignment. If possible, dosing should preferably take place on a dialysis day prior to two inter-dialysis days (e.g. Friday or Saturday), and will occur following that day's dialysis session. However, if not possible, then dosing may occur on a dialysis day not preceeding two inter-dialysis days. Patients will return to the study site on Days 4 and 6, then weekly for follow up assessments.

During follow up visits patients will undergo routine safety assessments and PK data will also be collected 85 days. Study visits may take place following the patient's scheduled dialysis visit, in order to fit with the dialysis schedule of the patient. All patients enrolled in Part 2 will be followed for 12 weeks following the dose of Ab (or placebo).

EPO Dose Management (Both Parts)

Individual EPO dose adjustments during both Parts will be managed as per each dialysis site's standard of care protocol. Site protocols will be reviewed as part of site assessment, and will be checked for compliance with standard of care guidelines (KDIGO Clinical Practice Guideline for Anemia in Chronic Kidney Disease Anemia Work Group 2012). Patients who achieve a Hgb level of ≥13 g/dL at any time during the study may be managed with therapeutic phlebotomy, at the discretion of the investigator, in addition to site-specific guidelines for managing Hgb values above target levels.

Intravenous Iron Management (Both Parts)

Patients receiving loading doses of IV iron (100 mg/week) will be excluded from the study. Patients receiving weekly maintenance IV iron (<100 mg/week) may be included in this study. The weekly maintenance IV iron dose will be held at the beginning of week 1 of Ab dosing. Iron indices will be monitored during the first week post-Ab dosing, and rescue iron therapy and maintenance IV iron management will follow standard of care guidelines as per the managing hemodialysis unit's protocol. Site protocols will be reviewed as part of site assessment, and will be checked for compliance with standard of care guidelines (KDIGO Clinical Practice Guideline for Anemia in Chronic Kidney Disease Anemia Work Group 2012).

Rationale of Study Design

Rationale for Two-Part Study Design

The rationale for two parts in the same patient population is to identify the minimum PAD safely and efficiently, aiming to minimize the number of patients and cohorts exposed to potentially sub-therapeutic doses. Part 2 will assess the efficacy of the minimum PAD, and one dose level above the minimum PAD (as determined in Part 1), in comparison with a placebo group.

Part 1 is designed to evaluate single-dose safety, tolerability, PK/PD, as well as the minimum PAD of Ab in an open label study. The minimum PAD will be determined based on each dose cohort's median change in Hgb at 29 days following Ab dosing. The rationale for the PAD determination criteria is that clinically meaningful responses to EPO may require up to 4 weeks following an EPO dose change. If Ab mobilizes iron in the target population, then that may enable the patient's current EPO dose to exert a more robust erythropoietic effect. The 29 days Hgb ranges listed in the PAD determination criteria are based on clinically significant & safe rates of increase in Hgb in response to an EPO dose (~0.5 g/dL over 29 days). The rationale for seeking the minimum PAD rather than a maximal effect is that an overly robust Hgb response is a safety risk in this patient population, as reflected by the target Hgb ranges in the current standard of care guidelines (Kidney Disease Improving Global Outcomes (KDIGO) Anemia Work Group 2012). The goals of the safety and tolerability assessments in Part 1 are (a) to identify safety signals, and (b) to inform dose adjustment decisions, ensuring that the doses selected for Part 2 (minimum PAD+1 dose higher) are suitable for further evaluation of both safety and efficacy relative to placebo. While Part 1 is inadequately powered to afford an unbiased assessment of safety, the placebo group and larger sample sizes in Part 2 will enable an unbiased safety assessment at the minimum PAD and one dose higher. In addition to safety, tolerability, and PK/PD, Part 2 is designed to assess efficacy vs. placebo in a double-blind study. Efficacy assessment will be based primarily on Hgb, with EPO resistance index (ERI=weekly weight-adjusted EPO dose divided by Hgb) as a key secondary endpoint. ERI provides a quantitative measure of the amount of EPO needed to achieve a given Hgb value, and therefore provides clinically important information in addition to Hgb alone.

Rationale for FIH in Dialysis Patients

This first-in-human (FIH) study will be conducted in chronic hemodialysis (HD) patients rather than healthy volunteers (HV). Evaluation of safety, tolerability, and PK/PD response to anti-human BMP6 Ab in HV is likely not translatable to chronic HD patients for several reasons:

Unlike HV, chronic HD patients with anemia, high serum ferritin, and low TSAT have chronically accumulated intracellular iron stores. Therefore, safety, tolerability, and pharmacological effects related to iron mobilization in response to low doses of Ab are most appropriately evaluated in chronic HD patients. In HV with normal renal function, hepcidin (of which BMP6 is a key regulator) is filtered by the kidney and is excreted efficiently in the urine, leading to low circulating levels. In contrast, hepcidin is filtered less efficiently and transiently by dialysis, leading to higher circulating levels in chronic HD patients (Zaritsky et al 2010). Furthermore, normal kidneys will adjust endogenous EPO levels dynamically and a change in Hgb may not be evident in response to Ab. Therefore, safety and tolerability related to modulation of hepcidin by the BMP6 pathway and the effect of Ab on Hgb are most appropriately evaluated in chronic HD patients.

Rationale for Target Patient Population

This study is designed to evaluate an anti-human BMP6 Ab in the setting of EPO-hypo-responsive, iron-restricted anemia. Established clinical guidelines (KDIGO Clinical Practice Guideline for Anemia in Chronic Kidney Disease Anemia Work Group 2012) define EPO hypo-responsiveness as the need for two increases in EPO dose, up to 50% above the stable dose, to maintain a stable Hgb concentration. The proposed eligibility criteria are designed to select for stable chronic HD patients with anemia, and clinical indicators of iron restriction: increased ferritin and low TSAT (TSAT=serum iron/total iron binding capacity; TSAT correlates very closely with serum iron). Furthermore, adjustments in EPO and IV iron doses will adhere to strict standard of care targets for Hgb, TSAT, and ferritin. This design reduces the risk of over-shooting desired Hgb targets because changes in iron and hematologic parameters will continue to be managed as per standard of care. Furthermore, patients receiving loading doses of IV iron within 1 week prior to baseline will be excluded. Patients receiving maintenance IV iron may be included (if all other eligibility criteria are met). The rationale for including these patients is that current standard of care in the USA dictates that Hgb and TSAT be maintained within narrow limits, and therefore, full withdrawal of maintenance iron therapy for the purpose of meeting lower TSAT eligibility criteria would place patients at risk for TSAT below 25%, necessitating a course of IV iron loading doses as per standard of care. However, eligible patients on maintenance IV iron will have their weekly IV iron dose held at the beginning of the week of Ab dosing, and will resume maintenance IV iron therapy only as determined by site's standard of care protocol, based on monitored iron indices.

Rationale of Dose/Regimen, Duration of Treatment Starting Dose Rationale

The maximum recommended starting dose (MRSD) was calculated based on the no adverse effect level (NOAEL) from the 13-week (14-dose) GLP toxicology studies conducted in rats and cynomolgus monkeys. Animals received weekly IV bolus doses of 0.1, 1, 10, and 100 mg/kg. The 1 and 100 mg/kg dose groups (only) were subsequently followed for 16 weeks in rats or 24 weeks in cynomolgus monkeys after the last dose of an isolated antibody or antigen-binding fragment thereof that binds human BMP6. The MRSD was estimated by first calculating the human equivalent dose (HED) for the NOAEL from these studies (0.1 mg/kg)—an approach deemed appropriate for drugs with a molecular weight >100 kDa—and subsequently applying a safety factor of 10 to account for differences between nonclinical species and patients, such as the amount of stored iron and the demand for erythropoiesis. PK parameters for the nonclinical species were inferred from the toxicokinetic (TK) data collected during the IND-enabling toxicology studies. Corresponding PK parameters in patients were then estimated using allometric scaling, and these parameters were used to predict free an isolated antibody or antigen-binding fragment thereof that binds human BMP6 concentration as a function of time in patients for a given dose. Comparing the TK data from the toxicology studies to the model-based an Ab PK in patients indicated that a dose 10-fold lower than the NOAEL/HED was predicted to yield a (minimum) 10-fold margin based on Ab concentration.

The maximal levels of serum iron observed in response to Ab in animal studies may underestimate the predicted human iron response to Ab, because HD patients who have been administered IV iron therapy likely have higher tissue stores of iron than healthy animals. However, unlike healthy, non-anemic animals, HD patients are expected to utilize the released serum iron for erythropoiesis; therefore animal models may overestimate the duration of iron elevation. The liver pathology observed in the 13-week studies was not observed in the 4-week studies, suggesting that the toxicities owe to the cumulative exposure to serum iron rather than a response to the acute release of iron.

To account for the anticipated differences in stored iron between nonclinical species and patients, MRSD was also predicted based on a model-based analysis of serum iron concentrations. The cumulative exposure to serum iron that resulted in the toxicology findings was represented as an iron area-under-the-curve (Fe AUC). In this approach, the Fe AUC calculated for the NOAEL dose (0.1 mg/kg) was regarded as being adequately safe. The Fe AUC at the proposed MRSD in patients was then predicted and compared to the Fe AUC in nonclinical species at the NOAEL. Because the model-predicted serum iron exposure at the MRSD in patients was >10-fold less than that at the NOAEL in nonclinical species, decreasing the NOAEL/HED by a safety factor of 10 was deemed adequate for the estimation of a MRSD. The proposed MRSD is therefore 0.01 mg/kg.

Dose Adjustment Rationale

For this study, the maximum test dose (xmax) will be the HED corresponding to the NOAEL in each of the 2 IND-enabling toxicology studies: 0.1 mg/kg. The minimum feasible test dose (xmin) is the lowest technically feasible dose based on compatibility studies: 0.001 mg/kg. The MRSD (x0) will be evaluated according to the safety, TSAT, and Hgb criteria (FIG. 7). If x0 results in a median change in Hgb <0.5 g/dL relative to pre-dose, selection of x+(FIG. 7) will be guided by linearly extrapolating on a natural base logarithmic scale (in anticipation of a sigmoidal dose-response relationship) between x0 and xmax. Provisional doses for this dose escalation are provided above. These provisional doses may be adjusted based on the review of data during the informal interim analysis between each cohort. This approach will continue until either the minimum PAD is identified or xmax is reached. If max results in a median change in Hgb <0.5 g/dL, the safety of this dose will be evaluated and a decision will be made whether to amend the protocol to add additional cohorts at doses that exceed the max, based on safety, PK, and PD data. If the highest dose tested in Part 1 results in a median increase in Hgb <0.5 g/dL, does not increase TSAT above 50%, and that dose is below xmax, the protocol may be amended to add additional cohorts.

If x0 instead results in a median change in Hgb ≥0.5 g/dL relative to pre-dose, the dose for the next cohort will be adjusted to xmin. If xmin also results in a median change in Hgb ≥0.5 g/dL, xmin will be deemed the minimum PAD, and xmin and x0 will be evaluated in Part 2. If min results in a median change in Hgb <0.5 g/dL and TSAT ≤50% (FIG. 7), doses will be increased by linear extrapolation within the interval (xmin, x0) on the natural base logarithmic scale until either the minimum PAD is identified or until 6 doses (cohorts) have been evaluated. Provisional doses within the interval (xmin, x0) are provided above. These provisional doses may be adjusted based on the review of data during the informal interim analysis between each cohort. The minimum PAD will be defined as the lowest dose tested that results in a median change in Hgb ≥0.5 g/dL relative to pre-dose.

The Ab will be administered as a single dose IV infusion to ensure serum iron exposure (Fe AUC) less than that associated with adverse findings in nonclinical toxicology studies. The Ab solution will be infused immediately following the hemodialysis session on Day 1 to minimize the potential impact of dialysis on PK or immediate post-dose iron bioavailability. The additional approximately 30 minutes of dosing infusion following dialysis (on dosing day only) is not expected to pose any significant risk or discomfort to patients.

Rationale for Choice of Comparator

Placebo is employed as a comparator in Part 2 to enable unbiased evaluation of clinical outcomes.

Purpose and Timing of Interim Analyses/Design Adaptations

In Part 1, after each cohort of 6 patients finishes the week 4 post-dose assessment, an informal interim analysis will be conducted to make the dose adjustment decision for the next cohort. Safety and PD markers will be reviewed by all members of the dose adjustment team, including the applicable Investigators and representative(s) from the Sponsor. New cohorts will be triggered only if safety and tolerability is confirmed, and if the PD conditions are met as described in FIG. 7. There will be up to 5 informal interim analyses in Part 1. A formal interim analysis is planned after all patients from the last cohort of Part 1 finish the week 4 post-dose assessment to evaluate the clinical effects of doses investigated, and potentially trigger additional non-clinical studies, and may inform subsequent clinical studies. Body temperature, blood pressure, pulse rate, ECG evaluation, blood chemistry, hematology iron indices, EPO resistance index, and adverse events collected through Day 29 of the last cohort conducted in Part 1 will be included.

The minimum PAD and a dose one level higher than the minimum PAD will be selected for Part 2. If the lowest possible tested dose induces a Hgb increase of ≥0.5 g/dL, the two lowest doses tested will be selected for Part 2.

Risks and Benefits

The potential benefit for patients participating in this study may include reduced EPO and IV iron needs, and improved Hgb levels during the time of treatment and for some time beyond.

The risk to patients in this trial will be minimized by adherence to the eligibility criteria, and close clinical monitoring of all patients (and domiciling the first two patients in Part 1) for the first 48 hours following administration Ab.

The potential risks associated with iron mobilization include (a) iron redistribution to tissues and organs such as the spleen, liver, heart, pancreas, and pituitary, and (b) a small increased susceptibility to bacterial infection, particularly in patients with indwelling vascular catheters. Several of the eligibility criteria reduce the risk of complications. Increased levels of liver function tests may be seen in association with iron redistribution. Liver function will be monitored in parallel with hematologic and iron parameters. Overshooting of standard of care Hgb targets may result in polycythemia. Management of Hgb, EPO therapy, and iron therapy may be undertaken HD patients who have been administered IV iron therapy may have higher tissue stores of iron than healthy animals; therefore the maximal levels of serum iron observed in patients treated with an isolated antibody or antigen-binding fragment thereof that binds human BMP6 may exceed those seen in animal studies. However, unlike healthy animals, HD patients are expected to utilize the released serum iron for erythropoiesis; therefore animal models may overestimate the duration of iron elevation. The model-predicted exposure to Ab (e.g., Cmax, AUC) at the MRSD is anticipated to be 10-fold less than that observed at the NOAEL in nonclinical studies. This exposure is not expected to result in serum iron exposure (AUC) levels associated with the elevated liver transaminases and single cell necrosis in the liver observed in preclinical studies. Escalation of Ab dose to the NOAEL will occur following; described safety evaluations. Clinical experience with patients with chronic iron overload as well as those who receive parenteral iron likely does not necessarily predict the effects that may occur from acute increases in intracellular iron induced by Ab. Therefore the potential risk Ab-induced acute iron toxicity is probably low. Acute iron toxicity may affect the heart, liver, and/or pancreas. Clinical manifestations of acute iron toxicity may include cardiac conduction defects, elevated liver transaminases, and glucose intolerance/hyperglycemia. Severe acute iron toxicity may also include metabolic acidosis, electrolyte abnormalities, and neurologic manifestations. In the event that acute iron toxicity occurs, patients may be emergently treated with iron chelation therapy such as deferoxamine combined with hemodialysis. A maximum of 134 mL (Part 1) and 172 mL (Part 2) of blood is planned to be collected over a period of 115 days, from each patient as part of the study. Additional samples for monitoring of any safety findings would be in addition to this. This is not considered to be a risk for this population.

No reproductive toxicity studies have been performed to date with the anti-human BMP6 antibodies. Potential effects on male or female reproductive organs have been assessed by careful standard histopathological examination of the ovaries and testes and accessory reproductive organs in the 13-week toxicity study in cynomolgus monkeys. No treatment-related effects were observed. BMP6 knock out mice showed delayed sternum ossification and iron overload (Meynard et al 2009).

Significant fetal and maternal morbidity and mortality is associated with chronic hemodialysis. In one retrospective cohort study comparing women on chronic hemodialysis (267 births) with women who received a renal transplant (264 births), women on hemodialysis demonstrated higher rates of placental abruption, blood transfusion, small-for-gestational-age babies, fetal deaths, and maternal deaths (Saliem et al 2015). Therefore, women of childbearing potential should use highly effective contraception to prevent pregnancy during an isolated antibody or antigen-binding fragment thereof that binds human BMP6 administration and for 125 days following the last dose.

Population

The study population will be comprised of patients with end-stage renal disease who require chronic hemodialysis therapy at least two times per week, and who have clinical evidence of functional iron-deficiency anemia, defined as anemia in the presence of apparently sufficient iron stores as determined by ferritin and transferrin saturation levels. Part 1 includes a plan to evaluate up to 36 patients initially in 6 cohorts (6 patients/cohort). If after 6 cohorts, no effects on TSAT and Hgb are seen, and there are no safety concerns (as determined by the applicable Investigators and representative(s) from the Sponsor), up to 2 additional 6-patient cohorts may be added (totaling 48 patients in Part 1). Part 2 consists of up to 3 arms (2 dose levels selected for further evaluation from Part 1, and a placebo group), with up to approximately 20 patients per arm (totaling 60 patients in Part 2). Therefore, enrollment of a total of approximately 96 patients (up to a maximum of 108) is planned, of which approximately 60 will be randomized in Part 2. Approximately 60 patients (12 in Part 1, 48 in Part 2) are expected to complete the study. The investigator must ensure that all patients being considered for the study meet the following eligibility criteria. No additional criteria should be applied by the investigator, in order that the study population will be representative of all eligible patients.

Patient selection is to be established by checking through all eligibility criteria at screening and first baseline. A relevant record (e.g. checklist) of the eligibility criteria must be stored with the source documentation at the study site. Deviation from any entry criterion excludes a patient from enrollment into the study.

Inclusion Criteria (Both Parts)

Patients eligible for inclusion in this study have to fulfill all of the following criteria:

Written informed consent must be obtained before any assessment is performed. If consent cannot be expressed in writing, it must be formally documented and witnessed, ideally via an independent trusted witness Age ≥18 years at screening.

Hemodialysis-dependent for at least 2 months prior to screening.

Receiving adequate hemodialysis at least 2 times per week for end stage renal disease; adequate is defined as Kt/V≥1.2 at the most recent monthly assessment prior to screening.

Receiving chronic erythropoietin (EPO) therapy, as per the dialysis site's anemia management protocol. EPO dose not increased by 50% or more during 14 days prior to baseline. EPO therapy must be short-acting formulation only (not darbepoetin) and administered IV (not SC).

Hgb ≥8.5, including Hgb ≥8.5 and <11.5 g/dL, and not increased by ≥0.5 g/dL at baseline vs. prior 14 days.

Ferritin <1500 ng/mL (inclusive) for at least 28 days prior to baseline (may include screening). Alternatively, Ferritin >500 ng/mL and ≤1000 ng/mL at screening.

TSAT ≤30% at a minimum of one time point during the 90 days prior to baseline, and TSAT ≤30% at baseline.

Exclusion Criteria (Both Parts)

Patients fulfilling, any of the following criteria are not eligible for inclusion in this study. No additional exclusions may be applied by the investigator, in order to ensure that the study population will be representative of all eligible patients.

1. Use of other investigational drugs within 5 half-lives of enrollment, or until the expected pharmacodynamic effect has returned to baseline, whichever is longer.
2. History of hypersensitivity to the study drug or to therapeutic antibodies.
3. Known diagnosis of hemochromatosis.
4. Known bone marrow malignancy, lymphatic malignancy or myelodysplastic syndrome.
5. History of dialysis AV fistula thrombosis within 2 months prior to screening, or 2 or more episodes of AV fistula thrombosis within 6 months prior to screening.
6. Severe co-morbid liver disease/dysfunction (Child-Pugh score ≥6) or prior liver transplant 7. Heart failure (New York Heart Association (NYHA) Functional Class III or IV)
8. Gastrointestinal bleeding requiring intervention within the past 2 months of screening. Patients with Hepatitis C Virus (HCV) infection may be included if all other liver function eligibility criteria are met.
9. ALT, AST or bilirubin ≥1.5×ULN within 4 weeks prior to baseline.
10. Uncontrolled renal osteodystrophy defined as intact PTH≥750 pg/mL at screening.
11. Conditions predisposing to an increased risk of serious infection, such as an indwelling vascular catheter (central venous line or hemodialysis catheter) or active infection requiring antibiotic therapy at any time during the 2 weeks prior to screening.
12. Blood transfusion administered within 4 weeks prior to baseline.
13. Receiving a loading dose (100 mg/week) IV iron within 1 week prior to baseline.
14. History of drug or alcohol abuse within the 12 months prior to dosing, or evidence of such abuse as indicated by the laboratory assays conducted during screening.
15. A positive Hepatitis B surface antigen test result.
16. History of immunodeficiency diseases, including a positive HIV (ELISA and Western blot) test result.
17. Women of childbearing potential may be enrolled in this study if highly effective contraception is used, for a minimum of 125 days following dosing with an antibody or antigen-binding fragment that binds human BMP6. Highly effective contraception is defined as one of the following: a. Total abstinence (when this is in line with the preferred and usual lifestyle of the patient. Periodic abstinence (e.g., calendar, ovulation, symptothermal, post-ovulation methods) and withdrawal are not acceptable methods of contraception) b. Male/female sterilization c. Use of oral, injected or implanted hormonal methods of contraception or placement of an intrauterine device (IUD) or intrauterine system (IUS) or other forms of hormonal contraception that have comparable efficacy (failure rate <1%), for example hormone vaginal ring or transdermal hormone contraception.

Treatment

Investigational Treatment

The investigational therapy in this study is an antibody or antigen-binding fragment that binds human BMP6, for example an anti-BMP6 IgG1, fully human antibody. The antibody is provided in liquid solution. The stock concentration will be diluted on site in accord with the dose to be administered. Infusion time will be maintained relatively constant across cohorts at approximately 30 minutes. Part 1 will be open label single dose, and Part 2 will be double-blinded, single dose, in comparison to a matching placebo (vehicle control). The anti-human BMP6 Ab active substance and placebo will be supplied as liquid in vials. The excipients in the active and placebo are identical.

Treatment Arms

In Part 1, patients will be assigned to one of up to 6 dose cohorts consisting of 6 patients each. Part 1 is an open label treatment. The starting dose, top dose, and dose adjustment rationale are described above. Provisional doses for Part 1 are given in Table 12 (Hgb <0.5 g/dL at MRSD) and Table 13 (Hgb ≥0.5 g/dL at MRSD).

TABLE 12

Provisional dose levels for Part 1

| For Hgb less than 0.5 g/dL at MRSD Dose level | Provisional dose | Increment from previous dose |
| --- | --- | --- |
| 1 (MRSD) | 0.010 mg/kg | starting dose |
| 2 | 0.016 mg/kg | 60% ↑ |
| 3 | 0.025 mg/kg | 60% ↑ |
| 4 | 0.040 mg/kg | 60% ↑ |
| 5 | 0.063 mg/kg | 60% ↑ |
| 6 (NOAEL) | 0.100 mg/kg | 60% ↑ |

This table is intended as an example of Part 1 dose adjustment for guidance only. Intermediate or higher dose levels may be used and some dose levels may be skipped based on data evaluation during the informal interim analyses between each cohort. Actual dose levels will be confirmed in writing by Novartis and provided to all participating study sites before treatment of patients in a new cohort.

TABLE 13

Provisional dose levels for Part 1

| For Hgb greater than or equal to 0.5 g/dL at MRSD Dose level | Provisional dose | Increment from previous dose |
| --- | --- | --- |
| 1 (MRSD) | 0.0100 mg/kg | starting dose |
| 2 | 0.0010 mg/kg | 90% ↓ |
| 3 | 0.0016 mg/kg | 60% ↑ |
| 4 | 0.0025 mg/kg | 60% ↑ |
| 5 | 0.0040 mg/kg | 60% ↑ |
| 6 | 0.0063 mg/kg | 60% ↑ |

This table is intended as an example of Part 1 dose adjustment for guidance only. Intermediate or higher dose levels may be used and some dose levels may be skipped based on data evaluation during the informal interim analyses between each cohort.

Study treatments are defined as:
A: single dose of placebo.
B: single dose of anti-human BMP6 Ab at minimum PAD, as determined in Part 1.
C: single dose of anti-human BMP6 Ab at one dose level above minimum PAD, as determined in Part 1.

Concomitant Treatment

All prescription medications, over-the-counter drugs and significant non-drug therapies (including physical therapy and blood transfusions) administered or taken within the timeframe defined in the entry criteria prior to the start of the study and during the study, must be recorded on the Concomitant medications/Significant non-drug therapies section of the CRF. Medication entries should be specific to trade name, the single dose and unit, the frequency and route of administration, the start and discontinuation date and the reason for therapy.

Efficacy/Pharmacodynamics

Efficacy assessments are specified below. Samples for efficacy assessments will be collected at various timepoints. Hematology labs will be assessed. Hgb and Fe indices will be reviewed during each inter-cohort informal interim analysis as part of the dose adjustment evaluation during Part 1 of the study. If the sample collection times set initially are deemed suboptimal for understanding the relationship between iron and PK, the sample collection times may be altered in subsequent cohorts in Part 1.

Iron Indices Panel

The anti-human BMP6 Ab is expected to mobilize Fe from body stores resulting in changes in serum Fe parameters including: serum Fe, transferrin saturation (TSAT), unbound Fe binding capacity (UIBC), total Fe binding capacity (TIBC), ferritin, and reticulocyte hemoglobin content (CHr). These will be measured in serum using validated assays.

Safety

Safety assessments are specified below.

Physical Examination

A complete physical examination will include the examination of general appearance, skin, neck (including thyroid), eyes, ears, nose, throat, lungs, heart, abdomen, back, lymph nodes, extremities, vascular and neurological. If indicated based on medical history and/or symptoms, rectal, external genitalia, breast, and/or pelvic exams may be performed.

Significant findings that are present prior to the start of study drug must be included in the Relevant Medical History/Current Medical Conditions screen on the patient's eCRF. Significant findings made after the start of study drug which meet the definition of an Adverse Event must be recorded on the Adverse Event screen of the patient's eCRF.

Vital Signs
Body temperature
Blood pressure (BP)
Pulse
Height and Weight
Height
Body weight
Body mass index (BMI) will be calculated (Body weight (kg)/[Height (m)]2)

Laboratory Evaluations

Clinically relevant deviations of laboratory test results will be evaluated for criteria defining an adverse event and reported as such if the criteria are met. Repeated evaluations are mandatory until normalization of the result(s) or until the change is no longer clinically relevant.

Hematology

Hemoglobin, hematocrit, red blood cell count, white blood cell count with differential and platelet count will be measured. Iron indices will be monitored.

Clinical Chemistry

Sodium, potassium, creatinine, urea, chloride, albumin, calcium, alkaline phosphatase, total bilirubin, LDH, GGT, AST, and ALT will be monitored. If the total bilirubin concentration is increased above 1.5 times the upper limit of normal, direct and indirect reacting bilirubin should be differentiated.

Electrocardiogram (ECG)

PR interval, QRS duration, heart rate, RR, QT, QTc

The Fridericia QT correction formula (QTcF) should be used for clinical decisions.

Pregnancy and Assessments of Fertility

Pregnancy tests are required of all female patients regardless of reported reproductive/menopausal status.

Serum pregnancy tests will be performed for this study. If positive, the patient must be discontinued from the trial.

When performed at screening and baseline, the result of this test must be received before the patient may be dosed.

Pharmacokinetics

PK samples will be collected. PK data will be reviewed during each inter-cohort informal interim analysis as part of the dose adjustment evaluation during Part 1 of the study. If the sample collection times set initially are deemed inadequate or inappropriate for characterizing the PK profile, the sample collection times may be altered in subsequent cohorts. The number of blood draws and total blood volume collected will not exceed those stated in the protocol.

PK samples will be collected and evaluated in all patients at all dose levels.

The concentration of free anti-human BMP6 Ab will be determined using an ELISA assay. The anticipated lower limit of quantification (LLOQ) is 10 pg/mL.

Untreated (placebo) samples will not be analyzed.

Free anti-human BMP6 Ab concentrations will be expressed at µg/mL. All concentrations below the LLOQ or missing data will be labeled as such in the concentration data listings. Concentrations below the LLOQ will be treated as zero in summary statistics for concentration data only. They will not be considered in the calculation of PK parameters.

PK samples remaining after determination of free anti-human BMP6 Ab may be used for exploratory assessments or other bioanalytical purposes (e.g. cross-check between different sites, stability assessment).

The following pharmacokinetic parameters will be determined (if feasible) using non-compartmental method(s) with Phoenix WinNonlin (Version 6.2 or higher): Cmax, tmax, AUC(0-t), AUC(0-tlast), Cmax/D, and AUC/D based on the serum concentration-time data. The linear trapezoidal rule will be used for AUC calculations. The terminal half-life of an antibody or antigen-binding fragment that binds human BMP6 ($t_{1/2}$) will also be estimated if feasible based on the data.

Other Assessments

Immunogenicity

An ELISA assay will be used to detect anti-human BMP6 antibodies. IG samples remaining after immunogenicity analysis may be used for exploratory assessment or other bioanalytical purposes (e.g., cross-check between different sites).

Exploratory Assessments

Biomarkers are objectively measured and evaluated indicators of normal biological processes, pathogenic processes, or pharmacologic responses to a therapeutic intervention (Biomarkers Definitions Working Group 2001).

The BMP6-hepcidin pathway is as follows: BMP6 signalling in hepatocytes is required for induced expression of hepcidin, inhibiting enterocyte iron absorption and macrophage iron export. BMP6-neutralizing antibody as a hepcidin-lowering therapy should benefit patients with iron-restricted anemia by reducing EPO requirement and increasing the number of patients who reach target Hgb level.

Based on the above described biology, exploratory biomarker assessments include, but not limited to hepcidin (measured using LC-MS assay).

Additional exploratory assessments may investigate potential roles of bone absorption markers, as well as address inflammation as a factor contributing to the mechanism of action.

The exploratory objectives are as follows:
To assess the relationships between hepcidin levels and several key measures such as ERI and iron indices:
To study the dynamics between primary and secondary endpoints and exploratory biomarkers longitudinally;
To assess pharmacogenetics;
To assess immunogenicity Sample(s) will be collected at various time point(s).

Further details on sample collection, numbering, processing and shipment will be provided in a central lab manual.

DNA

Exploratory DNA research studies are planned as a part of this study the objectives of identifying genetic factors which may (1) be related to erythropoietin-treated chronic hemodialysis patients with functional iron-deficiency anemia, (2) predict response to treatment with anti-human BMP6 Ab, or (3) predict genetic predisposition to side effects.

In addition, recent advances in genotyping technologies have made genome-wide approaches possible. Genome-wide approaches may also be undertaken within the restricted scope of these studies as described above.

Soluble Biomarkers

Hepcidin will be quantified in plasma as a potential PD/biomarker.

Detailed descriptions of the assays will be included in the bioanalytical data reports.

Other Biomarkers

Hypothesis-free platforms might be used to understand disease heterogeneity, mode of action and/or potential identification of stratification markers. Immunogenicity (IG) samples will be collected at various timepoints. Immunogenicity of anti-human BMP6 Ab will be assessed by measuring antibodies recognizing the anti-human BMP6 antibody.

REFERENCES

Fukuma S, Yamaguchi T, Hashimoto S et al (2012) Erythropoiesis-stimulating agent responsiveness and mortality in hemodialysis patients: results from a cohort study from the dialysis registry in Japan. Am J Kidney Dis; 59(1): p. 108-16.

Kilpatrick R D, Critchlow C W, Fishbane S et al (2008) Greater epoetin alfa responsiveness is associated with improved survival in hemodialysis patients. Clin J Am Soc Nephrol; 2008. 3(4):1077-83.

Lopez-Gomez J M, Portoles T M, and Aljama P (2008), Factors that condition the response to erythropoietin in patients on hemodialysis and their relation to mortality. Kidney Int Suppl; (111):S75-81.

Meynard D, Kautz L, Darnaud V et al (2009) Lack of the bone morphogenetic protein BMP6 induces massive iron overload. Nat Genet; 41(4):478-81.

Saliem S, Patenaude V, Abenhaim H A (2015) Pregnancy outcomes among renal transplant recipients and patients with end-stage renal disease on dialysis. J Perinat Med (Epiib ahead of print) ncbi.nlm.nih.gov/pubmed/25719292.

Suttorp M M, Hoekstra T, Rotmans J et al (2013) Eiythropoiesis-stimulating agent resistance and mortality in hemodialysis and peritoneal dialysis patients. BMC Nephrol; 14(1):200.

Zaritsk J, Young B, Gales B, et al (2010) Reduction of serum hepcidin by hemodialysis in pediatric and adult patients. Clin J Am Soc Nephrol; 5(6):1010-14.

Example 3

TSAT Levels for Patients Treated with 0.01 mg/kg Antibody 7

Data, including TSAT (iron saturation, %) levels were assessed for the first 10 patients treated according to the clinical protocol described in Example 2, with each patient receiving a single infusion of 0.01 mg/kg Antibody 7. None of these patients demonstrated any liver safety signals that defined the no observed adverse effect level (NOAEL) of 0.1 mg/kg/week. Cohort 1 included 5 anemic hemodialysis patients with low ferritin levels of less than or equal to 500 ng/mL, while Cohort 2 included 5 anemic hemodialysis patients higher ferritin levels (between 500 and 1000 ng/mL).

Figure 14:
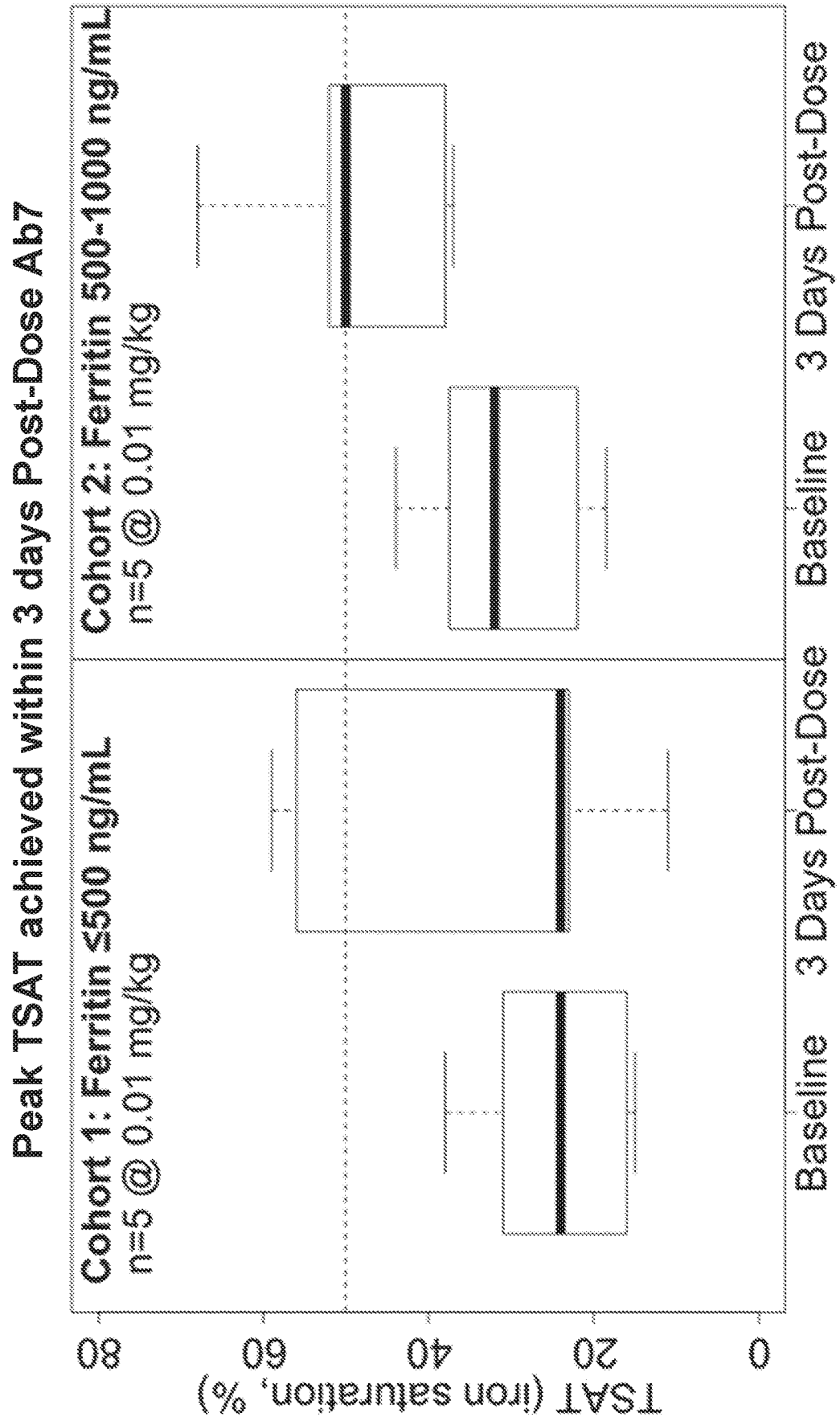
FIG. 14 shows the peak TSAT (iron saturation, %) for hemodialysis patients before treatment (Baseline) and during the 3 days following treatment with 0.01 mg/kg Antibody 7 (Ab7) (3 Days Post Dose). Cohort 1 patients all had pretreatment Ferritin levels less than or equal to 500 ng/mL. Cohort 2 patients all had pretreatment Ferritin levels between 500 and 1000 ng/mL. The bold line shows the median TSAT level for each group.

In the five Cohort 1 (low ferritin) patients who received 0.01 mg/kg Antibody 7, post-dose TSAT levels increased by an average of only 9.8% (mean 38.6% post-dose vs. 24.8% pre-dose). In contrast, post-dose TSAT levels increased by an average of 17.6% (mean 48.4% post-dose vs. 30.8% pre-dose) in five Cohort 2 (high ferritin) patients who received 0.01 mg/kg Antibody 7. The data are shown in FIG. 14, which shows the peak TSAT levels pre-Antibody 7 vs. within 72 hours post-Antibody 7 administration in the 2 cohorts. Surprisingly, in contrast to the Cohort 1 patients, the Cohort 2 anemia patients demonstrate a distinct TSAT increase in comparison to baseline. These data indicate that patients with ferritin levels greater than or equal to 500 ng/mL are good candidates for response to anti-BMP6 therapy, and that ferritin level, for example, a ferritin level greater than or equal to 500 ng/mL, may be an indicator of response.

Unless defined otherwise, the technical and scientific terms used herein have the same meaning as that usually understood by a specialist familiar with the field to which the disclosure belongs.

Unless indicated otherwise, all methods, steps, techniques and manipulations that are not specifically described in detail can be performed and have been performed in a manner known per se, as will be clear to the skilled person. Reference is for example again made to the standard handbooks and the general background art mentioned herein and to the further references cited therein. Unless indicated otherwise, each of the references cited herein is incorporated in its entirety by reference.

Claims to the invention are non-limiting and are provided below.

Although particular aspects and claims have been disclosed herein in detail, this has been done by way of example for purposes of illustration only, and is not intended to be limiting with respect to the scope of the appended claims, or the scope of subject matter of claims of any corresponding future application. In particular, it is contemplated by the inventors that various substitutions, alterations, and modifications may be made to the disclosure without departing from the spirit and scope of the disclosure as defined by the claims. The choice of nucleic acid starting material, clone of interest, or library type is believed to be a matter of routine for a person of ordinary skill in the art with knowledge of the aspects described herein. Other aspects, advantages, and modifications considered to be within the scope of the following claims. Those skilled in the art will recognize or be able to ascertain, using no more than routine experimentation, many equivalents of the specific aspects of the invention described herein. Such equivalents are intended to be encompassed by the following claims. Redrafting of claim scope in later filed corresponding applications may be due to limitations by the patent laws of various countries and should not be interpreted as giving up subject matter of the claims.

What is claimed is:

1. A method of selectively treating anemia in a patient in need thereof, comprising selectively administering a therapeutically effective amount of a bone morphogenetic protein 6 (BMP6) antagonist to the patient on the basis of a biological sample from the patient having a ferritin level of ≥500 ng/mL, wherein the BMP6 antagonist is an anti-BMP6 antibody or antigen-binding fragment thereof comprising:

(a) HCDR1, HCDR2, and HCDR3 sequences of SEQ ID NOs: 69, 70 and 71, respectively, and LCDR1, LCDR2, and LCDR3 sequences of SEQ ID NOs: 79, 80 and 81, respectively;

(b) HCDR1, HCDR2, and HCDR3 sequences of SEQ ID NOs: 72, 73 and 74, respectively, and LCDR1, LCDR2, and LCDR3 sequences of SEQ ID NOs: 82, 83 and 84, respectively;

(c) HCDR1, HCDR2, and HCDR3 sequences of SEQ ID NOs: 29, 30 and 31, respectively, and LCDR1, LCDR2, and LCDR3 sequences of SEQ ID NOs: 39, 40 and 41, respectively;

(d) HCDR1, HCDR2, and HCDR3 sequences of SEQ ID NOs: 32, 33 and 34, respectively, and LCDR1, LCDR2, and LCDR3 sequences of SEQ ID NOs: 42, 43 and 44, respectively;

(e) HCDR1, HCDR2, and HCDR3 sequences of SEQ ID NOs: 49, 50 and 51, respectively, and LCDR1, LCDR2, and LCDR3 sequences of SEQ ID NOs: 59, 60 and 61, respectively;

(f) HCDR1, HCDR2, and HCDR3 sequences of SEQ ID NOs: 52, 53 and 54, respectively, and LCDR1, LCDR2, and LCDR3 sequences of SEQ ID NOs: 62, 63 and 64, respectively;

(g) HCDR1, HCDR2, and HCDR3 sequences of SEQ ID NOs: 9, 10 and 11, respectively, and LCDR1, LCDR2, and LCDR3 sequences of SEQ ID NOs: 19, 20 and 21, respectively; or (h) HCDR1, HCDR2, and HCDR3 sequences of SEQ ID NOs: 12, 13 and 14, respectively, and LCDR1, LCDR2, and LCDR3 sequences of SEQ ID NOs: 22, 23 and 24, respectively.

2. The method of claim 1, wherein the ferritin level is ferritin protein level.

3. The method of claim 1, wherein the anemia is anemia associated with chronic disease.

4. The method of claim 3, wherein the chronic disease is chronic kidney disease, cancer or inflammation.

5. The method of claim 1, wherein the patient is being or has been treated with an erythropoiesis stimulating agent (ESA).

6. The method of claim 5, wherein the ESA is erythropoietin (EPO).

7. The method of claim 1, wherein the anemia is EPO-hyporesponsive anemia.

8. The method of claim 1, wherein the anemia is functional iron-restricted anemia.

9. The method of claim 1, wherein the patient is a chronic hemodialysis patient.

10. The method of claim 1, further comprising reducing the patient's iron dose requirement, reducing the patient's EPO dose requirement, or reducing both the patient's iron dose requirement and the patient's EPO dose requirement, relative to said EPO dose requirement and/or iron dose requirement in the absence of treatment with the therapeutically effective amount of the BMP6 antagonist.

11. The method of claim 1, wherein the anti-BMP6 antibody or antigen-binding fragment thereof comprises:
(a) A VH sequence of SEQ ID NO: 75;
(b) A VH sequence of SEQ ID NO: 35;
(c) A VH sequence of SEQ ID NO: 55; or
(d) A VH sequence of SEQ ID NO: 15.

12. The method of claim 1, wherein the anti-BMP6 antibody or antigen-binding fragment thereof comprises:
(a) A VL sequence of SEQ ID NO: 85;
(b) A VL sequence of SEQ ID NO: 45;
(c) A VL sequence of SEQ ID NO: 65; or
(d) A VL sequence of SEQ ID NO: 25.

13. The method of claim 1, wherein the anti-BMP6 antibody or antigen-binding fragment thereof comprises:
(a) A VH sequence of SEQ ID NO: 75; and a VL sequence of SEQ ID NO: 85;
(b) A VH sequence of SEQ ID NO: 35; and a VL sequence of SEQ ID NO: 45;
(c) A VH sequence of SEQ ID NO: 55; and a VL sequence of SEQ ID NO: 65; or
(d) A VH sequence of SEQ ID NO: 15; and a VL sequence of SEQ ID NO: 25.

14. The method of claim 1, wherein the anti-BMP6 antibody or antigen-binding fragment thereof comprises:
(a) A heavy chain sequence of SEQ ID NO: 77;
(b) A heavy chain sequence of SEQ ID NO: 37;
(c) A heavy chain sequence of SEQ ID NO: 57; or
(d) A heavy chain sequence of SEQ ID NO: 17.

15. The method of claim 1, wherein the anti-BMP6 antibody or antigen-binding fragment thereof comprises:
(a) A light chain sequence of SEQ ID NO: 87;
(b) A light chain sequence of SEQ ID NO: 47;
(c) A light chain sequence of SEQ ID NO: 67; or
(d) A light chain sequence of SEQ ID NO: 27.

16. The method of claim 1, wherein the anti-BMP6 antibody or antigen-binding fragment thereof comprises:
(a) A heavy chain sequence of SEQ ID NO: 77; and a light chain sequence of SEQ ID NO: 87;
(b) A heavy chain sequence of SEQ ID NO: 37; and a light chain sequence of SEQ ID NO: 47;
(c) A heavy chain sequence of SEQ ID NO: 57; and a light chain sequence of SEQ ID NO: 67; or
(d) A heavy chain sequence of SEQ ID NO: 17; and a light chain sequence of SEQ ID NO: 27.

17. The method of claim 1, wherein the anti-BMP6 antibody or antigen-binding fragment thereof:
a) binds human BMP6 with a KD of ≤1 nM; or
b) binds human BMP6 with a KD of ≤0.1 nM.

18. The method of claim 1, wherein the anti-BMP6 antibody or antigen-binding fragment thereof:
a) has at least about 100-fold greater affinity for human BMP6 than human BMP7;
b) has at least about 100-fold greater affinity for human BMP6 than human BMP2, human BMP5, or human BMP7;
c) has at least about 500-fold greater affinity for human BMP6 than human BMP2, human BMP5, or human BMP7; and/or
d) has no detectable binding to human BMP2 and/or BMP7 in an ELISA.

19. The method of claim 1, wherein the anti-BMP6 antibody or antigen-binding fragment thereof is an IgG selected from an IgG1, an IgG2, and IgG3 or an IgG4.

20. The method of claim 1, wherein the anti-BMP6 antibody or antigen-binding fragment thereof is selected from the group consisting of: a monoclonal antibody, a chimeric antibody, a single chain antibody, a Fab and a scFv.

21. The method of claim 1, wherein the anti-BMP6 antibody or antigen-binding fragment thereof is a component of an immunoconjugate.

22. The method of claim 1, wherein the anti-BMP6 antibody or antigen-binding fragment thereof has altered effector function through mutation of the Fc region.

23. The method of claim 1, wherein the anti-BMP6 antibody or antigen-binding fragment thereof binds to a human BMP6 epitope comprising the sequence QTLVHLMNPEYVPKP (SEQ ID NO: 98).

24. The method of claim 1, wherein the antibody or antigen-binding fragment thereof is administered:
a) intravenously; or
b) subcutaneously.

25. The method of claim 1, wherein the ferritin level is between 500 ng/mL and 2000 ng/mL.

* * * * *